(12) United States Patent
Opperman et al.

(10) Patent No.: US 9,540,389 B2
(45) Date of Patent: Jan. 10, 2017

(54) ANTIMICROBIAL POTENTIATORS

(71) Applicant: MICROBIOTIX, INC., Worcester, MA (US)

(72) Inventors: Timothy J. Opperman, Arlington, MA (US); Son T. Nguyen, West Boylston, MA (US); Steven M. Kwasny, Blackstone, MA (US); Xiaoyuan Ding, North Providence, RI (US)

(73) Assignee: Microbiotix, Inc., Worcester, MA (US)

( * ) Notice: Subject to any disclaimer, the term of this patent is extended or adjusted under 35 U.S.C. 154(b) by 0 days.

(21) Appl. No.: 14/888,022

(22) PCT Filed: May 3, 2014

(86) PCT No.: PCT/US2014/036712
§ 371 (c)(1),
(2) Date: Oct. 29, 2015

(87) PCT Pub. No.: WO2014/179784
PCT Pub. Date: Nov. 6, 2014

(65) Prior Publication Data
US 2016/0075714 A1    Mar. 17, 2016

Related U.S. Application Data

(60) Provisional application No. 61/819,054, filed on May 3, 2013.

(51) Int. Cl.

| | |
|---|---|
| A61K 31/5377 | (2006.01) |
| C07D 491/052 | (2006.01) |
| A61K 31/551 | (2006.01) |
| C07D 493/04 | (2006.01) |
| C07D 513/04 | (2006.01) |
| A61K 45/06 | (2006.01) |
| A61K 31/436 | (2006.01) |
| A61K 31/496 | (2006.01) |
| A61K 31/541 | (2006.01) |

(Continued)

(52) U.S. Cl.
CPC ........... *C07D 491/052* (2013.01); *A01N 43/90* (2013.01); *A01N 47/44* (2013.01); *A61K 31/436* (2013.01); *A61K 31/496* (2013.01); *A61K 31/5377* (2013.01); *A61K 31/5383* (2013.01); *A61K 31/541* (2013.01); *A61K 31/551* (2013.01); *A61K 31/553* (2013.01); *A61K 45/06* (2013.01); *C07D 493/04* (2013.01); *C07D 513/04* (2013.01)

(58) Field of Classification Search
CPC ... A61K 45/06; A61K 31/436; A61K 2300/00
USPC ............ 424/411; 514/196; 540/544; 544/127
See application file for complete search history.

(56) References Cited

U.S. PATENT DOCUMENTS

2009/0163545 A1* 6/2009 Goldfarb .............. A61K 31/122
                                                                514/312
2012/0040932 A1* 2/2012 Hirst ..................... A61K 31/69
                                                                514/64

FOREIGN PATENT DOCUMENTS

WO    2012171506 A1 * 12/2012

OTHER PUBLICATIONS

Richardson et al; Title: Identification of non-furan containing A2A antagonists using database mining and molecular similarity approaches; Bioorganic & Medicinal Chemistry Letters; vol. 16, Issue 23, Dec. 1, 2006, pp. 5993-5997.*

(Continued)

*Primary Examiner* — Yanzhi Zhang
(74) *Attorney, Agent, or Firm* — Leon R. Yankwich; David C. O'Brien; Yankwich & Associates, P.C.

(57) ABSTRACT

Novel compounds are disclosed having the structure of Formula I:

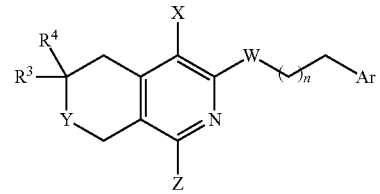

FORMULA I wherein,
n is an integer from 1 to 5;
X is —CN, —F, —Cl, —Br, —I, —NO$_2$;
W is S, SO, SO$_2$, O, NH, or NR$^5$;
R$^5$ is alkyl, aralkyl, alkenyl, or alkynyl;
Y is O, S;
Z is NR$^1$R$^2$ or heterocycloalkyl;
R$^1$, R$^2$ are, independently, hydrogen, alkyl, aralkyl, alkenyl, alkynyl, or cycloalkyl and may be optionally substituted with halo, hydroxy, alkoxy, amino, alkylamino, carboxy, alkoxycarbonyl, or nitrile groups;
R$^3$ and R$^4$ are, independently, hydrogen, alkyl, aralkyl, alkenyl, alkynyl, or cycloalkyl and may be optionally substituted with halo, hydroxy, alkoxy, amino, alkylamino, carboxy, alkoxycarbonyl, or nitrile groups, and may together form a cyclic structure; and
Ar is mono-, di-, or tri-substituted phenyl or heteroaryl,
a pharmaceutically acceptable salts thereof.
The compounds are potent bacterial efflux pump inhibitors (EPIs). Such compounds are useful to potentiate the antimicrobial activity of antimicrobial compounds such as beta-lactam antibiotics and quinolone antibiotics against Gram-negative bacteria.

17 Claims, 6 Drawing Sheets

(51) Int. Cl.
*A01N 43/90* (2006.01)
*A01N 47/44* (2006.01)
*A61K 31/5383* (2006.01)
*A61K 31/553* (2006.01)

(56) References Cited

OTHER PUBLICATIONS

Author: Paronikyan et al.; Title: Synthesis of 2-arylsubstituted pyrano[4,3-d]thieno-[2,3-b]pyridines and thieno[2,3-c]isoquinolines; Hayastani Kimiakan Handes, vol. 64, Issue: 2, pp. 265-271, 2011.*
Ballell et al., "Fueling Open-Source Drug Discovery: 177: Small Molecule Leads Against Tuberculosis", ChemMedChem, 8: 313-321 (2013) and Supporting Information at http://dx.doi.org./10.1002/cmdc.201200428.
Paronikyan et al. "Synthesis and Antibacterial Activity of Pyrano-(Thiopyrano) [3,4-c] Pyridine-2,7-Naphthyridine-, and 5,6,7,8,-Tetrahydro-Isoquinoline-3(2H)-Thione Derivatives", Pharm. Chem. J., 27(11): 1-4 (1993).

* cited by examiner a) *E. coli* AB1157
b) *E. coli* ATCC 25922
c) *K. pneumoniae* ATCC 700603
d) *S. flexneri* ATCC 12022
e) *S. enterica* ATCC 14028
f) *E. aerogenes* ATCC 13048

A) *E. coli* AB1157
B) *E. coli* 331
C) *Shigella flexneri* ATCC 12022
D) *Klebsiella pneumoniae* ATCC 13882
E) *Salmonella enterica* (typhimurium) ATCC 14028
F) *Enterobacter cloacae* subsp. cloacae ATCC 13047
G) *Proteus mirabilis* ATCC 25933
H) *Pseudomonas aeruginosa* ATCC 27835

US 9,540,389 B2

ANTIMICROBIAL POTENTIATORS

CROSS-REFERENCE TO RELATED APPLICATIONS

This application is a United States national stage filing under 35 U.S.C. §371 of international (PCT) application no. PCT/US2014/036712, filed May 3, 2014, and designating the US, which claims priority to U.S. Provisional Appln. No. 61/819,054 filed May 3, 2013.

STATEMENT OF FEDERALLY SPONSORED RESEARCH

This invention was made with government support under grants AI074116-01A2 and AI100332-02 awarded by the National Institutes of Health. The government has certain rights in the invention.

FIELD OF THE INVENTION

This invention is in the field of compounds that act in synergy with antimicrobial agents to enhance their effects. In particular, the invention provides organic compounds that work as efflux pump inhibitors, which enhance the efficacy of antibiotics.

BACKGROUND OF THE INVENTION

Multi-drug resistance (MDR) in Gram-negative pathogens, including the Enterobacteriaceae, *Pseudomonas aeruginosa*, *Acinetobacter* spp., and *Stenotrophomonas maltiphilia*, pose a significant threat to the effective treatment of infections caused by these organisms (Kibbey, et al.: An integrated process for measuring the physicochemical properties of drug candidates in a preclinical discovery environment. In J Pharm Sci, vol. 90, pp. 1164-1175, (2001); Kang et al.: Risk factors for antimicrobial resistance and influence of resistance on mortality in patients with bloodstream infection caused by *Pseudomonas aeruginosa*. In Microb Drug Resist, vol. 11, pp. 68-74, (2005); Kang, et al.: Clinical epidemiology of ciprofloxacin resistance and its relationship to broad-spectrum cephalosporin resistance in bloodstream infections caused by *Enterobacter* species. In Infect Control Hosp Epidemiol, vol. 26, pp. 88-92, (2005); Kang, et al.: Bloodstream infections caused by antibiotic resistant Gram-negative bacilli: risk factors for mortality and impact of inappropriate initial antimicrobial therapy on outcome Antimicrob Agents Chemother, vol. 49, pp. 760-766, (2005)). The MDR threat has been exacerbated by the recent decrease in commercial efforts to discover and develop new antibacterial agents. In addition, antibacterial agents that have been introduced recently into the clinic or are in development, such as daptomycin, gemifloxacin, telithromycin, and telavancin, are not active against Gram-negative pathogens. Recently approved agents with activity against Gram-negative bacteria include tigecycline and doripenem. While tigecycline is active against bacteria producing a tetracycline-specific pump in vitro, it is pumped out rapidly by the ubiquitous multidrug pumps, and its pharmacokinetic properties will limit its use for treating urinary tract and bloodstream infections (Peleg, et al.: Hospital acquired infections due to Gram-negative bacteria. In N Engl J Med, vol. 362, pp. 1804-1813, (2010)), as will the evolution of resistance during therapy (Anthony, et al.: Clinical and microbiological outcomes of serious infections with multi-drug-resistant Gram-negative organisms treated with tigecycline. Iu Clin Infect Dis, vol. 46, pp. 567-570, (2008)). Clearly, novel strategies for effectively treating infections caused by MDR Gram-negative pathogens are urgently needed.

The MDR phenotype has been attributed to both acquired and intrinsic mechanisms of resistance. Acquired resistance mechanisms include mutations that decrease the affinity of the target for an antibacterial agent, or through acquisition of mobile genetic elements that modify the target or inactivate the antibacterial agent. In recent years, the importance of the role that intrinsic resistance mechanisms play in the development of the MDR phenotype has been fully appreciated (Nikaido, et al.: Broad-specificity efflux pumps and their role in multidrug resistance of Gram-negative bacteria. In FEMS Microbiol Rev, vol. 36, pp. 340-363, (2012); Poole: Bacterial stress responses as determinants of antimicrobial resistance. In J Antimicrob Chemother, vol. 67, pp. 2069-2089, (2012)). Recent genome-wide screens for mutants with altered susceptibilities to antibacterial agents have identified several genes that play a role in intrinsic resistance in *E. coli* (Tamae, et al.: Determination of antibiotic hypersensitivity among 4,000 single-gene-knockout mutants of *Escherichia coli*. In J Bacteriol, vol. 190, pp. 5981-5988, (2008)) and *P. aeruginosa* (Breidenstein, et al.: Complex ciprofloxacin resistome revealed by screening a *Pseudomonas aeruginosa* mutant library for altered susceptibility. In Antimicrob Agents Chemother, vol. 52, pp. 4486-4491, (2008); Fajardo, et al.: The neglected intrinsic resistome of bacterial pathogens. In PLoS One, vol. 3, pp. e1619, (2008); Gallagher, et al.: Genome-scale identification of resistance functions in *Pseudomonas aeruginosa* using Tn-seq. In MBio, vol. 2, pp. e00315-00310, (2012)), including genes involved in heat shock, SOS response, membrane stress response, and efflux. A network of proteases FtsH and accessory proteins YccA, HtpX, HflK, HslUV, and HflC are involved in intrinsic resistance to aminoglycoside tobramycin (Hinz, et al.: Membrane proteases and aminoglycoside antibiotic resistance. In J Bacteriol, vol. 193, pp. 4790-4797, (2011)), presumably by removing misfolded proteins. In addition, the SOS has been implicated in intrinsic resistance to quinolone antibiotics (Piddock, et al.: Bactericidal activities of five quinolones for *Escherichia coli* strains with mutations in genes encoding the SOS response or cell division. In Antimicrob Agents Chemother, vol. 36, pp. 819-825, (1992)). However, the RND efflux pumps of Gram-negative bacteria play a major role in MDR. Because of their broad substrate specificity, overexpression of these efflux pumps results in decreased susceptibility to a wide range of antibacterial agents and biocides (Nikaido, et al.: Broad-specificity efflux pumps and their role in multidrug resistance of Gram-negative bacteria. In FEMS Microbiol Rev, vol. 36, pp. 340-363, (2012)).

The major efflux pump of *E. coli* is a typical Resistance-Nodulation-Division (RND) pump, which is a tripartite structure consisting of an integral membrane efflux transporter with broad substrate specificity (AcrB), an outer membrane channel (TolC), and a periplasmic protein adapter (AcrA). Antibiotics enter the periplasmic space through a porin or by diffusion through the lipid bilayer, where they interact with the substrate binding pocket of AcrB. The AcrB transporter uses proton motive force to extrude the compound into the TolC channel and to the exterior. These RND family pumps not only produce intrinsic levels of resistance to antibacterial agents, including the fluoroquinolones (FQs; e.g. ciprofloxacin and levofloxacin) and β-lactams (e.g., piperacillin, meropenem, and aztreonam) (Piddock: Clinically relevant chromosomally encoded multidrug resistance efflux pumps in bacteria. In Clin Microbiol Rev, vol. 19, pp. 382-402, (2006)), but also produce an MDR phenotype when overproduced. In addition, inhibition of RND pumps in *P. aeruginosa* by genetic deletion (Lomovskaya, et al.: Use of a genetic approach to evaluate the consequences of inhibition of efflux pumps in *Pseudomonas aeruginosa*. In Antimicrob Agents Chemother, vol. 43, pp. 1340-1346, (1999)) or with a potent efflux pump inhibitor (EPI) (Lomovskaya, et al.: Identification and characterization of inhibitors of multidrug resistance efflux pumps in *Pseudomonas aeruginosa*: novel agents for combination therapy. In Antimicrob Agents Chemother, vol. 45, pp. 105-116, (2001)) decreases the frequency of resistance to levofloxacin, and AcrAB-TolC is required for selection of target mutations for FQ resistance in *E. coli* (Singh, et al.: Temporal interplay between efflux pumps and target mutations in development of antibiotic resistance in *Escherichia coli*. Iu Antimicrob Agents Chemother, vol. 56, pp. 1680-1685, (2012)). In addition, RND pumps have been shown to play a role in virulence of the enteric pathogen *Salmonella enterica* serovar *Typhimurium* (Nishino, et al.: Virulence and drug resistance roles of multidrug efflux systems of *Salmonella enterica* serovar *Typhimurium*. In Mol Microbiol, vol. 59, pp. 126-141, (2006)), and EPIs that target RND pumps have been shown to inhibit biofilm formation in *E. coli* and *K. pneumoniae* (Kvist, et al.: Inactivation of efflux pumps abolishes bacterial biofilm formation. In Appl Environ Microbiol, vol. 74, pp. 7376-7382, (2008)). Therefore, EPIs could be used as adjunctive therapies with an FQ or β-lactam antibiotic to improve antibacterial potency at low antibiotic concentrations, prevent the emergence of resistance, inhibit biofilm formation, and decrease virulence of enteric pathogens.

Several potent efflux pump inhibitors have been described in the literature (Thorarensen, et al.: 3-Arylpiperidines as potentiators of existing antibacterial agents. In Bioorg Med Chem Lett, vol. 11, pp. 1903-1906, (2001); Lomovskaya, et al.: Practical applications and feasibility of efflux pump inhibitors in the clinic—a vision for applied use. In Biochem Pharmacol, vol. 71, pp. 910-918, (2006); Mahamoud, et al.: Quinoline derivatives as promising inhibitors of antibiotic efflux pump in multidrug resistant *Enterobacter aerogenes* isolates. In Curr Drug Targets, vol. 7, pp. 843-847, (2006); Mahamoud, et al.: Antibiotic efflux pumps in Gram-negative bacteria: the inhibitor response strategy. In J Antimicrob Chemother, vol. 59, pp. 1223-1229, (2007)), however, none have reached clinical development. A family of peptidomimetics, including PAβN (MC-207 110), that exhibited potent inhibition of efflux pumps in *P. aeruginosa* has been developed for use as an adjunctive therapy (Renau, et al.: Inhibitors of efflux pumps in *Pseudomonas aeruginosa* potentiate the activity of the fluoroquinolone antibacterial levofloxacin. In J Med Chem, vol. 42, pp. 4928-4931, (1999); Lomovskaya, et al.: Identification and characterization of inhibitors of multidrug resistance efflux pumps in *Pseudomonas aeruginosa*: novel agents for combination therapy. In Antimicrob Agents Chemother, vol. 45, pp. 105-116, (2001); Renau, et al.: Addressing the stability of C-capped dipeptide efflux pump inhibitors that potentiate the activity of levofloxacin in *Pseudomonas aeruginosa*. In Bioorg Med Chem Lett, vol. 11, pp. 663-667, (2001); Renau, et al.: Peptidomimetics of efflux pump inhibitors potentiate the activity of levofloxacin in *Pseudomonas aeruginosa*. In Bioorg Med Chem Lett, vol. 12, pp. 763-766, (2002); Renau, et al.: Conformationally restricted analogues of efflux pump inhibitors that potentiate the activity of levofloxacin in *Pseudomonas aeruginosa*. In Bioorg Med Chem Lett, vol. 13, pp. 2755-2758, (2003); Watkins, et al.: The relationship between physicochemical properties, in vitro activity and pharmacokinetic profiles of analogues of diamine-containing efflux pump inhibitors. In Bioorg Med Chem Lett, vol. 13, pp. 4241-4244, (2003); Yoshida, et al.: MexAB-OprM specific efflux pump inhibitors in *Pseudomonas aeruginosa*. Part 5: Carbon-substituted analogues at the C-2 position. In Bioorg Med Chem, vol. 14, pp. 1993-2004, (2006); Yoshida, et al.: MexAB-OprM specific efflux pump inhibitors in *Pseudomonas aeruginosa*. Part 6: exploration of aromatic substituents. In Bioorg Med Chem, vol. 14, pp. 8506-8518, (2006); Yoshida, et al.: MexAB-OprM specific efflux pump inhibitors in *Pseudomonas aeruginosa*. Part 7: highly soluble and in vivo active quaternary ammonium analogue D13-9001, a potential preclinical candidate. In Bioorg Med Chem, vol. 15, pp. 7087-7097, (2007)). In addition, pyridopyrimidine EPIs that are specific for the MexAB efflux pump of *P. aeruginosa* were advanced to the preclinical stage (Nakayama, et al.: MexAB-OprM-specific efflux pump inhibitors in *Pseudomonas aeruginosa*. Part 1: discovery and early strategies for lead optimization. In Bioorg Med Chem Lett, vol. 13, pp. 4201-4204, (2003); Nakayama, et al.: MexAB-OprM specific efflux pump inhibitors in *Pseudomonas aeruginosa*. Part 2: achieving activity in vivo through the use of alternative scaffolds. In Bioorg Med Chem Lett, vol. 13, pp. 4205-4208, (2003); Nakayama, et al.: MexAB-OprM specific efflux pump inhibitors in *Pseudomonas aeruginosa*. Part 3: Optimization of potency in the pyridopyrimidine series through the application of a pharmacophore model. In Bioorg Med Chem Lett, vol. 14, pp. 475-479, (2004); Nakayama, et al.: MexAB-OprM specific efflux pump inhibitors in *Pseudomonas aeruginosa*. Part 4: Addressing the problem of poor stability due to photoisomerization of an acrylic acid moiety. In Bioorg Med Chem Lett, vol. 14, pp. 2493-2497, (2004); Yoshida, et al.: MexAB-OprM specific efflux pump inhibitors in *Pseudomonas aeruginosa*. Part 5: Carbon-substituted analogues at the C-2 position. In Bioorg Med Chem, vol. 14, pp. 1993-2004, (2006); Yoshida, et al.: MexAB-OprM specific efflux pump inhibitors in *Pseudomonas aeruginosa*. Part 6: exploration of aromatic substituents. In Bioorg Med Chem, vol. 14, pp. 8506-8518, (2006); Yoshida, et al.: MexAB-OprM specific efflux pump inhibitors in *Pseudomonas aeruginosa*. Part 7: highly soluble and in vivo active quaternary ammonium analogue D13-9001, a potential preclinical candidate. In Bioorg Med Chem, vol. 15, pp. 7087-7097, (2007)). Some of these inhibitors were validated using in vivo infection models (Nakayama, et al.: MexAB-OprM specific efflux pump inhibitors in *Pseudomonas aeruginosa*. Part 2: achieving activity in vivo through the use of alternative scaffolds. In Bioorg Med Chem Lett, vol. 13, pp. 4205-4208, (2003); Yoshida, et al.: MexAB-OprM specific efflux pump inhibitors in *Pseudomonas aeruginosa*. Part 7: highly soluble and in vivo active quaternary ammonium analogue D13-9001, a potential preclinical candidate. In Bioorg Med Chem, vol. 15, pp. 7087-7097, (2007)); however, they were abandoned because of toxicity problems (Lomovskaya, et al.: Practical applications and feasibility of efflux pump inhibitors in the clinic—a vision for applied use. In Biochem Pharmacol, vol. 71, pp. 910-918, (2006)).

The following table lists the classes of reported EPIs and references.

| Compound Class | References |
|---|---|
| 1 Peptidomimetics | Renau, et al., J Med Chem, vol. 42, pp. 4928-4931, (1999);<br>Lomovskaya, et al., Antimicrob Agents Chemother, vol. 45, pp. 105-116, (2001);<br>Renau, et al., Bioorg Med Chem Lett, vol. 11, pp. 663-667, (2001);<br>Renau, et al., Bioorg Med Chem Lett, vol. 12, pp. 763-766, (2002);<br>Renau, et al., Bioorg Med Chem Lett, vol. 13, pp. 2755-2758, (2003);<br>Watkins, et al., Bioorg Med Chem Lett, vol. 13, pp. 4241-4244, (2003);<br>Yoshida, et al., Bioorg Med Chem, vol. 14, pp. 1993-2004, (2006);<br>Yoshida, et al., Bioorg Med Chem, vol. 14, pp. 8506-8518, (2006);<br>Yoshida, et al., Bioorg Med Chem, vol. 15, pp. 7087-7097, (2007)) |
| 2 Pyridopyrimidines | Nakayama, et al., Bioorg Med Chem Lett, vol. 13, pp. 4201-4204, (2003);<br>Nakayama, et al., Bioorg Med Chem Lett, vol. 13, pp. 4205-4208, (2003);<br>Nakayama, et al., Bioorg Med Chem Lett, vol. 14, pp. 475-479, (2004);<br>Nakayama, et al., Bioorg Med Chem Lett, vol. 14, pp. 2493-2497, (2004);<br>Yoshida, et al., Bioorg Med Chem, vol. 14, pp. 1993-2004, (2006);<br>Yoshida, et al., Bioorg Med Chem, vol. 14, pp. 8506-8518, (2006);<br>Yoshida, et al., Bioorg Med Chem, vol. 15, pp. 7087-7097, (2007) |
| 3 Quinolines | Chevalier, et al., J Med Chem, vol. 44, pp. 4023-4026, (2001);<br>Mallea, et al., Biochem J, vol. 376, pp. 801-805, (2003);<br>Chevalier, et al., Antimicrob Agents Chemother, vol. 48, pp. 1043-1046, (2004);<br>Mahamoud, et al., Curr Drug Targets, vol. 7, pp. 843-847, (2006) |
| 4 Quinazolines | Chevalier, et al., J Antimicrob Agents, vol. 36, pp. 164-168, (2010);<br>Mahamoud, et al., Microbiology, vol. 157, pp. 566-571, (2011)) |
| 5 3-Arylpiperidines | Thorarensen, et al., In Bioorg Med Chem Lett, vol. 11, pp. 1903-1906, (2001);<br>Bohnert, et al., Antimicrob Agents Chemother, vol. 49, pp. 849-852, (2005) |
| 6 Repurposed drugs | Piddock, et al., J Antimicrob Chemother, vol. 65, pp. 1215-1223, (2010);<br>Bohnert, et al., J Antimicrob Chemother, vol. 66, pp. 2057-2060, (2011);<br>Li, et al., J Antimicrob Chemother, vol. 66, pp. 769-777, (2011) |

The need remains for more effective efflux pump inhibitors as a means of combatting bacterial infection.

SUMMARY OF THE INVENTION

Accordingly, the present invention provides a new family of novel compounds that are effective to inhibit efflux pumps in bacteria. These novel compounds are effective as antibiotic or antimicrobial potentiators. Structures of these compounds are distinctive from other reported efflux pump inhibitors and antibiotic potentiators.

Also disclosed are methods for inhibiting bacterial efflux pumps with the novel compounds described herein. In another embodiment, the present invention discloses the use of these novel compounds for the inhibition of bacterial efflux pumps. In yet another embodiment, the present invention discloses the use of these novel compounds for treating or inhibiting bacterial infection.

The novel bacterial efflux pump inhibitory compounds of the present invention are represented by the following Formula I:

FORMULA I

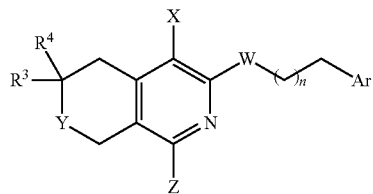

wherein,
n is an integer from 1 to 5;
X is —CN, —F, —Cl, —Br, —I, —NO$_2$;
W is S, SO, SO$_2$, O, NH, or NR$^5$;
R$^5$ is alkyl, aralkyl, alkenyl, or alkynyl;
Y is O, S;
Z is NR$^1$R$^2$ or heterocycloalkyl;
R$^1$, R$^2$ are, independently, hydrogen, alkyl, aralkyl, alkenyl, alkynyl, or cycloalkyl and may be optionally substituted with halo, hydroxy, alkoxy, amino, alkylamino, carboxy, alkoxycarbonyl, or nitrile groups;
R$^3$ and R$^4$ are, independently, hydrogen, alkyl, aralkyl, alkenyl, alkynyl, or cycloalkyl and may be optionally substituted with halo, hydroxy, alkoxy, amino, alkylamino, carboxy, alkoxycarbonyl, or nitrile groups, and may together form a cyclic structure; and
Ar is mono-, di-, or tri-substituted phenyl or heteroaryl.

In a preferred embodiment, the present invention is directed to a novel compound having the structure of Formula I wherein:
n is 1;
X is —CN;
W is S;
Y is O;
Z is heterocycloalkyl;
R$^3$ and R$^4$ are methyl; and
Ar is mono-, di-, or tri-substituted phenyl or heteroaryl.

In a particularly preferred embodiment, the novel bacterial efflux inhibitor compounds of Formula I include the following:

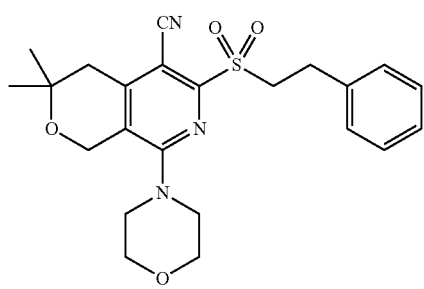
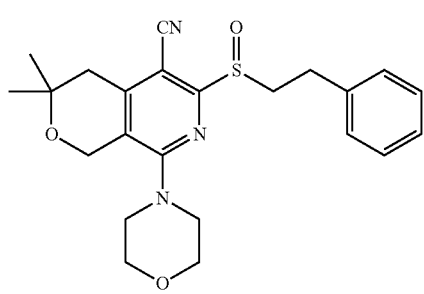
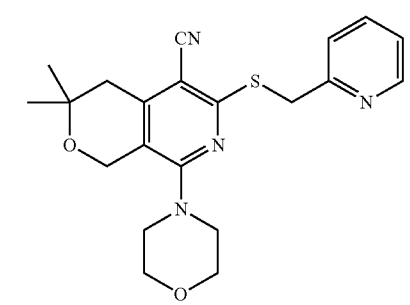
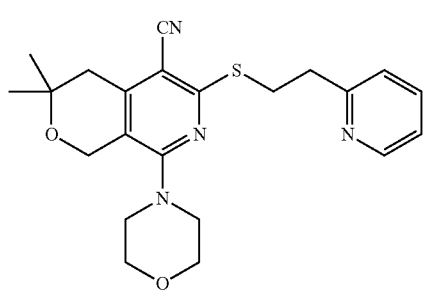
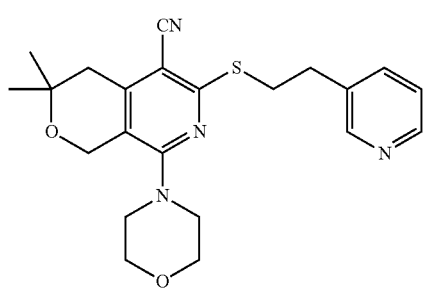
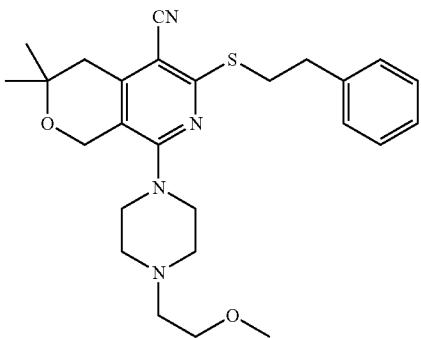
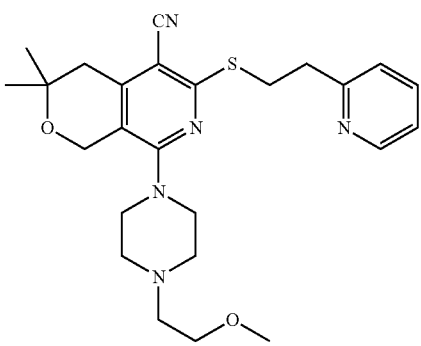
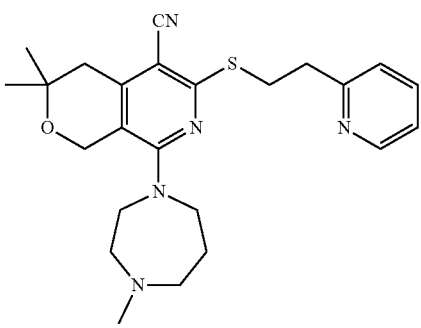
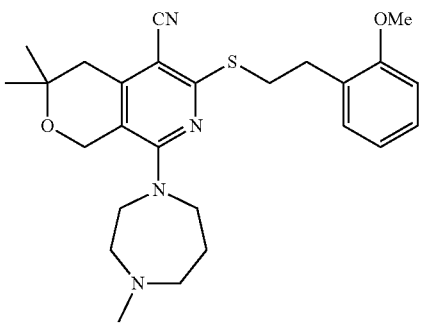
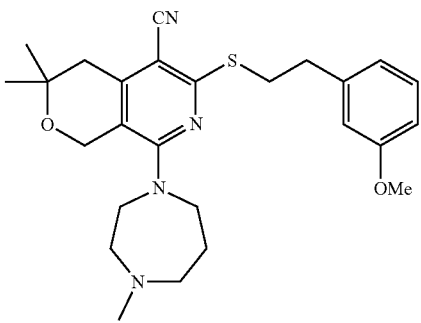

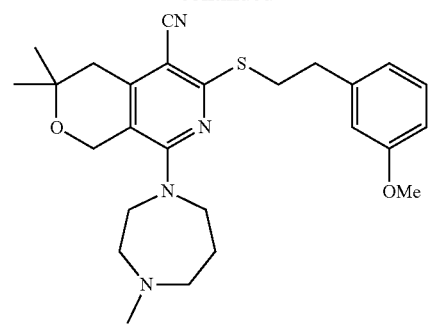
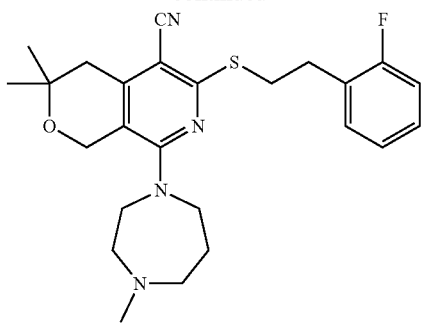
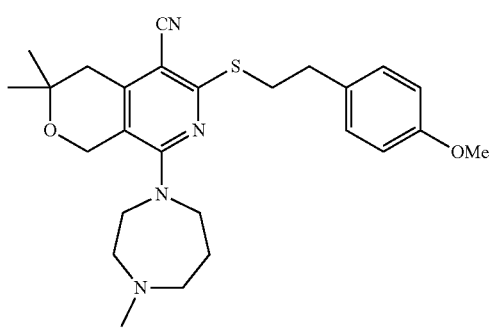
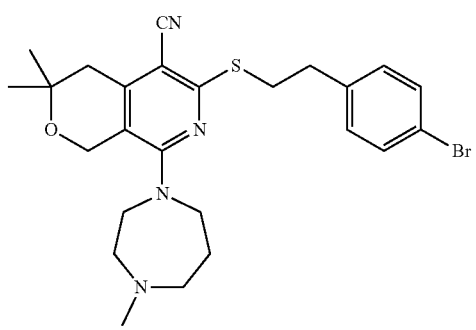
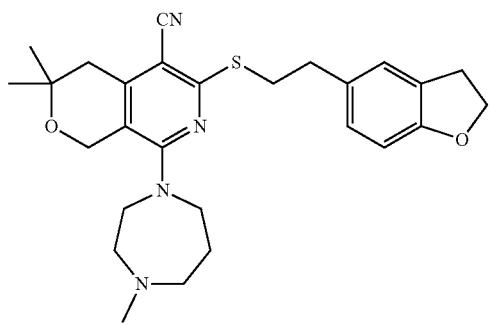
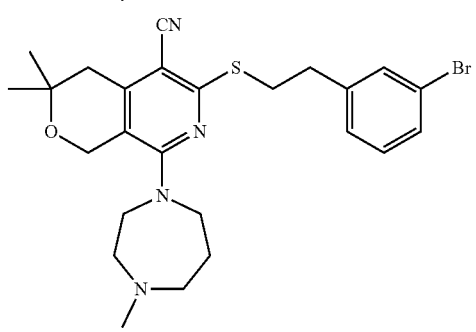
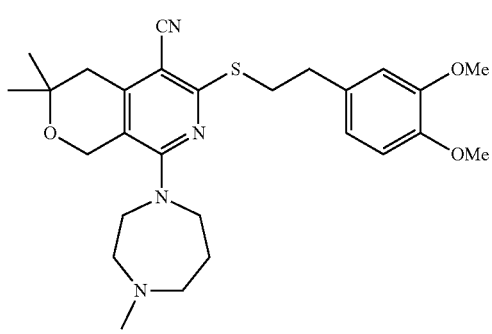
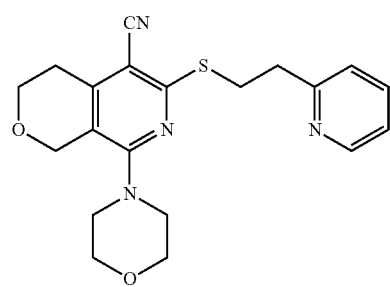
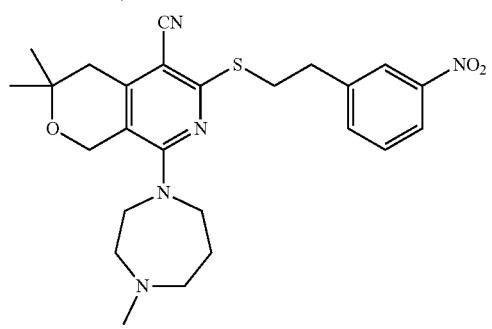
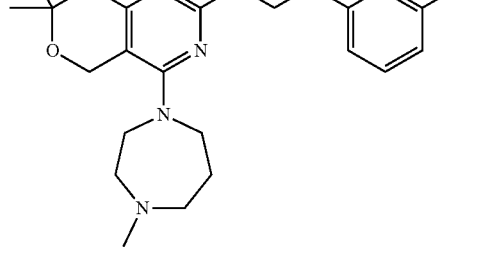

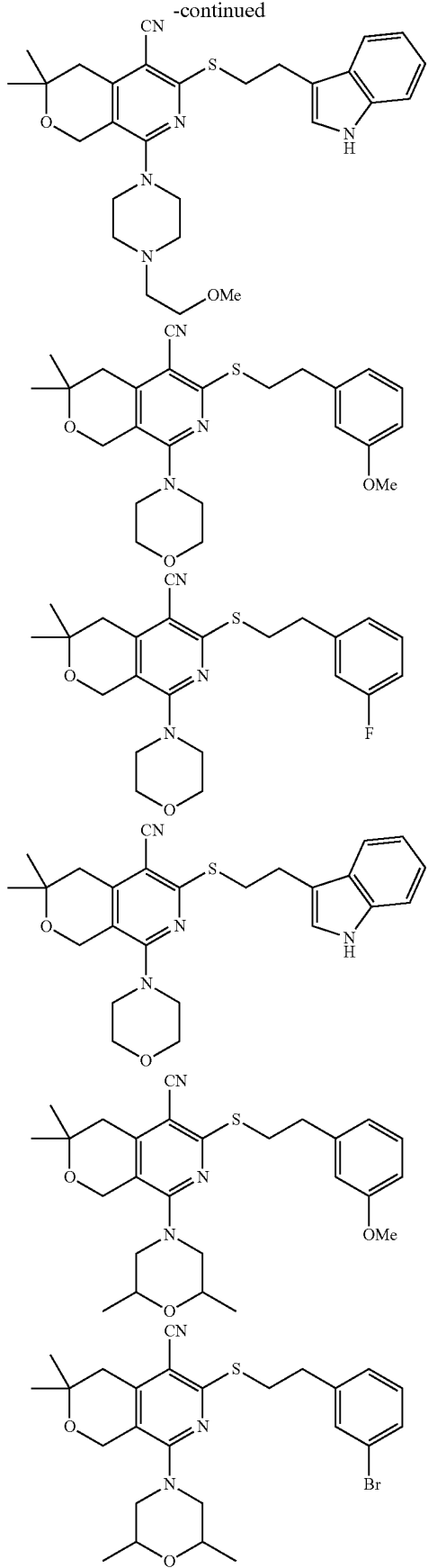
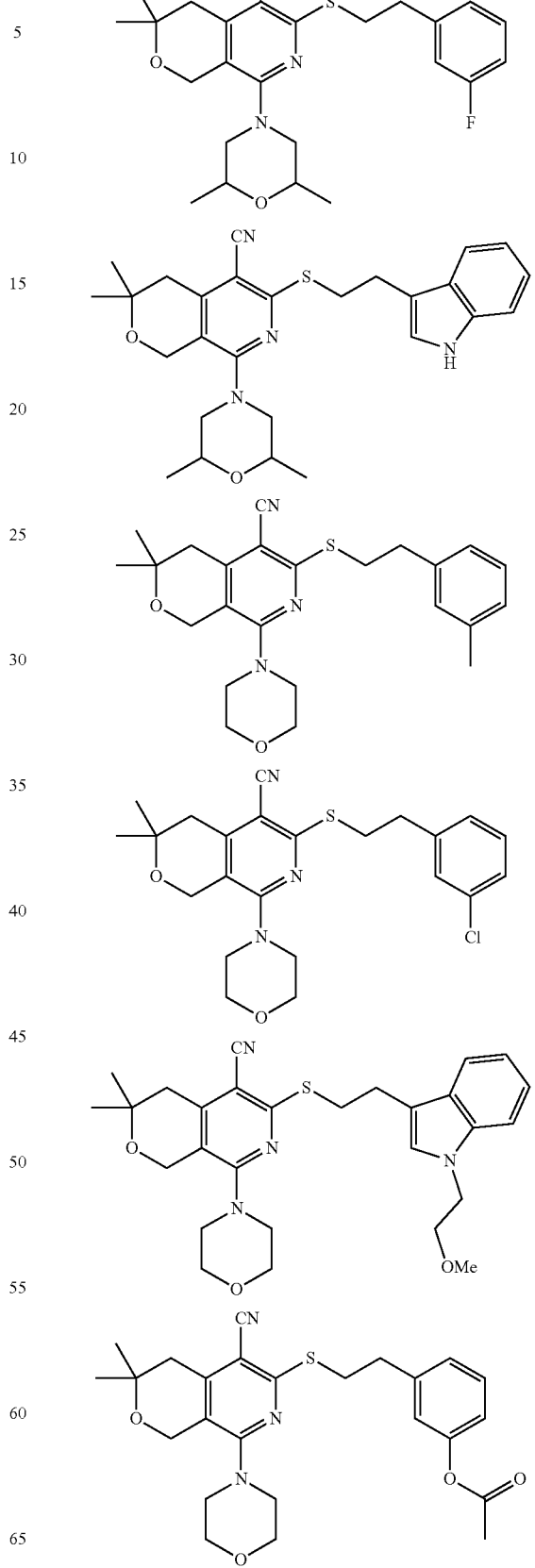

-continued
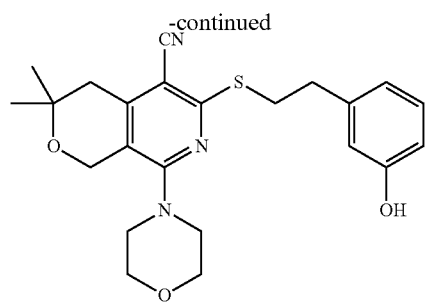
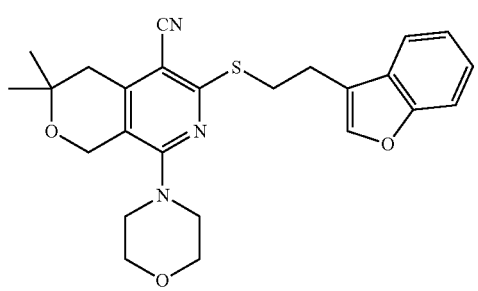
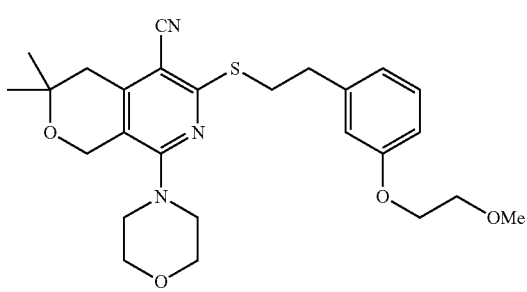
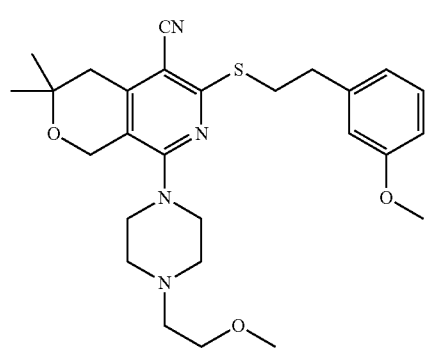
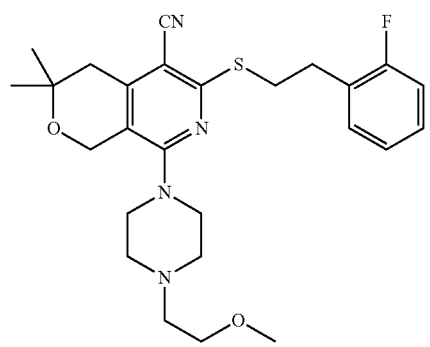
-continued
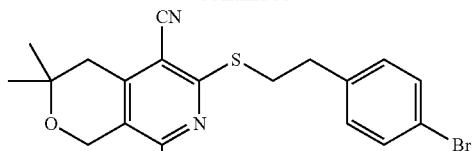
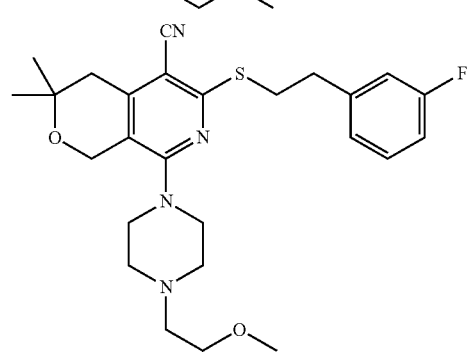
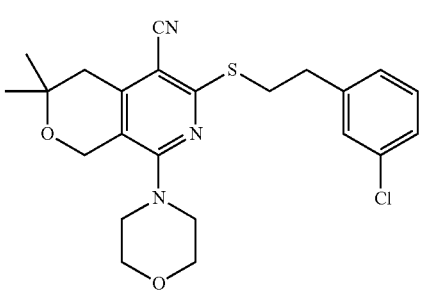
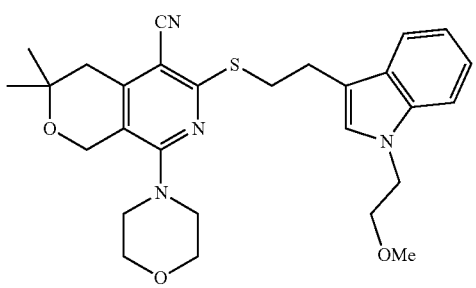
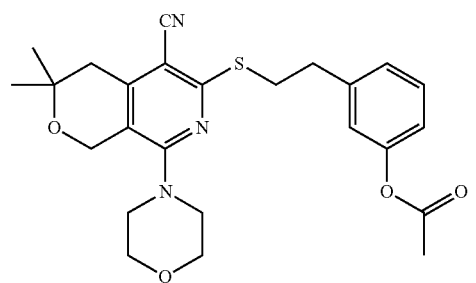

-continued
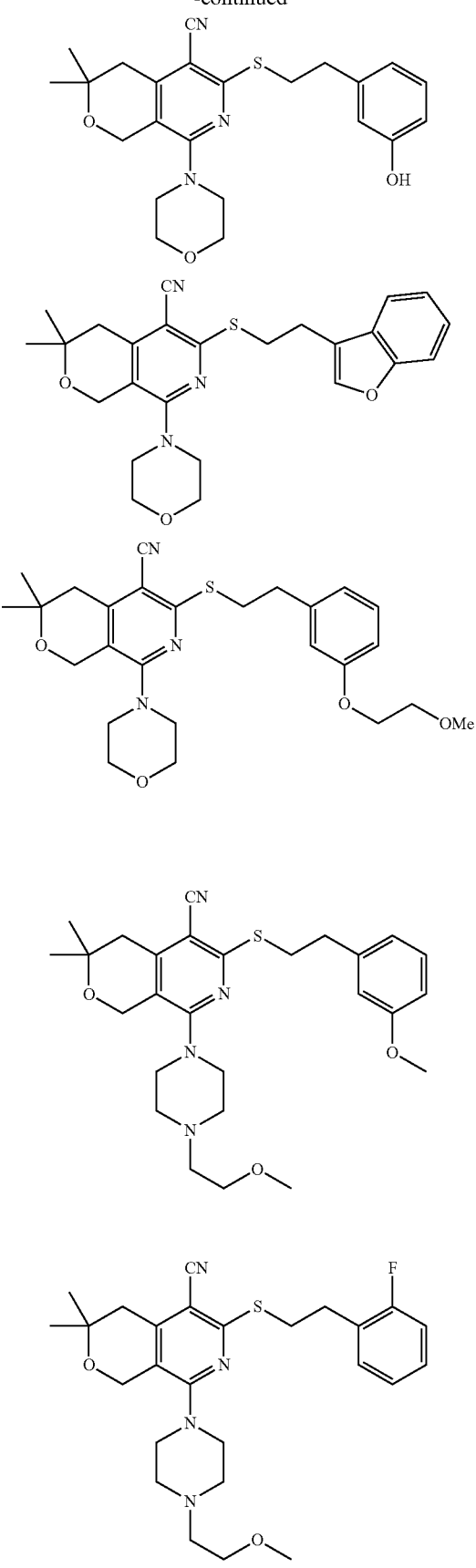
-continued
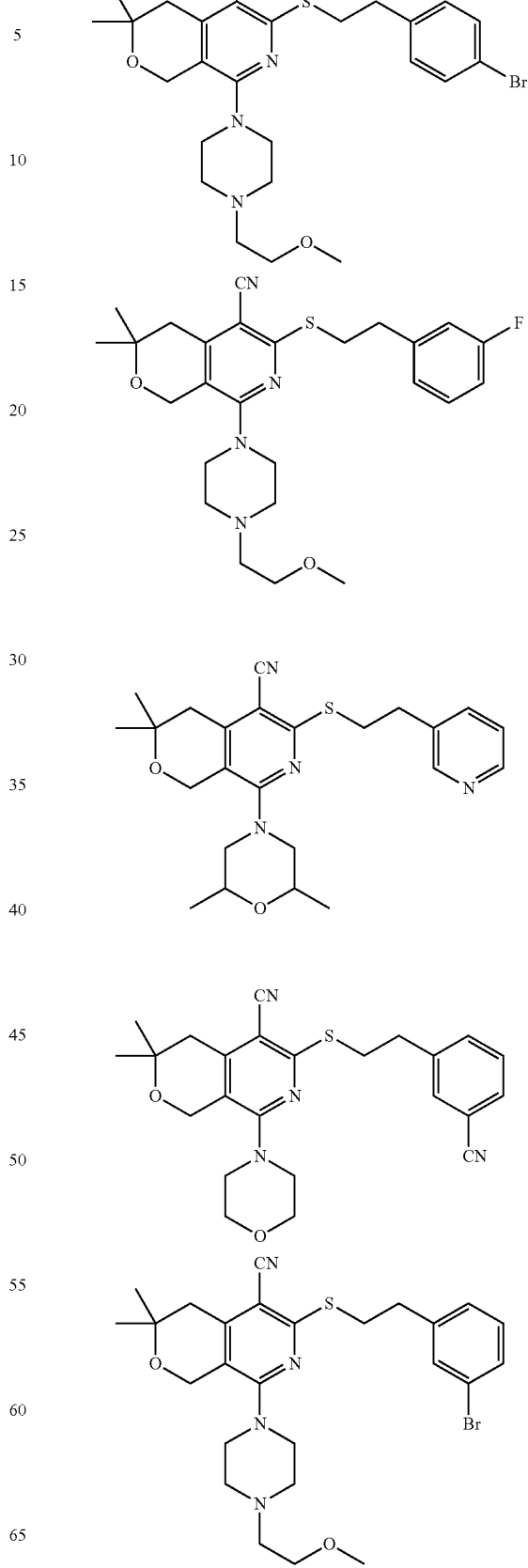

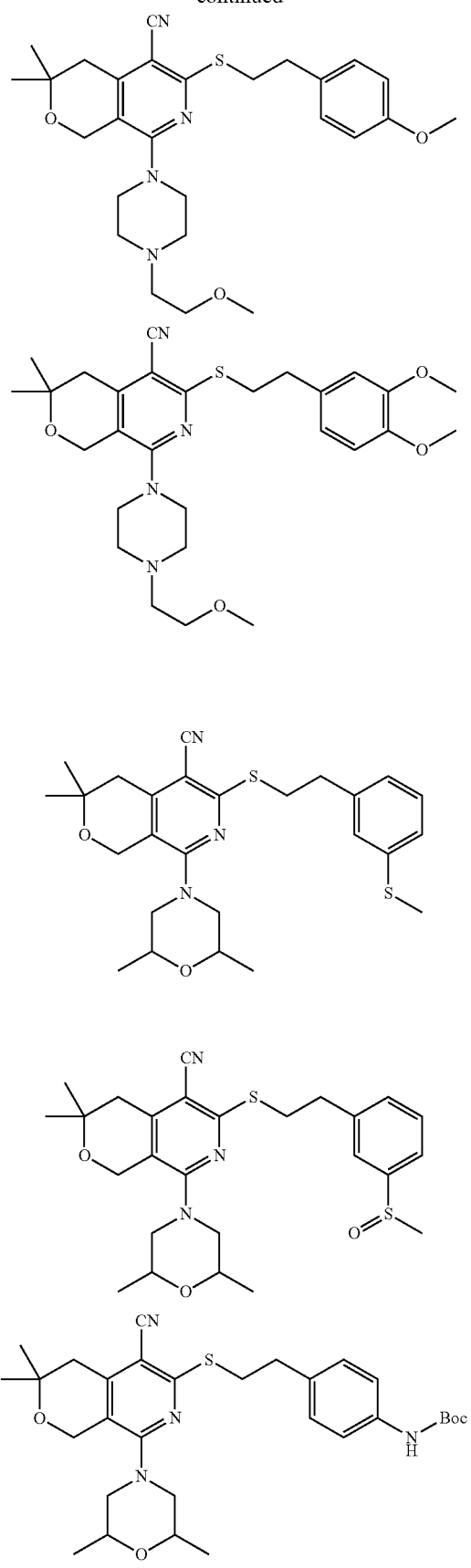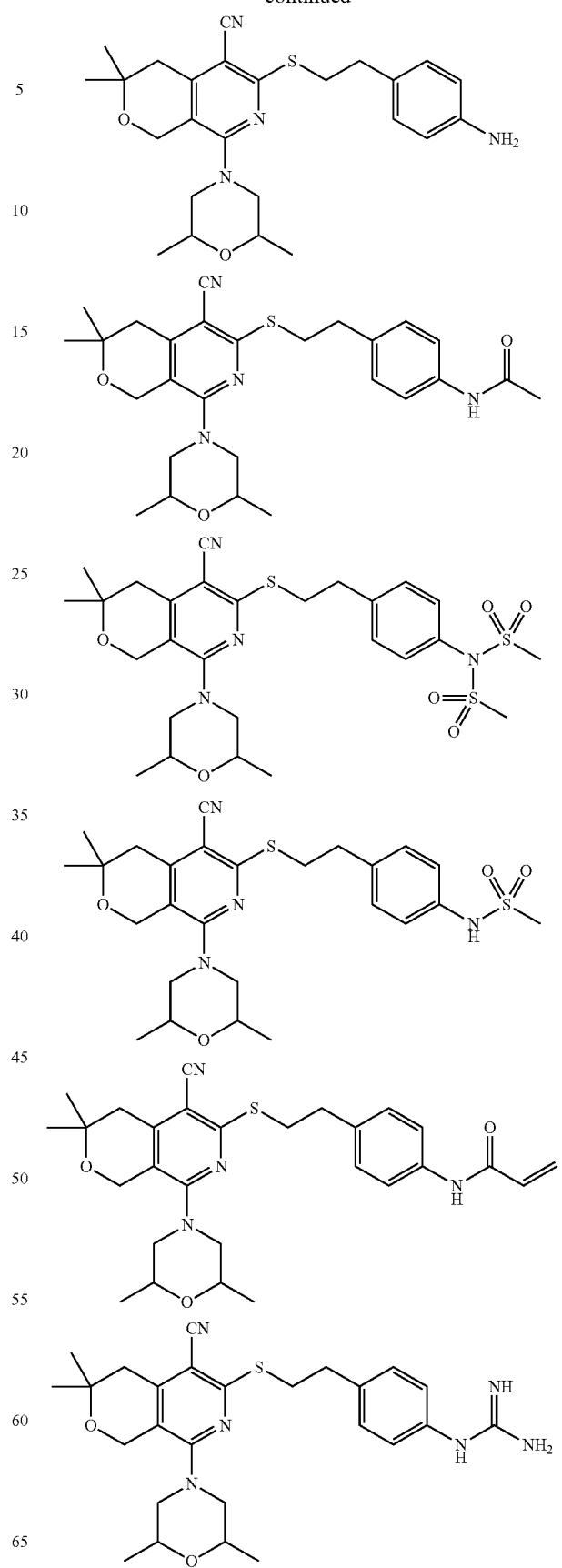

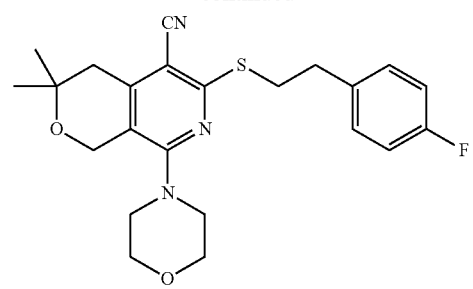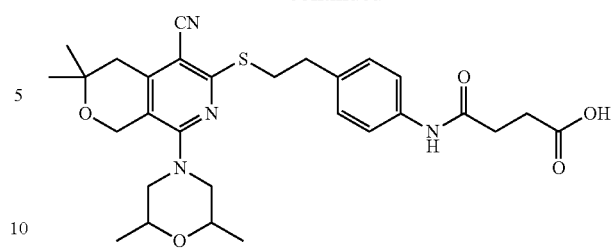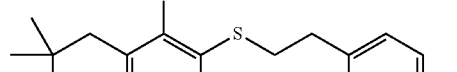

21
-continued
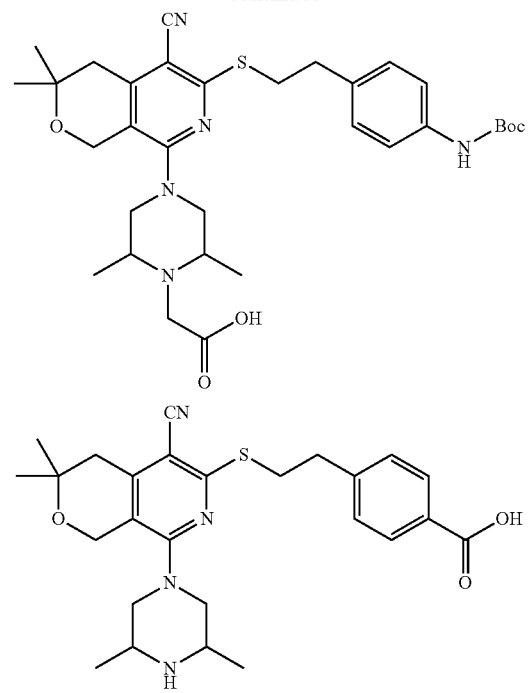
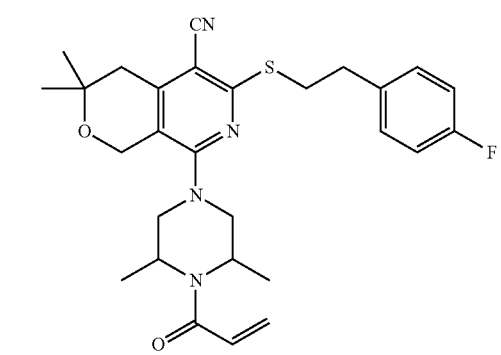
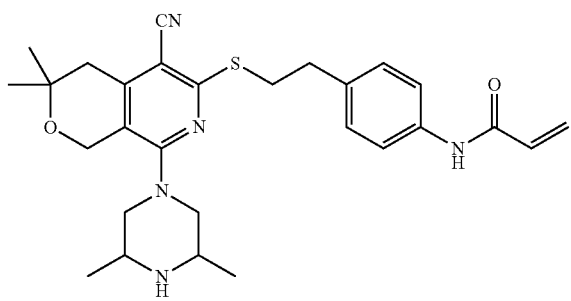
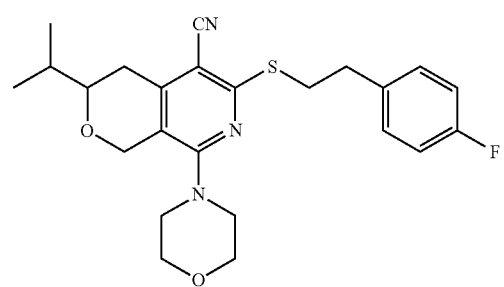
22
-continued
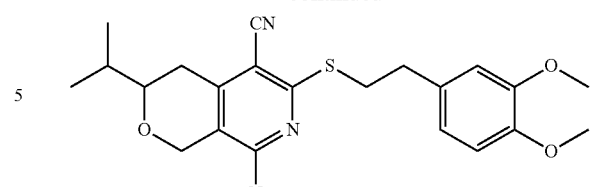
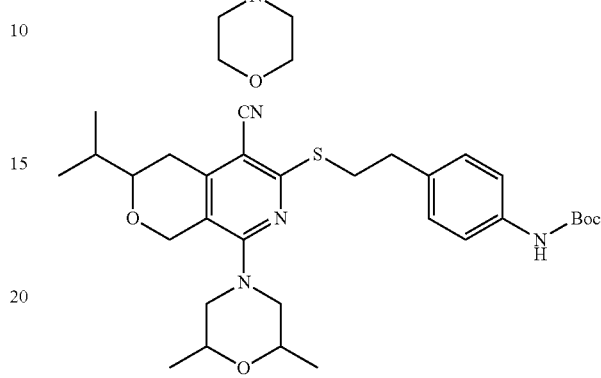
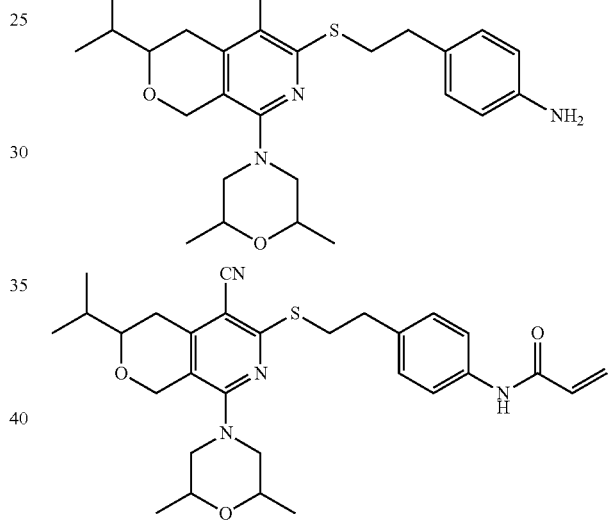
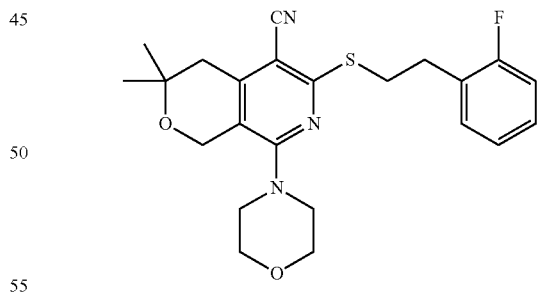
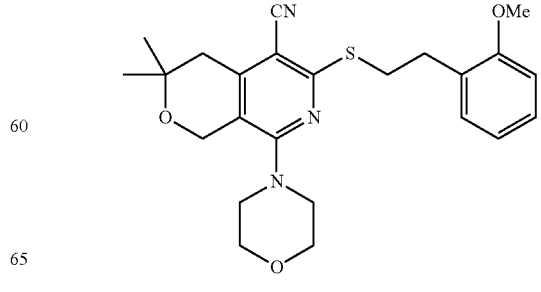

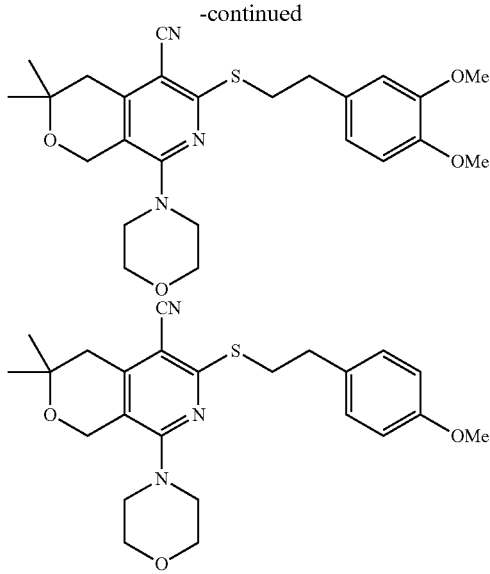

A potentiator or combination of potentiators described herein may be used as a supporting or adjunctive therapy for the treatment of bacterial infection in humans or other animals. The potentiator may be administered in admixture, sequentially, or simultaneously with an antibacterial agent to provide more effective bacterial killing or microbial growth inhibition. This adjunctive therapy may provide the following benefits: increased antibiotic efficacy that leads to lower dosage and/or shorter treatment period, minimizing the side effects of antibiotics to patients and decreasing evolution of bacterial resistance in the community.

Also disclosed are antimicrobial compositions comprising a potentiator of the invention and an antimicrobial agent. The antimicrobial component of the compositions can be, but is not limited to, a beta-lactam (with or without beta-lactamase inhibitors) and/or a quinolone antibiotic. These compositions kill or inhibit growth of bacteria more effectively than the antimicrobial agent alone.

Compositions comprising an antimicrobial component and a potentiator according to Formula I may be used to treat in vivo infections, or to disinfect devices and surfaces such as bandages, bodily appliances, catheters, surgical instruments, patient examination tables, counters, etc.

In a further embodiment, a new utility for additional compounds having structural similarity to the compounds of Formula I has been discovered. In working with the compounds of Formula I, additional analogs were discovered to be effective as bacterial efflux pump inhibitors.

Accordingly, in another aspect of the present invention, a method of treating bacterial infection is provided comprising administration of a compound of Formula II, or a pharmaceutically acceptable salt thereof:

FORMULA II

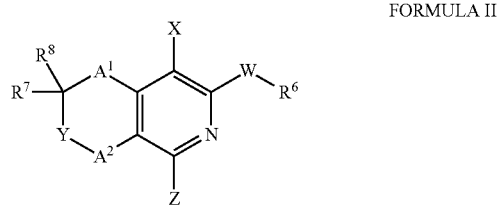

wherein:

X is cyano, amido, sulfonamido, imino, amidino, acyl, carboxy, alkoxycarbonyl, halo, or nitro;

W is a sulfur, SO (sulfoxide), $SO_2$ (sulfone), oxygen, nitrogen, or alkyl-substituted nitrogen;

$R^6$ is optionally substituted aralkyl, alkyl, aryloxyalkyl, alkoxyalkyl, haloalkyl, alkenyl, or alkynyl;

Z is $NR^1R^2$ or heterocycloalkyl;

$R^1$, $R^2$ are, independently, hydrogen, alkyl, aralkyl, alkenyl, alkynyl, or cycloalkyl, and may be optionally substituted with halo, hydroxy, alkoxy, amino, alkylamino, carboxy, alkoxycarbonyl, or nitrile groups $A^1$ and $A^2$ are, independently, carbon, or optionally substituted carbon;

Y is oxygen, sulfur, or optionally substituted nitrogen;

$R^7$ and $R^8$ are, independently, hydrogen, alkyl, aralkyl, alkenyl, alkynyl, or cycloalkyl and may be optionally substituted with halo, hydroxy, alkoxy, amino, alkylamino, carboxy, alkoxycarbonyl, or nitrile groups, and may together form a cyclic structure.

Also disclosed in the use of a compound according to Formula II, or a pharmaceutically acceptable salt thereof, for inhibiting bacterial efflux pumps.

In another embodiment of the methods and uses herein, the compound of Formula II (or salt thereof) may be used in combination with an antimicrobial agent. Such antimicrobial agent is preferably a beta-lactam antibiotic with or without a beta-lactamase inhibitor, or a quinolone antibiotic.

The compounds according to Formula II may be used to disinfect devices and surfaces. In particular, the compounds of Formula II may be used to disinfect devices or surfaces colonized by Gram-negative pathogens.

In another embodiment of the methods and uses described herein, the compounds have the structure of Formula II, wherein:

X is cyano;

W is S $R^6$ is optionally substituted aralkyl or aryloxyalkyl;

Z is $NR^1R^2$ or heterocycloalkyl;

$R^1$, $R^2$ are, independently, hydrogen, alkyl, aralkyl, alkenyl, alkynyl, or cycloalkyl, and may be optionally substituted with halo, hydroxy, alkoxy, amino, alkylamino, carboxy, alkoxycarbonyl, or nitrile groups;

$A^1$, $A^2$ are CH2; and

Y is oxygen;

or pharmaceutically acceptable salts thereof.

In preferred embodiments, the compounds of Formula II are those having the following structures:

-continued
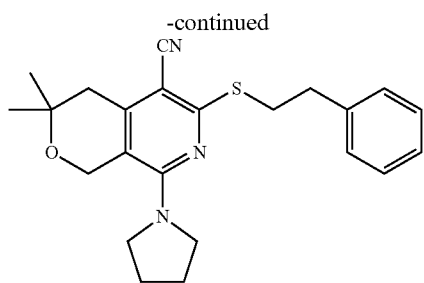
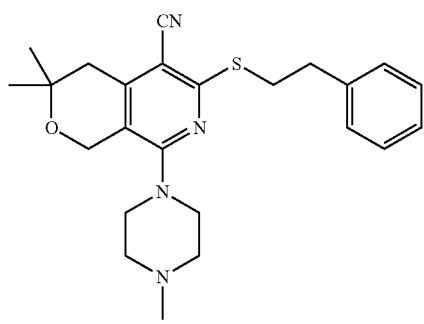
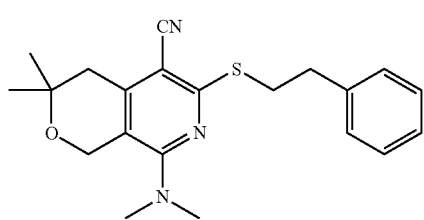
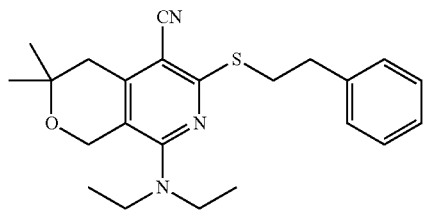
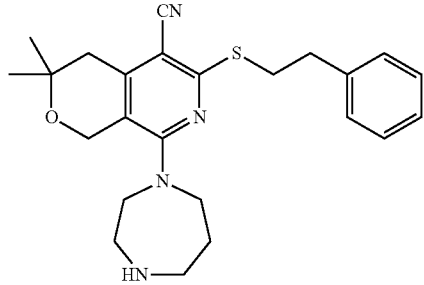
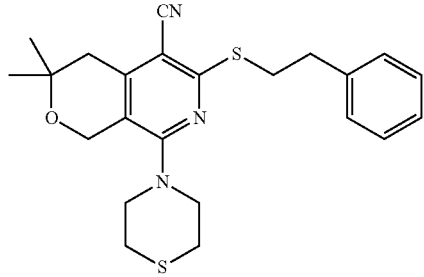
-continued
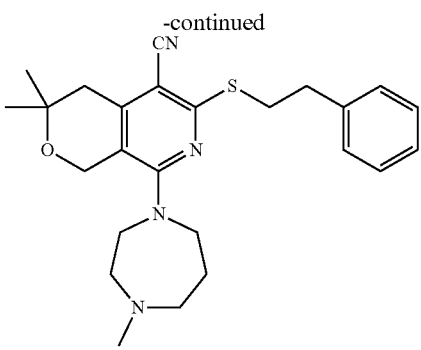
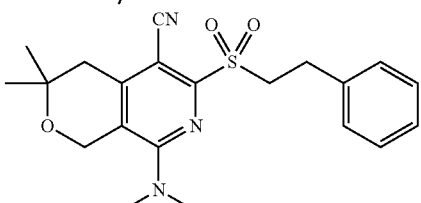
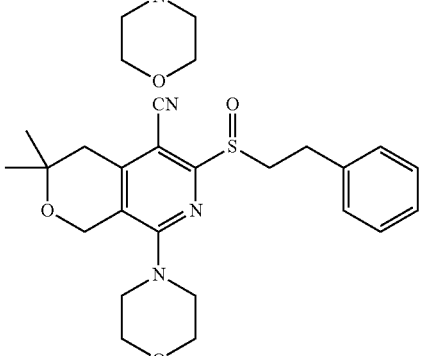
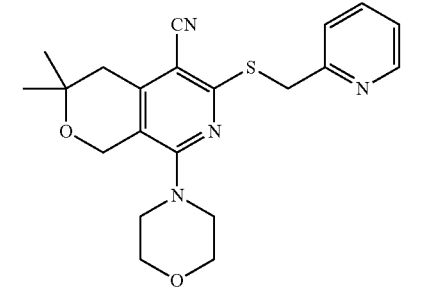
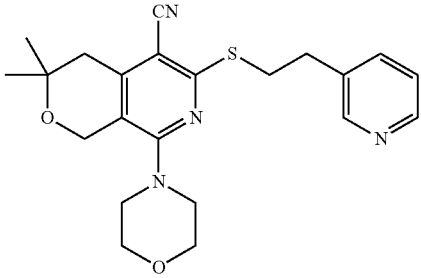
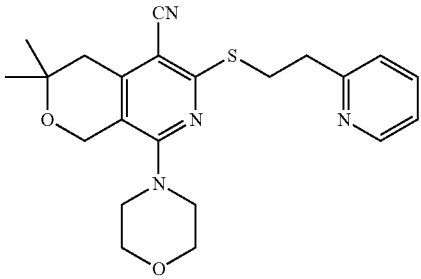

27
-continued
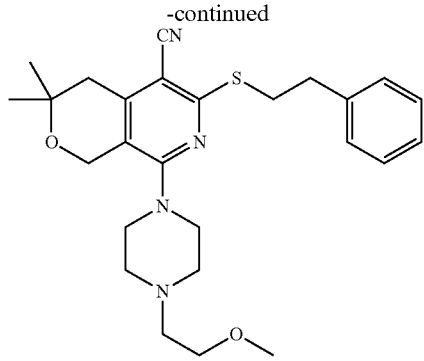
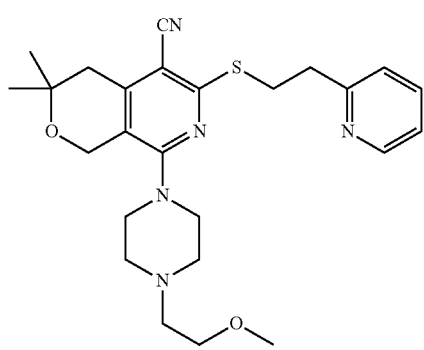
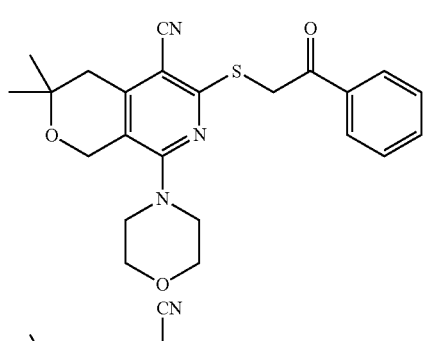
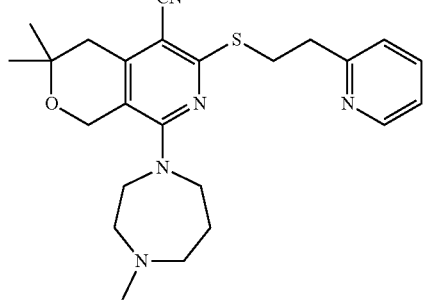
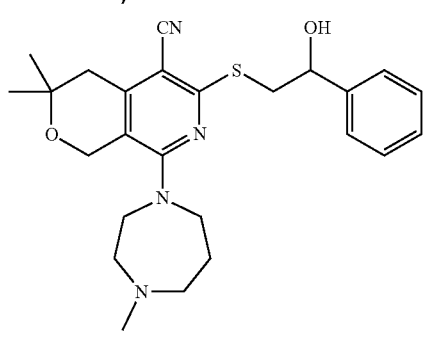
28
-continued
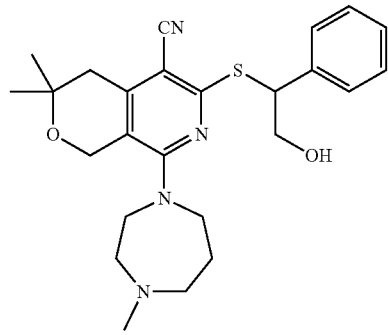
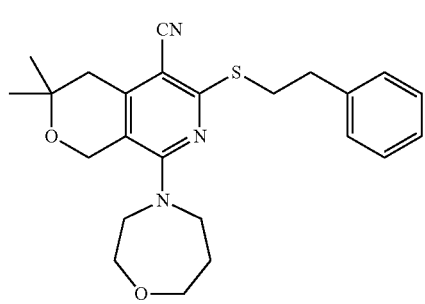
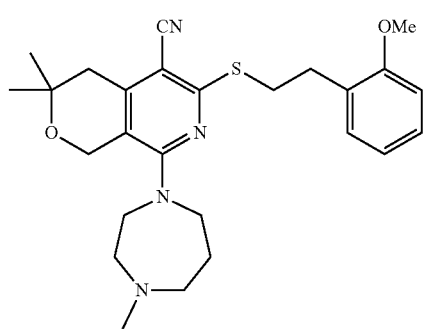
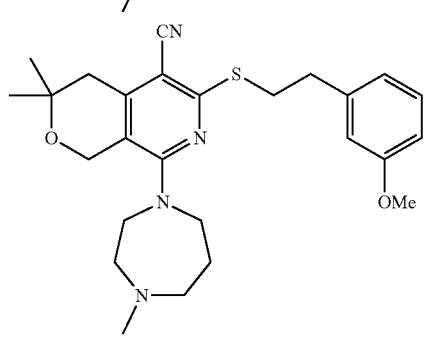
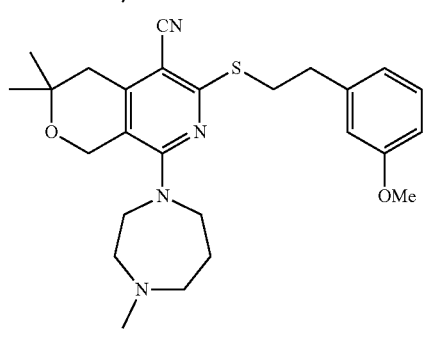

29
-continued
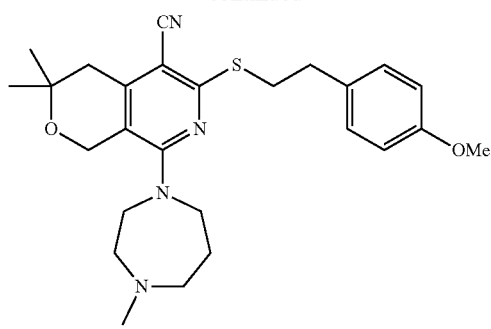
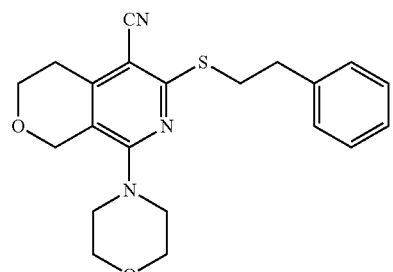
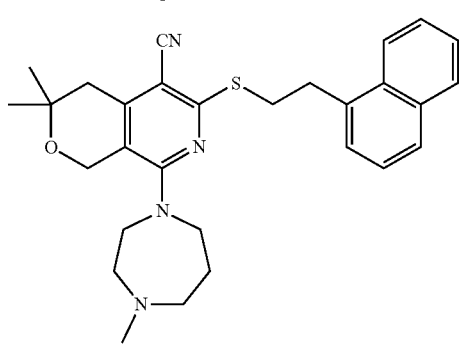
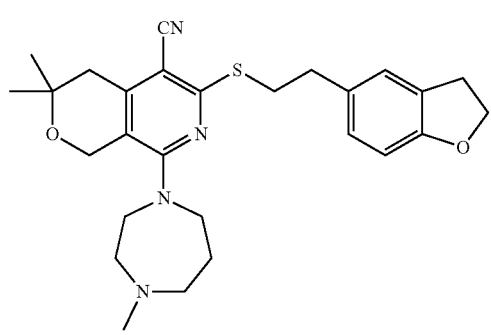
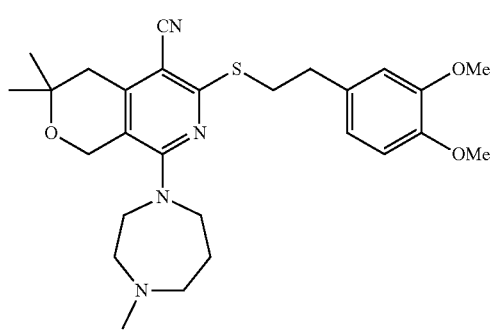
30
-continued
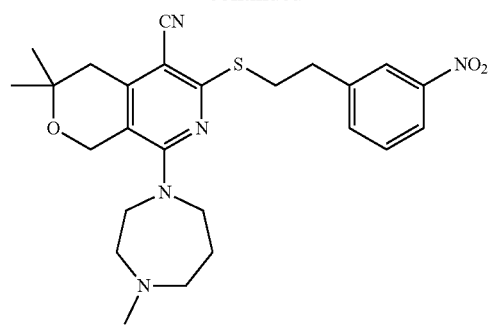
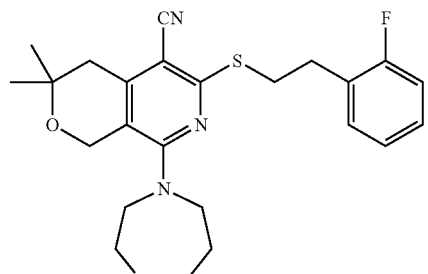
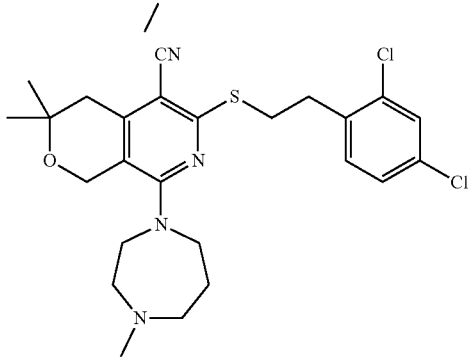
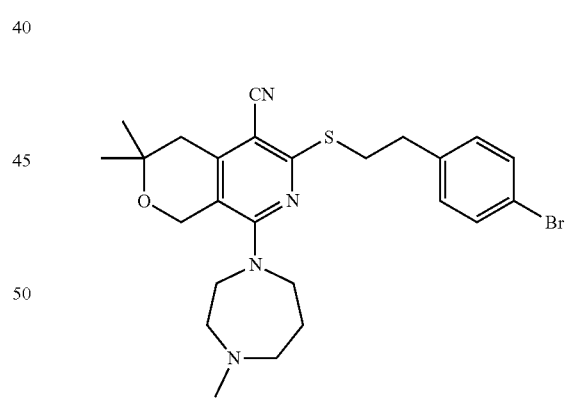
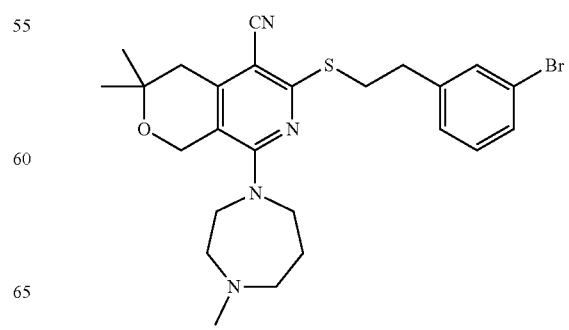

31
-continued
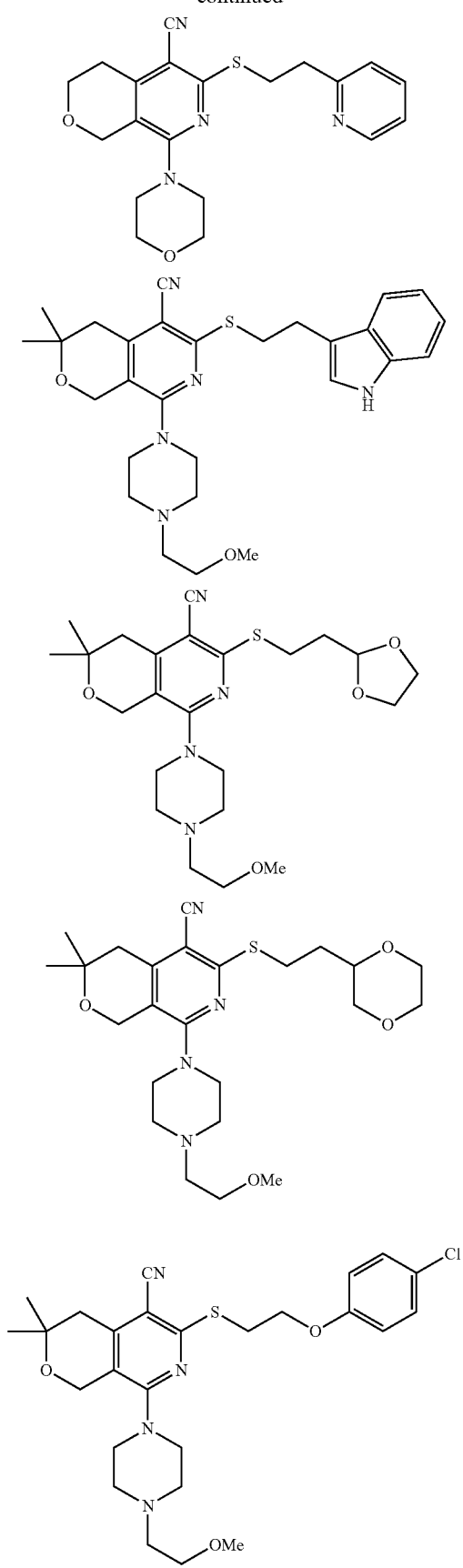
32
-continued
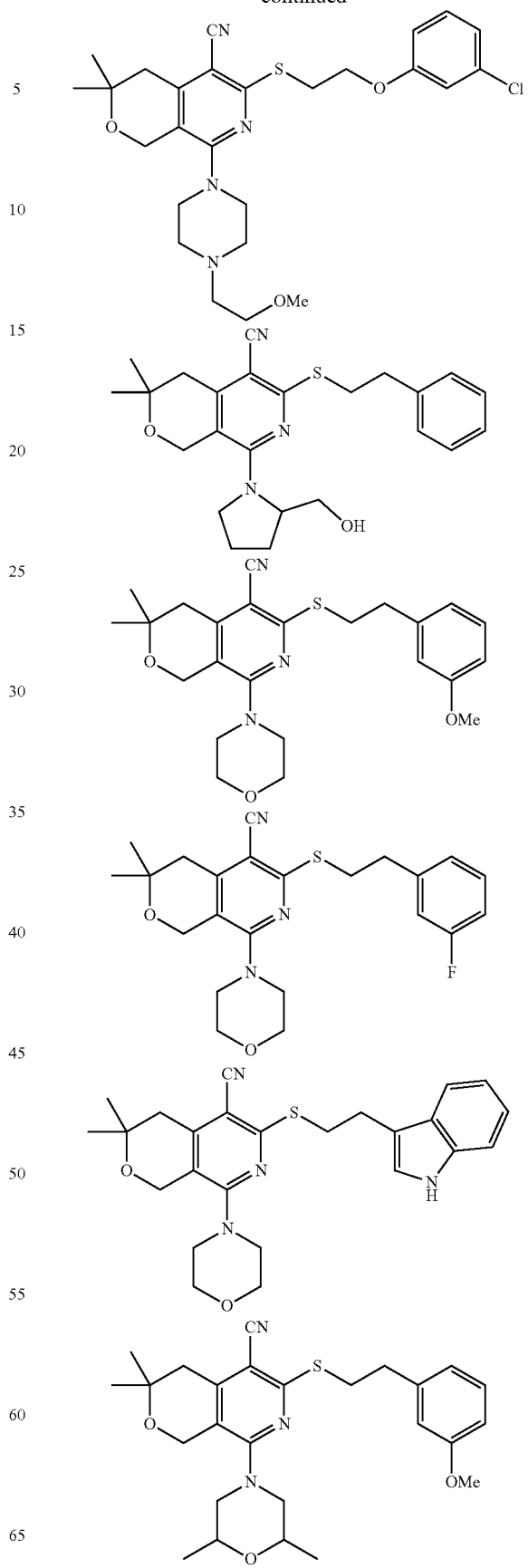

33
-continued
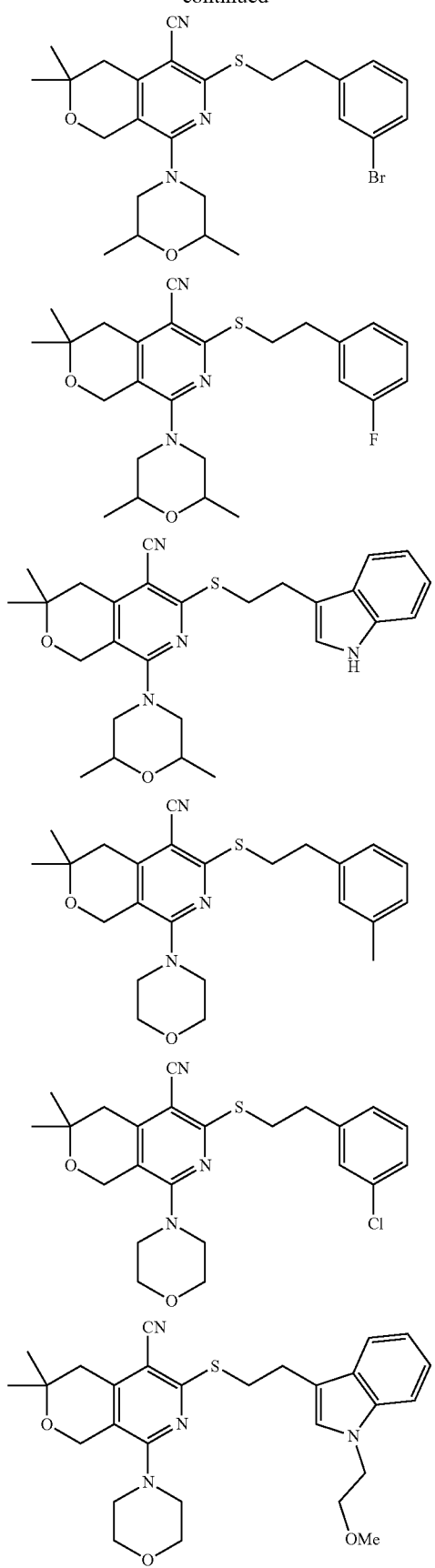
34
-continued
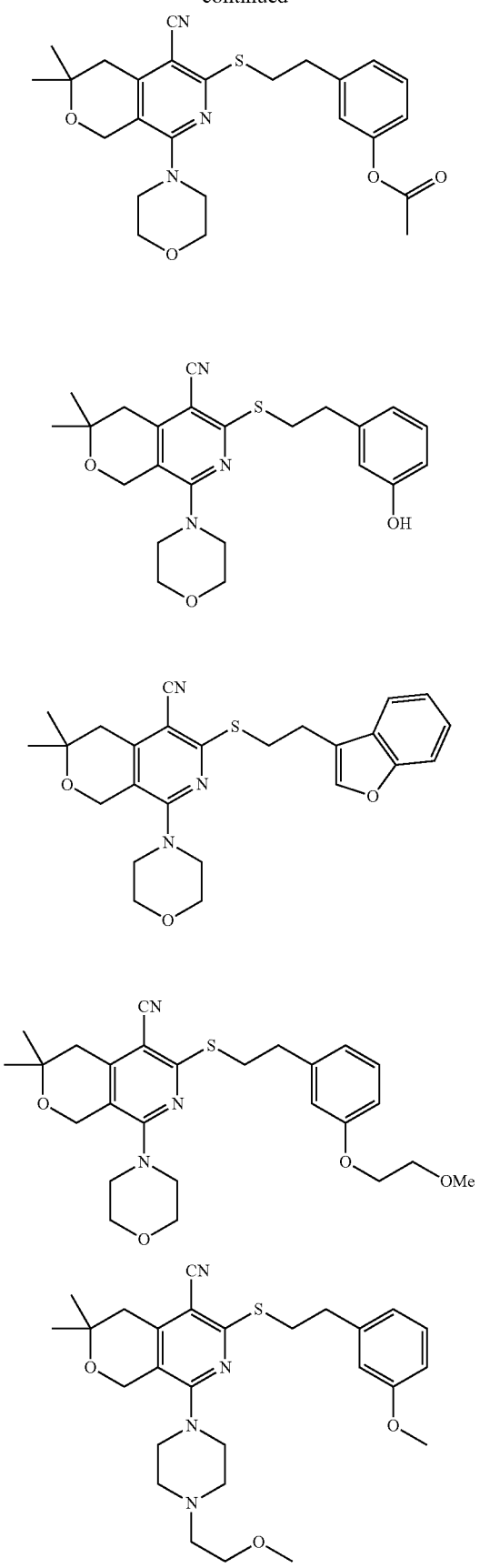

35
-continued
36
-continued
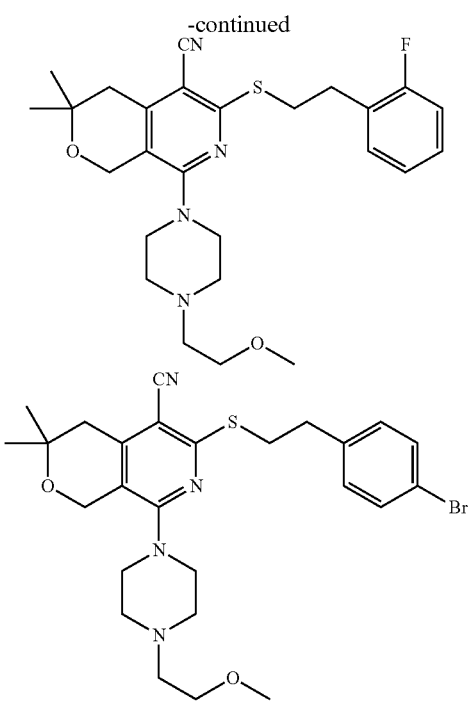
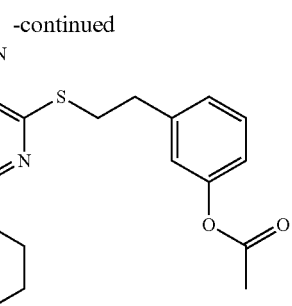
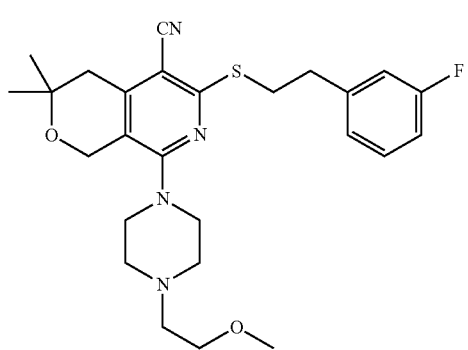
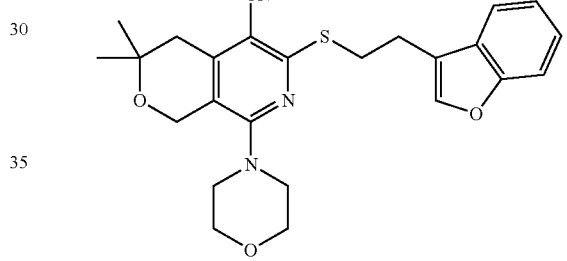
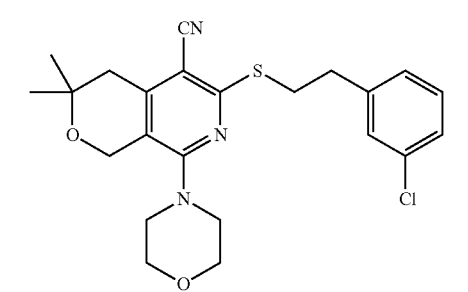
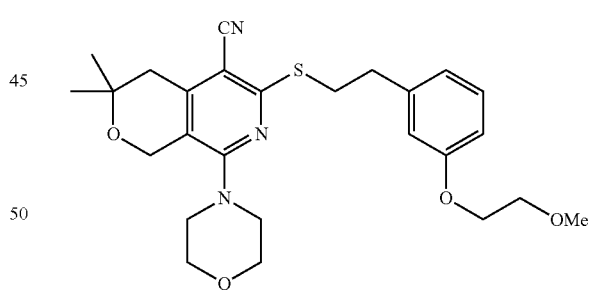
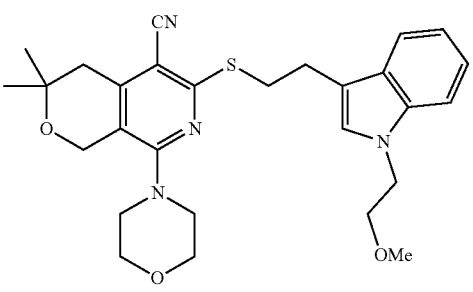
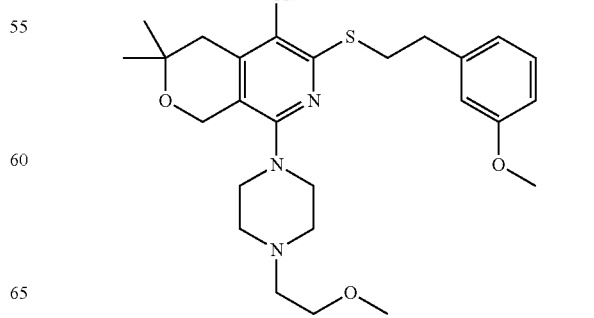

37
-continued
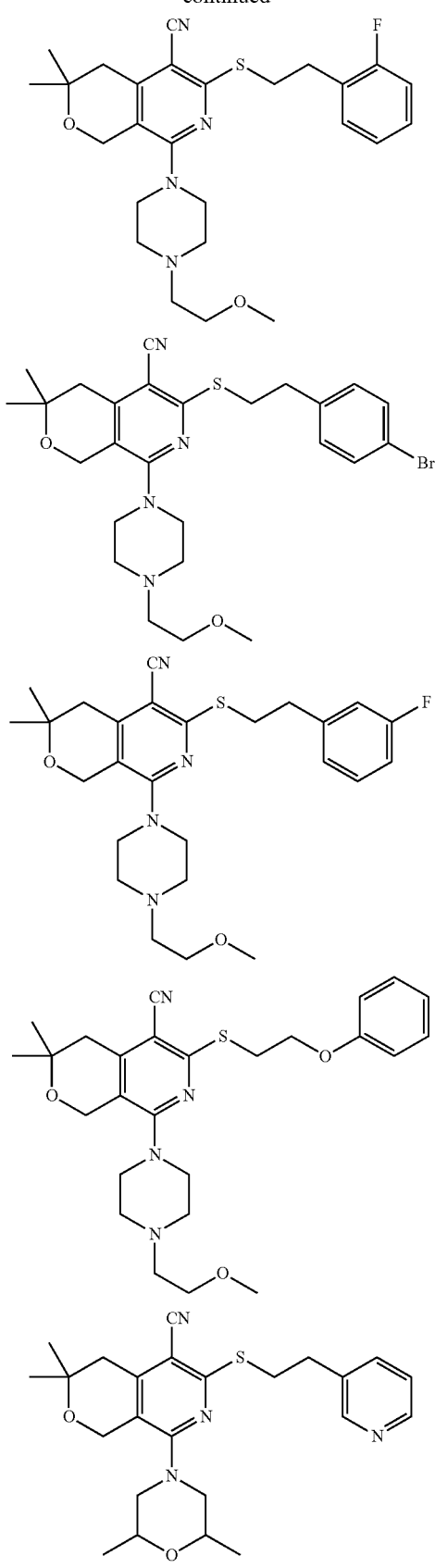
38
-continued
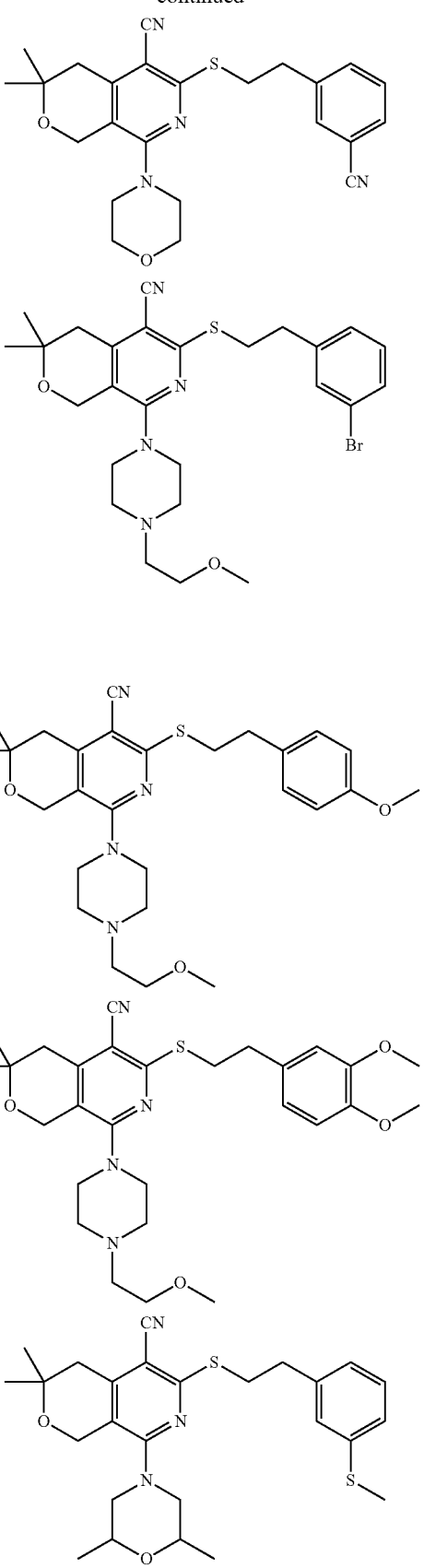

39
-continued
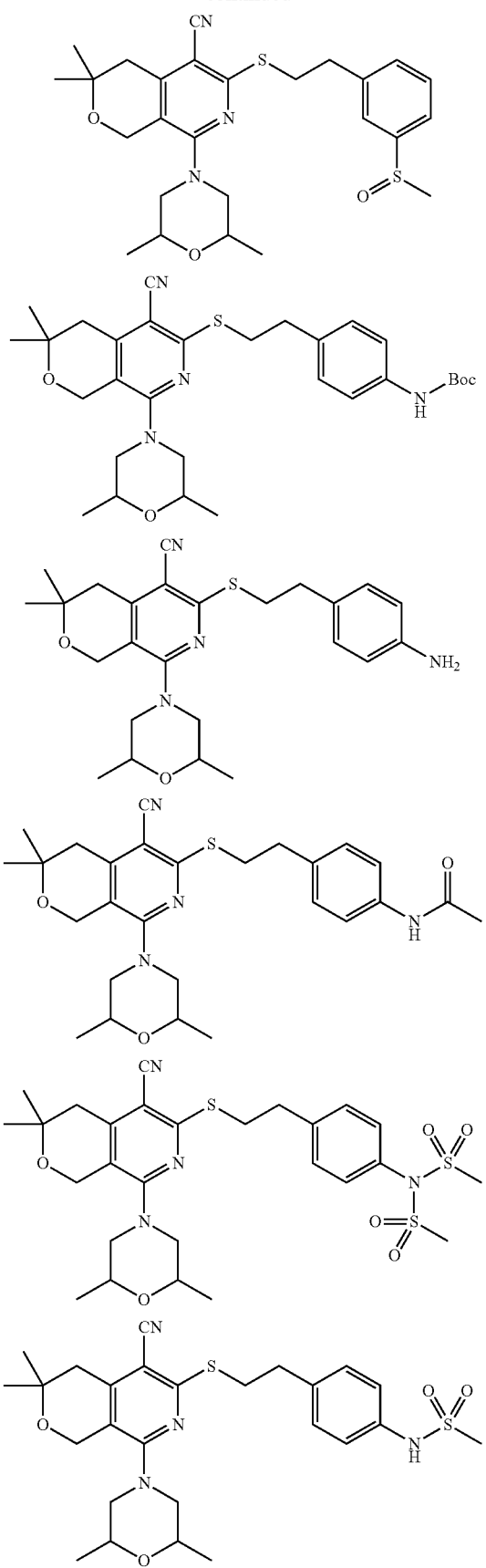
40
-continued
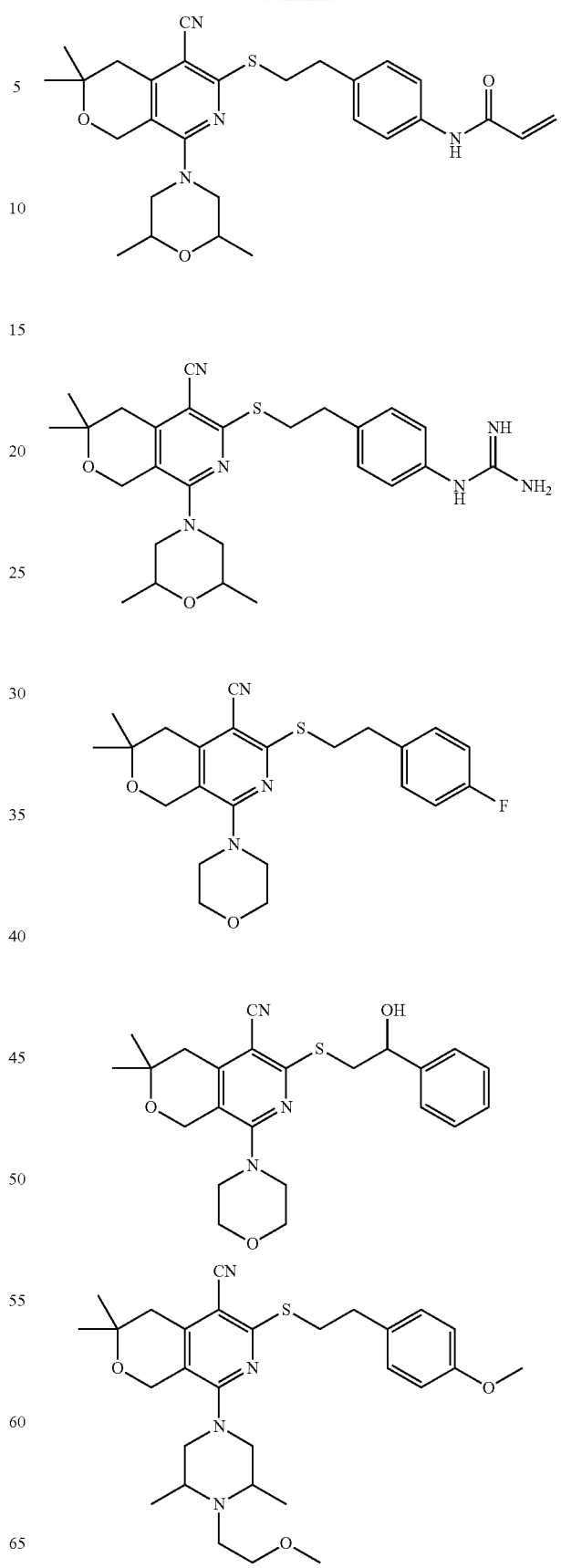

-continued
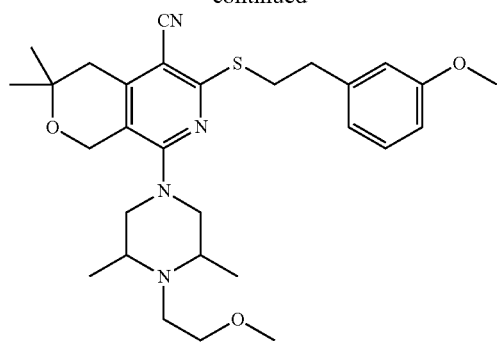
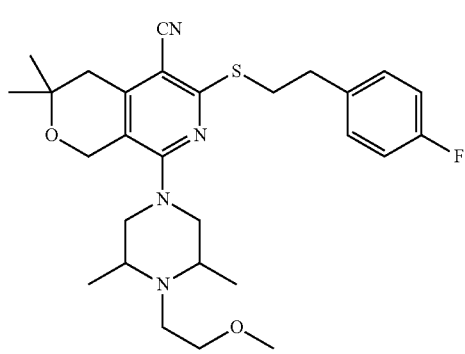
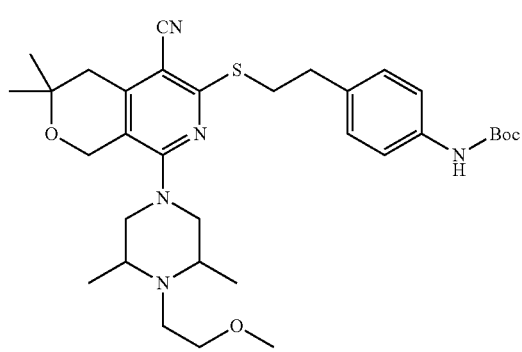
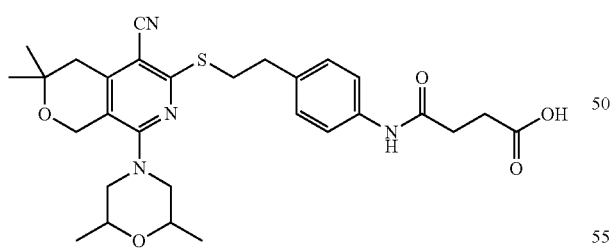
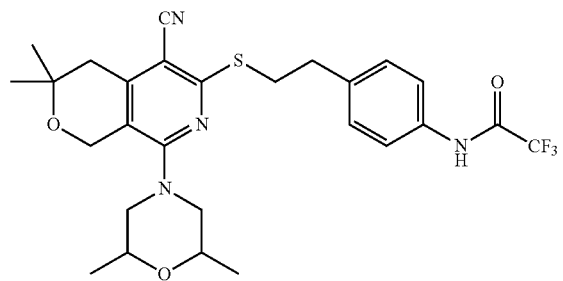
-continued
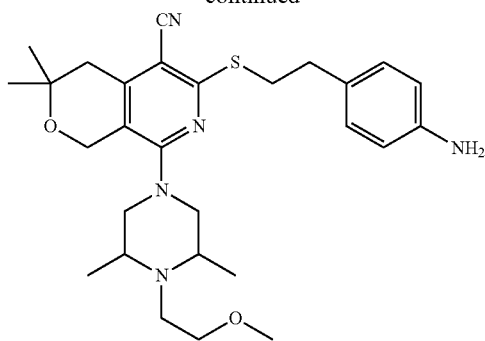
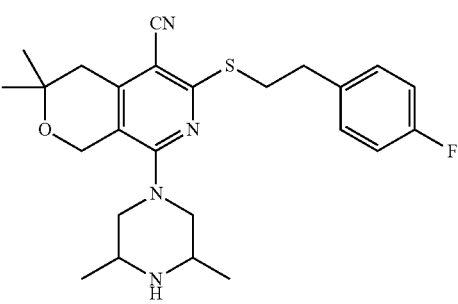
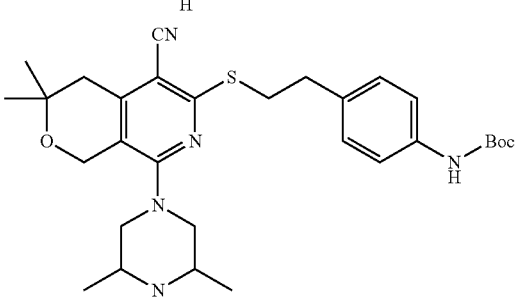
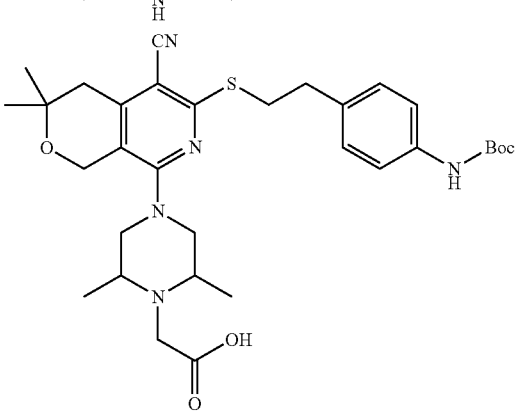
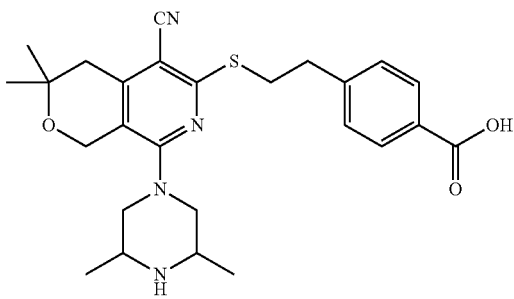

43
-continued
44
-continued
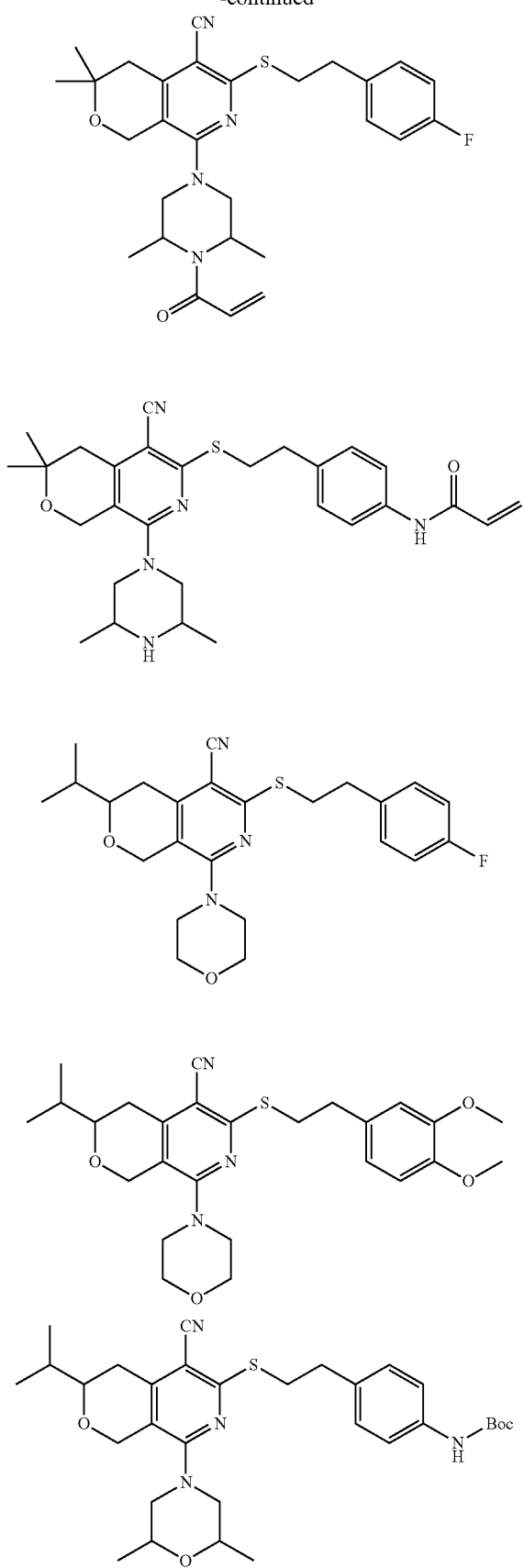
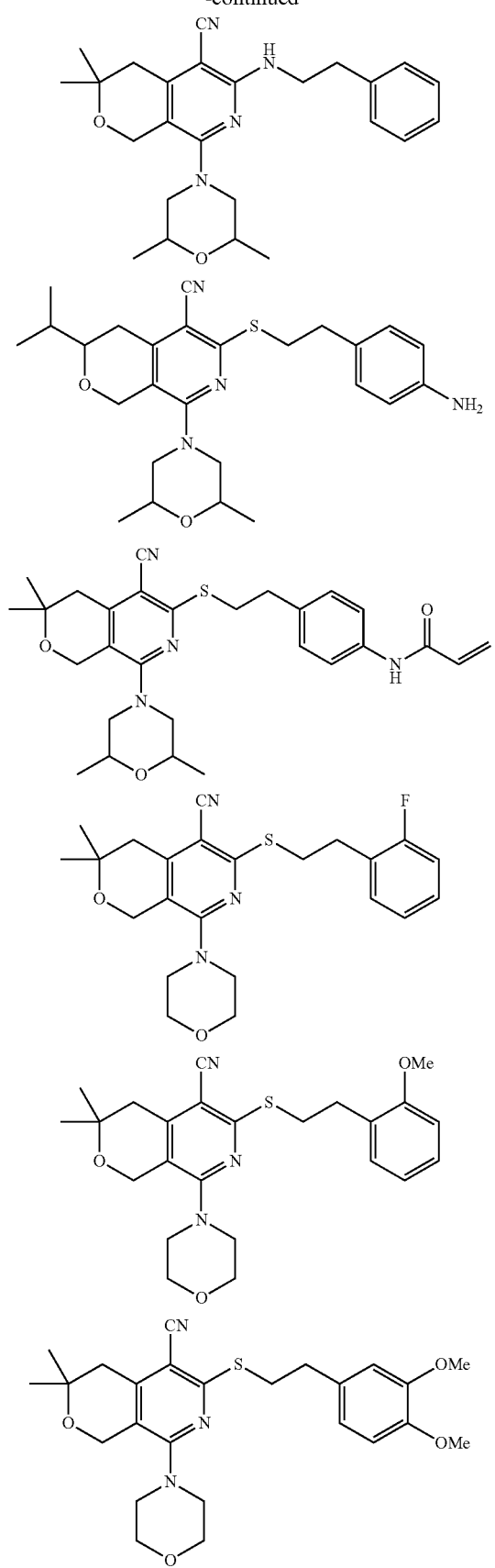

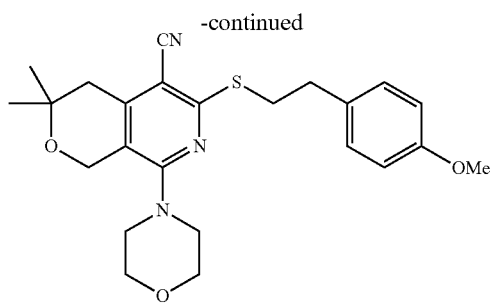

and salts thereof.

The present invention also provides pharmaceutical compositions comprising one or more compounds of Formula I or Formula II and a pharmaceutically acceptable carrier or excipient. The use of one or more of the compounds of Formula I or Formula II in the preparation of a medicament for inhibiting bacterial efflux pumps is also disclosed.

Compositions comprising an antibacterial potentiator compound of Formula I or Formula II described herein may be formulated for administration to an individual (human or other animal) by any of a variety of routes including, but not limited to, intravenous, intramuscular, subcutaneous, intraarterial, parenteral, intraperitoneal, sublingual (under the tongue), buccal (cheek), oral (for swallowing), topical (epidermis), transdermal (absorption through skin and lower dermal layers to underlying vasculature), nasal (nasal mucosa), intrapulmonary (lungs), intrauterine, vaginal, intracervical, rectal, intraretinal, intraspinal, intrasynovial, intrathoracic, intrarenal, nasojejunal, and intraduodenal.

Additionally, the invention contemplatesprovides salts, (especially, pharmaceutically acceptable salts) of the compounds of Formula I and Formula II described herein; solvated forms of the antimicrobial compounds described herein; multimeric forms of the antimicrobial compounds described herein; and prodrugs of the antimicrobial compounds described herein.

DEFINITIONS

Figure 1:
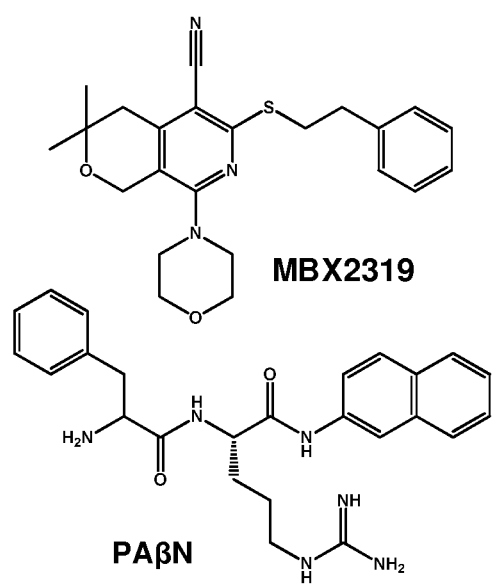
FIG. 1 shows the chemical structures of efflux pump inhibitor compounds MBX2319 and PAβN.

So that the invention may be more clearly understood, the following terms and abbreviations are used as defined below.

Unless indicated otherwise, when the terms "about" and "approximately" are used in combination with an amount, number, or value, then that combination describes the recited amount, number, or value alone as well as the amount, number, or value plus or minus 10% of that amount, number, or value. By way of example, the phrases "about 40%" and "approximately 40%" disclose both "40%" and "from 36% to 44%, inclusive".

"Alkyl" means a straight or branched chain monovalent hydrocarbon radical of the formula $C_nH_{2n+1}$. Examples of an alkyl radical include, but are not limited to, methyl (abbreviated "Me"), ethyl ("Et"), propyl ("Pr"), isopropyl ("iPr"), butyl ("Bu"), isobutyl ("iBu"), sec-butyl (sBu), tert-butyl (tBu), and the like.

"Alkenyl" means a straight-chain or branched, monovalent hydrocarbon radical having at least one carbon-carbon double bond, e.g., ethenyl, 3-buten-1-yl, 3-hexen-1-yl, cyclopent-1-en-3-yl, and the like.

"Alkynyl" means a straight-chain or branched, monovalent hydrocarbon radical having at least one triple bond, e.g., ethynyl, 3-butyn-1-yl, 2-butyn-1-yl, 3-pentyn-1-yl, and the like.

"Cycloalkyl" means a nonaromatic monovalent monocyclic or polycyclic hydrocarbon radical, e.g., cyclopropyl, cyclobutyl, cyclopentyl, cyclohexyl, decalinyl, and the like. A cycloalkyl radical may also be fused to one or more aryl groups, heteroaryl groups, or heterocycloalkyl groups. "Cycloalkenyl" and "cycloalkynyl" refer similarly to monovalent or divalent, monocyclic or polycyclic alkenyl and alkynyl radicals, respectively.

"Heterocycloalkyl" means a nonaromatic monovalent, monocyclic or polycyclic radical composed of carbon and hydrogen atoms wherein one or more carbon atom is substituted by a heteroatom selected from nitrogen (N), oxygen (O), or sulfur (S), e.g., pyrrolodinyl, tetrahydropyranyl, morpholinyl, piperazinyl, oxiranyl, and the like. A heterocycloalkyl radical may also be fused to one or more aryl groups, heteroaryl groups, or heterocycloalkyl groups.

"Aryl" means any monovalent or divalent monocyclic or polycyclic radical derived from aromatic ring members, e.g., phenyl, biphenyl, naphthyl, phenanthryl, and the like. An aryl radical may also be fused to one or more heteroaryl groups or heterocycloalkyl groups, which themselves may be unsubstituted or substituted with one or more suitable substituents found herein.

"Heteroaryl" means a monovalent or divalent, monocyclic or polycyclic aromatic radical comprising carbon atoms, hydrogen atoms, and one or more heteroatoms selected from nitrogen (N), oxygen (O), or sulfur (S), e.g., pyridyl, pyrazinyl, pyridizinyl, pyrimidinyl, furanyl, thienyl, triazolyl, quinolinyl, imidazolinyl, benzimidazolinyl, indolyl, and the like. A heteroaryl radical may also be fused to one or more aryl groups, heteroaryl groups, or heterocycloalkyl groups.

"Heterocycle" means a closed ring of atoms, at least one of which is not a carbon atom. A heterocycle can be aromatic or nonaromatic.

"Amidino" means the radical —C(=NR)NR'R", wherein R, R', and R" are, independently, hydrogen, alkyl, alkenyl, alkynyl, cycloalkyl, aryl, or heteroaryl, and wherein R, R', and R" may form heterocycloalkyl rings, e.g., carboxamido, imidazolinyl, tetrahydropyrimidinyl.

"Imino" means the radical —C(=NR)R', wherein R, and R' are, independently, hydrogen, alkyl, alkenyl, alkynyl, cycloalkyl, aryl, or heteroaryl, and wherein R and R' may form heterocycloalkyl rings.

"Amino" means the radical —NRR', wherein R and R' are, independently, hydrogen, alkyl, alkenyl, alkynyl, cycloalkyl, aryl, heteroaryl, or heterocycloalkyl, acyl, and wherein R and R' may form heterocycloalkyl rings.

"Guanidino" means the radical —NHC(=NR)NR'R", wherein R, R', and R" are, independently, hydrogen, alkyl, alkenyl, alkynyl, cycloalkyl, aryl, or heteroaryl, and wherein R, R', and R" may form heterocycloalkyl rings.

"Halo" or "halogen" means fluorine, chlorine, bromine, or iodine.

"Haloalkyl" means an alkyl radical wherein one or more hydrogen atoms is replaced by an identical or different halogen atoms, e.g., —$CH_2Cl$, —$CF_3$, —$CH_2CF_3$, —$CH_2CCl_3$, —$CHCl$—$CF_3$, and the like.

"Hydroxy" means the radical —OH.

"Alkoxy" means the radical —OR, wherein R is an alkyl or cycloalkyl group.

"Aryloxy" means the radical —OAr, wherein Ar is an aryl group.

"Heteroaryloxy" means the radical —O(HAr), wherein HAr is a heteroaryl group.

"Acyl" means a —C(=O)R radical, wherein R is alkyl, alkenyl, alkynyl, cycloalkyl, aryl, heteroaryl, or heterocycloalkyl, e.g., acetyl, benzoyl, and the like.

"Carboxy" means the radical —C(=O)OH.

"Alkoxycarbonyl" means a —C(=O)OR radical wherein R is alkyl or cycloalkyl.

"Aryloxycarbonyl" means a —C(=O)OR radical wherein R is aryl or heteroaryl.

"Acylamino" means the radical —NHC(=O)R, wherein R is alkyl, alkenyl, alkynyl, cycloalkyl, aryl, heteroaryl, or heterocycloalkyl, e.g., acetylamino, benzoylamino, and the like.

"Amido" means the radical —C(=O)NRR', wherein R and R' are, independently, hydrogen, alkyl, alkenyl, alkynyl, cycloalkyl, aryl, heteroaryl, or heterocycloalkyl.

"Sulfonylamino" means the radical —$NHSO_2R$, wherein R is alkyl, alkenyl, alkynyl, cycloalkyl, aryl, heteroaryl, or heterocycloalkyl.

"Mercapto" means the radical —SH.

"Alkylthio" means the radical —SR, wherein R is an alkyl or cycloalkyl group.

"Arylthio" means the radical —SAr, wherein Ar is an aryl group.

"Hydroxamate" means the radical —C(=O)NHOR, wherein R is an alkyl or cycloalkyl group.

"Thioacyl" means a —C(=S)R radical, wherein R is alkyl, alkenyl, alkynyl, cycloalkyl, aryl, heteroaryl, or heterocycloalkyl.

"Alkylsulfonyl" means the radical —$SO_2R$, wherein R is alkyl, alkenyl, alkynyl, cycloalkyl, aryl, heteroaryl, or heterocycloalkyl.

"Aminosulfonyl" means the radical —$SO_2NRR'$, wherein R and R' are, independently, hydrogen, alkyl, alkenyl, alkynyl, cycloalkyl, aryl, heteroaryl, or heterocycloalkyl.

As described herein, where the moieties or functional groups specified in the various structural formulas of compounds of the invention are described as "optionally substituted" by one or more suitable "substituents", the term "substituent" or "suitable substituent" means any suitable substituent or suitable organic moiety, that may be recognized or selected, such as through routine testing, by those skilled in the art. Illustrative examples of "suitable substituents" are those found in the exemplary compounds that are described herein, including but not limited to halogen; $C_{1-6}$ alkyl; $C_{1-6}$ alkenyl; $C_{1-6}$ alkynyl; hydroxyl; $C_{1-6}$ alkoxy; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or nonfused polycyclic alkyl (e.g., cyclopropyl, cyclobutyl, cyclopentyl, or cyclohexyl) or a heterocycloalkyl, which may be monocyclic or fused or nonfused polycyclic (e.g., pyrrolidinyl, tetrahydropyranyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, aryloxy (—OM; aralkyl (—RAr, where R is alkanediyl); and the like. Such moieties may also be optionally substituted by a fused ring structure or bridge, for example —O— $CH_2$—O—. All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, substituted amino groups, disubstituted amino groups, carbamoyl groups, aryloxyl groups, heteroaryloxyl groups, arylthio groups, heteroarylthio groups, and the like.

The term "optionally substituted" is intended to expressly indicate that the specified group may be unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

DETAILED DESCRIPTION OF THE INVENTION

The present invention describes a novel class of organic compounds which are effective as bacterial efflux pump inhibitors. In one embodiment, the novel compounds can be used or administered in combination with antimicrobial agents to enhance their efficacy in inhibiting growth or to kill bacteria on contact. Compounds of the present invention are thus referred to as "antimicrobial potentiator" compounds, i.e., compounds that may be administered in combination, either before, during, or after, with one or more antimicrobial compounds and that enhance or complement the effect of the antimicrobial compounds. Antimicrobial potentiator compounds described herein may be used in compositions and methods to treat an individual (human or other mammal) who is infected with, at risk of infection by, or suspected of being infected with a pathogenic microbial species. Antimicrobial potentiator compounds described herein may also be used in combination with antimicrobial agents to treat or disinfect a device, a solid surface, or a material composition, which can be liquid, solid, or semisolid, that is contaminated with or susceptible to contamination by cells of a pathogenic microbial species.

The novel bacterial efflux pump inhibitory compounds of the present invention are represented by the following Formula I:

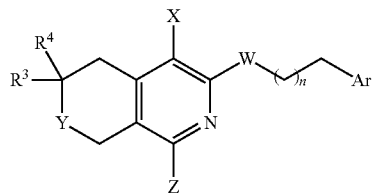

FORMULA I wherein,
n is 1, 2, 3, 4 or 5;
X is —CN, —F, —Cl, —Br, —I, —NO$_2$;
W is S, SO, SO$_2$, O, NH, or NR$^5$;
R$^5$ is alkyl, aralkyl, alkenyl, or alkynyl;
Y is O, S;
Z is NR$^1$R$^2$ or heterocycloalkyl;
R$^1$, R$^2$ are, independently, hydrogen, alkyl, aralkyl, alkenyl, alkynyl, or cycloalkyl and may be optionally substituted with halo, hydroxy, alkoxy, amino, alkylamino, carboxy, alkoxycarbonyl, or nitrile groups;
R$^3$ and R$^4$ are, independently, hydrogen, alkyl, aralkyl, alkenyl, alkynyl, or cycloalkyl and may be optionally substituted with halo, hydroxy, alkoxy, amino, alkylamino, carboxy, alkoxycarbonyl, or nitrile groups, and may together form a cyclic structure; and
Ar is mono-, di-, or tri-substituted phenyl or heteroaryl, and pharmaceutically acceptable salts thereof.

In a particularly preferred embodiment, the novel bacterial efflux inhibitor compounds of Formula I include the following:

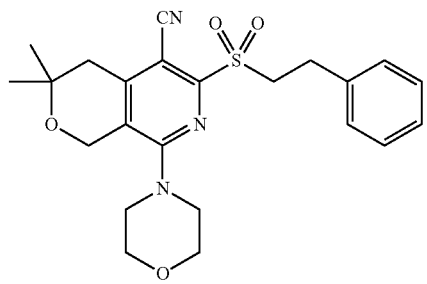

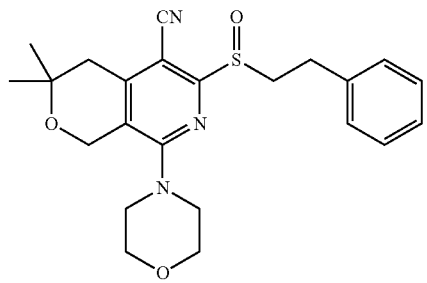

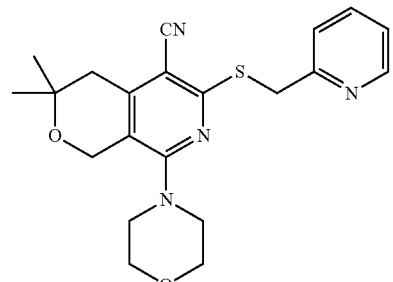

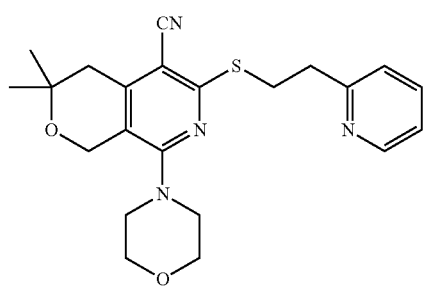

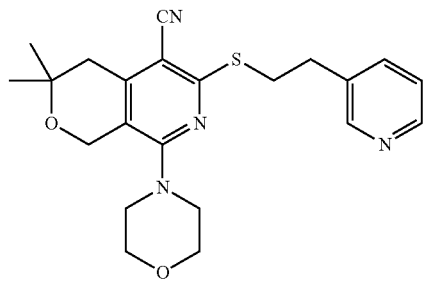

51
-continued
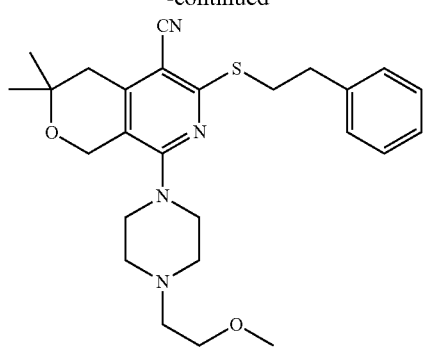
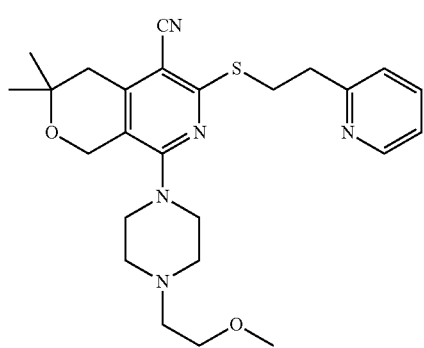
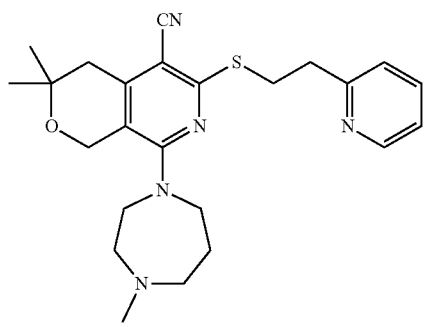
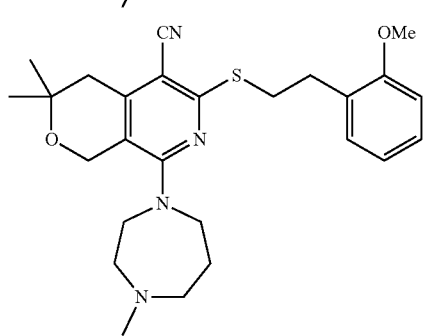
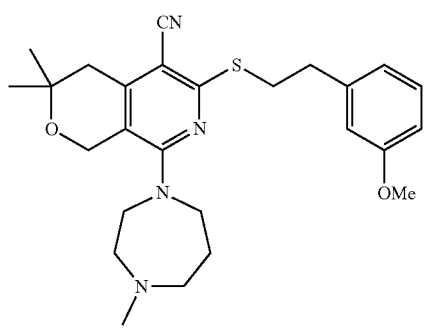
52
-continued
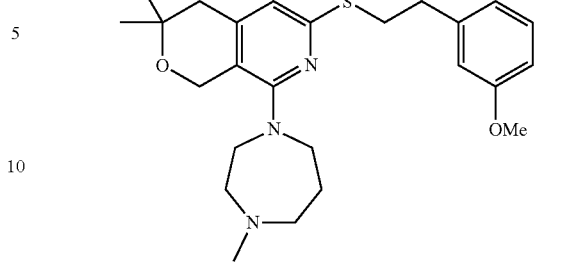
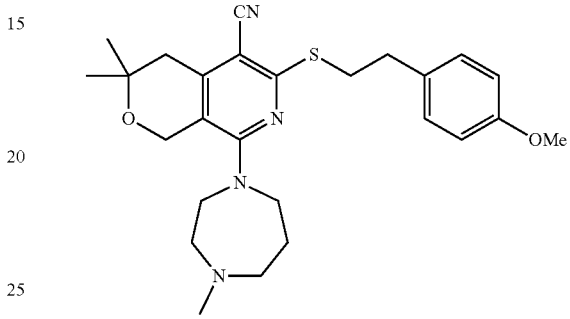
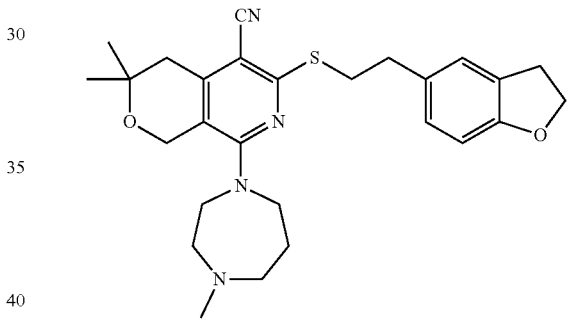
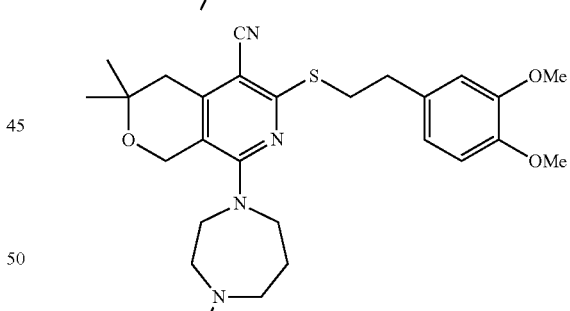
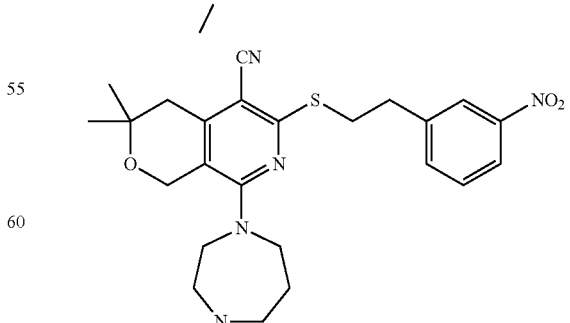

53
-continued
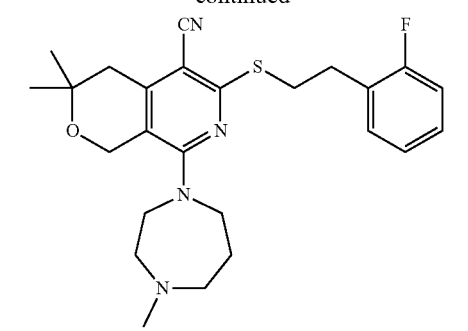
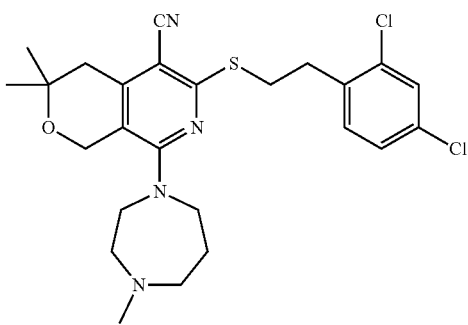
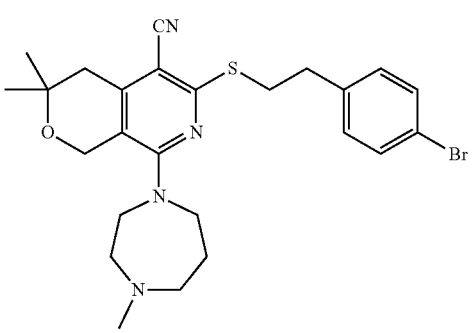
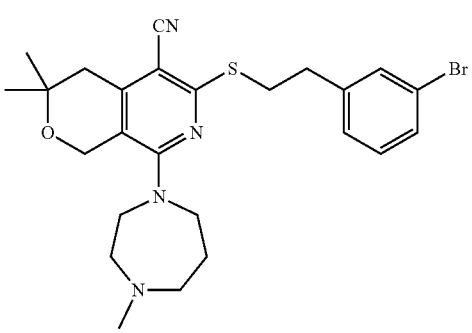
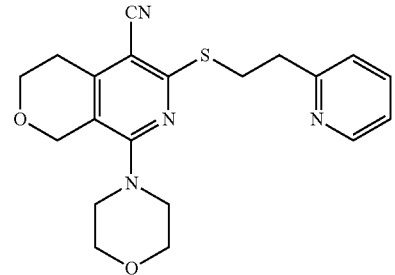
54
-continued
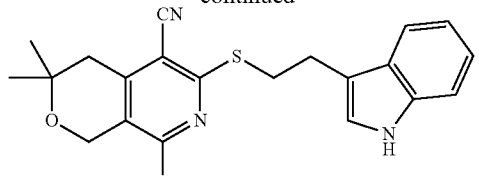
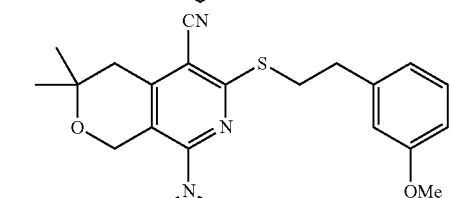
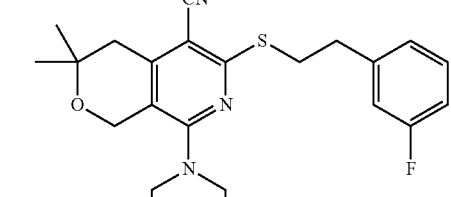
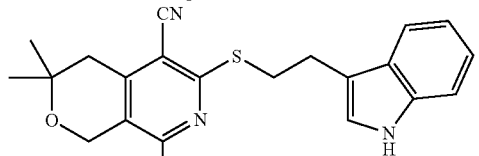
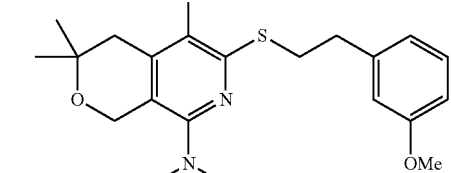
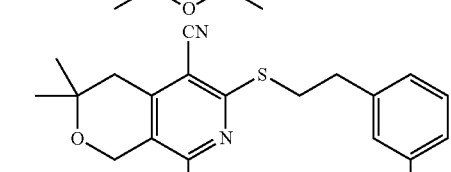
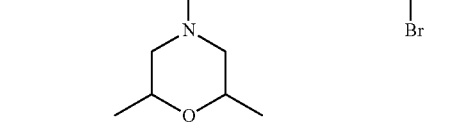

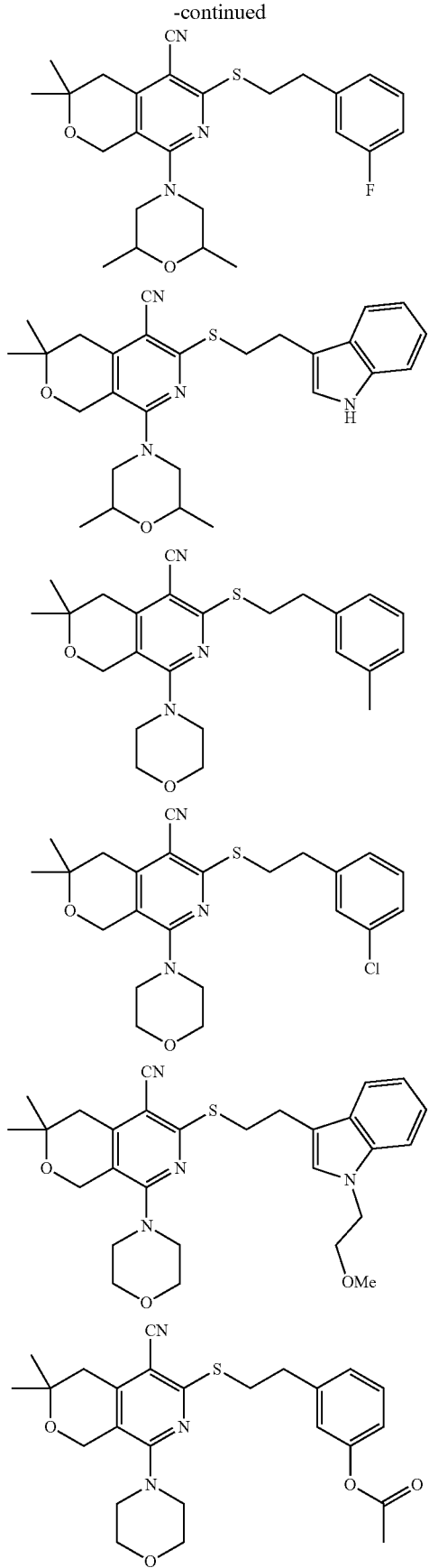

57
-continued
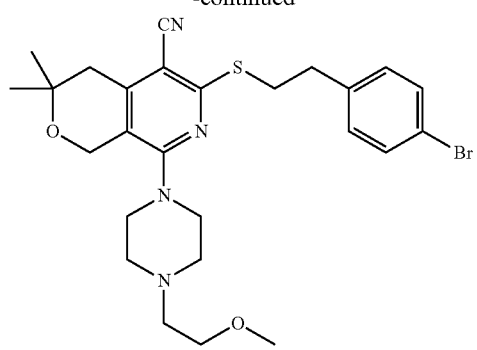
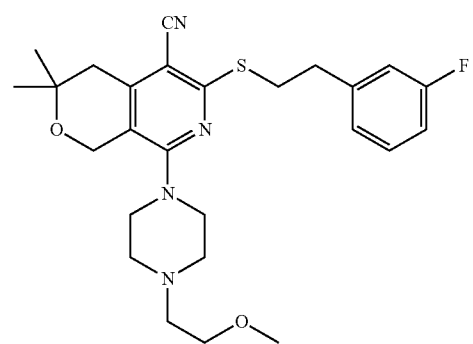
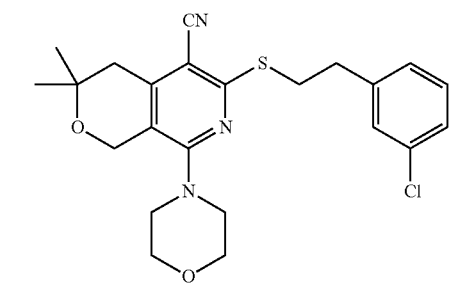
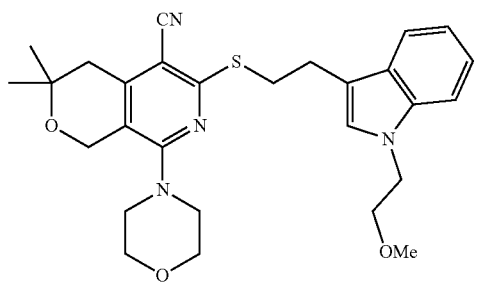
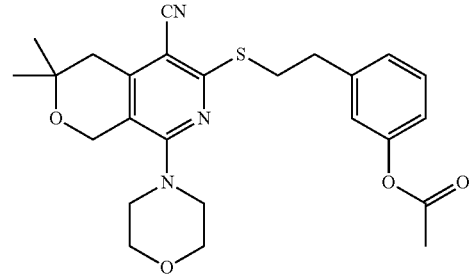
58
-continued
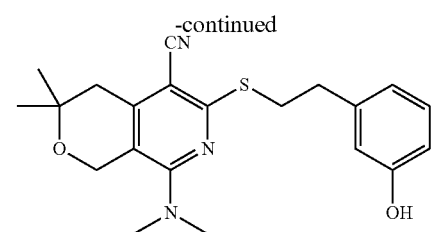
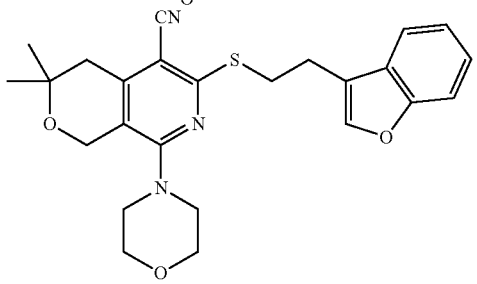
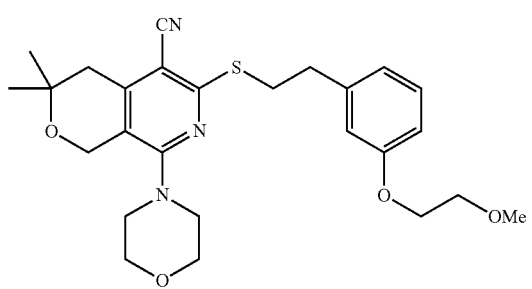
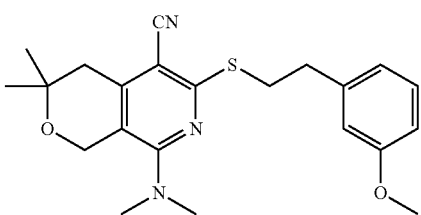
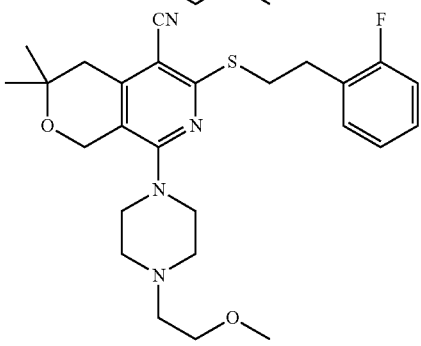

59
-continued
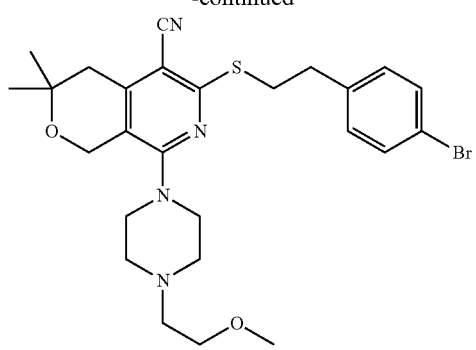
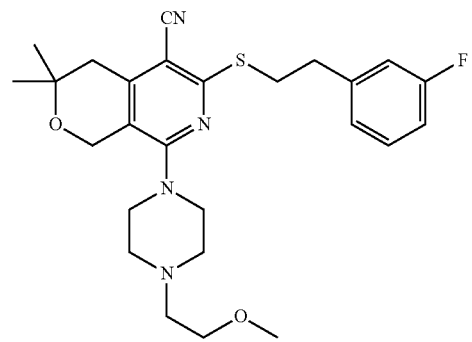
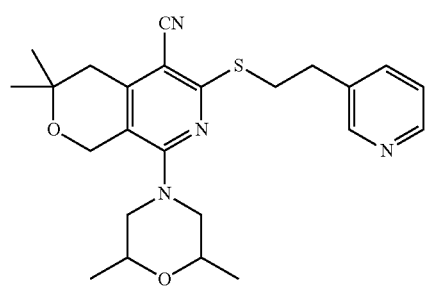
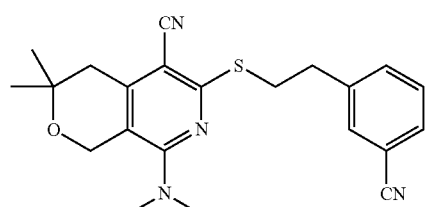
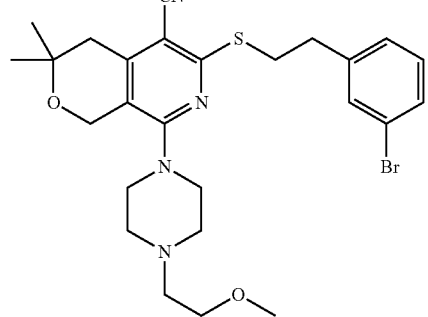
60
-continued
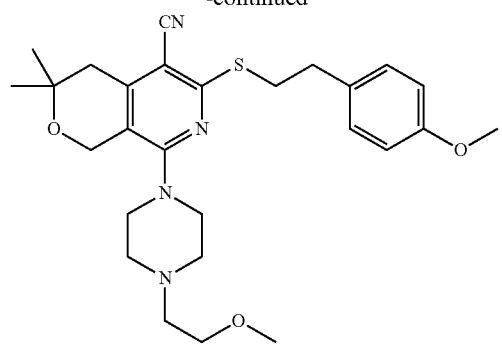
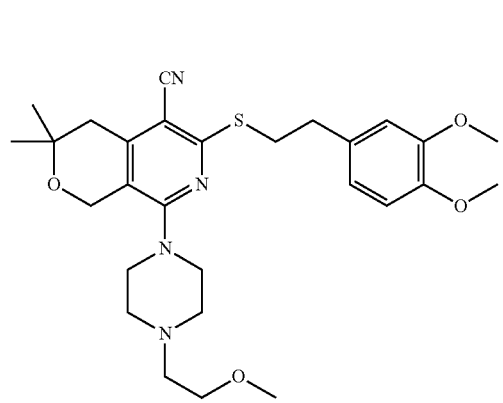
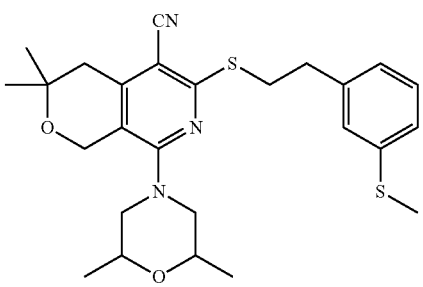
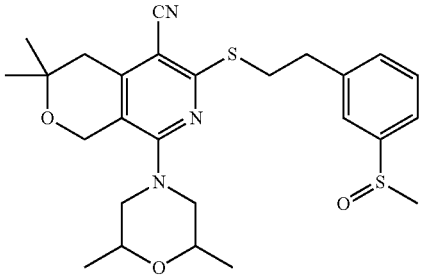
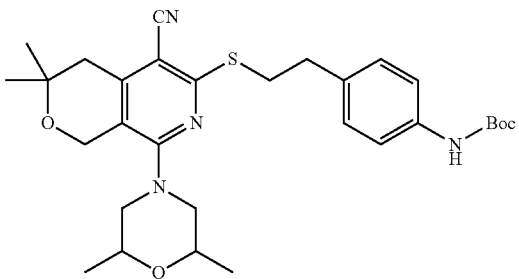

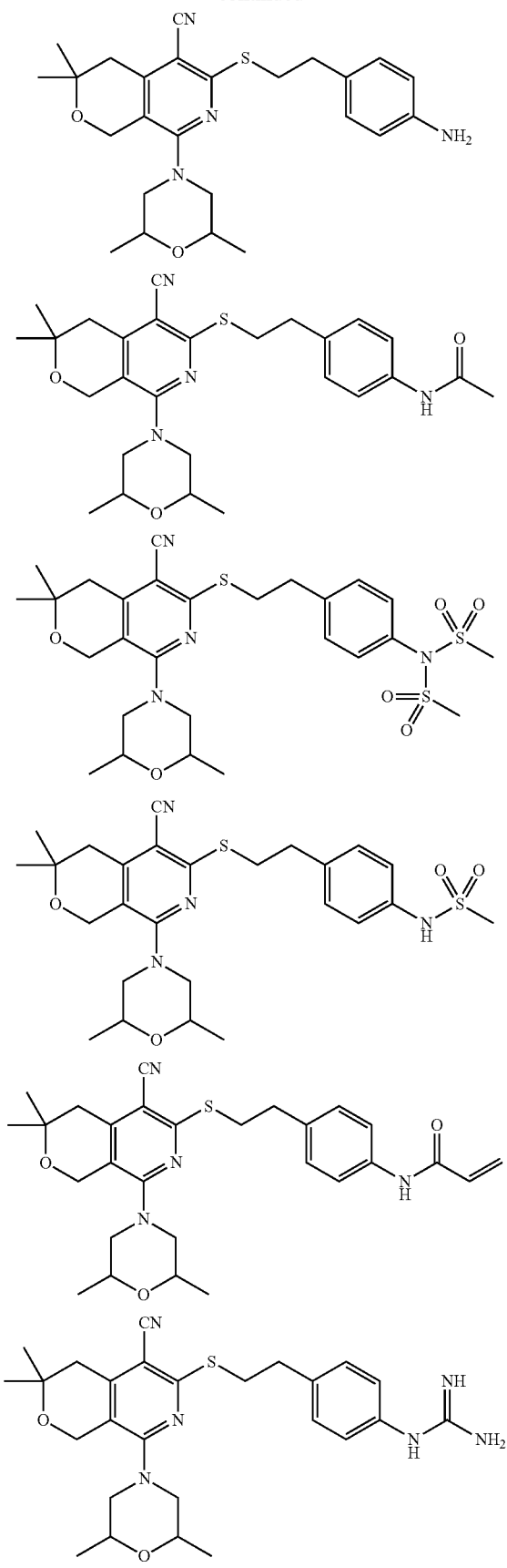

63
-continued
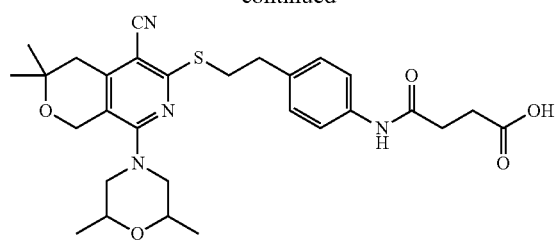
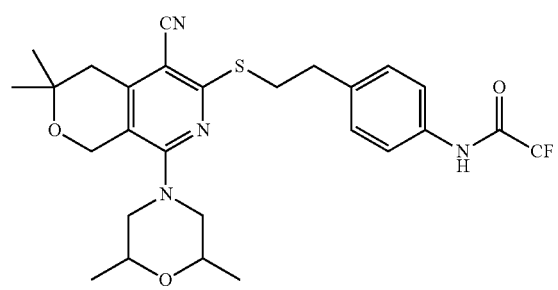
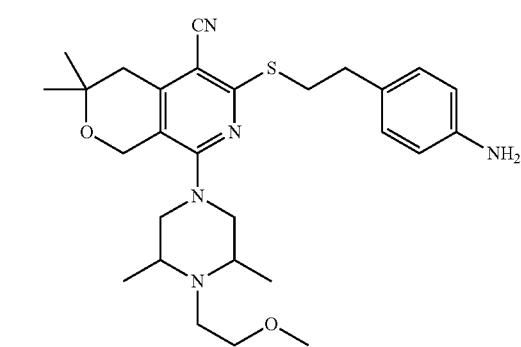
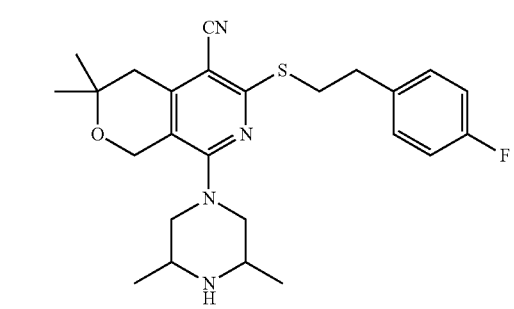
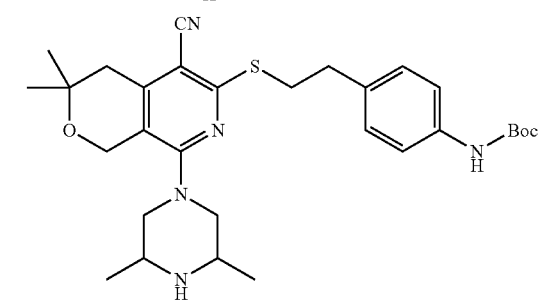
64
-continued
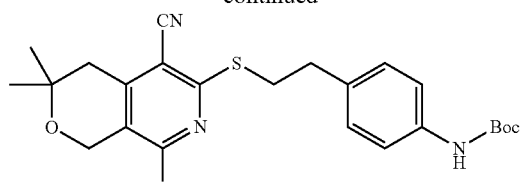
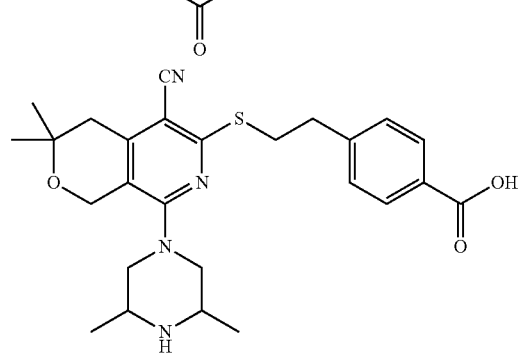
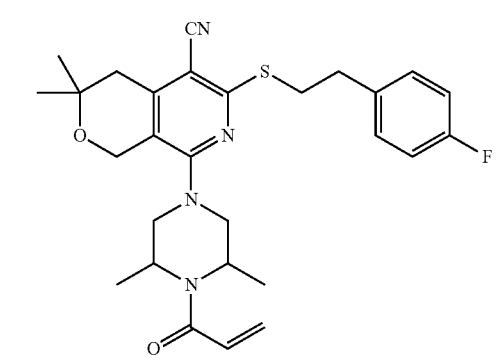
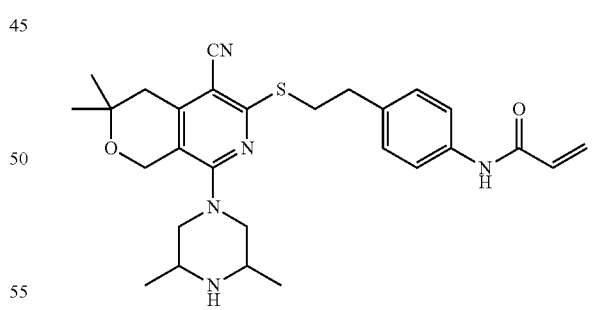
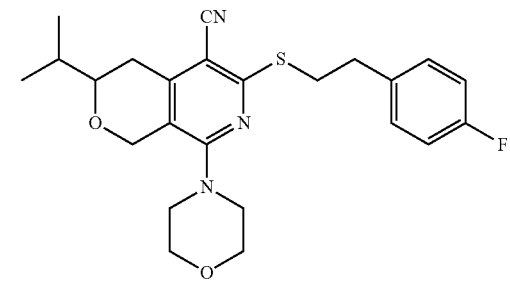

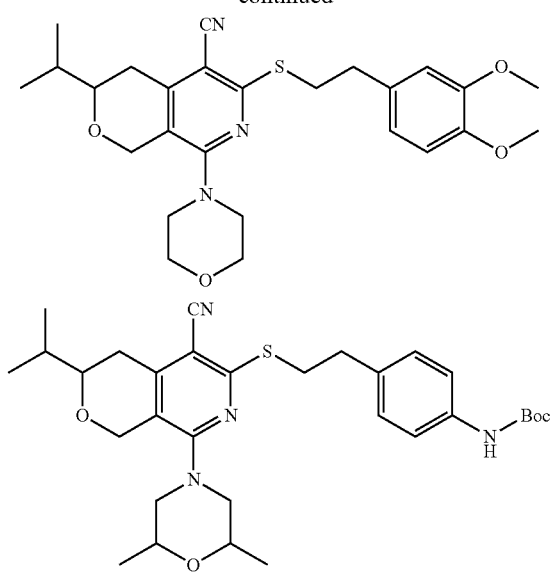
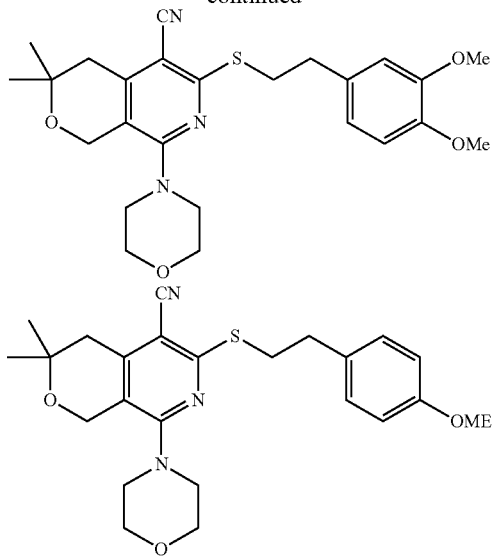
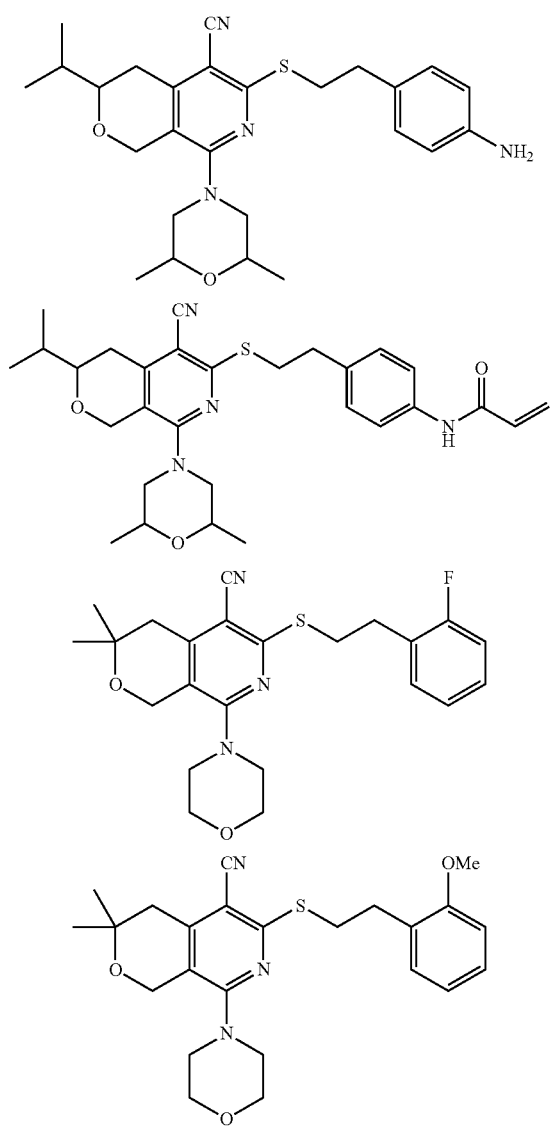

A potentiator or combination of potentiators described herein may be used as a supporting or adjunctive therapy for the treatment of bacterial infection in humans or other animals. The potentiator may be administered in admixture, sequentially, or simultaneously with an antibacterial agent to provide more effective bacterial killing or microbial growth inhibition. This adjunctive therapy may provide the following benefits: increased antibiotic efficacy that leads to lower dosage and/or shorter treatment period, minimizing the side effects of antibiotics to patients and decreasing evolution of bacterial resistance in the community.

Also disclosed are antimicrobial compositions comprising a potentiator of the invention and an antimicrobial agent. The antimicrobial component of the compositions can be, but is not limited to, a beta-lactam (with or without beta-lactamase inhibitors) and/or a quinolone antibiotic. These compositions kill or inhibit growth of bacteria more effectively than the antimicrobial agent alone.

Compositions comprising an antimicrobial component and a potentiator according to Formula I may be used to treat in vivo infections, or to disinfect devices and surfaces such as bandages, bodily appliances, catheters, surgical instruments, patient examination tables, counters, etc.

In addition to the compounds of Formula I that have been discovered and found to act as bacterial efflux pump inhibitors, additional analogs have been tested and found to also be useful as bacterial efflux pump inhibitors. Such analogs would also be useful as antimicrobial potentiator compounds. Accordingly, uses and methods are described herein for compounds having following Formula II:

FORMULA II

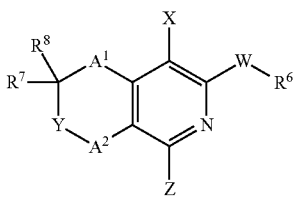

wherein:

X is cyano, amido, sulfonamido, imino, amidino, acyl, carboxy, alkoxycarbonyl, halo, or nitro;

W is a sulfur, SO (sulfoxide), $SO_2$ (sulfone), oxygen, nitrogen, or alkyl-substituted nitrogen;

$R^6$ is optionally substituted aralkyl, alkyl, aryloxyalkyl, alkoxyalkyl, haloalkyl, alkenyl, or alkynyl;

Z is $NR^1R^2$ or heterocycloalkyl;

$R^1$, $R^2$ are, independently, hydrogen, alkyl, aralkyl, alkenyl, alkynyl, or cycloalkyl, and may be optionally substituted with halo, hydroxy, alkoxy, amino, alkylamino, carboxy, alkoxycarbonyl, or nitrile groups $A^1$ and $A^2$ are, independently, carbon, optionally substituted carbon, or are absent;

Y is oxygen, sulfur, or optionally substituted nitrogen; and $R^7$ and $R^8$ are, independently, hydrogen, alkyl, aralkyl, alkenyl, alkynyl, or cycloalkyl and may be optionally substituted with halo, hydroxy, alkoxy, amino, alkylamino, carboxy, alkoxycarbonyl, or nitrile groups, and may together form a cyclic structure, and pharmaceutically acceptable salts thereof.

In another embodiment, the antimicrobial potentiator compounds of the present invention have the structure of Formula II, wherein:

X is cyano;

W is S $R^6$ is optionally substituted aralkyl or aryloxyalkyl;

Z is $NR^1R^2$ or heterocycloalkyl;

$R^1$, $R^2$ are, independently, hydrogen, alkyl, aralkyl, alkenyl, alkynyl, or cycloalkyl, and may be optionally substituted with halo, hydroxy, alkoxy, amino, alkylamino, carboxy, alkoxycarbonyl, or nitrile groups;

$A^1$, $A^2$ are $CH_2$;

Y is oxygen;

and pharmaceutically acceptable salts thereof.

Particularly preferred embodiments of the compounds of Formula II according to the present invention having the following structures:

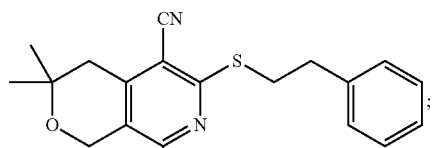

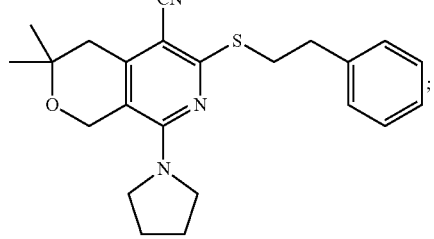

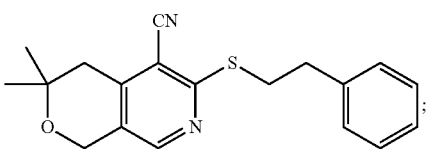

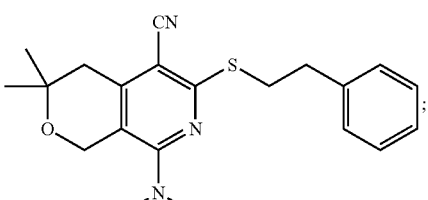

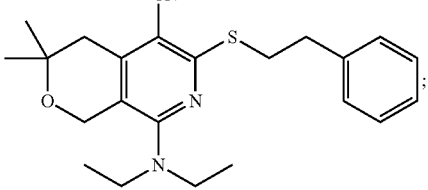

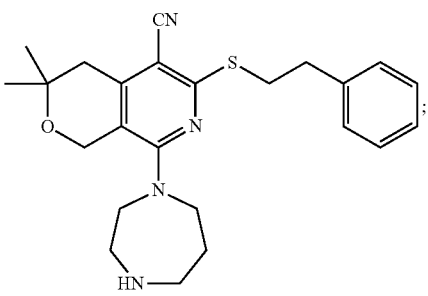

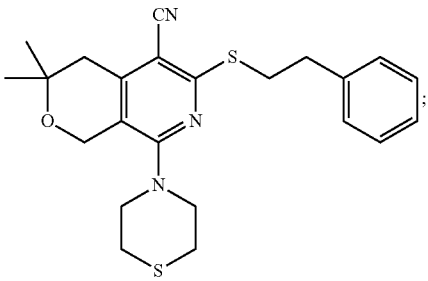

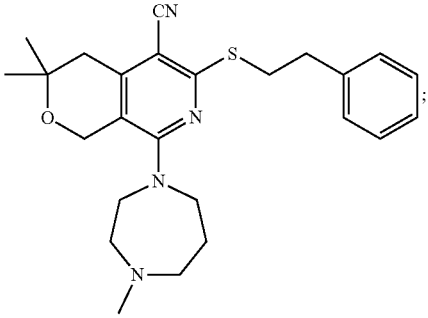

69
-continued
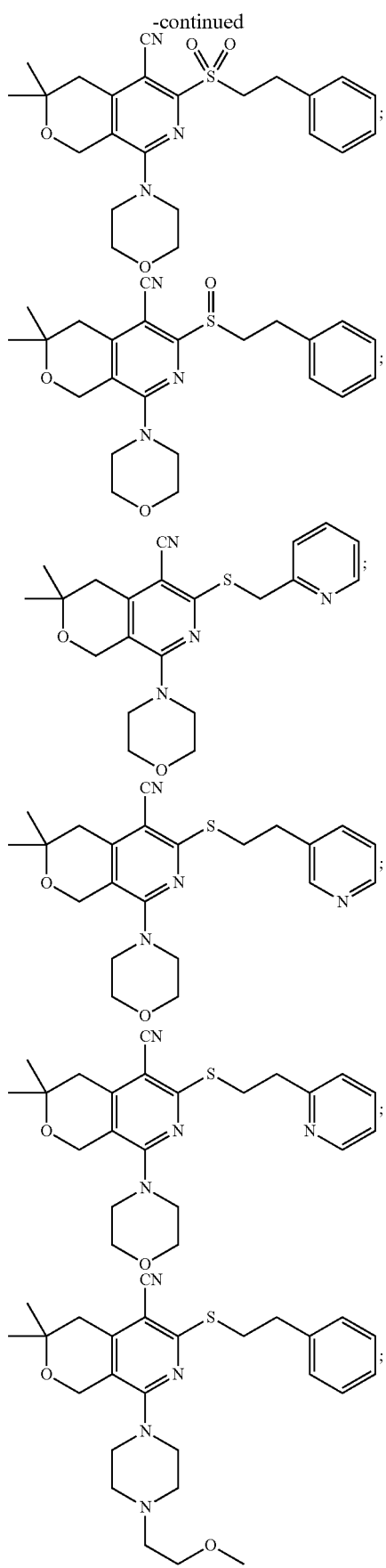
70
-continued
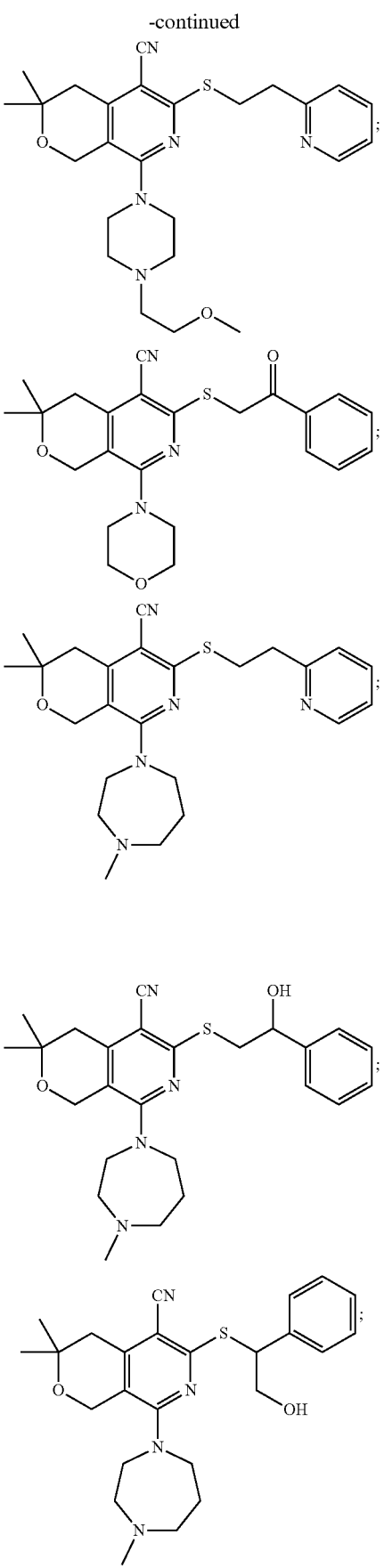

71
-continued
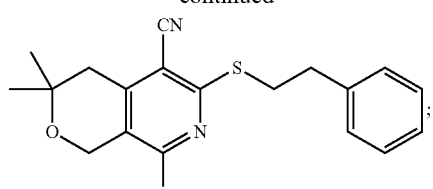
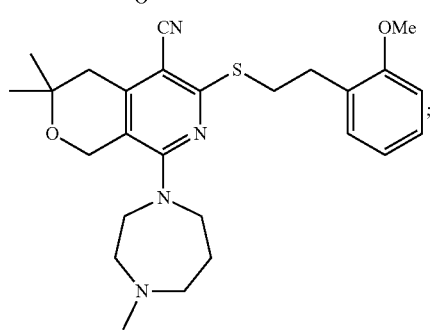
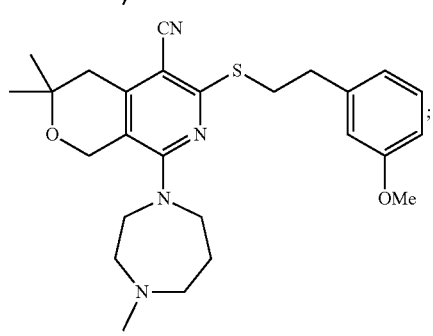
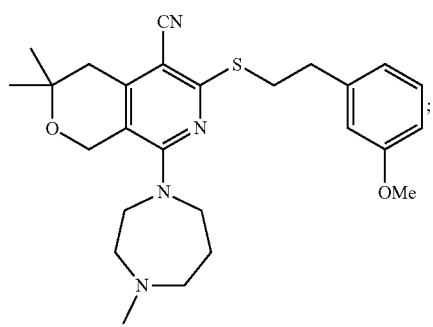
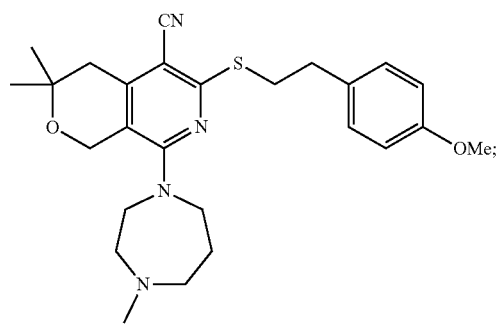
72
-continued
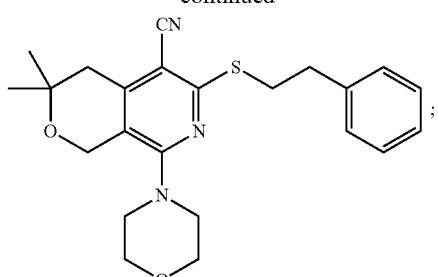
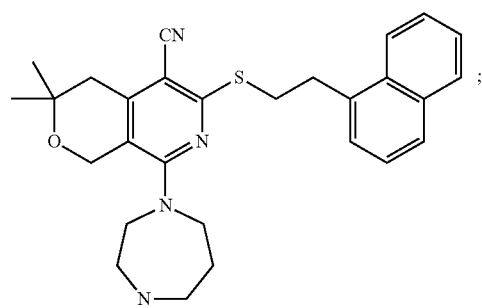
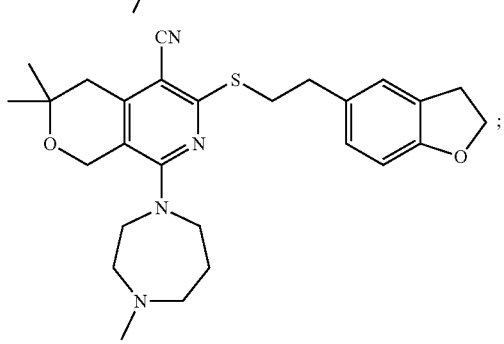
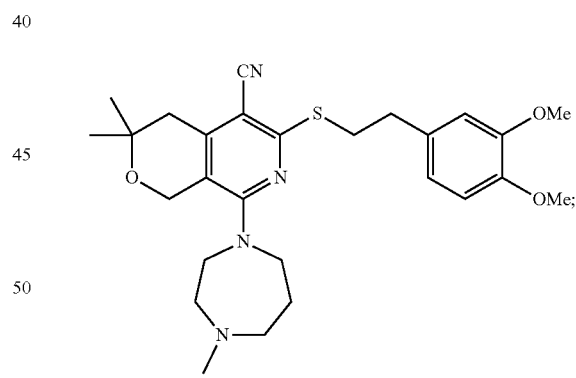
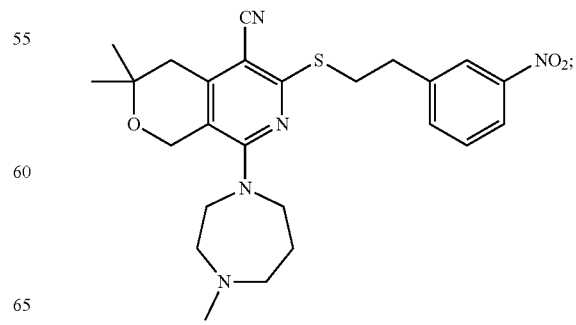

73
-continued
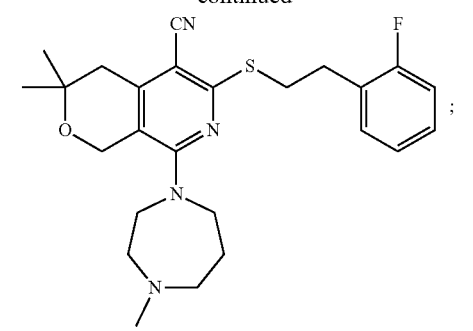
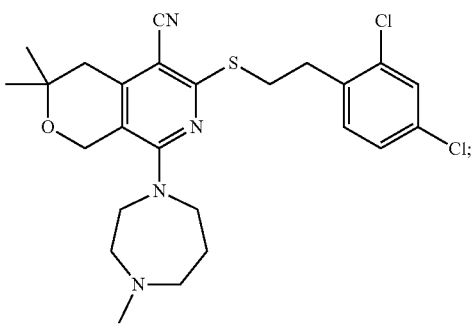
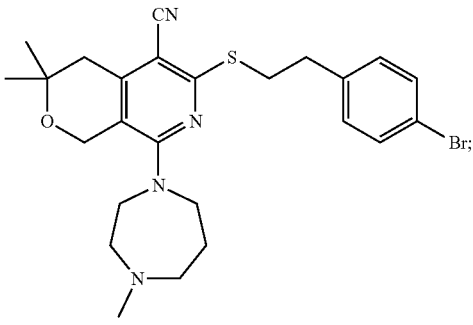
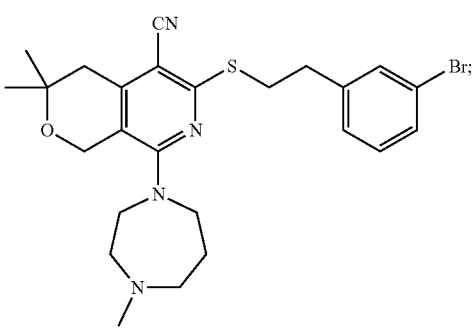
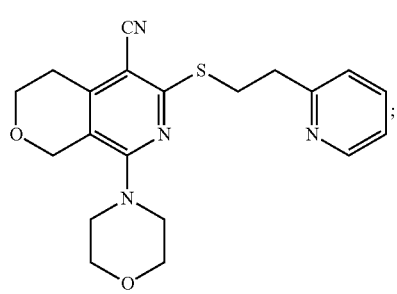
74
-continued
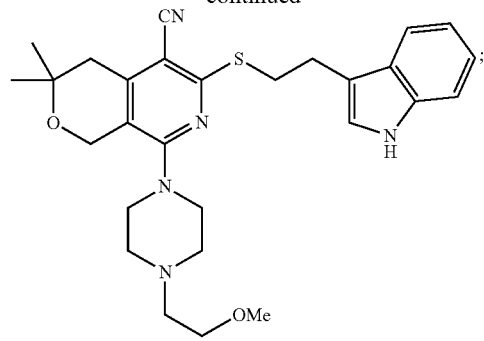
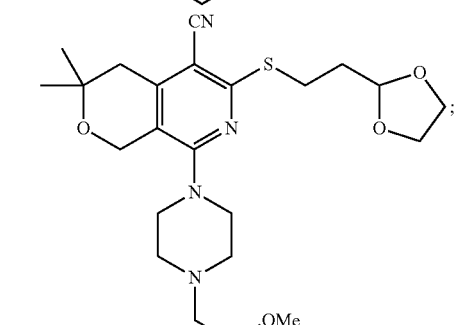
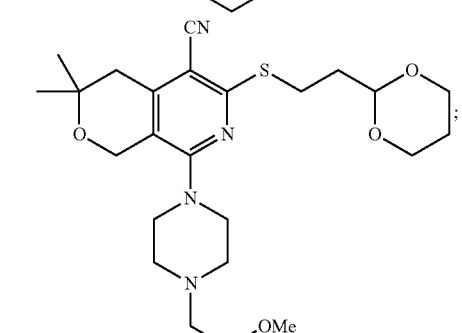
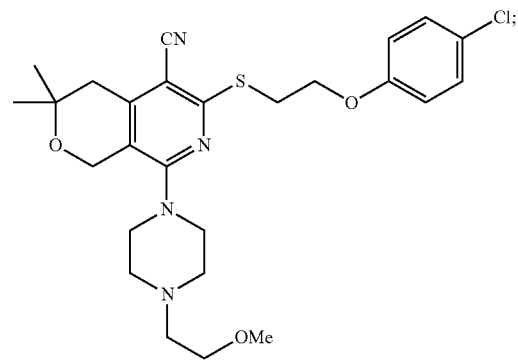
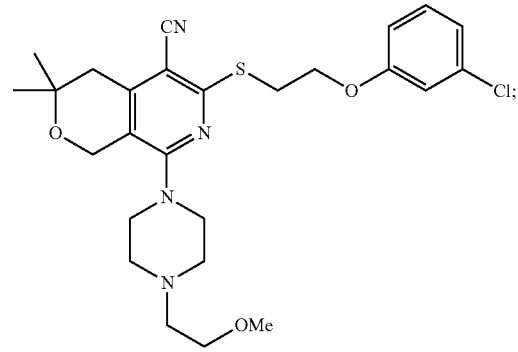

75
-continued
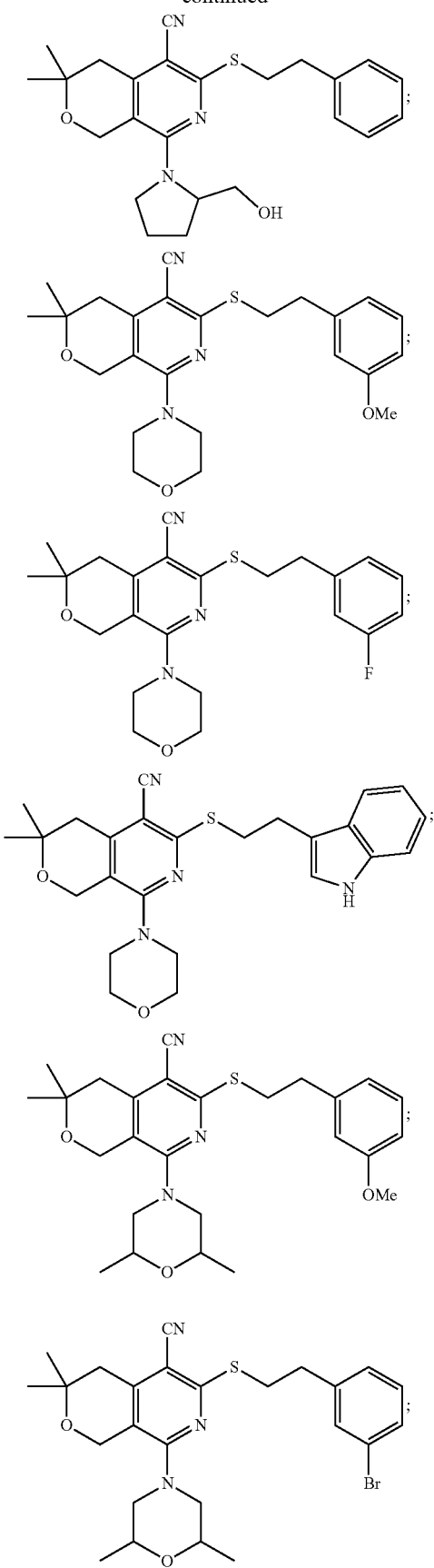
76
-continued
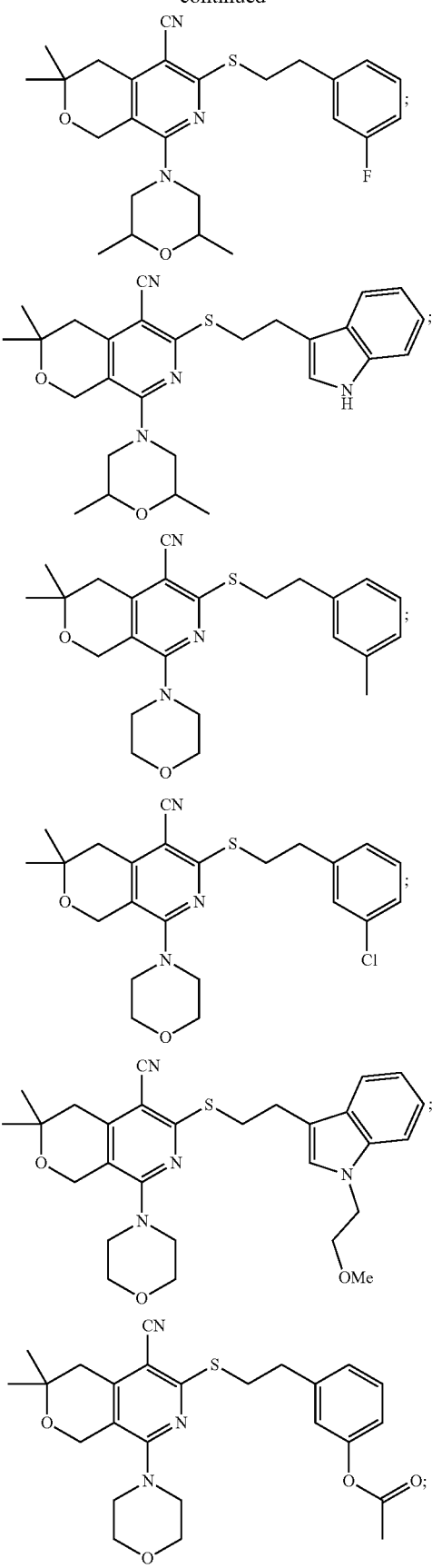

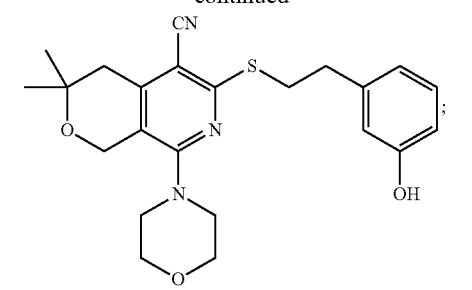
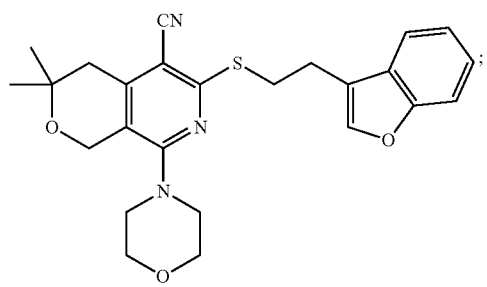
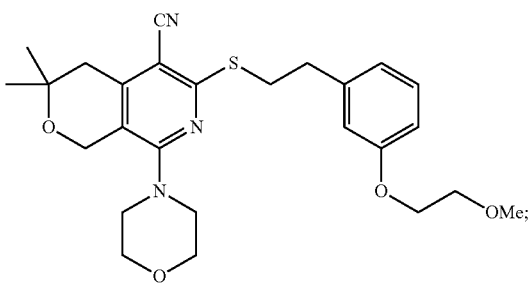
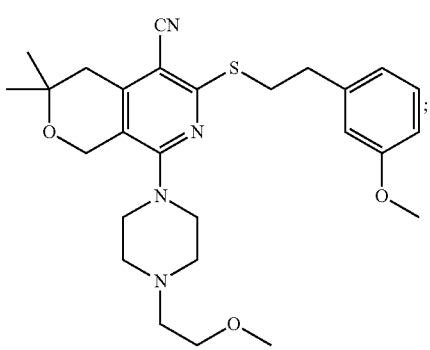
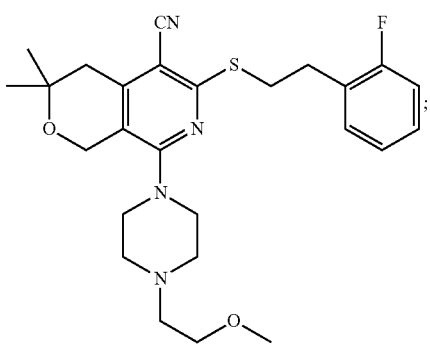
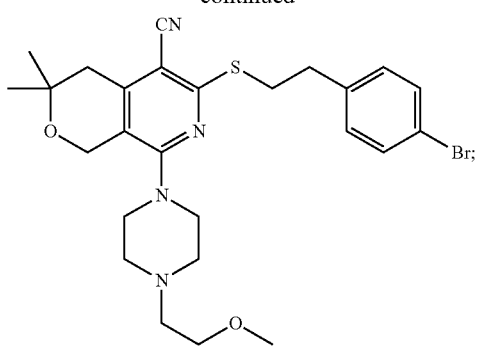
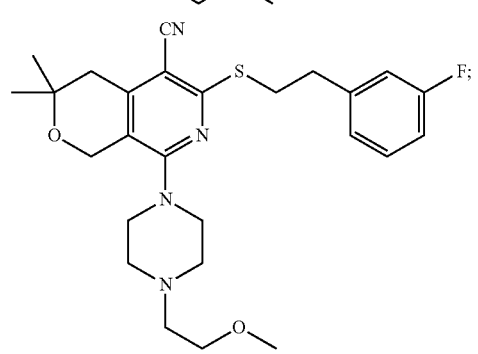
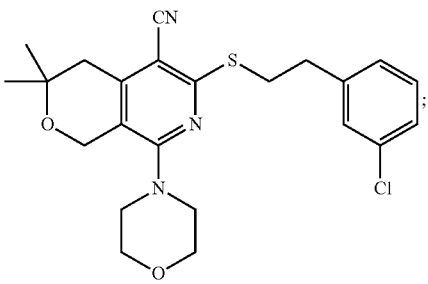
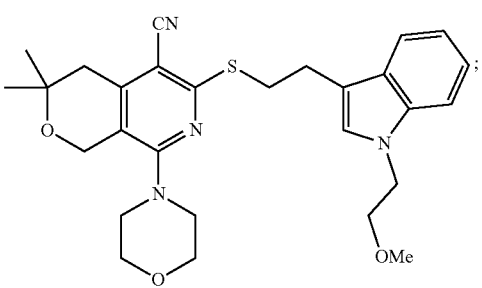
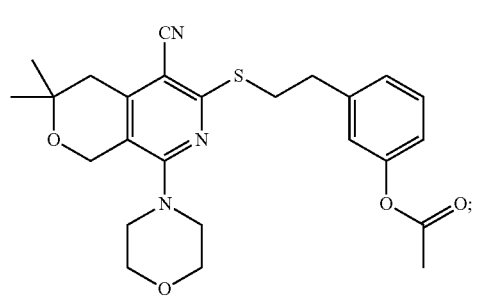

79
-continued
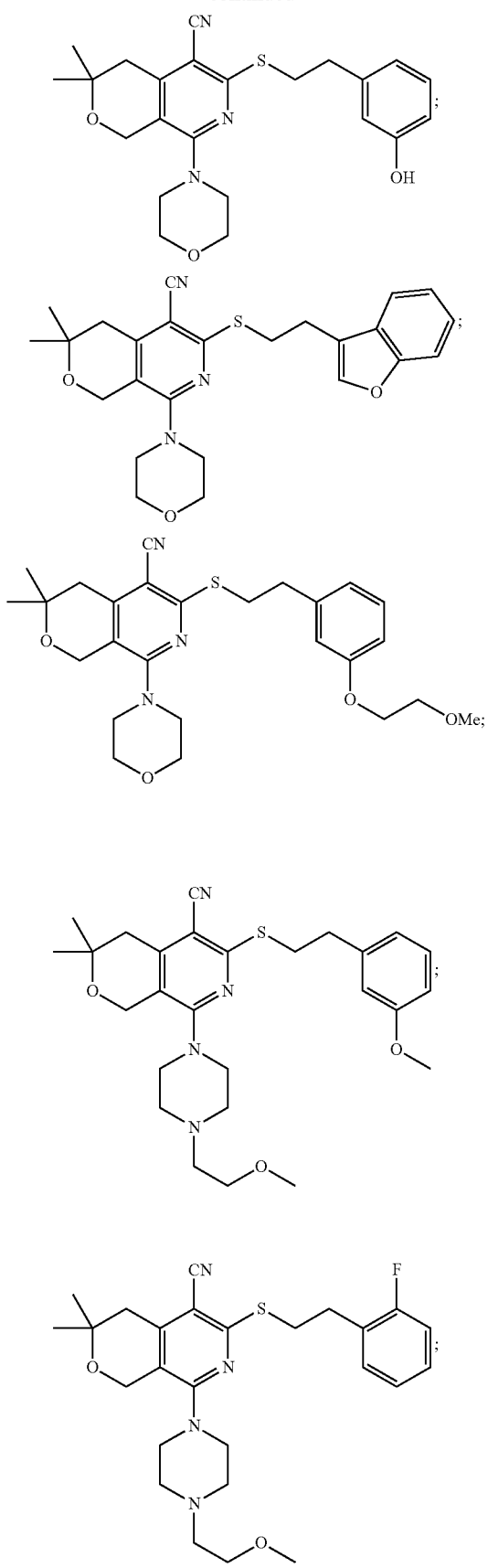
80
-continued
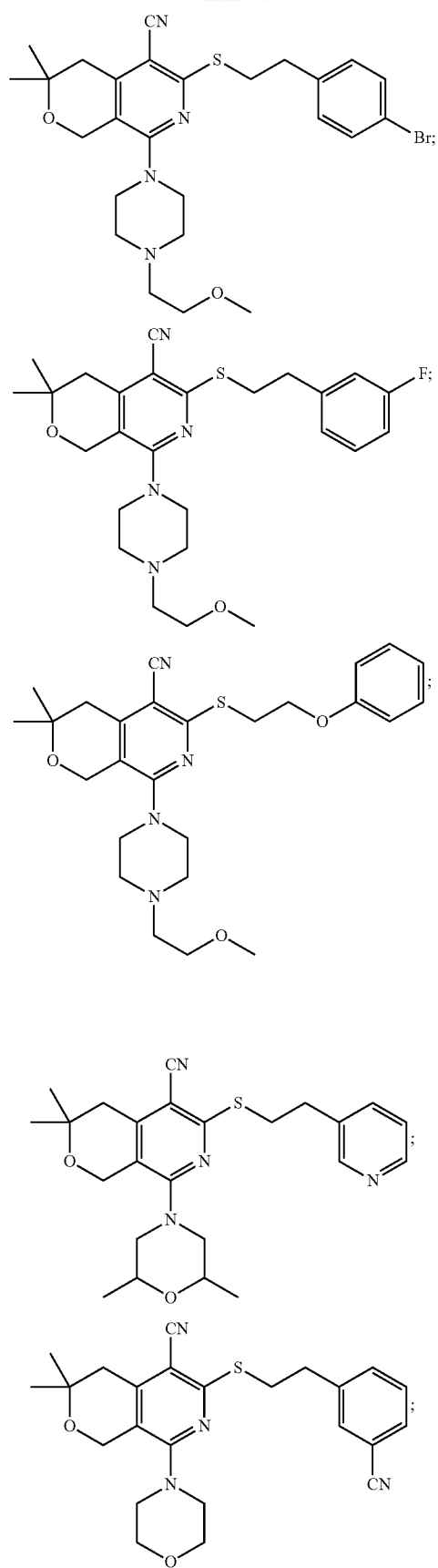

81
-continued
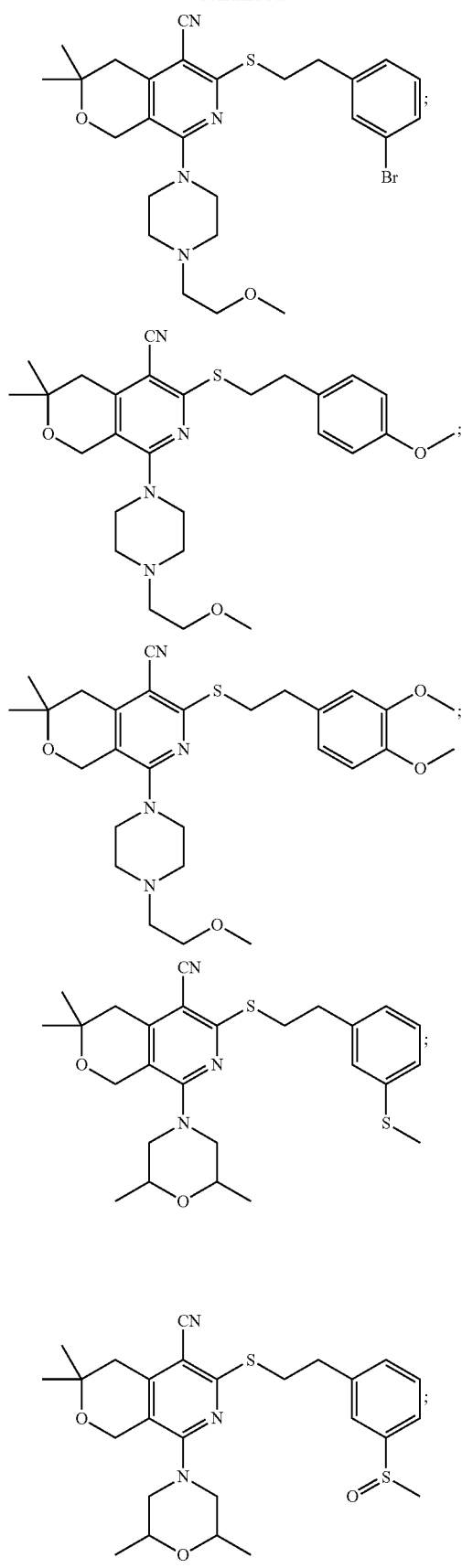
82
-continued
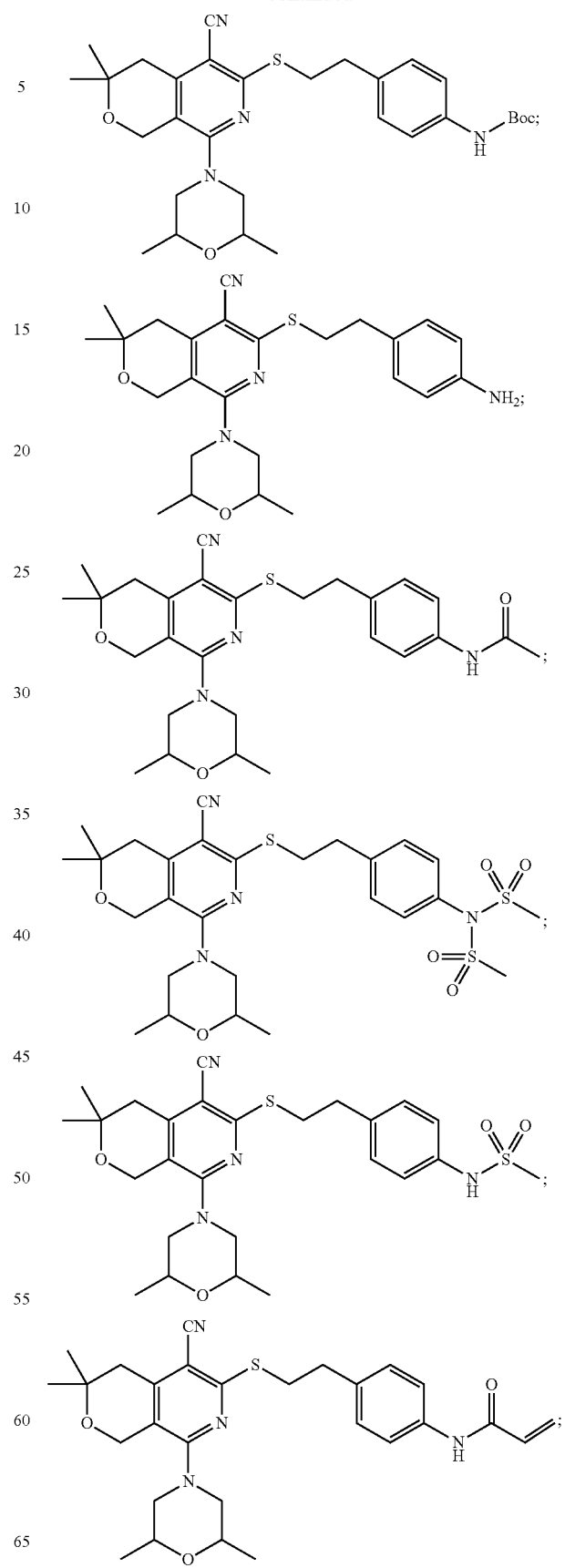

83
-continued
84
-continued
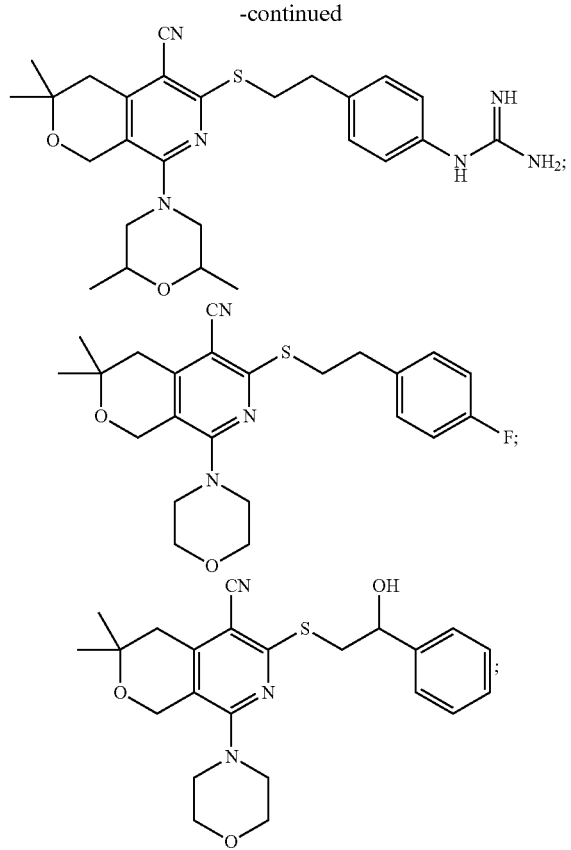
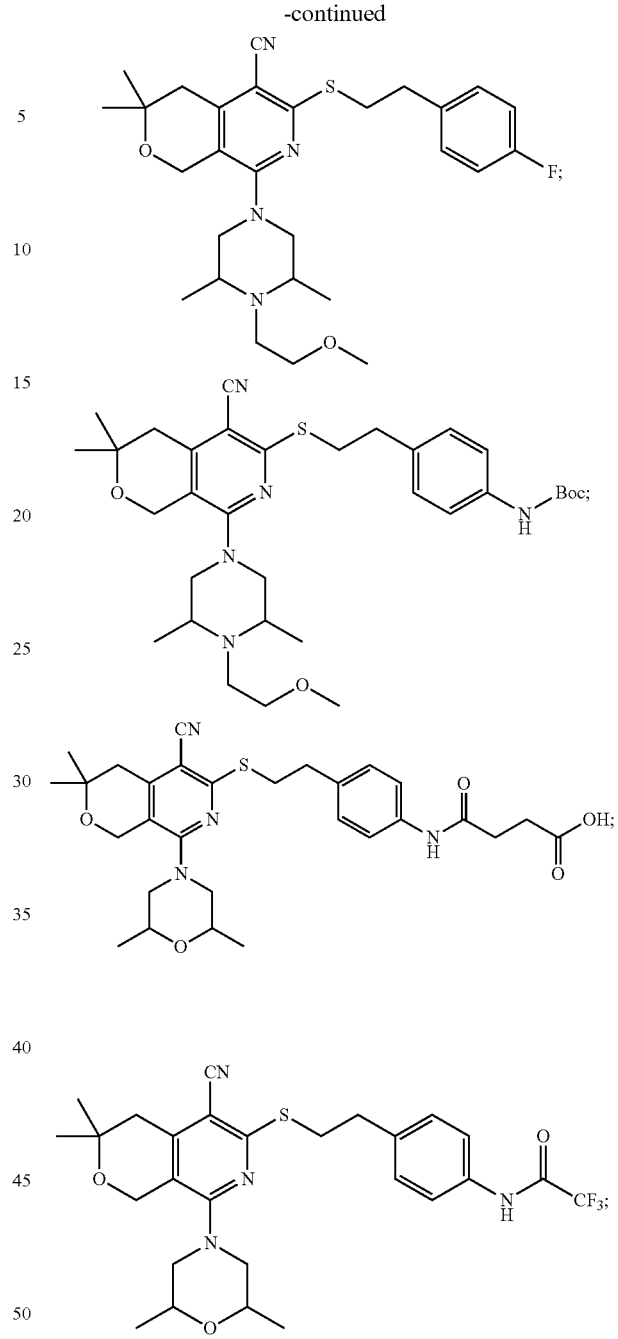
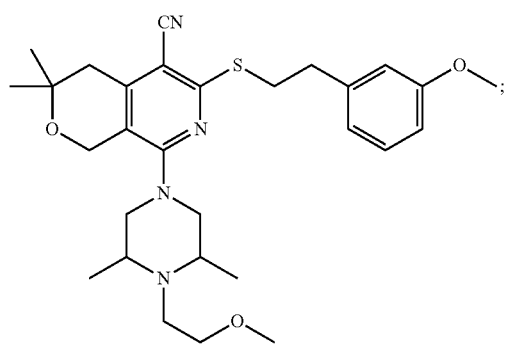

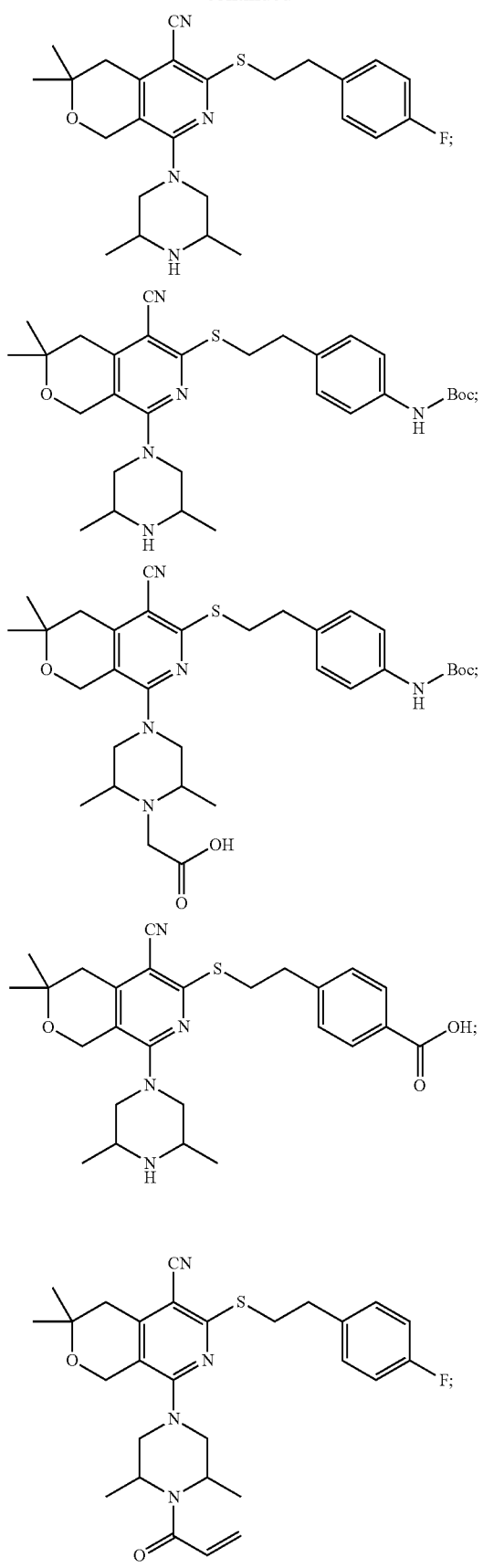
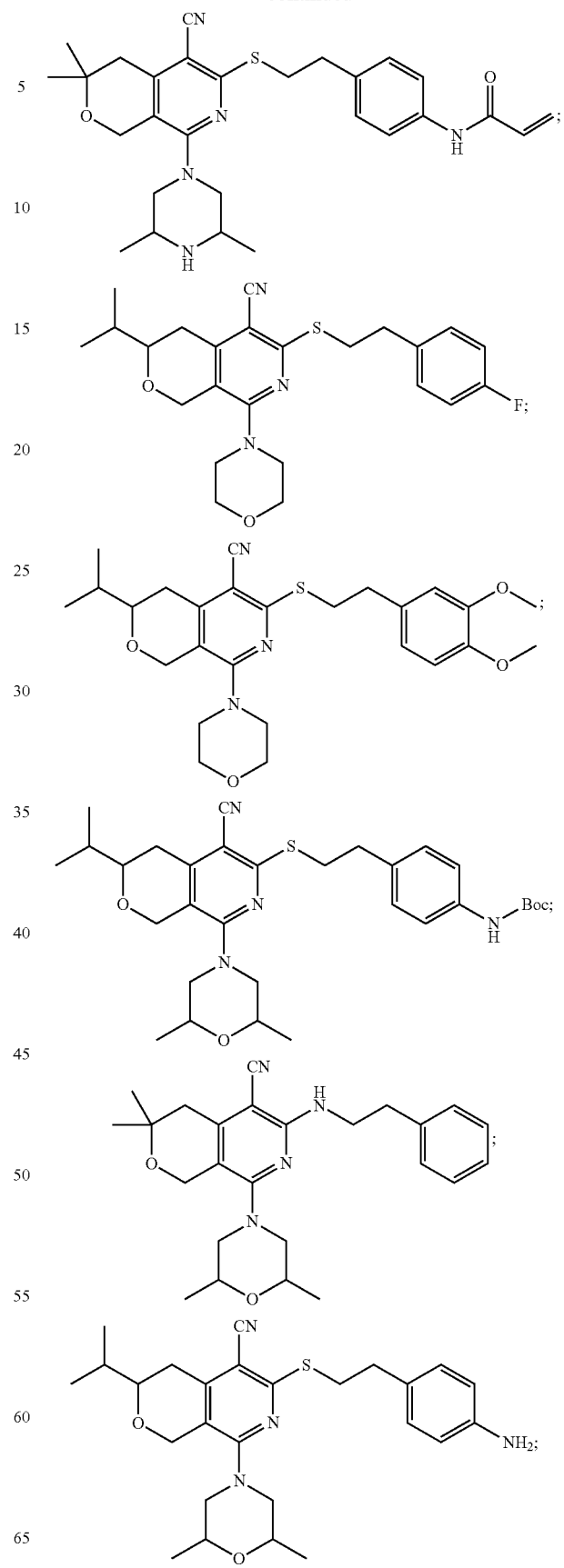

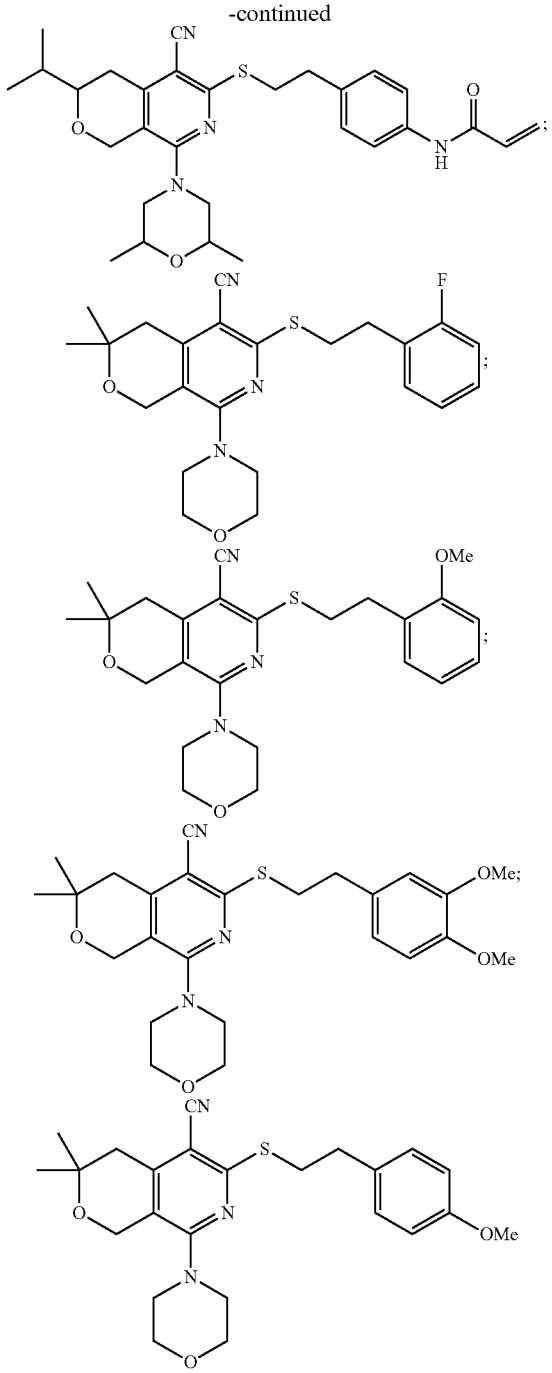

and salts thereof.

Compositions comprising a potentiator described herein may be formulated for administration to an individual (human or other animal) by any of a variety of routes including, but not limited to, intravenous, intramuscular, subcutaneous, intra-arterial, parenteral, intraperitoneal, sublingual (under the tongue), buccal (cheek), oral (for swallowing), topical (epidermis), transdermal (absorption through skin and lower dermal layers to underlying vasculature), nasal (nasal mucosa), intrapulmonary (lungs), intrauterine, vaginal, intracervical, rectal, intraretinal, intraspinal, intrasynovial, intrathoracic, intrarenal, nasojejunal, and intraduodenal.

Additionally, the invention provides salts, (especially, pharmaceutically acceptable salts) of the compounds described herein; solvated forms of the antimicrobial compounds described herein; multimeric forms of the antimicrobial compounds described herein; and prodrugs of the antimicrobial compounds described herein.

It is understood that the structure of an inhibitor compound described herein includes solvated forms of the compound. Examples of solvated forms of a compound of the invention include the compound as solute in a complex with solvent molecules of a solvent including, but not limited to, water, isopropanol, ethanol, methanol, dimethyl sulfoxide, ethyl acetate, acetic acid, ethanolamine, and acetone.

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and are not to be limited to one of plural possible forms depicted by the same structural formula.

It is also understood that the structural formula for a compound appearing herein is intended to represent any configurational form of the depicted compound and is not to be limited to a specific configuration of the compound form depicted by the structural formula. Some of the compounds of the present invention may exist as single stereoisomers (i.e., essentially free of other stereoisomers), racemates, or mixtures of enantiomers, diastereomers, or both when they contain one or more stereogenic centers as designated by R or S according to the Cahn-Ingold-Prelog rules, whether the absolute or relative configuration is known. All such configurational forms of a given compound are encompassed by the formulas appearing herein.

Some of the compounds in the present invention may exist as geometric isomers as the result of containing a stereogenic double bond. In such cases, they may exist either as pure or mixtures of cis or trans geometric isomers, or (E) and (Z) designated forms according to the Cahn-Ingold-Prelog rules, and may include compounds that adopt a double bond configuration as a result of electronic delocalization.

As is generally understood by those skilled in the art, an optically pure compound having one or more chiral centers (i.e., one asymmetric atom producing unique tetrahedral configuration) is one that consists essentially of one of the two possible enantiomers (i.e., is enantiomerically pure), and an optically pure compound having more than one chiral center is one that is both diastereomerically pure and enantiomerically pure. If the compounds of the present invention are made synthetically, they may be used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

As noted above, compounds of the invention include active tautomeric and stereoisomeric forms of the compounds of the present invention, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques, such as a chemical method (usingchiral salt forms if salt formation is feasible), or a chromatographic method, such as supercritical fluid chromatography (SFC).

If a compound of the present invention is a base, the desired salt of the compound may be prepared by any suitable method available in the art, for example, treatment of the free base with an inorganic acid or with an organic acid along with appropriate counter ion. Inorganic acids that may be used to form salts of compounds of the invention include, but are not limited to, hydrochloric acid, hydrobromic acid, sulfuric acid, nitric acid, and phosphoric acid. Organic acids that may be used to form salts of compounds of the invention include, but are not limited to, acetic acid, maleic acid, succinic acid, mandelic acid, fumaric acid, malonic acid, pyruvic acid, oxalic acid, glycolic acid, salicylic acid, a pyranosidyl acid (such as glucuronic acid or galacturonic acid), an alpha-hydroxy acid (such as citric acid or tartaric acid), an amino acid (such as aspartic acid or glutamic acid), an aromatic acid (such as benzoic acid or cinnamic acid), and a sulfonic acid (such as p-toluenesulfonic acid or ethanesulfonic acid).

If a compound of the present invention is an acid, then the desired salt form may be prepared by any suitable method, for example, treatment of the free acid with an inorganic or organic base. Examples of bases that may be used to form salts of compounds of the invention include, but are not limited to, amines (primary, secondary or tertiary), an alkali metal hydroxide, and an alkaline earth metal hydroxide. Illustrative examples of suitable salts of compounds of the invention include, but are not limited to, organic salts derived from basic amino acids (such as lysine and arginine, ammonia, primary, secondary, and tertiary amines) and from cyclic amines (such as piperidine, morpholine and piperazine), and inorganic salts derived from sodium, calcium, potassium, magnesium, manganese, iron, copper, zinc, aluminum, and lithium.

Salts of a compound of the invention include pharmaceutically acceptable salts of the compound. By the term "pharmaceutically acceptable salts of the compound" as understood and used herein, is meant those salts of any compound of the invention derived from an inorganic or organic acid or base recognized in the art as compatible for pharmaceutical compositions. For convenience, the terms "pharmaceutical" and "pharmaceutically acceptable" also are understood to encompass compounds acceptable for the practice of medicine, including veterinary medicine as well. It is understood that pharmaceutically acceptable salts of the compounds described herein are not limited to only pharmaceutical uses. Examples of suitable acids for pharmaceutically acceptable salts of antimicrobial compounds of the invention include, but are not limited to, hydrochloric acid, hydrobromic acid, sulfuric acid, nitric acid, perchloric acid, fumaric acid, maleic acid, hydroxymaleic acid, malonic acid, glutamic acid, phosphoric acid, glycolic acid, lactic acid, salicylic acid, succinic acid, p-toluenesulfonic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, tartaric acid, acetic acid, methanesulfonic acid, formic acid, naphthalene-2-sulfonic acid, benzenesulfonic acid, ethanedisulfonic acid, and sulfanilic acid. Salts of other acids, such as oxalic acid or isethionic acid, may not be pharmaceutically acceptable, but may find use in a variety of compositions and methods that are used to provide the benefit of the antimicrobial activity of a compound of the invention to a solution, semisolid, or solid composition that is not a pharmaceutical composition. Salts derived from appropriate bases include alkali metal (e.g., sodium, potassium), alkaline earth metal (e.g., magnesium), ammonium and $NR_4^+$ (where R is a $C_{1-4}$ alkyl) salts, and the like. Reference herein to a compound according to the invention (or an equivalent term) is understood to include any and all corresponding salts, including pharmaceutically acceptable salts, thereof.

The term "multimer" refers to multivalent or multimeric forms of antimicrobial compound potentiating compounds of the invention. Such "multimers" may be made by linking or placing multiple copies of an active compound (i.e., possessing antimicrobial compound potentiating activity) as described herein in close proximity to each other, e.g., using a scaffold provided by a carrier moiety. Multimers of various dimensions (i.e., bearing varying numbers of copies of an active compound) may be tested to arrive at a multimer of optimum size with respect to binding site interactions. Provision of such multivalent forms of active compounds may enhance binding site interactions. See, e.g., Lee et al., *Biochem.*, 23: 4255 (1984). The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers including, but not limited to, proteins such as bovine serum albumin (BSA); peptides such as pentapeptides, decapeptides, pentadecapeptides, and the like having functional side chains (e.g., the $\epsilon$-amino containing side chain of lysine); and nonbiological compounds selected for their beneficial effects on absorbability, transport, or persistence within or on a target microbial cell. Functional groups on the carrier moiety, such as amino, sulfhydryl, hydroxyl, and substituted amino groups, may be selected to obtain stable linkages to the compounds of the invention, optimal spacing between the immobilized compounds, and optimal biological properties.

By "pharmaceutically acceptable" is meant any compound or mixture that is not biologically, chemically, or in any other way, incompatible with body chemistry and metabolism and also does not significantly adversely affect the desired, effective antimicrobial potentiating activity of a compound of the invention or the activity of any other component of a composition comprising an antimicrobial compound and a potentiator compound described herein that may be administered to an individual to effectively kill or inhibit growth of cells of a microbial pathogen infecting an individual.

The terms "oral", "orally", "enteral", "enterally", "nonparenteral", "nonparenterally", and the like, refer to a route or mode for administering an effective amount of an antimicrobial potentiating compound described herein, or composition thereof, to an individual anywhere along the alimentary canal of the individual. Examples of such "enteral" routes of administration include, without, limitation, from the mouth, e.g., swallowing a solid (e.g., pill, tablet, capsule) or liquid (e.g., syrup, elixir) composition; nasojejunal or gastrostomy tubes (into the stomach); intraduodenal administration; and rectal (e.g., using suppositories for release and absorption of a compound or composition in the lower intestinal tract of the alimentary canal). One or more enteral routes of administration may be employed in the invention. Thus, unless a particular type of "oral" formulation described herein is specified or indicated by the context, "oral" formulations are the same as "enteral" formulations and broadly encompass formulations that may be swallowed from the mouth as well as those that permit administration of an antimicrobial compound of the invention anywhere along the alimentary canal. For the purposes of this discussion, sublingual (absorption under the tongue) and buccal (absorption through the inner cheek) administration of an antimicrobial compound of the invention may also be considered oral routes of administration.

The terms "parenteral" and "parenterally" refer to routes or modes of administration of an antimicrobial potentiating compound of the invention, or composition thereof, to an individual other than along the alimentary canal. Examples of parenteral routes of administration include, without limitation, intravenous (i.v.), intramuscular (i.m.), intra-arterial (i.a.), intraperitoneal (i.p.), subcutaneous (s.c.), transdermal (absorption through the skin or dermal layer), nasal or pulmonary (e.g., via inhalation or nebulization, for absorption through the respiratory mucosa or lungs), intra-articular, direct injections or infusions into body cavities or organs, as well as by implantation of any of a variety of devices into the body that permit active or passive release into the body of an individual of an antimicrobial compound described herein.

A "prodrug" is a compound that may be converted under physiological conditions or by solvolysis to the specified compound or to a salt of such compound, or a compound that is biologically active with respect to an intended pharmacodynamic effect. A "metabolite" means a pharmacologically active product produced through metabolism in the body of a specified compound or salt thereof. Prodrugs and active metabolites of a compound may be identified using routine techniques known in the art. See, e.g., Bertolini et al., *J. Med. Chem.*, 40: 2011-2016 (1997); Shan et al., *J. Pharm. Sci.*, 86(7):765-767 (1997); Bagshawe, *Drug Dev. Res.*, 34: 220-230 (1995); Bodor, *Advances in Drug Res.*, 13: 224-331 (1984); Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

In the case where a compound of the invention is present in a solid form, it is understood by those skilled in the art that the compound and salts thereof may exist in different crystal or polymorphic forms, all of which are intended to be within the scope of the present invention and specified structural formulas.

The terms "patient" and "individual" and "subject" are synonymous, unless noted otherwise, and mean any mammal, including without limitation, a human, who receives or may be a candidate to receive an antimicrobial compound and/or an antimicrobial potentiator compound as described herein or composition thereof. Thus, as used herein, a "patient" may or may not present a recognizable symptom of a microbial disease, but merely be at risk for infection by cells of a pathogenic microbial species that may cause a disease, e.g., due to exposure to a source of cells of the microbial pathogen.

As provided herein, an "effective amount" is intended to mean that amount of a compound that is sufficient to reduce, prevent or inhibit bacterial growth as compared with a negative control. A "therapeutically effective amount" of an antimicrobial composition including an antimicrobial potentiator of the present invention is a quantity sufficient to, when administered to an individual, to kill or inhibit growth of cells of a microbial pathogen. A therapeutically effective amount of a compound of the present invention is an amount which prevents, inhibits, suppresses, eliminates, or reduces a given clinical condition or disease symptom in an individual that is associated with microbial infection, as known and understood by a skilled healthcare provider or as compared to a control, such as an individual that is not infected with a microbial pathogen. As defined herein, a therapeutically effective amount of a compound of the present invention may be readily determined by one skilled in the art by routine methods known in the art.

"Therapy" and "therapeutic" as understood and used herein refer to treatment of a patient for a microbial infection or disease due to the microbial infection. For convenience, the terms are also understood to encompass prophylactic or precautionary use or administration of a compound of the invention. Such precautionary or prophylactic use is exemplified by administration of an antibiotic to an immunocompromised or immunodeficient patient to protect the patient from an infection; to a patient suspected, but not proven, of having a microbial infection; or to a patient that is susceptible to contracting a disease caused by infection of cells of a pathogenic species, for example, at open wounds; by contact with water, food, body fluids, corpses, or carcasses contaminated with cells of a pathogenic microbial species; or by contact with or other exposure to infected individuals or body fluids of infected individuals containing cells of a pathogenic microbial species.

In the context of therapeutic use of the antimicrobial compounds described herein, the terms "treatment", "to treat", or "treating" will refer to any use of the antimicrobial compounds calculated or intended to arrest or inhibit the growth of or kill cells of a pathogenic microbial species. Thus, treating an individual may be carried out after any diagnosis indicating possible bacterial, fungal, or protozoan infection, i.e., whether an infection by a particular microbe has been confirmed or whether the possibility of infection is only suspected, for example, after exposure to the microbe or to another individual infected by the microbe.

A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or which "consists of") the named elements or steps to the exclusion of any other unnamed element or step. In any composition or method disclosed herein, known or disclosed equivalents of any named essential element or step may be substituted for that element or step.

It is also understood that an element or step "selected from the group consisting of" or otherwise recited in a list of elements or steps refers to one or more of the elements or steps in the list that follows, including combinations of any two or more of the listed elements or steps, unless otherwise stated.

The meaning of other terms will be understood by the context as understood by the skilled practitioner in the art, including the fields of organic chemistry, pharmacology, pharmaceuticals, and microbiology.

Synthesis of Compounds

General method for synthesis of these compounds is shown in Scheme 1, below. Related procedures are described in the following articles: Paronikyan, E. G.; Noravyan, A. S. "Synthesis of Fused Thiopyrans and Pyridines on the Base of Six-Membered Saturated Heterocycles," *Chem. Heterocycl. Comp.* 35: 799-803 (1999); and Hunt, J. C., E. Briggs, E. D. Clarke, and W. G. Whittingham "Synthesis and SAR studies of novel antifungal 1,2,3-triazines," *Bioorg. Med. Chem. Lett.* 17: 5222-5226 (2007); and references cited therein.

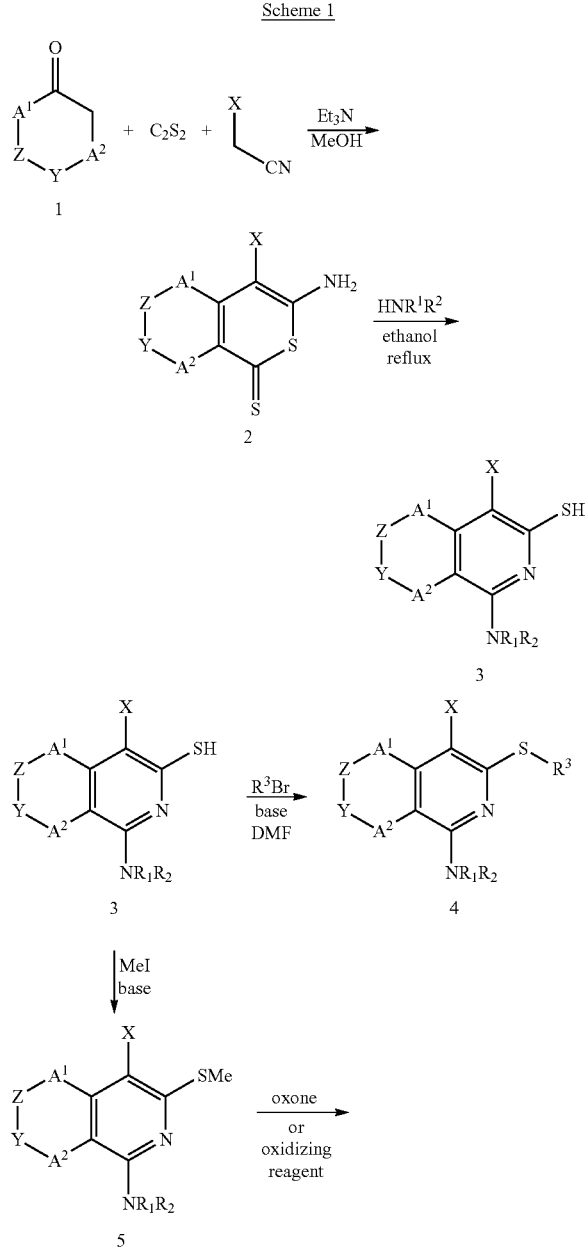

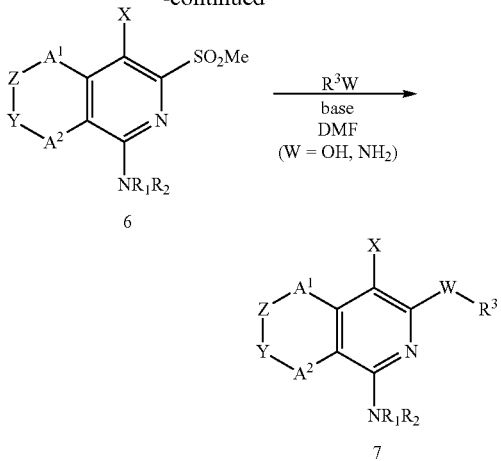

Uses and Compositions

Compounds of the invention possess bacterial efflux pump inhibitory activity. Accordingly, the compounds described herein are useful as efflux pump inhibitors. Preferably, they can be used as efflux pump inhibitors against Gram-negative pathogens, including, but not limited to, *Escherichia coli, Hemophilus influenzae, Klebsiella pneumoniae, Legionella pneumophila, Pseudomonas aeruginosa, Proteus mirabilis, Enterobacter cloacae, Enterobacter aerogenes, Serratia marcescens, Helicobacter pylori, Salmonella enterica, Salmonella enteritidis, Salmonella typhi, Acinetobacter baumanii,* and *Neisseria gonorrhoroeae.*

Compounds of the invention when brought in contact with bacteria will make the bacteria more susceptible to antimicrobial agents. Therefore, they can be used as antimicrobial potentiators. While not intending to be limited to any particular theory of the mode of action, the antimicrobial-potentiating effect of the compounds disclosed herein may be related to the efflux pump inhibitory activity of the compounds. The potentiating effect may be measured by a decrease in the minimum inhibitory concentration (MIC) of an antimicrobial agent or by an increase in the bactericidal activity of an antibacterial agent at concentrations that are bacteriostatic.

Compounds of the invention can enhance the efficacy of antimicrobial agents against strains of bacteria that are resistant to multiple antibacterial agents due to overexpression of efflux pumps. For example, we have shown that the compound of formula I designated MBX2319 (see FIG. 1) potentiates the activity of fluoroquinolone antibiotics ciprofloxacin and levofloxacin against resistant *E. coli* strains 331, 285, and 287, through efflux pump inhibition (see Tables 2 and 5).

A compound or combination of compounds described herein may be used as a supporting or adjunctive therapy for the treatment of bacterial infection in human or other animal. The potentiator may be administered in admixture, sequentially, or simultaneously with an antibacterial agent to provide more effective bacterial killing or microbial growth inhibition. This adjunctive therapy may provide the following benefits: increased antibiotic efficacy that leads to lower dosage and/or shorter treatment period, minimizing the side effects of antibiotics to patients and decreasing evolution of bacterial resistance in the community.

The present invention also provides antimicrobial compositions comprising an antimicrobial (bactericidal or bacteriostatic) agent and one or more compounds of the invention. Especially, compositions comprise a quinolone antibiotic or a beta-lactam antibiotic and one or more compounds of the invention. These compositions provide more effective bacterial killing or microbial growth inhibition than the microbial agent alone.

Preferred antibiotics that can be potentiated by compounds of the invention are: norfloxacin, ciprofloxacin, ofloxacin, levofloxacin, gatifloxacin, trovafloxacin, moxifloxacin, azlocillin. piperacillin, mezlocillin, cefazolin, cefacetrile, cefadroxil, cefalexin, cefaloglycin, cefalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefprozil, cefbuperazone, cefuroxime, cefuzonam, cefoxitin, cefotetan, cefmetazole, cefixime, ceftriaxone, ceftazidime, cefoperazone, cefcapene, cefdaloxime, cefdinir, cefodizime, cefotaxime, cefpimizole, cefpiramide, cefpodoxime, cefsulodin, cefteram, ceftibuten, ceftiolene, ceftizoxime, cefepime, cefozopran, cefpirome, cefquinome, ceftobiprole, biapenem, ertapenem, doripenem, imipenem, meropenem, panipenem, aztreonam, tigemonam, carumonam, tetracycline, and minocycline.

There are a variety of pathogenic microbial species and strains that are known etiological agents for various diseases that can occur once an infection has become established in or on the body of an individual. In some cases, a microbial species may be an opportunistic microbial pathogen, i.e., cause a disease only under certain conditions. For example, cells of an opportunistic pathogenic microbial species may not normally be pathogenic or only mildly pathogenic in the case of a healthy individual whose immune system can effectively identify the invading microbial cells and mount an effective response to inactivate and/or otherwise remove the cells from the individual's body. However, cells of the same microbial species may be able to establish an infection resulting in significant pathology in an individual whose immune system has been weakened or otherwise suppressed. Weakened or compromised immune systems may result from a variety of conditions including, but not limited to, prior (primary) illness, cancer of the immune system, exposure to toxins, exposure to radiation, exposure to chemotherapy drugs, and use of immunosuppressive drugs. Such individuals include, without limitation, patients of acquired immunodeficiency syndrome (AIDS), cancer patients undergoing radiation therapy, cancer or transplant patients receiving immunosuppressive chemotherapy drugs, and also individuals who take drugs designed to inhibit or suppress the activity of one or more cytokines, for example, to treat diseases associated with an overactive cytokine, such as rheumatoid arthritis, psoriasis, and Crohn's disease.

The potentiator compounds described herein when used along with antibacterial agents in separate dosing or in preformed antimicrobial compositions as mentioned above may be useful to kill or inhibit growth of cells of one more species of bacteria. Bacterial cells which may be advantageously treated in this way include, but are not limited to, *Acinetobacter* (for example, *A. baumannii*), *Burkholderia* (for example, *B. mallei, B. pseudomallei*, and *B. cepacia*), *Chlamydia* (for example, *C. trachomatis*), *Chlamydophila* (for example, *C. pneumoniae* and *C. psittiaci*), *Enterobacter* (for example, *E. aerogenes* and *E. cloacae*), *Escherichia* (for example, *E. coli*), *Haemaphilus* (for example, *H. influenzae*), *Helicobacter* (for example, *H. pylori*), *Klebsiella* (for example, *K. pneumoniae*), *Legionella* (for example, *L. pneumophila*), *Neisseria* (for example, *N. gonorrhoeae*), *Pseudomonas* (for example, *P. aeruginosa*), *Proteus* (for example, *P. mirabilis*), *Salmonella* (for example, *S. typh-imurium* and *S. typhi*), *Shigella* (for example, *S. dysenteriae*), *Stenotrophomonas* (for example, *S. maltophilia*), *Vibrio* (for example, *V. cholerae*), and *Yersinia* (for example, *Y. pestis*).

Potentiator compounds and antimicrobial compositions described herein may be formulated for pharmaceutical and nonpharmaceutical uses.

In pharmaceutical uses, a potentiator compound or the antimicrobial compositions containing a potentiator may provide new treatments for a variety of diseases, including those for which drug resistance by the etiological agent is a problem.

For nonpharmaceutical uses, the potentiator compounds or the antimicrobial compositions containing a potentiator described herein can be applied to catheters, lock solutions, pumps (including cardiopulmonary bypass pumps, implantable patient pumps), nonimplantable (exterior) patient pumps (e.g., for drug or hormone delivery), and industrial pumps), dialysis equipment, water pipes, plumbing fixtures, fuel lines, air ducts, gas lines (including air lines, oxygen lines, respirators), cosmetic products (including cosmetic skin products, cosmetic hair products), foods, eye products (eye drops, contact lenses, implantable lenses), ear products (e.g., ear drops, hearing aids), oral products (e.g., mouthwashes, toothpastes, dental appliances, dentures, teeth, dental implants, etc.), nasal products (e.g., nose drops, nose gels, nose swabs), vaginal care products, medical and veterinarian clothing (e.g., face masks, caps, gowns, gloves, footwear, gloves, aprons), gas masks, adhesives, soaps, detergents, and paints.

A compound or an antimicrobial composition described herein may be formulated into solutions, suspensions, dry mixtures, ointments, creams, gels, jellies, lotions, pastes, toothpastes, petroleum products, porous membranes, porous filters, microparticles, microspheres, liposomes, micelles, lipid bilayers, resin particles, plastics, paints, glues, adhesives, cellulose products, textiles (fiber, yarn, or cloth), and nanoparticles.

A compound or an antimicrobial composition described herein may also be formulated by standard methods for delivery to a surface in an aerosol of fine solid particles or liquid droplets mixed with a gas.

A compound or an antimicrobial composition described herein may be brought into contact with a solid surface composed of or comprising any of a variety of materials that are capable of retaining and/or transmitting viable cells of one or more microbial pathogens that may be present on the solid surface. Such materials include, but are not limited to, enamel, plastic, glass, silicon, rubber, metal, stone, cement, nylon, cellulose, polymeric resin (including various cellulose and agarose resins), composites, calcium phosphate (for example, as in, but not limited to, hydroxyapatite and bone), calcium carbonate (for example, as in, but not limited to, mollusk shells and mother-of-pearl), keratin (for example, as in, but not limited to, skin, hair, fur, wool, nails, claws, hooves, scales, beaks, and feathers), collagen (for example, as in, but not limited to, animal hides, tendons, and ligaments), chitin (for example, as in, but not limited to, exoskeletons and fungal cell walls), skin, teeth, and combinations thereof. They may be applied to a solid surface by any of a variety of methods available in the art for applying an organic compound to a particular surface. Such methods include methods of "treating" a surface, wherein it is understood that the terms "treat", "treating", and "treatment" in this context of combining a compound or composition with a surface is distinct from a medical treatment of an individual for a disease. Such methods of treating a surface with a compound or composition described herein include, but are not limited to, contacting, coating, absorbing, adsorbing the compound or the compositions to the surface, covalently conjugating the compound to the surface, applying a solution of the compound or antimicrobial composition to the surface, and the like.

For some applications, a carrier may be needed. A carrier is any compound that provides a medium for using the potentiator compound described herein. A carrier may be liquid, solid, or semisolid. To retain its utility, it will be necessary that the carrier (and any other component of a composition) does not significantly neutralize, inhibit, or block the activity of a compound of the invention. A suitable carrier includes, but is not limited to, an organic solvent, an aqueous buffer, water, an emulsifying agent, and a solid dispersing agent. Solutions and suspensions comprising an antimicrobial potentiator compound described herein may also be prepared using an appropriate organic solvent or emulsifying agent. A preferred organic solvent is dimethyl sulfoxide (DMSO). DMSO-based solutions comprising a compound or composition described herein are particularly useful in providing required concentrations of the compound in various compositions, assays (including growth assays), and procedures. Other organic solvents may also be used including, but not limited to, an alcohol, N-methylpyrrolidone (NMP), and N,N-dimethylacetamide (DMA). For most in vitro purposes, DMSO is preferred. As a general guide for using an alcohol as a solvent for a compound described herein, ethanol is more preferred than isopropanol, which is more preferred than butanol or an aryl alcohol, which are more preferred than methanol.

For solid compositions, conventional solid carriers are preferred and include, but are not limited to, mannitol, lactose, starch, magnesium stearate, sodium saccharin, talc, cellulose, glucose, sucrose, magnesium carbonate, and the like.

A composition comprising a compound described herein may also comprise a dispersing agent. The dispersing agent may be employed to disperse the compound more uniformly in a composition and/or to enhance dispersion of the composition containing an antimicrobial compound described herein over a surface to which the composition is applied. A dispersing agent may be a solid or liquid. Solid dispersing agents may include, without limitation, talc, starch, cellulose, metal oxide (e.g., zinc oxide, titanium oxide), graphite, and combinations thereof. A preferred dispersing agent for liquid compositions is a surfactant, which may be an anionic, cationic, amphoteric, or nonionic surfactant. See, for example, U.S. Pat. No. 6,921,745. Preferably, a surfactant is employed at the lowest concentration that provides optimal dispersion of the antimicrobial compound throughout the composition or optimal dispersion of the composition on a surface.

Preferred anionic surfactants useful in the compositions and methods described herein include, without limitation, linear alkyl benzene sulfonic acid; alkyl sulfate; polyoxyethylene alkyl ether sulfate 10 having 1 to 10 moles of ethylene oxide; polyoxyethylene alkyl ether carboxylic acid having 1 to 10 moles ethylene oxide; polyoxyethylene alkyl amide ether carboxylic or fatty acid having 1 to 10 moles ethylene oxide; and potassium, sodium, magnesium, or alkanolamine salts thereof. Preferably, the alkyl and fatty groups in an anionic surfactant are, independently, 8 to 22 carbon atoms, and more preferably 10 to 18 carbon atoms.

Preferably, a nonionic surfactant useful in the compositions and methods described herein is a nonionic polyoxyethylene ether, including, but not limited to, a polyoxyethylene alkyl ether having an alkyl chain containing 8 to 22 carbon atoms, more preferably 10 to 18 carbon atoms, and having 1 to 30 moles, and more preferably 4 to 20 moles, of ethylene oxide; a polyoxyethylene oxypropylene alkyl ether having 1 to 30 moles, and more preferably 1 to 20 moles, of ethylene oxide, and having 1 to 10 moles, more preferably 1 to 5 moles, of propylene oxide; a fatty acid alkanol amide containing 8 to 22 carbon atoms, and more preferably 10 to 18 carbon atoms to which 1 to 3 moles of ethylene oxide or propylene oxide may be added; and an alkyl polyglucoside having an alkyl chain containing 8 to 22 carbon atoms, and more preferably 10 to 18 carbon atoms, and preferably having 1 to 10 sugars, and more preferably 1 to 2 sugars, condensed therein. A preferred species of nonionic surfactant useful in compositions and methods described herein is t-octylphenoxypolyethoxyethanol (e.g., brand name TRITON® X-100 nonionic surfactant, Sigma-Aldrich, St. Louis, Mo., US).

Another nonionic surfactant useful in the compositions and methods described herein may be an ester between a fatty acid containing 8 to 22 carbon atoms, and preferably 10 to 18 carbon atoms, and a polyvalent alcohol having a hydrocarbon group containing 2 to 10 carbon atoms and 2 to 8 hydroxy groups. More preferably, the ester is a glycerin fatty acid ester, a polyglycerin fatty acid ester, a sorbitan fatty acid ester, a sucrose fatty acid ester, or a propylene glycol fatty acid ester.

Amphoteric surfactants that may find use in the compositions and methods described herein include, without limitation, those having an alkyl group containing 8 to 22 carbon atoms, such as alkylamidopropyl-N,N-dimethyl acetate betaine (N-alkanoy aminopropyl-N,N-dimethyl-N-carboxymethylammonium carbobetaine), alkyl amidopropyl-N,N-dimethyl-2-hydroxypropyl sulfobetaine (N-alkanoylaminopropyl-N,N-dimethyl-N-(2-hydroxy-3-sulfopropyl) ammonium sulfobetaine), alkyl-N,N-dimethyl acetate betaine (N-alkyl-N,N-dimethyl-N-carboxymethy ammonium carbobetaine), alkyl amidopropyl-N,N-dimethyl-2-propyl sulfobetaine (N-alkanoyl aminopropyl-N,N-dimethyl-N-(2-sulfopropyl)ammonium sulfobetaine), lauryl-N,N-dimethylhydroxypropyl sulfobetaine (N-lauryl-5 N,N-dimethyl-N-(2-hydroxy-3-sulfopropyl)ammonium sulfobetaine), and alky amine oxide. Among these, preferred species include lauric acid amidopropyl-N,N-dimethyl acetate betaine (N-lauroylaminopropyl-N,N-dimethyl-N-carboxymethylammonium carbobetaine), myristic acid amidopropyl-N,N-dimethyl acetate betaine (N-myristyloylaminopropyl-N,N-dimethyl-N-carboxymethylammonium carbobetaine), cocamide amide propyl-N,N-dimethyl acetate betaine (N-coconut composition alkanoylaminopropyl-N,N-dimethyl-N-carboxymethylammonium carbobetaine), lauryl-N,N-dimethyl-2-hydroxypropyl sulfobetaine (N-lauryl-N,N-dimethyl-N-(2-hydroxy-3-sulfopropyl)ammonium sulfobetaine), lauric acid amide propyl-N,N-dimethyl-23-hydroxypropyl betaine (N-lauroylaminopropyl-N,N-dimethyl-N-(2-hydroxy-3-sulfopropyl) ammonium sulfobetaine), and an alkylamine oxide having two alkyl groups containing 2 or less carbon atoms and one long-chain alkyl group containing 8 to 22 carbon atoms, which optionally may have an amide linkage.

Cationic surfactants that may be used in compositions and methods described herein include, but are not limited to, a long-chain dialkyl dimethyl ammonium salt, long-chain monoalkyl monobenzyldimethyl ammonium salt, and monoalkyl trimethyl ammonium salt having a long alkyl chain containing 6 to 24 carbon atoms, and preferably 6 to 18 carbon atoms, which may be interrupted therein with an amide or ester linkage. The counterion of such cationic species is preferably a halogen ion, sulfate ion, or an alkylsulfate containing 1 to 3 carbon atoms. The cationic surfactants of the amine type, useful in compositions and methods described herein, include long-chain dialkyl monomethylamine salts having a long alkyl chain containing 8 to 24 carbon atoms, which optionally may be interrupted therein with an amide or ester linkage. Preferred counterions of such species include hydrochlorides, sulfates, and phosphates thereof. Pharmaceutical compositions of the invention comprise at least one antimicrobial compound described herein and may be prepared in a unit-dosage form appropriate for a desired mode of administration.

Where any compositions containing compounds of the invention are used as pharmaceutical compositions, they may be administered for therapy (including for preventive therapy) by any suitable route including, but not limited to, oral, buccal, sublingual, rectal, mucosal (mucosa), nasal, topical, dermal, vaginal and parenteral (including, but not limited to, subcutaneous, intramuscular, intravenous, and intradermal). It will be appreciated that the preferred route will vary with the condition and age of the individual receiving the pharmaceutical composition, the nature of the condition to be treated, the microbial pathogen to be targeted, and the chosen antimicrobial compound of the present invention to be employed. A pharmaceutically acceptable carrier used in a pharmaceutical composition of the invention must be "acceptable" in the sense of being compatible with the other agents and ingredients of the composition and not prohibitively deleterious to the patient to whom the pharmaceutical composition is administered.

A potentiator compound or an antimicrobial composition of the invention may be administered alone, but will generally be administered as a pharmaceutical formulation suitable for administration. Pharmaceutical formulations of this invention comprise a therapeutically effective amount of at least one compound of the present invention, and an inert, pharmaceutically acceptable (which includes cosmetically acceptable) carrier or diluent. As used herein the language "pharmaceutically acceptable carrier" is intended to include any and all solvents, dispersion media, coatings, antibacterial and antifungal agents, isotonic and absorption delaying agents, and the like, compatible with pharmaceutical or cosmetic administration, respectively. Except insofar as any conventional media or agent is incompatible with an antimicrobial composition of the invention, use thereof in the formulation is contemplated.

Descriptions of suitable pharmaceutically acceptable carriers, formulations, and factors involved in their selection, are familiar to those skilled in the art and may be found in a variety of readily available sources, e.g., Remington's Pharmaceutical Sciences, 17th ed., (Mack Publishing Company, Easton, Pa., 1985), which is incorporated herein by reference.

A preferred pharmaceutical composition comprises an effective amount of one or more antimicrobial compounds described herein in combination with a pharmaceutically acceptable carrier, and, optionally, one or more other active agents, diluents, fillers, or excipients. An excipient is a compound that improves or provides a desirable physical property to a composition. An excipient useful in a composition described herein includes, but is not limited to, emulsifying agents, pH buffering agents, approved dyes and colorants; dispersing agents, cosolvents, gelling agents, and drying agents.

While it is possible that, for use in therapy, a compound of the invention may be administered as the raw chemical, preferably the compound is present as an active ingredient in a pharmaceutical composition. The invention thus further provides a pharmaceutical composition comprising a compound described herein, or a pharmaceutically acceptable salt thereof, together with one or more pharmaceutically acceptable carriers and, optionally, one or more other therapeutic or beneficial agents known in the art, such as, an antibiotic, an antifungal drug, an antiprotozoan drug, an antiviral compound, an anticancer compound, a vitamin, a trace metal supplement, or an ion supplement to restore or maintain proper ionic balance in blood or other tissues. Other examples of suitable therapeutic agents that may be used in combination with potentiator compounds of this invention include, without limitation, penicillins and other beta lactamase inhibitors, carbapenems, cephalosporins, macrolides (including erythromycin and ketolides), sulfonamides, quinolones (such as fluoroquinolones), oxazolidinones, tetracyclines, ancomycin, erythromycin, lactoferrins, and cationic peptides. Such agents may be administered to an individual in the same pharmaceutical composition comprising a compound of this invention or in a separate composition.

A composition comprising a compound of the invention may further comprise one or more antibiotics such as, but not limited to, penicillin, cephalosporin, cloxacillin, dicloxacillin, methicillin, nafcillin, oxacillin, ampicillin, amoxicillin, bacampicillin, azlocillin, carbenicillin, mezlocillin, piperacillin, ticarcillin, azithromycin, clarithromycin, clindamycin, erythromycin, lincomycin, demeclocycline, doxycycline, minocycline, oxytetracycline, tetracycline, quinolone, cinoxacin, nalidixic acid, fluoroquinolone, ciprofloxacin, enoxacin, grepafloxacin, levofloxacin, lomefloxacin, norfloxacin, ofloxacin, sparfloxacin, trovafloxacin, bacitracin, colistin, polymyxin B, sulfonamide, trimethoprim-sulfamethoxazole, co-amoxyclav, cephalothin, cefuroxime, ceftriaxone, chloramphenicol, nitrofurantoin, co-trimoxazole, rifampicin, isoniazid, pyrazinamide, kirromycin, thiostrepton, micrococcin, fusidic acid, thiolactomycin, fosmidomycin, and the like.

Additional combination therapies may also include a compound of this invention. Clearly, the combination therapies described herein are merely exemplary and are not meant to exclude other combination treatments or coadministration regimens.

Pharmaceutical compositions according to the invention include those suitable for administration to an individual by any medically acceptable route including, but not limited to, parenteral, subcutaneous, intramuscular, intravenous, auricular (ear), ocular, intra-articular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary (e.g., by inhalation or insufflation), intrarectal, intrarenal, intraretinal, intraspinal, intrasynovial, intrathoracic, intrauterine, intravesical, bolus, vaginal, oral, rectal, buccal, sublingual, intranasal, and transdermal. The pharmaceutical compositions may, where appropriate, be conveniently presented in discrete dosage units and may be prepared by any of the methods well known in the art of pharmaceutical compositions.

Pharmaceutical compositions suitable for oral administration may conveniently be presented as discrete units such as capsules, cachets, or tablets each containing a predetermined amount of a compound of the invention in a powder or granule form, in a solution, in a suspension, or as an emulsion. A compound of the invention may also be presented as a bolus, electuary, or paste. Tablets and capsules for oral administration may contain conventional excipients such as binding agents, fillers, lubricants, disintegrants, or wetting agents. The tablets may be coated according to methods well known in the art.

Oral liquid preparations may be in the form of, for example, aqueous or oily suspensions, solutions, emulsions, syrups, or elixirs, or may be presented as a dry product for constitution with water or other suitable vehicle before use. Such liquid preparations may contain conventional additives such as suspending agents, emulsifying agents, nonaqueous vehicles (which may include edible oils), or preservatives.

The compounds according to the invention may also be formulated for parenteral administration (e.g., by injection as a bolus or by continuous infusion) and may be presented in unit dose form in ampoules, prefilled syringes, small volume infusion, or in multidose containers with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form, obtained by aseptic isolation of sterile solid or by lyophilization from solution, for constitution with a suitable vehicle, e.g., sterile, pyrogen-free water or pharmaceutically acceptable buffer, prior to use.

For topical administration to the epidermis, antimicrobial compounds according to the invention may be formulated as ointments, creams, gels, jellies, or lotions. A compound of the invention may also be incorporated into a transdermal patch. Such transdermal patches may contain penetration enhancers such as linalool, carvacrol, thymol, citral, menthol, t-anethole, and the like. Ointments and creams may, for example, be formulated with an aqueous or oily base comprising one or more suitable thickening and/or gelling agents. Lotions may be formulated with an aqueous or oily base and will in general also contain one or more emulsifying agents, stabilizing agents, dispersing agents, suspending agents, thickening agents, or coloring agents. Compositions suitable for topical administration of an antimicrobial compound of the invention in the mouth include lozenges comprising the compound, optionally, in a flavored base, usually sucrose and acacia or tragacanth; pastilles comprising the compound in an inert base such as gelatin and glycerin or sucrose and acacia; and mouthwashes comprising the active ingredient in a suitable liquid carrier.

Pharmaceutical compositions suitable for rectal administration wherein the carrier is a solid are presented as unit dose suppositories. Suitable carriers include cocoa butter and other materials commonly used in the art, and the suppositories may be conveniently formed by admixture of a compound of the invention with the softened or melted carrier(s) followed by chilling and shaping in molds.

Pharmaceutical compositions suitable for vaginal administration may be presented as pessaries, tampons, creams, gels, pastes, foams, or sprays containing in addition to a compound of the invention such carriers as are known in the art to be appropriate.

For intranasal administration the compounds of the invention may be used as a liquid spray or dispersible powder or in the form of drops. Drops may be formulated with an aqueous or nonaqueous base also comprising one more dispersing agents, solubilizing agents, or suspending agents. Liquid sprays may conveniently be delivered from pressurized packs.

For administration by inhalation, the compounds according to the invention may conveniently be delivered from an insufflator, nebulizer, a pressurized pack, or other convenient means of delivering an aerosol spray. Pressurized packs may comprise a suitable propellant, such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example, a powder mix of a compound of the invention and a suitable powder base such as lactose or starch. The powder composition may be presented in unit dosage form in, for example, capsules or cartridges, or, for example, gelatin or blister packs from which the powder may be administered with the aid of an inhalator or insufflator.

An antimicrobial composition comprising a compound of the invention may also be formulated into a pharmaceutical composition for treating an eye or ear infection. Diseases of the eye that may be treated by administering antimicrobial compound of the invention to a patient include, but are not limited to, bacterial keratitis, infectious keratoconjunctivitis, bacterial conjunctivitis, ocular tuberculosis, and suppurative uveitis.

When desired, the above described compositions may be adapted to give a sustained or time-delayed release of compound of the invention using any of the sustained or time-delayed formats available in art.

When a compound of the invention or a pharmaceutically acceptable salt thereof is used in combination with an antimicrobial agent, the dose of each compound may be either the same as or differ from that when the compound is used alone. Appropriate doses will be readily calculated by those skilled in the art. The appropriate ratio between a compound of the present invention and a second therapeutic compound for coadministration to a patient will be readily determined by those skilled in the art. For example, one may use a ratio in the range from about 50:1 to about 1:50 (by weight) of a compound of the invention:an antimicrobial agent. In additional embodiments, the ranges of ratios that may be used in preparing a composition for coadministration of a compound of the invention with a second therapeutic compound include, without limitation: about 30:1 to about 1:30 (by weight), about 20:1 to about 1:20 (by weight), about 15:1 to about 1:15 (by weight), about 10:1 to about 1:10 (by weight), about 5:1 to about 1:5 (by weight), and about 3:1 to about 1:3 (by weight) of a compound of the invention:antimicrobial agent. If yet (a) further therapeutic compound(s) is (are) added, ratios are adjusted accordingly.

Antimicrobial compositions containing a potentiator compound of the invention may be provided and packaged in any of a variety of forms as described above, including in a powder or lyophilized state for reconstitution with sterile water or buffer, in unit doses for convenient administration, with one or more pharmaceutically acceptable buffers or salts, and/or with instructions for using the packaged compound as an antibiotic to treat an infection by a microbial pathogen.

Toxicity and therapeutic efficacy of such compounds can be determined by standard pharmaceutical procedures in cell cultures or experimental animals, e.g., for determining the LD50 (the dose lethal to 50% of the population) and the ED50 (the therapeutically effective dose in 50% of the population). The dose ratio between toxic and therapeutic effects is the therapeutic index, and it can be expressed as the ratio LD50/ED50. Compounds that exhibit larger therapeutic indices are preferred. While compounds that exhibit toxic side effects may be used, care should be taken to design a delivery system that targets such compounds to the site of affected tissue to minimize potential damage to uninfected cells of an individual and, thereby, reduce undesired side effects.

Data obtained from cell culture assays and animal studies can be used in formulating a range of dosages for use in humans. The dosage of such compounds lies preferably within a range of circulating concentrations that include the ED50 value with little or no toxicity. The dosage may vary within this range depending upon the dosage form employed and the route of administration utilized. For any compound used in a method of the invention, the therapeutically effective dose can be estimated initially from cell culture assays. A dose may be formulated in animal models to achieve a circulating plasma concentration range that includes the IC50 (i.e., the concentration of the test antimicrobial compound that achieves a half-maximal inhibition of microbial growth). Such information can be used to more accurately determine useful doses for humans. Levels in plasma may be measured, for example, by high performance liquid chromatography.

The following examples are provided to illustrate various embodiments of the present invention and shall not be considered as limiting the scope of the invention as fully disclosed herein.

EXAMPLES

Example 1

Synthesis of Exemplary Antimicrobial Potentiator Compounds

Specific compounds were prepared following the syntheses of Scheme 1:

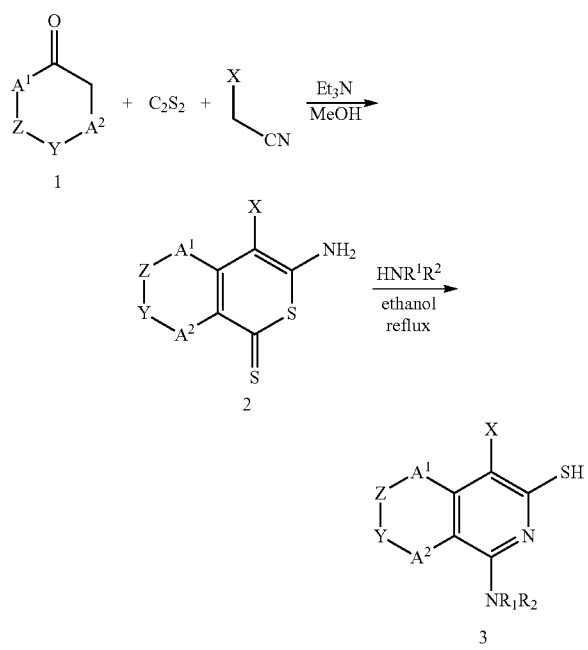

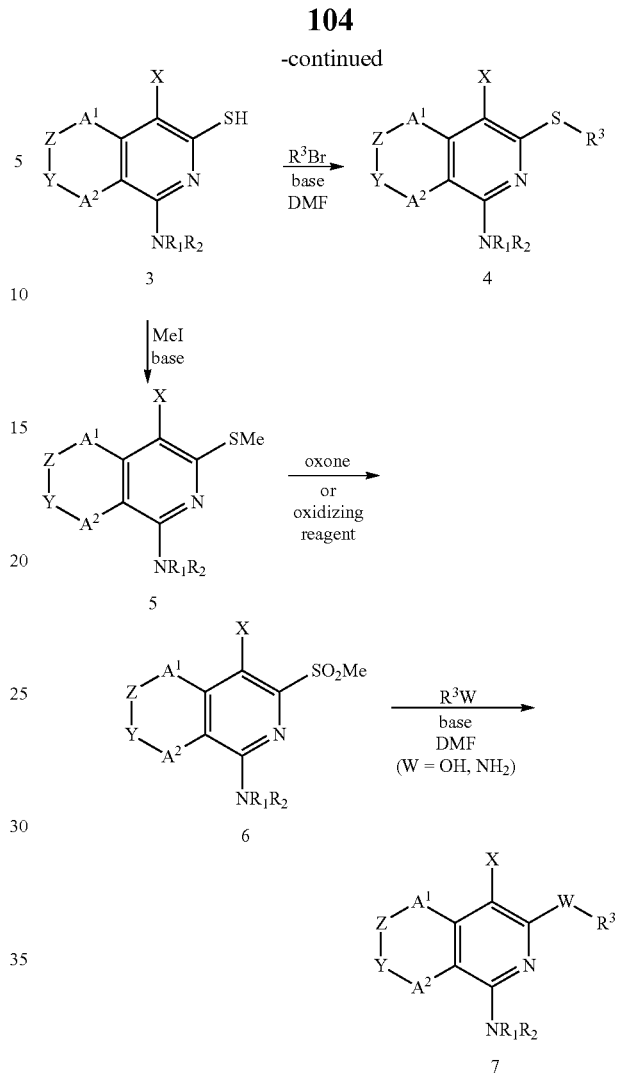

1.1. Procedures for Synthesis of Compound 2 (in Scheme 1):

To a stirred solution of compound 1 (3.2 g, 25 mmol) in methanol (8 mL) was added malononitrile (1.65 g, 25 mmol), followed by carbon disulfide (3 mL, 50 mmol). Triethylamine (1.5 mL, 10.8 mmol) was added dropwise. The reaction was exothermic. After stirring for 24 hr, the formed solid was filtered, rinsed with diethyl ether and dried in vacuum to provide compound 2 (2.7 g, 43%) as an orange-colored solid.

$^1$H NMR (DMSO-$d_6$): 8.91 (br s, 2H), 4.46 (s, 2H), 2.57 (s, 2H), 1.19 (s, 6H).

(ESI) MS: 253.0 [M+1]

1.2. General Procedures for Synthesis of Compound 3 (in Scheme 1):

To the suspension of compound 2 (1 mmol) in ethanol (5 mL) was added the amine $R^1R^2$NH (10 mmol). The reaction mixture was heated at reflux under nitrogen for 18-50 hr (reaction progress could be analyzed by LCMS). The reaction mixture was evaporated under reduced pressure. The residue was purified by silica gel column chromatography to provide compound 3.

1.3. General Procedures for Synthesis of Compound 4 (in Scheme 1):

To a solution of 3 (1 mmol) in DMF (4 mL) was added cesium carbonate (2 mmol), followed by the bromide ($R^3$Br) (1.5 mmol). The mixture was heated at 40-45° C. for 16 hr.

The reaction mixture was poured into water (3 mL) and product was extracted with ethyl acetate or dichloromethane. The combined organic phases were dried over Na$_2$SO$_4$ or MgSO$_4$, filtered and concentrated. The residue was purified by silica gel column chromatography or by reversed phase (C18) HPLC to provide compound 4.

1.4. Compound Characterizations:

| | MBX # | Structure | $^1$H NMR | Mass Spec. | Melting point | R$_f$ (eluents) |
|---|---|---|---|---|---|---|
| 1 | 2319 | 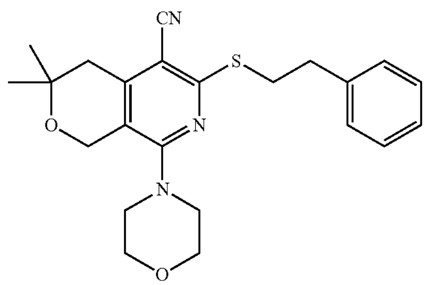 [SMILES: CC1(C)Cc2c(C#N)c(SCCc3ccccc3)nc(N3CCOCC3)c2CO1] | (DMSO): 7.32-7.19 (m, 5H), 4.49 (s, 2H), 3.68 (t, 4H), 3.45 (t, 2H), 3.32 (t, 4H), 2.96 (t, 2H), 2.68 (s, 2H), 1.24 (s, 6H). | 410.1 (M + 1) | 123-125° C. | 0.54 (1:1, EtOAc:Hexane) |
| 2 | 2403 | 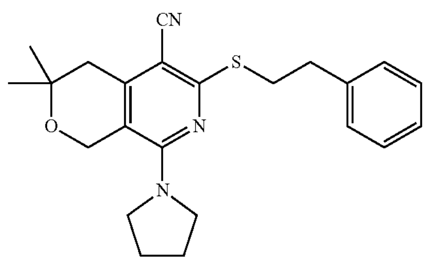 [SMILES: CC1(C)Cc2c(C#N)c(SCCc3ccccc3)nc(N3CCCC3)c2CO1] | (DMSO): 7.32-7.19 (m, 5H), 4.75 (s, 2H), 3.64 (m, 4H), 3.41 (t, 2H), 2.95 (t, 2H), 2.56 (s, 2H), 1.85 (m, 4H), 1.23 (s, 6H). | 394.2 (M + 1) | 135-136° C. | 0.66 (1:1, EtOAc:Hexane) |
| 3 | 2408 | 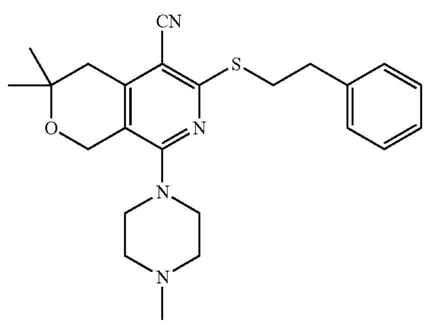 [SMILES: CN1CCN(c2nc(SCCc3ccccc3)c(C#N)c3c2COC(C)(C)C3)CC1] | (DMSO): 7.32-7.19 (m, 5H), 4.46 (s, 2H), 3.43 (t, 2H), 3.33 (m, 4H), 2.95 (t, 2H), 2.66 (s, 2H), 2.39 (m, 4H), 2.18 (s, 3H), 1.23 (s, 6H). | 423.3 (M + 1) | 145-147° C. | 0.51 (86:13:1, CHCl$_3$:MeOH:NH$_3$) |
| 4 | 2440 | 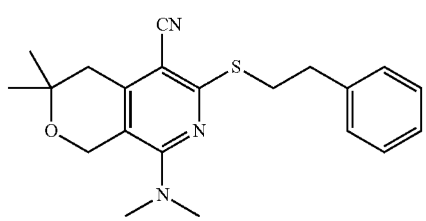 | (MeOD): 7.27-7.15 (m, 5H), 4.65 (s, 2H), 3.48 (t, 2H), 3.06 (s, 6H), 3.01 (t, 2H), 2.70 (s, 2H), 1.32 (s, 6H) | 368.3 (M + 1) | 106-108° C. | 0.68 (1:1, EtOAc:Hexane) |
| 5 | 2441 | 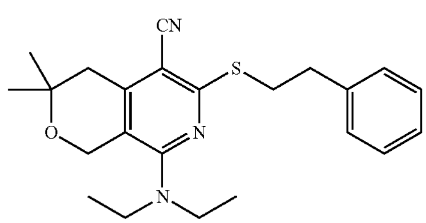 | (MeOD): 7.29-7.15 (m, 5H), 4.56 (s, 2H), 3.48-3.38 (m, 6H), 2.97 (t, 2H), 2.69 (s, 2H), 1.30 (s, 6H), 1.17 (t, 6H) | 396.4 (M + 1) | wax at room temp. | 0.73 (1:1, EtOAc:Hexane) |

-continued

Compound Characterization Data

| MBX # | | Structure | ¹H NMR | Mass Spec. | Melting point | R_f (eluents) |
|---|---|---|---|---|---|---|
| 6 | 2452 | 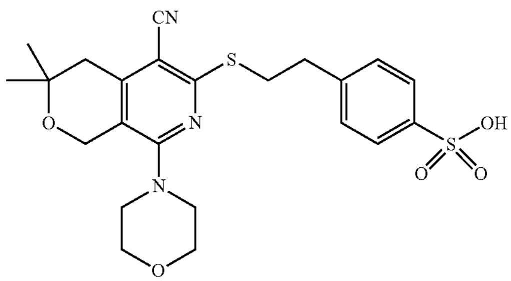 [SMILES: CC1(C)Cc2c(C#N)c(SCCc3ccc(S(=O)(=O)O)cc3)nc(N3CCOCC3)c2CO1] | (DMSO): 7.53 (d, 2H), 7.23 (d, 2H), 4.51 (s, 2H), 3.98 (bs, 1H), 3.70 (t, 4H), 3.45 (t, 2H), 3.33 (t, 4H), 2.97 (t, 2H), 2.69 (s, 2H), 1.26 (s, 6H) | 490.4 (M + 1) | Waxy solid at room temp. | 0.0 (EtOAc) |
| 7 | 2453A | 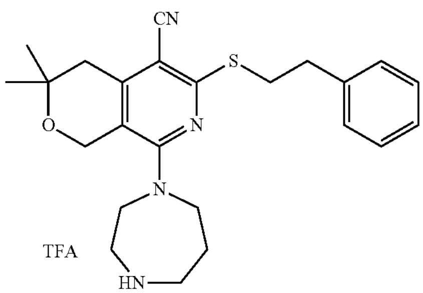 [SMILES: CC1(C)Cc2c(C#N)c(SCCc3ccccc3)nc(N3CCCNCC3)c2CO1 ; "TFA"] | (MeOD): 7.29-7.19 (m, 5H), 4.65 (s, 2H), 3.89 (t, 2H), 3.66 (t, 2H), 3.48 (t, 2H), 3.42 (t, 2H), 3.34 (m, 2H), 3.01 (t, 2H), 2.73 (s, 2H), 2.17 (pent, 2H), 1.32 (s, 6H) | 423.5 (M + 1) | grease at room temp. | 0.52 (83:16:1, CHCl₃:MeOH:NH₃) |
| 8 | 2471 | 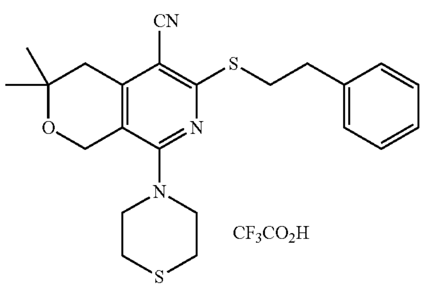 [SMILES: CC1(C)Cc2c(C#N)c(SCCc3ccccc3)nc(N3CCSCC3)c2CO1 ; "CF3CO2H"] | (Acetone-d₆): 7.38-7.19 (m, 5H), 4.59 (s, 2H), 3.66-3.63 (m, 4H), 3.56-3.51 (m, 2H), 3.08-3.00 (m, 2H), 2.80-2.77 (m, 4H), 2.73 (s, 2H), 1.32 (s, 6H) | 426.3 (M + 1) | 140-143° C. | 0.74 (1:1, EtOAc:Hexane) |
| 9 | 2503 | 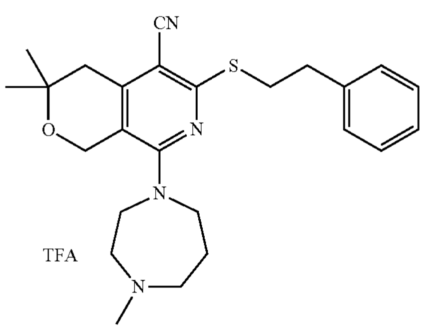 [SMILES: CN1CCCN(c2nc(SCCc3ccccc3)c(C#N)c3c2COC(C)(C)C3)CC1 ; "TFA"] | (MeCN): 11.95 (br s, 1H), 7.36-7.21 (m, 5H), 4.64 (br s, 1H), 4.57 (br s, 1H), 3.97 (br s, 1H), 3.86 (br s, 1H), 3.71 (br s, 1H), 3.60-3.30 (br m, 3H), 3.49 (t, 2H), 3.20-3.00 (br m, 2H), 3.04 (t, 2H), 2.75 (s, 3H), 2.72 (s, 2H), 2.30 (br m, 2H, overlap with solvent peak), 1.30 (s, 6H) | 437.3 (M + 1) | Grease at room temp. | 0.43 (83:16:1, CHCl₃:MeOH:NH₃) |
| 10 | 2574 | 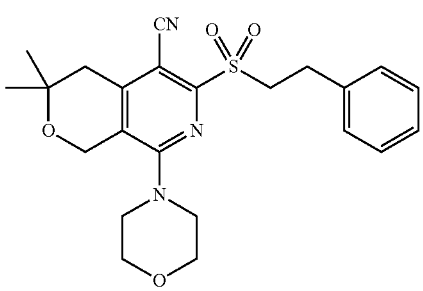 [SMILES: CC1(C)Cc2c(C#N)c(S(=O)(=O)CCc3ccccc3)nc(N3CCOCC3)c2CO1] | (CDCl₃): 7.26-7.13 (m, 5H), 4.57 (s, 2H), 3.81 (t, 4H), 3.77 (t, 2H), 3.34 (t, 4H), 3.18 (t, 2H), 2.86 (s, 2H), 1.35 (s, 6H) | 442.1 (M + 1) | 162-164° C. | 0.21 (1:1, EtOAc:Hexanes) |

| MBX # | | Structure | ¹H NMR | Mass Spec. | Melting point | R_f (eluents) |
|---|---|---|---|---|---|---|
| 11 | 2575 | 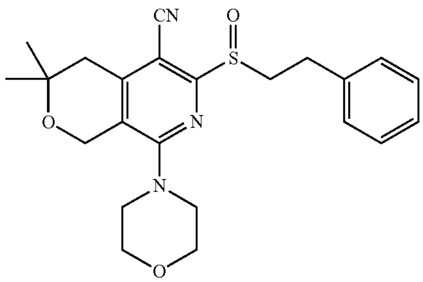 [SMILES: CC1(C)Cc2c(C#N)c(S(=O)CCc3ccccc3)nc(N3CCOCC3)c2CO1] | (CDCl₃): 7.29-7.17 (m, 5H), 4.57 (s, 2H), 3.81 (t, 4H), 3.48-3.31(m, 6H), 3.20-3.03 (m, 2H), 2.84 (s, 2H), 1.35 (s, 6H) | 425.8 (M + 1) | 146-147° C. | 0.34 (1:1, EtOAc:CH₂Cl₂) |
| 12 | 2685 | 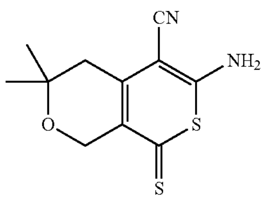 [SMILES: CC1(C)Cc2c(C#N)c(N)sc(=S)c2CO1] | (DMSO): 8.94 (bs, 2H), 4.48 (s, 2H), 2.59 (s, 2H), 1.21 (s, 6H) | 253.0 (M + 1) | 269-273° C. (decomp.) | 0.54 (1:1, EtOAc:Hexanes) |
| 13 | 2687 | 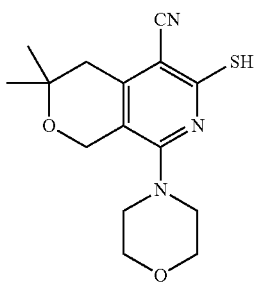 [SMILES: CC1(C)Cc2c(C#N)c(S)nc(N3CCOCC3)c2CO1] | (CDCl₃): 4.53 (s, 2H), 3.80 (t, 3H), 3.68 (t, 1H), 3.30-3.24 (m, 4H), 2.79 (s, 0.5H), 2.76 (s, 1.5H), 1.33 (s, 6H) | 306.2 (M + 1) | 235-238° C. | 0.49 (EtOAc) |
| 14 | 2697 | 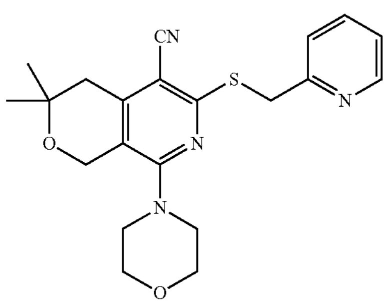 [SMILES: CC1(C)Cc2c(C#N)c(SCc3ccccn3)nc(N3CCOCC3)c2CO1] | (CDCl₃): 8.54 (d, 1H), 7.63 (t, 1H), 7.45 (d, 1H), 7.17 (t, 1H), 4.60 (s, 2H), 4.52 (s, 2H), 3.74 (d, 2H), 3.72 (d, 3.19 (d, 2H), 3.17 (d, 2H), 2.77 (s, 2H), 1.32 (s, 6H) | 397.1 (M + 1) | 130-131° C. | 0.41 (EtOAc) |
| 15 | 2698 | 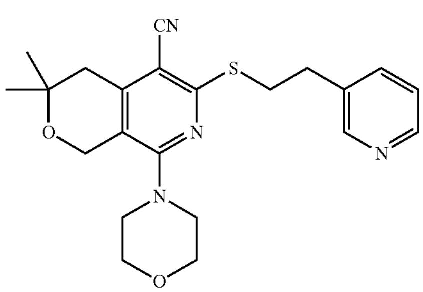 | (CDCl₃): 8.50 (s, 1H), 8.48 (s, 1H), 7.56 (d, 1H), 7.24 (dd, 1H), 4.56 (s, 2H), 3.82 (d, 2H), 3.80 (d, 2H), 3.47 (t, 2H), 3.29 (d, 2H), 3.27 (d, 2H), 3.04 (t, 2H), 2.77 (s, 2H), 1.33 (s, 6H) | 411.2 (M + 1) | 140-142° C. | 0.19 (EtOAc) |

-continued

Compound Characterization Data

| MBX # | | Structure | ¹H NMR | Mass Spec. | Melting point | R_f (eluents) |
|---|---|---|---|---|---|---|
| 16 | 2699 | 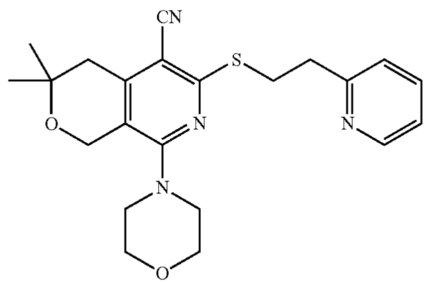 [SMILES: CC1(C)Cc2c(C#N)c(SCCc3ccccn3)nc(N3CCOCC3)c2CO1] | (CDCl₃): 8.54 (d, 1H), 7.61 (dt, 1H), 7.18-7.12 (m, 2H), 4.55 (s, 2H), 3.80 (t, 4H), 3.63 (t, 2H), 3.32 (t, 4H), 3.20 (t, 2H), 2.76 (s, 2H), 1.32 (s, 6H) | 411.2 (M + 1) | 107-108° C. | 0.46 (EtOAc) |
| 17 | 2741 | 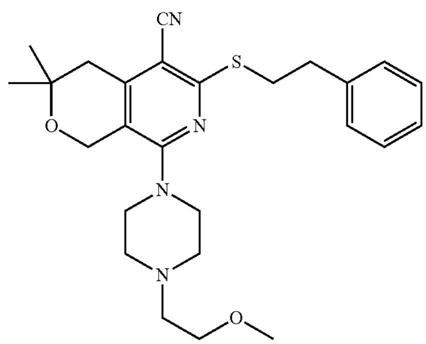 [SMILES: COCCN1CCN(c2nc(SCCc3ccccc3)c(C#N)c3c2COC(C)(C)C3)CC1] | (CDCl₃): 7.33-7.20 (m, 5H), 4.55 (s, 2H), 3.54 (t, 2H), 3.44 (t, 2H), 3.38-3.35 (m, 7H), 3.02 (t, 2H), 2.75 (s, 2H), 2.65-2.60 (m, 6H), 1.32 (s, 6H) | 467.3 (M + 1) | waxy solid at room temp. | 0.08 (1:1, EtOAc:Hexanes) |
| 18 | 2742 | 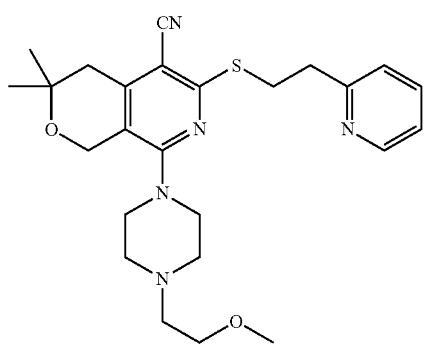 [SMILES: COCCN1CCN(c2nc(SCCc3ccccn3)c(C#N)c3c2COC(C)(C)C3)CC1] | (CDCl₃): 8.54 (d, 1H), 7.61 (dt, 1H), 7.18-7.12 (m, 2H), 4.55 (s, 2H), 3.62 (t, 2H), 3.53 (t, 2H), 3.38-3.35 (m, 7H), 3.18 (t, 2H), 2.74 (s, 2H), 2.65-2.60 (m, 6H), 1.32 (s, 6H) | 468.0 (M + 1) | waxy solid at room temp. | 0.70 (86:13:1, CHCl₃:MeOH:NH₃) |
| 19 | 2743 | 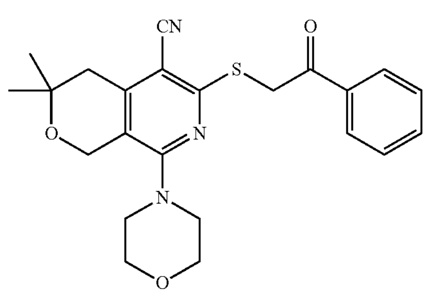 [SMILES: CC1(C)Cc2c(C#N)c(SCC(=O)c3ccccc3)nc(N3CCOCC3)c2CO1] | (CDCl₃): 7.84 (dd, 2H), 7.51-7.43 (m, 3H), 7.31 (br s, 2H), 4.75 (s, 2H), 3.83 (t, 4H), 3.21 (t, 4H), 3.16 (s, 2H), 1.41 (s, 6H) | 424.4 (M + 1) | 247-249° C. | 0.40 (1:1, EtOAc:Hexanes) |

-continued

Compound Characterization Data

| MBX # | Structure | ¹H NMR | Mass Spec. | Melting point | $R_f$ (eluents) |
|---|---|---|---|---|---|
| 20 2789 | | (CDCl$_3$): 8.53 (d, 1H), 7.60 (dt, 1H), 7.18-7.11 (m, 2H), 4.60 (s, 2H), 3.73-3.67 (m, 2H), 3.65-3.57 (m, 4H), 3.18 (t, 2H), 2.75-2.72 (m, 4H), 2.58 (t, 2H), 2.36 (s, 3H), 1.99 (pent, 2H), 1.32 (s, 6H) | 438.1 (M + 1) | Brown waxy solid at room temp. | 0.40 (83:16:1, CHCl$_3$:MeOH:NH$_3$) |
| 21 2802 | | (CDCl$_3$): 7.41-7.26 (m, 5H), 4.90 (dd, 1H), 4.59 (s, 2H), 3.70 (dd, 2H), 3.66-3.60 (m, 3H), 3.49 (dd, 1H), 2.76 (t, 2H), 2.74 (s, 2H), 2.64 (t, 2H), 2.39 (s, 3H), 2.01 (pent, 2H), 1.32 (s, 6H) | 453.2 (M + 1) | 128-132° C. | 0.49 (CHCl$_3$:MeOH:NH$_3$, 1:1) |
| 22 2803 | | (CDCl$_3$): 7.43-7.27 (m, 5H), 5.15 (t, 1H), 4.58 (s, 2H), 4.03 (d, 2H), 3.75-3.66 (m, 2H), 3.60 (t, 2H), 2.87-2.81 (m, 2H), 2.72 (s, 2H), 2.66 (t, 2H), 2.43 (s, 3H), 2.04 (pent, 2H), 1.32 (s, 6H) | 453.2 (M + 1) | 63-68° C. | 0.44 (CHCl$_3$:MeOH:NH$_3$, 1:1) |
| 23 2804 | | (CDCl$_3$): 7.30-7.20 (m, 5H), 4.59 (s, 2H), 3.82 (t, 2H), 3.77 (t, 2H), 3.70-3.62 (m, 4H), 3.42 (t, 2H), 3.00 (t, 2H), 2.76 (s, 2H), 1.99 (pent, 2H), 1.32 (s, 6H) | 424.2 (M + 1) | 103-105° C. | 0.35 (1:1, Hexanes:EtOAc) |

-continued

Compound Characterization Data

| MBX # | Structure | ¹H NMR | Mass Spec. | Melting point | $R_f$ (eluents) |
|---|---|---|---|---|---|
| 24 2807 | 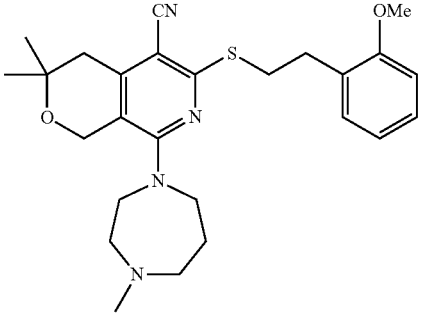 [SMILES: COc1ccccc1CCSc1nc(N2CCCN(C)CC2)c2c(c1C#N)CC(C)(C)OC2] | (CDCl₃): 7.27-7.13 (m, 2H), 6.92-6.84 (m, 2H), 4.70 (s, 0.3H, rotamer-1), 4.59 (s, 1.7H, rotamer-2), 3.82-3.79 (m, 5H), 3.61 (t, 2H), 3.41 (t, 2H), 3.02-2.97 (m, 4H), 2.84 (m, 2H), 2.74 (s, 2H), 2.59 (s, 0.45H, rotamer-1), 2.52 (s, 2.55H, rotamer-2), 2.15 (pent, 2H), 1.32 (s, 6H) | 467.2 (M + 1) | 53-57° C. | 0.64 (83:16:1, CHCl₃:MeOH:NH₃) |
| 25 2808 | 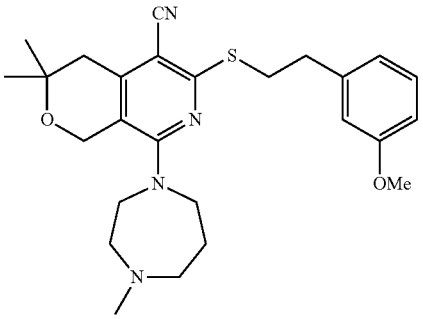 [SMILES: COc1cccc(CCSc2nc(N3CCCN(C)CC3)c3c(c2C#N)CC(C)(C)OC3)c1] | (CDCl₃): 7.21 (t, 1H), 6.82-6.75 (m, 3H), 4.60 (s, 2H), 3.80 (s, 3H), 3.69 (m, 2H), 3.62 (t, 2H), 3.43 (t, 2H), 2.98 (t, 2H), 2.84 (m, 2H), 2.73-2.71 (m, 4H), 2.59 (t, 2H), 2.36 (s, 3H), 1.98 (pent, 2H), 1.32 (s, 6H) | 467.3 (M + 1) | Red grease at room temp. | 0.64 (83:16:1, CHCl₃:MeOH:NH₃) |
| 26 2809 | 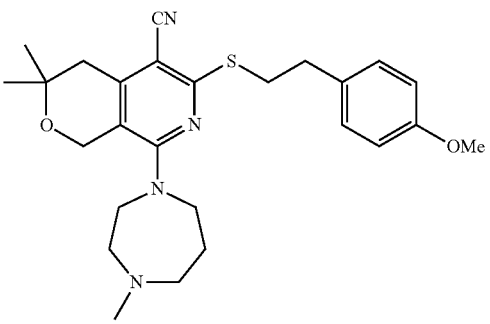 [SMILES: COc1ccc(CCSc2nc(N3CCCN(C)CC3)c3c(c2C#N)CC(C)(C)OC3)cc1] | (CDCl₃): 7.15 (d, 2H), 7.82 (d, 2H), 4.59 (s, 2H), 3.79 (s, 3H), 3.76 (m, 2H), 3.61 (t, 2H), 3.39 (t, 2H), 2.94 (t, 2H), 2.74 (m, 2H), 2.73-2.71 (m, 4H), 2.45 (s, 3H), 2.09 (pent, 2H), 1.32 (s, 6H) | 467.3 (M + 1) | 53-57° C. | 0.64 (83:16:1, CHCl₃:MeOH:NH₃) |
| 27 2810 | 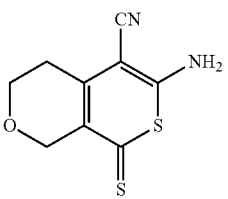 [SMILES: N#Cc1c(N)sc(=S)c2c1CCOC2] | (DMSO) 8.93 (s, 2H), 4.73 (s, 2H), 3.80 (t, 2H), 2.71 (t, 2H) | 224.9 (M + 1) | 242-247° C. | 0.50 (3% MeOH in CH₂Cl₂) |
| 28 2813 | 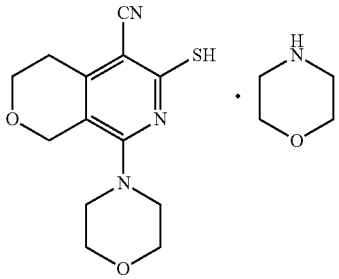 | (DMSO) 8.41 (s, 2H), 4.36 (s, 2H), 3.84 (t, 2H), 3.73 (t, 4H), 3.66 (t, 4H), 3.05 (t, 4H), 2.98 (t, 4H), 2.62 (t, 2H) | 278.1 (M + 1) | 209-216° C. | 0.36 (5% MeOH in CH₂Cl₂) |

-continued

Compound Characterization Data

| MBX # | | Structure | $^1$H NMR | Mass Spec. | Melting point | $R_f$ (eluents) |
|---|---|---|---|---|---|---|
| 29 | 2814 | 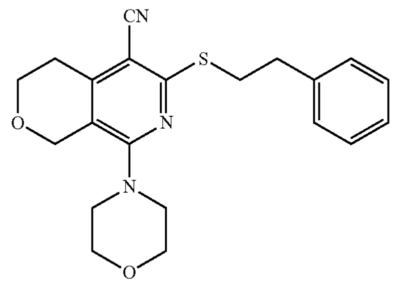 [SMILES: N#Cc1c(SCCc2ccccc2)nc(N2CCOCC2)c2c1CCOC2] | (CDCl$_3$) 7.34-7.21 (m, 5H), 4.52 (s, 2H), 4.02 (t, 2H), 3.81 (t, 4H), 3.48 (t, 2H), 3.30 (t, 4H), 3.05 (t, 2H), 2.96 (t, 2H) | 382.1 (M + 1) | 132-134° C. | 0.30 (1:1 Hexanes:EtOAc) |
| 30 | 2816 | 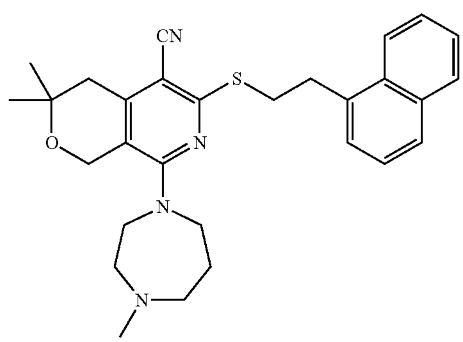 [SMILES: CN1CCCN(c2nc(SCCc3cccc4ccccc34)c(C#N)c3c2COC(C)(C)C3)CC1] | (CDCl$_3$): 8.02 (d, 1H), 7.76 (d, 1H), 7.73 (d, 1H), 7.54-7.36 (m, 4H), 4.57 (s, 2H), 3.60-4.36 (m, 8H), 2.74 (s, 2H), 2.60 (m, 2H), 2.50 (m, 2H), 2.25 (s, 3H), 1.89 (pent, 2H), 1.32 (s, 6H) | 487.2 (M + 1) | grease | 0.67 (83:16:1, CHCl$_3$:MeOH:NH$_3$) |
| 31 | 2817 | 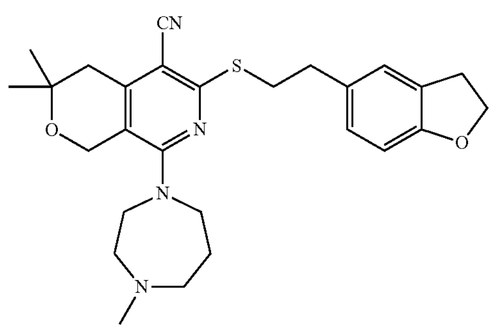 [SMILES: CN1CCCN(c2nc(SCCc3ccc4c(c3)CCO4)c(C#N)c3c2COC(C)(C)C3)CC1] | (CDCl$_3$): 7.03 (s, 1H), 6.92 (d, 1H), 6.68 (d, 1H), 4.58 (s, 2H), 4.53 (t, 2H), 3.68 (m, 2H), 3.60 (t, 2H), 3.37 (t, 2H), 3.16 (t, 2H), 2.90 (t, 2H), 2.74 (m, 2H), 2.71 (s, 2H), 2.58 (m, 2H), 2.36 (s, 3H), 1.98 (pent, 2H), 1.30 (s, 6H) | 479.2 (M + 1) | grease | 0.67 (83:16:1, CHCl$_3$:MeOH:NH$_3$) |
| 32 | 2818 | 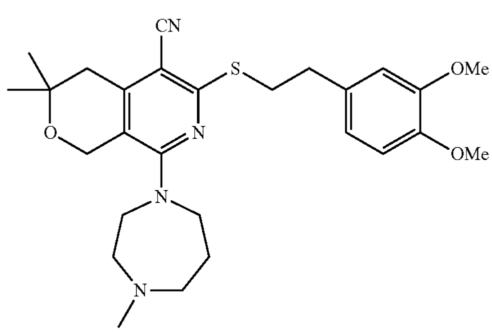 [SMILES: COc1ccc(CCSc2nc(N3CCCN(C)CC3)c3c(c2C#N)CC(C)(C)OC3)cc1OC] | (CDCl$_3$): 6.82-6.75 (m, 3H), 4.60 (s, 2H), 3.89 (s, 3H), 3.88 (s, 3H), 3.69 (m, 2H), 3.62 (t, 2H), 3.41 (t, 2H), 2.95 (t, 2H), 2.74-2.72 (m, 4H), 2.59 (m, 2H), 2.38 (s, 3H), 1.99 (pent, 2H), 1.33 (s, 6H) | 497.1 (M + 1) | 111-113° C. | 0.66 (83:16:1, CHCl$_3$:MeOH:NH$_3$) |

-continued

Compound Characterization Data

| MBX # | | Structure | ¹H NMR | Mass Spec. | Melting point | R_f (eluents) |
|---|---|---|---|---|---|---|
| 33 | 2825 | 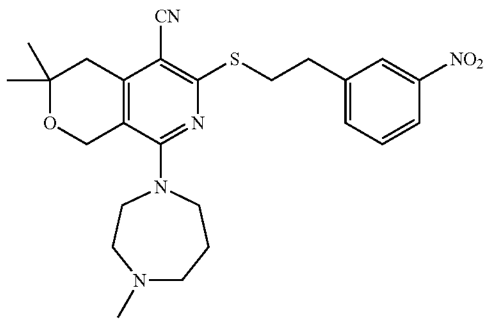 [SMILES: CN1CCCN(c2nc(SCCc3cccc([N+](=O)[O-])c3)c(C#N)c3c2COC(C)(C)C3)CC1] | (CDCl₃): 8.10-8.08 (m, 2H), 7.57 (d, 1H), 7.48 (t, 1H), 4.60 (s, 2H), 3.69 (m, 2H), 3.63 (t, 2H), 3.49 (t, 2H), 3.13 (t, 2H), 2.76-2.74 (m, 4H), 2.60 (m, 2H), 2.38 (s, 3H), 1.99 (pent, 2H), 1.33 (s, 6H) | 482.0 (M + 1) | grease | 0.68 (83:16:1, CHCl₃:MeOH:NH₃) |
| 34 | 2826A | 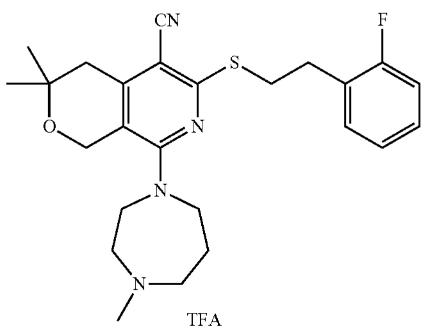 [SMILES: CN1CCCN(c2nc(SCCc3ccccc3F)c(C#N)c3c2COC(C)(C)C3)CC1 ; "TFA"] | (CDCl₃): 7.25-7.18 (m, 2H), 7.09 (t, 1H), 7.01 (t, 1H), 4.66 (d, 1H), 4.48 (d, 1H), 4.05 (m, 1H), 3.87 (d, 1H), 3.77 (d, 1H), 3.62 (m, 2H), 3.44-3.30 (m, 4H), 3.04-2.97 (m, 3H), 2.83 (s, 3H), 2.74 (d, 2H), 2.59 (m, 1H), 2.21 (m, 1H), 1.32 (s, 6H) | 455.3 (M + 1) | grease | 0.68 (83:16:1, CHCl₃:MeOH:NH₃) |
| 35 | 2827 | 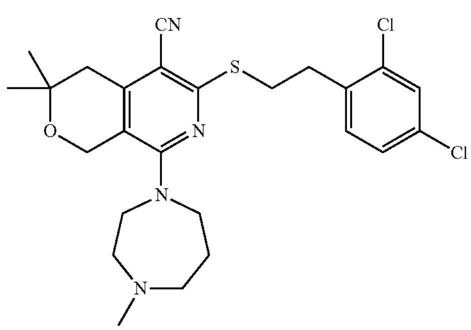 [SMILES: CN1CCCN(c2nc(SCCc3ccc(Cl)cc3Cl)c(C#N)c3c2COC(C)(C)C3)CC1] | (CDCl₃): 7.35 (d, 1H), 7.18-7.16 (m, 2H), 4.59 (s, 2H), 3.67 (m, 2H), 3.60 (t, 2H), 3.46 (t, 2H), 3.09 (t, 2H), 2.74-2.70 (m, 4H), 2.60 (m, 2H), 2.37 (s, 3H), 1.99 (pent, 2H), 1.32 (s, 6H) | 505.1 (M + 1) | grease | 0.70 (83:16:1, CHCl₃:MeOH:NH₃) |
| 36 | 2828 | 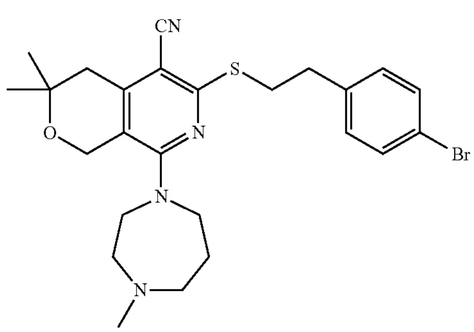 [SMILES: CN1CCCN(c2nc(SCCc3ccc(Br)cc3)c(C#N)c3c2COC(C)(C)C3)CC1] | (CDCl₃): 7.41 (d, 2H), 7.09 (d, 2H), 4.59 (s, 2H), 3.67 (m, 2H), 3.60 (t, 2H), 3.41 (t, 2H), 2.96 (t, 2H), 2.74-2.69 (m, 4H), 2.59 (t, 2H), 2.37 (s, 3H), 1.99 (pent, 2H), 1.32 (s, 6H) | 515.1 (M + 1) | 151-153° C. | 0.57 (83:16:1, CHCl₃:MeOH:NH₃) |

-continued

Compound Characterization Data

| MBX # | Structure | $^1$H NMR | Mass Spec. | Melting point | $R_f$ (eluents) |
|---|---|---|---|---|---|
| 37 2829A | | (CDCl$_3$): 12.55 (br s, 1H), 12.20 (br s, 1H), 7.36-7.33 (m, 2H), 7.20-7.12 (m, 2H), 4.64 (d, 1H), 4.48 (d, 1H), 3.98 (m, 1H), 3.87-3.64 (m, 4H), 3.48-3.20 (m, 4H), 3.02 (m, 1H), 2.99 (t, 2H), 2.85 (s, 3H), 2.75 (d, 2H), 2.54 (m, 1H), 2.20 (m, 1H), 1.32 (s, 6H) | 515.3 (M + 1) | 63-67° C. | 0.57 (83:16:1, CHCl$_3$:MeOH:NH$_3$) |
| 38 2831 | | (CDCl$_3$) 8.48 (d, 1H), 7.56 (td, 1H), 7.11-7.05 (m, 2H), 4.44 (s, 2H), 3.94 (t, 2H), 3.74 (t, 4H), 3.58 (t, 2H), 3.25 (t, 4H), 3.15 (t, 2H), 2.88 (t, 2H) | 383.0 (M + 1) | 158-159° C. | 0.20 (1:4 Hexanes:EtOAc) |
| 39 2842 | | (CDCl$_3$): 8.20 (br s, 1H), 7.59 (d, 1H), 7.35 (d, 1H), 7.18 (t, 1H), 7.10 (t, 1H), 7.04 (d, 1H), 4.53 (s, 2H), 3.56-3.48 (m, 4H), 3.38 (s, 3H), 3.33 (m, 4H), 3.17 (t, 2H), 2.74 (s, 2H), 2.61-2.54 (m, 6H), 1.32 (s, 6H) | 506.2 (M + 1) | grease | 0.28 (5% MeOH in CH$_2$Cl$_2$) |
| 40 2843 | | (CDCl$_3$): 4.99 (t, 1H), 4.54 (s, 2H), 4.00-3.96 (m, 2H), 3.89-3.86 (m, 2H), 3.55 (t, 2H), 3.38 (m, 4H), 3.37 (s, 3H), 3.28 (m, 2H), 2.74 (s, 2H), 2.67-2.62 (m, 6H), 2.12-2.05 (m, 2H), 1.32 (s, 6H) | 463.1 (M + 1) | grease | 0.26 (5% MeOH in CH$_2$Cl$_2$) |

-continued
Compound Characterization Data
| MBX # | | Structure | ¹H NMR | Mass Spec. | Melting point | $R_f$ (eluents) |
|---|---|---|---|---|---|---|
| 41 | 2844 | 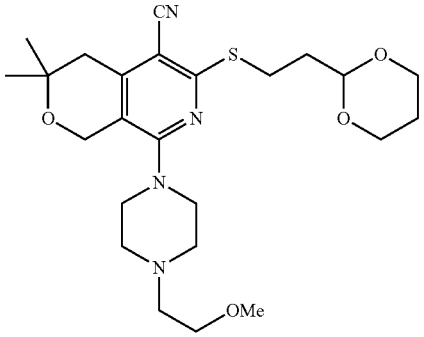 [SMILES: COCCN1CCN(c2nc(SCCC3OCCCO3)c(C#N)c3c2COC(C)(C)C3)CC1] | (CDCl₃): 4.69 (t, 1H), 4.53 (s, 2H), 4.09 (dd, 2H), 3.78 (t, 2H), 3.56 (t, 2H), 3.37 (m, 7H), 3.27 (t, 2H), 2.74 (s, 2H), 2.67-2.62 (m, 6H), 2.15-1.97 (m, 4H), 1.32 (s, 6H) | 477.1 (M + 1) | grease | 0.20 (5% MeOH in CH₂Cl₂) |
| 42 | 2845 | 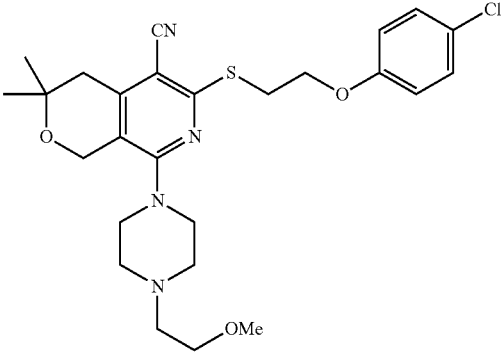 [SMILES: COCCN1CCN(c2nc(SCCOc3ccc(Cl)cc3)c(C#N)c3c2COC(C)(C)C3)CC1] | (CDCl₃): 7.21 (d, 2H), 6.80 (d, 2H), 4.52 (s, 2H), 4.16 (t, 2H), 3.55 (t, 2H), 3.48 (t, 2H), 3.35 (s, 3H), 3.33-3.30 (m, 4H), 2.74 (s, 2H), 2.56-2.52 (m, 6H), 1.31 (s, 6H) | 517.3 (M + 1) | grease | 0.23 (5% MeOH in CH₂Cl₂) |
| 43 | 2846 | 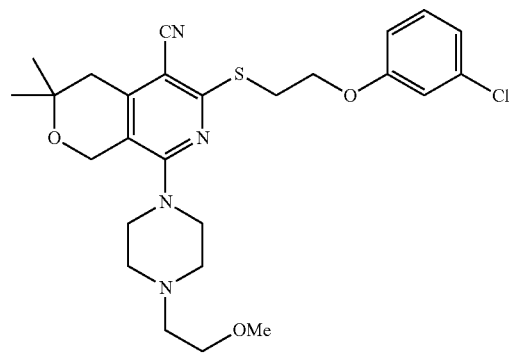 [SMILES: COCCN1CCN(c2nc(SCCOc3cccc(Cl)c3)c(C#N)c3c2COC(C)(C)C3)CC1] | (CDCl₃): 7.19 (t, 1H), 6.93 (d, 1H), 6.87 (s, 1H), 6.78 (d, 1H), 4.53 (s, 2H), 4.18 (t, 2H), 3.57 (t, 2H), 3.49 (t, 2H), 3.36 (s, 3H), 3.37-3.32 (m, 4H), 2.75 (s, 2H), 2.58-2.53 (m, 6H), 1.32 (s, 6H) | 517.3 (M + 1) | grease | 0.23 (5% MeOH in CH₂Cl₂) |
| 44 | 2847 | 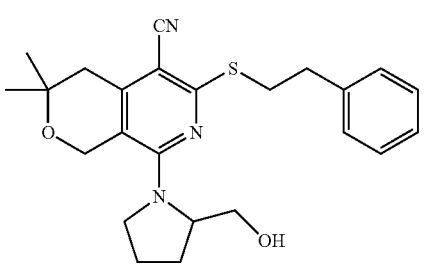 [SMILES: CC1(C)Cc2c(C#N)c(SCCc3ccccc3)nc(N3CCCC3CO)c2CO1] | (CDCl₃): 7.30-7.22 (m, 5H), 4.74 (d, 1H), 4.61 (br t, 1H), 4.52 (d, 1H), 3.72-3.63 (m, 2H), 3.54-3.34 (m, 3H), 3.02 (t, 2H), 2.76 (d, 1H), 2.69 (d, 1H), 2.13-1.80 (m, 6H), 1.32 (s, 6H) | 424.2 (M + 1) | grease | 0.08 (40% EtOAc in Hexanes) |

-continued

Compound Characterization Data

| MBX # | Structure | ¹H NMR | Mass Spec. | Melting point | $R_f$ (eluents) |
|---|---|---|---|---|---|
| 45 2854 | | (CDCl₃): 7.23 (t, 1H), 6.82-6.76 (m, 3H), 4.55 (s, 2H), 3.82-3.79 (m, 7H), 3.45 (t, 2H), 3.29 (t, 4H), 2.99 (t, 2H), 2.76 (s, 2H), 1.33 (s, 6H) | 440.3 (M + 1) | 95-97° C. | 0.37 (1:1 EtOAc:Hexanes) |
| 46 2864 | | (CDCl₃): 7.25 (m, 1H), 6.99 (d, 1H), 6.95-6.85 (m, 2H), 4.55 (s, 2H), 3.81 (t, 4H), 3.45 (t, 2H), 3.29 (t, 4H), 3.02 (t, 2H), 2.76 (s, 2H), 1.33 (s, 6H) | 428.2 (M + 1) | grease | 0.15 (1:3 EtOAc:Hexanes) |
| 47 2865 | | (CDCl₃): 8.07 (br s, 1H), 7.59 (d, 1H), 7.35 (d, 1H), 7.19 (t, 1H), 7.35 (d, 1H), 7.19 (t, 1H), 7.11 (t, 1H), 7.06 (d, 1H), 4.54 (s, 2H), 3.75 (t, 4H), 3.56 (t, 2H), 3.24 (t, 4H), 3.18 (t, 2H), 2.76 (s, 2H), 1.28 (s, 6H) | 449.0 (M + 1) | 202-205° C. | 0.36 (1:1 EtOAc:Hexanes) |
| 48 2870 | | (CDCl₃): 7.19 (t, 1H), 6.82 (d, 1H), 6.78 (s, 1H), 6.76 (d, 1H), 4.54 (s, 2H), 3.80 (s, 3H), 3.55 (m, 2H), 3.47-3.40 (m, 4H), 2.99 (t, 2H), 2.76 (s, 2H), 2.71 (t, 2H), 1.33 (s, 6H), 1.18 (d, 6H) | 468.1 (M + 1) | grease | 0.24 (1:3 EtOAc:Hexanes) |
| 49 2871 | | (CDCl₃): 7.36-7.33 (m, 2H), 7.16-7.13 (m, 2H), 4.54 (s, 2H), 3.76 (m, 2H), 3.45-3.40 (m, 4H), 2.99 (t, 2H), 2.76 (s, 2H), 2.71 (t, 2H), 1.33 (s, 6H), 1.19 (d, 6H) | 516.2 (M + 1) | Waxy solid | 0.28 (1:3 EtOAc:Hexanes) |

| MBX # | Structure | ¹H NMR | Mass Spec. | Melting point | R_f (eluents) |
|---|---|---|---|---|---|
| 50 2872 | | (CDCl₃): 7.26 (m, 1H), 7.23 (d, 1H), 6.92-6.89 (m, 2H), 4.54 (s, 2H), 3.76 (m, 2H), 3.46-3.41 (m, 4H), 3.02 (t, 2H), 2.76 (s, 2H), 2.71 (t, 2H), 1.33 (s, 6H), 1.19 (d, 6H) | 456.2 (M + 1) | 117-119° C. | 0.31 (1:3 EtOAc:Hexanes) |
| 51 2873 | | (CDCl₃): 8.15 (br s, 1H), 7.58 (d, 1H), 7.34 (d, 1H), 7.19 (t, 1H), 7.13 (t, 1H), 7.06 (d, 1H), 4.52 (s, 2H), 3.71 (m, 2H), 3.55 (t, 2H), 3.39 (d, 2H), 3.17 (t, 2H), 2.76 (s, 2H), 2.67 (t, 2H), 1.33 (s, 6H), 1.11 (d, 6H) | 477.0 (M + 1) | 169-172° C. | 0.48 (1:1 EtOAc:Hexanes) |
| 52 2884 | | (CDCl₃): 7.19 (t, 1H), 7.03-7.00 (m, 3H), 4.56 (s, 2H), 3.81 (t, 4H), 3.44 (t, 2H), 3.30 (t, 4H), 2.98 (t, 2H), 2.76, (s, 2H), 2.33 (s, 3H), 1.33 (s, 6H) | 424.3 (M + 1) | 122-124° C. | 0.22 (1:3 EtOAc:Hexanes) |
| 53 2855 | | (CDCl₃): 7.23-7.09 (m, 4H), 4.56 (s, 2H), 3.81 (t, 4H), 3.45 (t, 2H), 3.29 (t, 4H), 3.00 (t, 2H), 2.76 (s, 2H), 1.33 (s, 6H) | 444.3 (M + 1) | 132-134° C. | 0.22 (1:3 EtOAc:Hexanes) |
| 54 2856 | | (CDCl₃): 7.57 (d, 1H), 7.32 (d, 1H), 7.20 (t, 1H), 7.10 (t, 1H), 7.02 (s, 1H), 4.54 (s, 2H), 4.24 (t, 2H), 3.75 (t, 4H), 3.69 (t, 2H), 3.54 (t, 2H), 3.32 (s, 3H), 3.25 (t, 4H), 3.16 (t, 2H), 2.76 (s, 2H), 1.32 (s, 6H) | 507.0 (M + 1) | glassy solid | 0.25 (1:1 EtOAc:Hexanes) |

-continued

Compound Characterization Data

| MBX # | Structure | $^1$H NMR | Mass Spec. | Melting point | $R_f$ (eluents) |
|---|---|---|---|---|---|
| 55 2885 | | (CDCl$_3$): 7.23-7.09 (m, 4H), 4.56 (s, 2H), 3.81 (t, 4H), 3.45 (t, 2H), 3.29 (t, 4H), 3.00 (t, 2H), 2.76 (s, 2H), 1.33 (s, 6H) | 444.3 (M + 1) | White solid | 0.22 (1:3 EtOAc:Hexane) |
| 56 2886 | | (CDCl$_3$): 7.57 (d, 1H), 7.32 (d, 1H), 7.20 (t, 1H), 7.10 (t, 1H), 7.02 (s, 1H), 4.54 (s, 2H), 4.24 (t, 2H), 3.75 (t, 4H), 3.69 (t, 2H), 3.54 (t, 2H), 3.32 (s, 3H), 3.25 (t, 4H), 3.16 (t, 2H), 2.76 (s, 2H), 1.32 (s, 6H) | 507.0 (M + 1) | Pale yellow glassy solid | 0.25 (1:1 EtOAc:Hexane) |
| 57 2893 | | (CDCl$_3$): 7.28 (t, 1H), 7.09 (d, 1H), 6.97 (s, 1H), 6.95 (d, 1H), 4.56 (s, 2H), 3.80 (t, 4H), 3.44 (t, 2H), 3.27 (t, 4H), 3.02 (t, 2H), 2.76 (s, 2H), 2.30 (s, 3H), 1.33 (s, 6H) | 468.1 (M + 1) | Pale yellow grease | 0.09 (1:3 EtOAc:Hexane) |
| 58 2894 | | (CDCl$_3$): 7.16 (t, 1H), 6.77 (d, 1H), 6.73 (s, 1H), 6.69 (d, 1H), 5.47 (br s, 1H), 4.56 (s, 2H), 3.82 (t, 4H), 3.43 (t, 2H), 3.30 (t, 4H), 2.97 (t, 2H), 2.77 (s, 2H), 1.33 (s, 6H) | 426.2 (M + 1) | Colorless solid | 0.44 (1:1 EtOAc:Hexane) |
| 59 2895 | | (CDCl$_3$): 7.55 (d, 1H), 7.49 (s, 1H), 7.46 (d, 1H), 7.32-7.21 (m, 2H), 4.53 (s, 2H), 3.75 (t, 4H), 3.55 (t, 2H), 3.22 (t, 4H), 3.11 (t, 2H), 2.76 (s, 2H), 1.32 (s, 6H) | 450.1 (M + 1) | Yellow grease | 0.16 (1:3 EtOAc:Hexane) |

| MBX # | Structure | ¹H NMR | Mass Spec. | Melting point | R$_f$ (eluents) |
|---|---|---|---|---|---|
| 60 2896 | | (CDCl$_3$): 7.23 (t, 1H), 6.82-6.77 (m, 3H), 4.56 (s, 2H), 4.11 (t, 2H), 3.81 (t, 4H), 3.76 (t, 2H), 3.45 (s, 3H), 3.43 (t, 2H), 3.29 (t, 4H), 2.98 (t, 2H), 2.76 (s, 2H), 1.33 (s, 6H) | 484.2 (M + 1) | Yellow grease | 0.32 (1:1 EtOAc:Hexane) |
| 61 2897 | | (CDCl$_3$) 7.25 (t, 1H), 6.83-6.72 (m, 3H), 4.54 (s, 2H), 3.81 (s, 3H), 3.56 (t, 2H), 3.46 (dd, 2H), 3.39-3.35 (m, 7H), 3.02 (dd, 2H), 2.75 (s, 2H), 2.66-2.61 (m, 6H), 1.33 (s, 6H) | 497.3 (M + 1) | Red waxy Solid | 0.36 (4% MeOH-EtOAc) |
| 62 2898 | | (CDCl$_3$) 7.25-7.18 (m, 2H), 7.10-6.99 (m, 2H), 4.54 (s, 2H), 3.56 (t, 2H), 3.49 (t, 2H), 3.38-3.31(m, 7H), 3.09 (t, 2H), 2.75 (s, 2H), 2.66-2.62 (m, 6H), 1.33 (s, 6H) | 485.3 (M + 1) | Red waxy Solid | 0.50 (4% MeOH-EtOAc) |
| 63 2900 | | (CDCl$_3$) 7.42 (d, 2H), 7.11 (d, 2H), 4.54 (s, 2H), 3.57 (t, 2H), 3.45-3.33 (m, 9H), 3.00 (t, 2H), 2.75 (s, 2H), 2.67-2.60 (m, 6H), 1.32 (s, 6H) | 545.3 (M + 1) | Red waxy Solid | 0.50 (8% MeOH-EtOAc) |

-continued

Compound Characterization Data

| MBX # | Structure | $^1$H NMR | Mass Spec. | Melting point | $R_f$ (eluents) |
|---|---|---|---|---|---|
| 64  2901 | | (CDCl$_3$) 7.25-7.22 (m, 1H), 7.01 (d, 1H), 6.94-6.88 (m, 2H), 4.54 (s, 2H), 3.57 (t, 2H), 3.47 (t, 2H), 3.39-3.35 (m, 7H), 3.05 (t, 2H), 2.75 (s, 2H), 2.68-2.63 (m, 6H), 1.32 (s, 6H) | 485.3 (M + 1) | Red waxy Solid | 0.50 (8% MeOH-EtOAc) |
| 65  2903 | | (CDCl$_3$) 7.30-7.25 (m, 2H), 6.98-6.87 (m, 3H), 4.53 (s, 2H), 4.20 (t, 2H), 3.60 (t, 2H), 3.50 (t, 2H), 3.35-3.33 (m, 7H), 2.75 (s, 2H), 2.58-2.55 (m, 6H), 1.32 (s, 6H) | 483.3 (M + 1) | Red waxy Solid | 0.50 (8% MeOH/EtOAc) |
| 66  2913 | | (CDCl$_3$): 9.77 (b s, 1H), 8.85 (s, 1H), 8.84 (d, 1H), 8.37 (d, 1H), 7.97 (dd, 1H), 4.55 (s, 2H), 3.78 (m, 2H), 3.58 (t, 2H), 3.45 (d, 2H), 3.32 (t, 2H), 2.92 (s, 6H), 2.75 (s, 2H), 2.73 (dd, 2H), 2.02 (s, 1H), 1.34 (s, 6H), 1.22 (d, 6H) | 439.2 (M + 1) | Brown grease | 0.26 (1:1 EtOAc:Hexane) |
| 67  2923 | | (CDCl$_3$): 7.51-7.39 (m, 4H), 4.56 (s, 2H), 3.83 (t, 4H), 3.48 (t, 2H), 3.28 (t, 4H), 3.08 (t, 2H), 2.76 (s, 2H), 1.33 (s, 6H) | 435.3 (M + 1) | Glassy yellow solid | 0.5 (1:1 EtOAc:Hexane) |

-continued

Compound Characterization Data

| MBX # | Structure | ¹H NMR | Mass Spec. | Melting point | R$_f$ (eluents) |
|---|---|---|---|---|---|
| 68  2927 | | (CDCl$_3$) 7.37-7.34 (m, 2H), 7.18-7.15 (m, 2H), 4.54 (s, 2H), 3.57 (t, 2H), 3.49-3.36 (m, 9H), 3.02 (t, 2H), 2.75 (s, 2H), 2.67-2.58 (m, 6H), 1.33 (s, 6H) | 545.6 (M + 1) | Red waxy Solid | 0.53 (10% MeOH-EtOAc) |
| 69  2928 | | (CDCl$_3$) 7.15 (d, 2H), 6.85 (d, 2H), 4.54 (s, 2H), 3.80 (s, 3H), 3.57 (t, 2H), 3.43-3.30 (m, 9H), 2.98 (t, 2H), 2.75 (s, 2H), 2.69-2.60 (m, 6H), 1.32 (s, 6H) | 497.5 (M + 1) | Red waxy Solid | 0.47 (10% MeOH-EtOAc) |
| 70  2931 | | (CDCl$_3$) 6.83-6.75 (m, 3H), 4.55 (s, 2H), 3.88 (s, 3H), 3.87 (s, 3H), 3.56 (t, 2H), 3.45-3.30 (m, 9H), 2.99 (t, 2H), 2.75 (s, 2H), 2.99 (t, 2H), 2.70-2.60 (m, 6H), 1.32 (s, 6H) | 527.4 (M + 1) | Red waxy Solid | 0.30 (10% MeOH-EtOAc) |
| 71  3097 | | (CDCl$_3$): 7.22 (t, 1H), 7.12 (s, 1H), 7.11 (d, 1H), 7.00 (d, 1H), 4.54 (s, 2H), 3.74 (m, 2H), 3.46-3.38 (m, 4H), 2.98 (t, 2H), 2.76 (s, 2H), 2.71 (t, 2H), 2.48 (s, 3H), 1.33 (s, 6H), 1.18 (d, 6H) | 484.3 (M + 1) | Brown wax | 0.40 (1:3 EtOAc:Hexane) |

-continued

Compound Characterization Data

| | MBX # | Structure | $^1$H NMR | Mass Spec. | Melting point | $R_f$ (eluents) |
|---|---|---|---|---|---|---|
| 72 | 3098 | 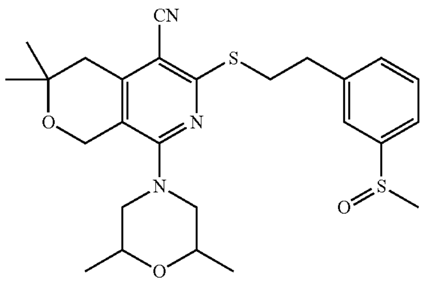 | (CDCl$_3$): 7.55 (s, 1H), 7.47-7.44 (m, 2H), 7.38 (m, 1H), 4.54 (s, 2H), 3.75 (m, 2H), 3.49 (t, 2H), 3.43 (d, 2H), 3.12 (t, 2H), 2.76 (s, 2H), 2.75 (s, 3H), 2.71 (dd, 2H), 1.34 (s, 6H), 1.19 (d, 6H) | 500.2 (M + 1) | Brown wax | 0.51 (1:1 EtOAc:Hexane) |
| 73 | 3099 | 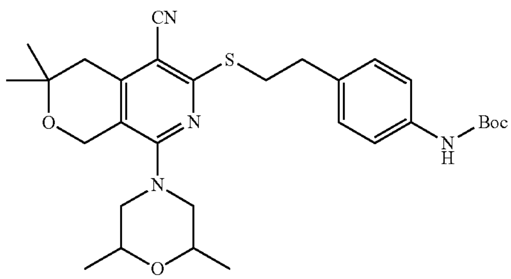 [SMILES: CC1CN(c2nc(SCCc3ccc(NC(=O)OC(C)(C)C)cc3)c(C#N)c3c2COC(C)(C)C3)CC(C)O1] | (CDCl$_3$): 7.28 (d, 2H), 7.14 (d, 2H), 6.46 (b s, 1H), 4.54 (s, 2H), 3.75 (m, 2H), 3.46-3.37 (m, 4H), 2.96 (t, 2H), 2.76 (s, 2H), 2.71 (dd, 2H), 1.51 (s, 9H), 1.33 (s, 6H), 1.19 (d, 6H) | 553.1 (M + 1) | Purple solid | 0.60 (1:1 EtOAc:Hexane) |
| 74 | 3106 | 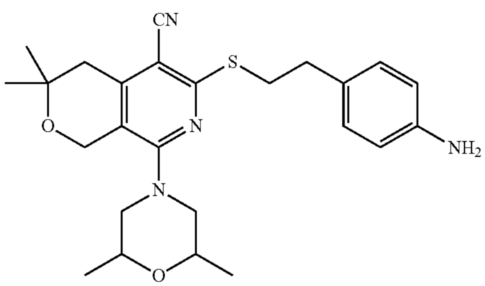 [SMILES: CC1CN(c2nc(SCCc3ccc(N)cc3)c(C#N)c3c2COC(C)(C)C3)CC(C)O1] | (CDCl$_3$): 7.02 (d, 2H), 6.64 (d, 2H), 6.46 (b s, 1H), 4.54 (s, 2H), 3.76 (m, 2H), 3.46-3.34 (m, 4H), 3.08 (b s, 2H), 2.90 (t, 2H), 2.76 (s, 2H), 2.72 (dd, 2H), 1.33 (s, 6H), 1.20 (d, 6H) | 453.1 (M + 1) | Light brown solid | 0.35 (1:1 EtOAc:Hexane) |
| 75 | 3132 | 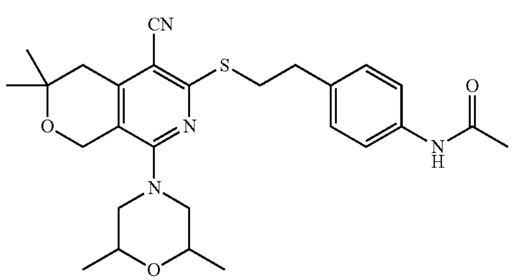 [SMILES: CC(=O)Nc1ccc(CCSc2nc(N3CC(C)OC(C)C3)c3c(c2C#N)CC(C)(C)OC3)cc1] | (CDCl$_3$): 7.43 (d, 2H), 7.39 (b s, 1H), 7.18 (d, 2H), 4.54 (s, 2H), 3.76 (m, 2H), 3.46-3.38 (m, 4H), 2.97 (t, 2H), 2.75 (s, 2H), 2.72 (dd, 2H), 2.17 (s, 3H), 1.33 (s, 6H), 1.20 (d, 6H) | 495.1 (M + 1) | Yellow solid | 0.17 (1:1 EtOAc:Hexane) |
| 76 | 3133 | 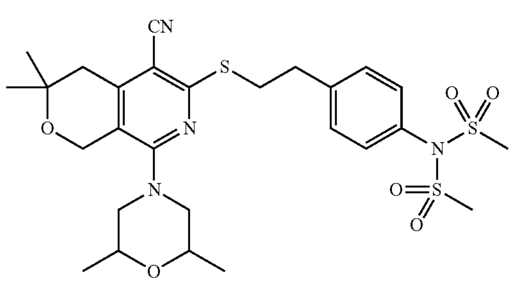 | (CDCl$_3$): 7.35 (d, 2H), 7.29 (d, 2H), 4.54 (s, 2H), 3.77 (m, 2H), 3.45 (m, 4H), 3.40 (s, 6H), 3.07 (t, 2H), 2.76 (s, 2H), 2.71 (dd, 2H), 1.34 (s, 6H), 1.19 (d, 6H) | 609.1 (M + 1) | Yellow glassy solid | 0.47 (1:1 EtOAc:Hexane) |

Compound Characterization Data

| MBX # | Structure | ¹H NMR | Mass Spec. | Melting point | R$_f$ (eluents) |
|---|---|---|---|---|---|
| 77 3134 | | (CDCl$_3$): 7.23 (d, 2H), 7.17 (d, 2H), 6.57 (b s, 1H), 4.54 (s, 2H), 3.76 (m, 2H), 3.45-3.40 (m, 2H), 3.03-2.98 (m, 4H), 2.76 (s, 2H), 2.71 (dd, 2H), 1.34 (s, 6H), 1.19 (d, 6H) | 531.2 (M + 1) | White solid | 0.36 (1:1 EtOAc:Hexane) |
| 78 3135 | | (CDCl$_3$): 7.51 (b d, 2H), 7.30 (b s, 1H), 7.20 (d, 2H), 6.44 (dd, 1H), 6.24 (dd, 1H), 5.76 (dd, 1H), 4.53 (s, 2H), 3.76 (m, 2H), 3.46-3.39 (m, 4H), 2.99 (t, 2H), 2.76 (s, 2H), 2.71 (dd, 2H), 1.33 (s, 6H), 1.19 (d, 6H) | 507.1 (M + 1) | Off-white powder | 0.39 (1:1 EtOAc:Hexane) |
| 79 3157 | | (CD$_3$CN): 9.54 (b s, 1H), 7.36 (d, 2H), 7.18 (d, 2H), 6.82 (b s, 4H), 4.53 (s, 2H), 3.70 (m, 2H), 3.57-3.45 (m, 4H), 3.04 (t, 2H), 2.71 (s, 2H), 2.65 (t, 2H), 1.28 (s, 6H), 1.11 (d, 6H) | 495.3 (M + 1) | White crystal solid | 0.0 (EtOAc) |
| 80 3193 | | (CDCl$_3$): 7.18 (m, 2H), 6.99 (m, 2H), 4.55 (s, 2H), 3.81 (t, 4H), 3.43 (t, 2H), 3.28 (t, 4H), 3.00 (t, 2H), 2.76 (s, 2H), 1.33 (s, 6H) | 428.1 (M + 1) | White powder | 0.21 (1:3 EtOAc:Hexane) |
| 81 3221 | | (CDCl$_3$) 7.43-7.29 (m, 5H), 4.97 (dt, 1H), 4.56 (s, 2H), 3.83 (t, 4H), 3.67-3.63 (m, 2H), 3.46 (dd, 1H), 3.32 (m, 4H), 2.78 (s, 2H), 1.33 (s, 6H) | 426.0 (M + 1) | Light yellow crystalline solid | 0.33 (1:1 Hexanes:EtOAc) |

| MBX # | | Structure | ¹H NMR | Mass Spec. | Melting point | R_f (eluents) |
|---|---|---|---|---|---|---|
| 82 | 3223 | 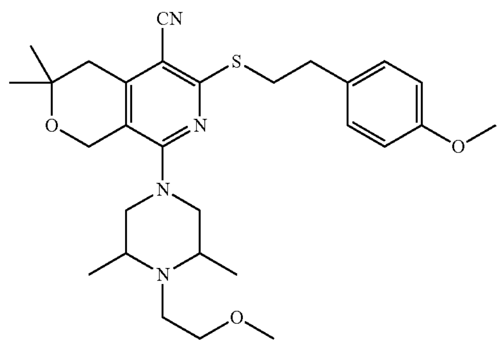 | (CDCl₃) 7.15 (d, 2H), 6.82 (d, 2H), 4.54 (s, 2H), 3.79 (s, 3H), 3.49-3.37 (m, 6H), 3.34 (s, 3H), 2.98-2.88 (m, 4H), 2.80-2.74 (m, 6H), 1.32 (s, 6H), 1.15 (d, 6H) | 525.1 (M + 1) | Green solid | 0.11 (1:1 Hexanes:EtOAc) |
| 83 | 3224 | 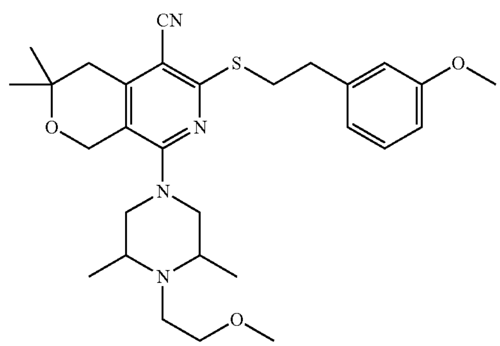 | (CDCl₃) 7.21 (t, 1H), 6.84-6.74 (m, 3H), 4.54 (s, 2H), 3.80 (s, 3H), 3.49-3.41 (m, 6H), 3.34 (s, 3H), 2.99 (t, 2H), 2.89 (t, 2H), 2.88-2.75 (m, 6H), 1.33 (s, 6H), 1.10 (d, 6H) | 525.2 (M + 1) | Brown wax | 0.11 (1:1 Hexanes:EtOAc) |
| 84 | 3225 | 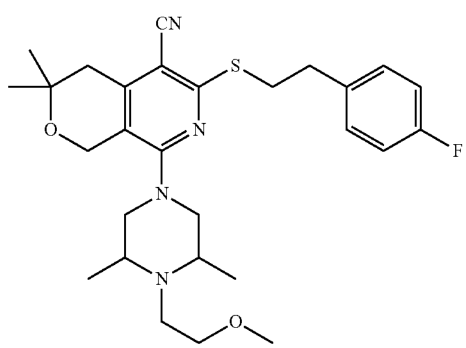 [SMILES: COCCN1C(C)CN(c2nc(SCCc3ccc(F)cc3)c(C#N)c3c2COC(C)(C)C3)CC1C] | (CDCl₃) 7.18 (m, 2H), 6.95 (m, 2H), 4.54 (s, 2H), 3.47-3.38 (m, 6H), 3.34 (s, 3H), 2.99 (t, 2H), 2.90 (t, 2H), 2.80-2.75 (m, 6H), 1.33 (s, 6H), 1.11 (d, 6H) | 513.2 (M + 1) | Brown solid | 0.14 (1:1 Hexanes:EtOAc) |
| 85 | 3226 | 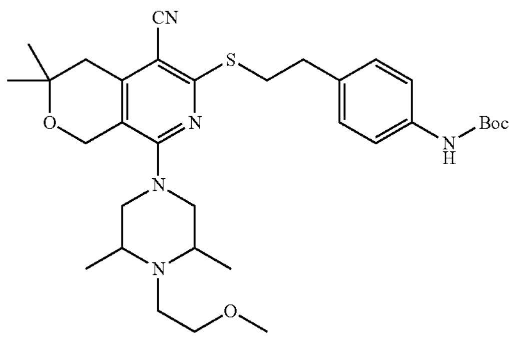 [SMILES: COCCN1C(C)CN(c2nc(SCCc3ccc(NC(=O)OC(C)(C)C)cc3)c(C#N)c3c2COC(C)(C)C3)CC1C] | (CDCl₃) 7.28 (d, 2H), 7.15 (d, 2H), 6.49 (b s, 1H), 4.54 (s, 2H), 3.49-3.37 (m, 6H), 3.34 (s, 3H), 2.98-2.86 (m, 4H), 2.80-2.74 (m, 6H), 1.52 (s, 9H), 1.32 (s, 6H), 1.12 (d, 6H) | 610.2 (M + 1) | Brown wax | 0.11 (1:1 Hexanes:EtOAc) |

-continued

Compound Characterization Data

| MBX # | Structure | ¹H NMR | Mass Spec. | Melting point | R$_f$ (eluents) |
|---|---|---|---|---|---|
| 86  3229 | | (MeOD) 7.43 (d, 2H), 7.18 (d, 2H), 4.54 (s, 2H), 3.85 (m, 2H), 3.55-3.43 (m, 4H), 2.96 (t, 2H), 2.72-2.64 (m, 8H), 1.32 (s, 6H), 1.15 (d, 6H) | 553.2 (M + 1) | Light brown crystals | 0.68 (100:10:1, EtOAc:MeOH:AcOH) |
| 87  3230 | | (CDCl$_3$) 7.98 (b s, 1H), 7.49 (d, 2H), 7.26 (d, 2H), 4.53 (s, 2H), 3.75 (m, 2H), 3.46-3.41 (m, 4H), 3.02 (t, 2H), 2.76 (s, 2H), 2.71 (dd, 2H), 1.33 (s, 6H), 1.19 (d, 6H) | 549.2 (M + 1) | Light brown solid | 0.78 (1:3 Hexanes:EtOAc) |
| 88  3249 | | (CDCl$_3$) 7.03 (d, 2H), 6.62 (d, 2H), 4.54 (s, 2H), 3.58-3.36 (m, 6H), 3.34 (s, 3H), 2.95-2.85 (m, 4H), 2.80-2.73 (m, 6H), 1.32 (s, 6H), 1.12 (d, 6H) | 510.2 (M + 1) | Brown wax | 0.80 (86:13:1 CHCl$_3$:MeOH:NH$_3$) |
| 89  3262 | | (CDCl$_3$) 7.20 (m, 2H), 6.98 (t, 2H), 4.54 (s, 2H), 3.49 (d, 2H), 3.42 (t, 2H), 2.99 (t, 4H), 2.75 (s, 2H), 2.56 (t, 2H), 1.33 (s, 6H), 1.08 (d, 6H) | 455.2 (M + 1) | White solid | 0.60 (86:13:1 CHCl$_3$:MeOH:NH$_3$) |
| 90  3263 | | (CDCl$_3$) 7.27 (d, 2H), 7.15 (d, 2H), 4.53 (s, 2H), 3.51 (d, 2H), 3.39 (t, 2H), 3.03-2.93 (m, 4H), 2.75 (s, 2H), 2.57 (t, 2H), 1.51 (s, 9H), 1.33 (s, 6H), 1.08 (d, 6H) | 552.0 (M + 1) | White solid | 0.57 (86:13:1 CHCl$_3$:MeOH:NH$_3$) |

-continued

Compound Characterization Data

| | MBX # | Structure | ¹H NMR | Mass Spec. | Melting point | R_f (eluents) |
|---|---|---|---|---|---|---|
| 91 | 3269A | (structure shown: 3,3-dimethyl-pyrano-pyridine core with CN, S-CH2CH2-C6H4-NHBoc, and 2,6-dimethylpiperazine-N-CH2COOH; CF3CO2H salt) | (DMSO) 9.24 (bs, 1H), 7.37 (d, 2H), 7.15 (d, 2H), 4.50 (s, 2H), 3.80 (bs, 2H), 3.67 (d, 2H), 3.41 (b m, 4H), 3.05 (m, 2H), 2.89 (t, 2H), 2.69 (s, 2H), 1.47 (s, 9H), 1.26 (s, 6H), 1.11 (d, 6H) | 609.9 (M + 1) | White solid | 0.11 (86:13:1 CHCl₃:MeOH:NH₃) |
| 92 | 3309A | (structure shown: 3,3-dimethyl-pyrano-pyridine core with CN, S-CH2CH2-C6H4-COOH, and 2,6-dimethylpiperazine; CF3CO2H salt) | (DMSO): 9.12 (br d, 1H), 8.48 (br q, 1H), 7.89 (d, 2H), 7.43 (d, 2H), 4.56 (s, 2H), 3.80 (d, 2H), 3.52 (t, 2H), 3.46 (m, 2H), 3.09 (t, 2H), 2.92 (dd, 2H), 2.73 (s, 2H), 1.28 (s, 6H), 1.19 (d, 6H) | 481.1 (M + 1) | White solid | 0.0 (10:1 EtOAc:MeOH) |
| 93 | 3310 | (structure shown: 3,3-dimethyl-pyrano-pyridine core with CN, S-CH2CH2-C6H4-F, and 2,6-dimethylpiperazine with N-acryloyl) | (DMSO): 7.17 (dd, 2H), 6.98 (dd, 2H), 6.60 (dd, 1H), 6.39 (d, 1H), 5.74 (d, 1H), 4.71 (s, 2H), 4.55 (br m, 2H), 3.44 (d, 2H), 3.42 (d, 2H), 3.01 (m, 2H), 2.98 (t, 2H), 2.78 (s, 2H), 1.46 (d, 6H), 1.34 (s, 6H) | 509.2 (M + 1) | White solid | 0.19 (1:1 EtOAc:Hexanes) |
| 94 | 3311A | (structure shown: 3,3-dimethyl-pyrano-pyridine core with CN, S-CH2CH2-C6H4-NHC(O)CH=CH2, and 2,6-dimethylpiperazine; CF3CO2H salt) | (DMSO): 10.12 (s, 1H), 9.06 (br d, 1H), 8.44 (br q, 1H), 7.61 (d, 2H), 7.25 (d, 2H), 6.44 (dd, 1H), 6.25 (d, 1H), 5.75 (d, 1H), 4.56 (s, 2H), 3.79 (d, 2H), 3.45 (m, 4H), 2.95 (m, 4H), 2.73 (s, 2H), 1.28 (s, 6H), 1.21 (d, 6H) | 506.2 (M + 1) | White solid | 0.50 (86:13:1 CHCl₃:MeOH:NH₃) |

| | MBX # | Structure | $^1$H NMR | Mass Spec. | Melting point | $R_f$ (eluents) |
|---|---|---|---|---|---|---|
| 95 | 3324 | 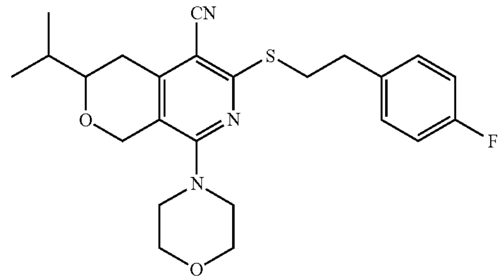 [SMILES: CC(C)C1Cc2c(C#N)c(SCCc3ccc(F)cc3)nc(N3CCOCC3)c2CO1] | (CDCl$_3$) 7.18 (dd, 2H), 6.99 (t, 2H), 4.64 (d, 1H), 4.48 (d, 1H), 3.88-3.70 (m, 4H), 3.45-3.19 (m, 7H), 2.99 (t, 2H), 2.85 (dd, 1H), 2.72 (dd, 1H), 1.82 (m, 1H), 1.04 (d, 3H), 1.00 (d, 3H) | 442.2 (M + 1) | yellow crystalline solid | 0.69 (1:1 Hexanes:EtOAc) |
| 96 | 3325 | 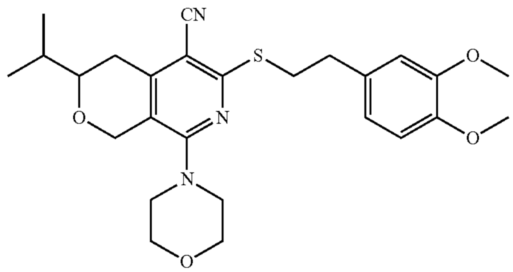 [SMILES: COc1ccc(CCSc2nc(N3CCOCC3)c3c(c2C#N)CC(C(C)C)OC3)cc1OC] | (DMSO) 6.86 (d, 1H), 6.85 (s, 1H), 6.75 (d, 1H), 4.60 (d, 1H), 4.50 (d, 1H), 3.77-3.71 (m, 8H), 3.67-3.60 (m, 2H), 3.46-3.20 (m, 7H), 2.89 (t, 2H), 2.80 (dd, 1H), 2.49 (dd, 1H), 1.75 (m, 1H), 0.97 (d, 3H), 0.94 (d, 3H) | 484.2 (M + 1) | Red-brown solid | 0.43 (1:1 Hexanes:EtOAc) |
| 97 | 3327 | 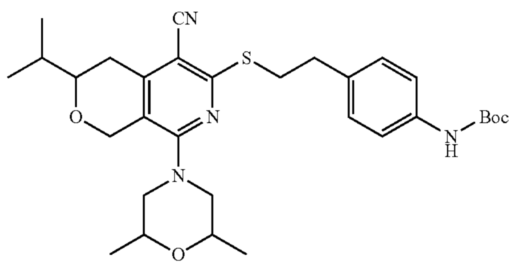 [SMILES: CC1CN(c2nc(SCCc3ccc(NC(=O)OC(C)(C)C)cc3)c(C#N)c3c2COC(C(C)C)C3)CC(C)O1] | (CDCl$_3$) 7.27 (d, 2H), 7.14 (d, 2H), 6.43 (br s, 1H), 4.60 (d, 1H), 4.49 (d, 1H), 3.82 (m, 1H), 3.66 (m, 1H), 3.47-3.34 (m, 5H), 2.98-2.80 (m, 4H), 2.70 (dd, 1H), 2.55 (dd, 1H), 1.82 (m, 1H), 1.51 (s, 9H), 1.20 (d, 3H), 1.17 (d, 3H), 1.04 (d, 3H), 1.00 (d, 3H) | 567.0 (M + 1) | Brown foamy solid | 0.74 (1:1 Hexanes:EtOAc) |
| 98 | 3330 | 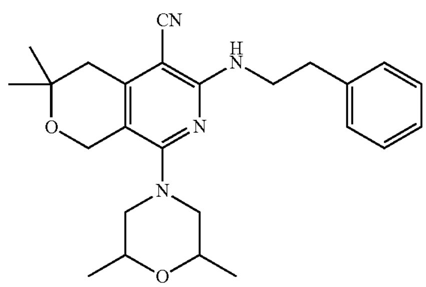 [SMILES: CC1CN(c2nc(NCCc3ccccc3)c(C#N)c3c2COC(C)(C)C3)CC(C)O1] | (CDCl$_3$) 7.31-7.21 (m, 5H), 5.08 (t, 1H), 4.50 (s, 2H), 3.75 (m, 2H), 3.68 (dd, 2H), 3.42 (d, 2H), 2.90 (t, 2H), 2.69 (s, 2H), 2.67 (dd, 2H), 1.32 (s, 6H), 1.24 (d, 6H) | 421.3 (M + 1) | Pale yellow solid | 0.62 (1:1 EtOAc:Hexanes) |
| 99 | 3335 | 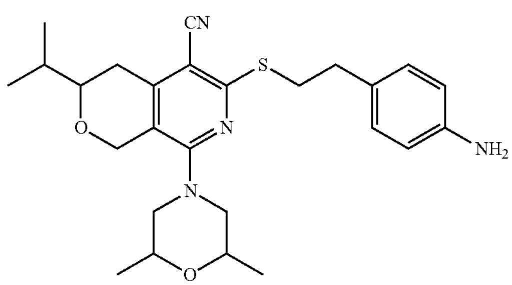 [SMILES: CC1CN(c2nc(SCCc3ccc(N)cc3)c(C#N)c3c2COC(C(C)C)C3)CC(C)O1] | (CDCl$_3$) 7.02 (d, 2H), 6.63 (d, 2H), 4.62 (d, 1H), 4.49 (d, 1H), 3.82 (m, 1H), 3.66 (m, 1H), 3.75-3.45 (br s, 2H), 3.47-3.28 (m, 5H), 2.91-2.81 (m, 4H), 2.71 (dd, 1H), 2.55 (dd, 1H), 1.81 (sep, 1H), 1.21 (d, 3H), 1.18 (d, 3H), 1.04 (d, 3H), 1.00 (d, 3H) | 467.1 (M + 1) | Yellow solid | 0.30 (1:1 Hexanes:EtOAc) |

Compound Characterization Data

| MBX # | | Structure | ¹H NMR | Mass Spec. | Melting point | R_f (eluents) |
|---|---|---|---|---|---|---|
| 100 | 3336 | 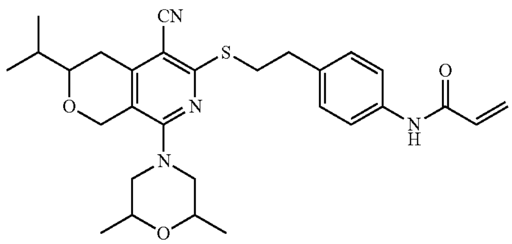 [SMILES: C=CC(=O)Nc1ccc(CCSc2nc(N3CC(C)OC(C)C3)c3c(c2C#N)CC(C(C)C)OC3)cc1] | (CDCl₃) 7.50 (d, 2H), 7.39 (s, 1H), 7.19 (d, 2H), 6.43 (d, 1H), 6.24 (dd, 1H), 5.76 (d, 1H), 4.60 (d, 1H), 4.48 (d, 1H), 3.83 (m, 1H), 3.65 (m, 1H), 3.47-3.34 (m, 5H), 2.98 (t, 2H), 2.86 (dd, 1H), 2.80 (d, 1H), 2.70 (dd, 1H), 2.55 (dd, 1H), 1.81 (sep, 1H), 1.22 (d, 3H), 1.18 (d, 3H), 1.04 (d, 3H), 1.00 (d, 3H) | 521.2 (M + 1) | Pale yellow solid | 0.39 (1:1 Hexanes:EtOAc) |
| 101 | 3347 | 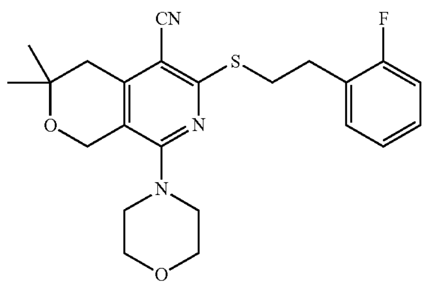 [SMILES: CC1(C)Cc2c(C#N)c(SCCc3ccccc3F)nc(N3CCOCC3)c2CO1] | (CDCl₃) 7.25-7.18 (m, 2H), 7.10-6.99 (m, 2H), 4.56 (s, 2H), 3.81 (t, 4H), 3.46 (t, 2H), 3.30 (t, 4H), 3.06 (t, 2H), 2.76 (s, 2H), 1.33 (s, 6H) | 428.2 (M + 1) | Pale yellow solid | 0.66 (1:1 Hexanes:EtOAc) |
| 102 | 3348 | 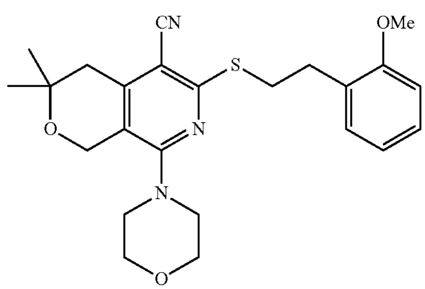 [SMILES: COc1ccccc1CCSc1nc(N2CCOCC2)c2c(c1C#N)CC(C)(C)OC2] | (CDCl₃) 7.24-7.13 (m, 2H), 6.92-6.84 (m, 2H), 4.56 (s, 2H), 3.83 (s, 3H), 3.80 (t, 4H), 3.45 (t, 2H), 3.29 (t, 4H), 3.02 (t, 2H), 2.76 (s, 2H), 1.32 (s, 6H) | 440.1 (M + 1) | Pale yellow grease | 0.66 (1:1 Hexanes:EtOAc) |
| 103 | 3353 | 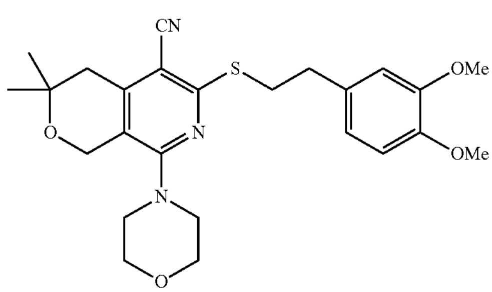 [SMILES: COc1ccc(CCSc2nc(N3CCOCC3)c3c(c2C#N)CC(C)(C)OC3)cc1OC] | (CDCl₃) 6.83-6.75 (m, 3H), 4.56 (s, 2H), 3.88 (s, 3H), 3.86 (s, 3H), 3.80 (t, 4H), 3.43 (t, 2H), 3.29 (t, 4H), 2.96 (t, 2H), 2.76 (s, 2H), 1.33 (s, 6H) | 470.2 (M + 1) | Foamy white solid | 0.43 (1:1 Hexanes:EtOAc) |
| 104 | 3354 | 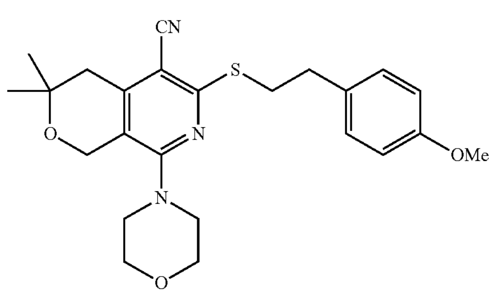 [SMILES: COc1ccc(CCSc2nc(N3CCOCC3)c3c(c2C#N)CC(C)(C)OC3)cc1] | (CDCl₃) 7.17 (d, 2H), 7.10 (d, 2H), 4.55 (s, 2H), 3.81 (t, 4H), 3.79 (s, 3H), 3.41 (t, 2H), 3.29 (t, 4H), 2.96 (t, 2H), 2.76 (s, 2H), 1.32 (s, 6H) | 440.2 (M + 1) | Pale yellow solid | 0.56 (1:1 Hexanes:EtOAc) |

Example 2

Determination of Efflux Pump Inhibitory Effect and Antimicrobial Potentiating Effect of Select Compounds Strains and Reagents. The bacterial strains used in this study are listed in Table 1. The following strains were obtained from the Keio collection (Baba, et al.: Construction of *Escherichia coli* K-12 in-frame, single-gene knockout mutants: the Keio collection. In Mol Syst Biol, vol. 2, pp. 2006 0008, (2006)): JW0451 (ΔacrB::kan), JW5503 (ΔtolC::kan), JW3234 (ΔacrF::kan), JW2661 (ΔemrB::kan), JW0863 (ΔmacB::kan). The deletion mutations in each of these strains were transferred to AB1157 using P1 phage transduction (see Table 1). The construction of the *E. coli* cell-based reporter strain (SOS-XXX) that was used for high throughput screening is described in detail in the supplementary information. Ciprofloxacin was purchased from ICN Biomedicals (Aurora, Ohio). Irgasan was a generous gift from Ciba Speciality Chemicals, Inc. (High Point, N.C.). Hoechst 33342 (H33342) was purchased from Molecular Probes (Eugene, Oreg.). The following reagents were purchased from Sigma Aldrich (St. Louis, Mo.): phenyl-arginine-β-naphthylamide (PAβN), cyanide-m-chlorophenyl hydrazone (CCCP), Levofloxacin, Norfloxacin, Naladixic acid, Piperacillin, Cloxacillin, Oxacillin, Cloramphenicol, Tetracycline, Ethidium Bromide, Gentamicin, Crystal violet, Cephalexin, Amoxacillin, Rifampicin, and Cefotaxime. Luria Broth (Miller) and agar were purchased as prepared dehydrated media from Becton Dickenson (Franklin Lakes, N.J.). The compound libraries used in high-throughput screens were purchased from Chembridge (San Diego, Calif.), ChemDiv (San Diego, Calif.), and TimTec (Newark, Del.). MBX2319 was synthesized by Microbiotix, Inc.

Antibacterial Activity Assays. The minimal inhibitory concentration (MIC) of antibacterial agents and biocides were determined using the microbroth dilution method essentially as described in the CLSI protocol M7-A7 (CLSI: Method for dilution antimicrobial susceptibility testing for bacteria that grow aerobically; Approved standard-document M7-A7. In Clinical and Laboratory Standards Institute document M7-A7, Clinical and Laboratory Standards Institute, Wayne, Pa., (2006)), with the following exceptions. LB media was used instead of MHB. Serial two-fold dilutions of test compounds were made in DMSO at concentrations 50-fold higher than the final concentration: the diluted compounds were added to the assay plates, and 100 µl of the inocula was added to each well. The final concentration of DMSO in each assay was 2%. When indicated, MIC assays were performed in the presence of an efflux pump inhibitor (EPI) at a final concentration of 25 µM. MIC assays were performed in triplicate and the geometric mean was calculated. Checkerboard MIC assays using an EPI and an antibacterial agent were performed essentially as described (Pillai, et al.: Antimicrobial Combinations. In Antibiotics in Laboratory Medicine, ed. by V. Lorian, pp. 365-440, Lippincott Williams & Wilkins, Philadelphia, Pa., (2005)), with the same modifications used for the MIC assays described above.

Time-Kill Assays. Killing curve assays were performed essentially as described (Pillai, et al.: Antimicrobial Combinations. In Antibiotics in Laboratory Medicine, ed. by V. Lorian, pp. 365-440, Lippincott Williams & Wilkins, Philadelphia, Pa., (2005)). Exponential bacterial cultures grown in LB were diluted to a cell density of ~1×10$^7$ in LB followed by addition of CIP and/or an EPI. Viability was monitored over 2-4 hours by making serial dilutions in saline and spotting 5 µl of each dilution onto the surface of an LB agar plate in triplicate. Colonies were counted after the plates were incubated at 37° C. for 16-18 hr, colony forming units (CFU) per ml were calculated, and the average and standard deviation for the three replicates was determined. For treatments that decreased CFU/ml below the limit of detection for the spot plating method, the 100 µl samples were diluted into 5 ml LB top agar, were poured onto LB agar plates, and incubated for 18 hr at 37° C. To calculate the fraction of the control for each sample, the average CFU/ml values for treated samples were divided by those from the same sample at 0 h (time=0). Each experiment was repeated at least three times, and a representative experiment is shown.

H33342 Accumulation Assay. The rate of accumulation of the fluorescent dye Hoechst 33342 (H33342), which is a substrate of a wide variety of bacterial efflux pumps (van den Berg van Saparoea, et al., Biochemistry, vol. 44, pp. 16931-16938, (2005)), can be used to estimate the activity of the major efflux pumps in *E. coli* and many other bacterial species. The H33342 accumulation assay was used to evaluate the effect of EPIs on the activity of the AcrAB-TolC efflux pump in several bacterial species essentially as described (Coldham, et al., J Antimicrob Chemother, vol. 65, pp. 1655-1663, (2010)). Briefly, bacterial cultures were grown overnight in LB (Miller) with aeration at 37° C. and were used to inoculate fresh cultures (1:100 dilution) that were grown in LB (Miller) with aeration until an optical density at 600 nm (OD$_{600}$) of 0.4-0.6 was reached. Bacterial cells were harvested by centrifugation, and the cell pellet was washed with a volume of PBSM+G (PBS containing 1 mM MgSO$_4$ and 20 mM glucose) equivalent to the original volume of the culture. After centrifugation, the cell pellets were resuspended in PBSM+G and the OD600 of each suspension was adjusted to 0.2. Aliquots of 190 µl were transferred to the wells of a 96-well assay plate (Costar 3515, Corning, N.Y.; flat bottom, black plate). Various concentrations of test compounds dissolved in DMSO or an equivalent volume of solvent alone were added to a total of 8 assay wells (one column of wells) for each condition tested. The final concentration of DMSO in all assays was 2%. The assay plates were incubated at 37° C. for 15 min, and 10 µl of a solution of 50 µM H33342 in PBSM+G was added to each assay well, resulting in a final dye concentration of 2.5 µM. Fluorescence (excitation and emission filter of 355 and 460 nm, respectively) of each well was measured at 37° C. every 5 min for 30 min using a Victor$^2$ V 1420 Multilabel HTS Counter (Perkin Elmer, Waltham, Mass.). The average values and standard deviations for the eight replicates for each condition were calculated using Microsoft Excel. Each experiment was repeated at least three times, and a representative experiment is shown.

2.2. MBX2319 Potentiates the Antibacterial Activity of Fluoroquinolone and β-Lactam Antibiotics Against *E. coli*.

Figure 2:
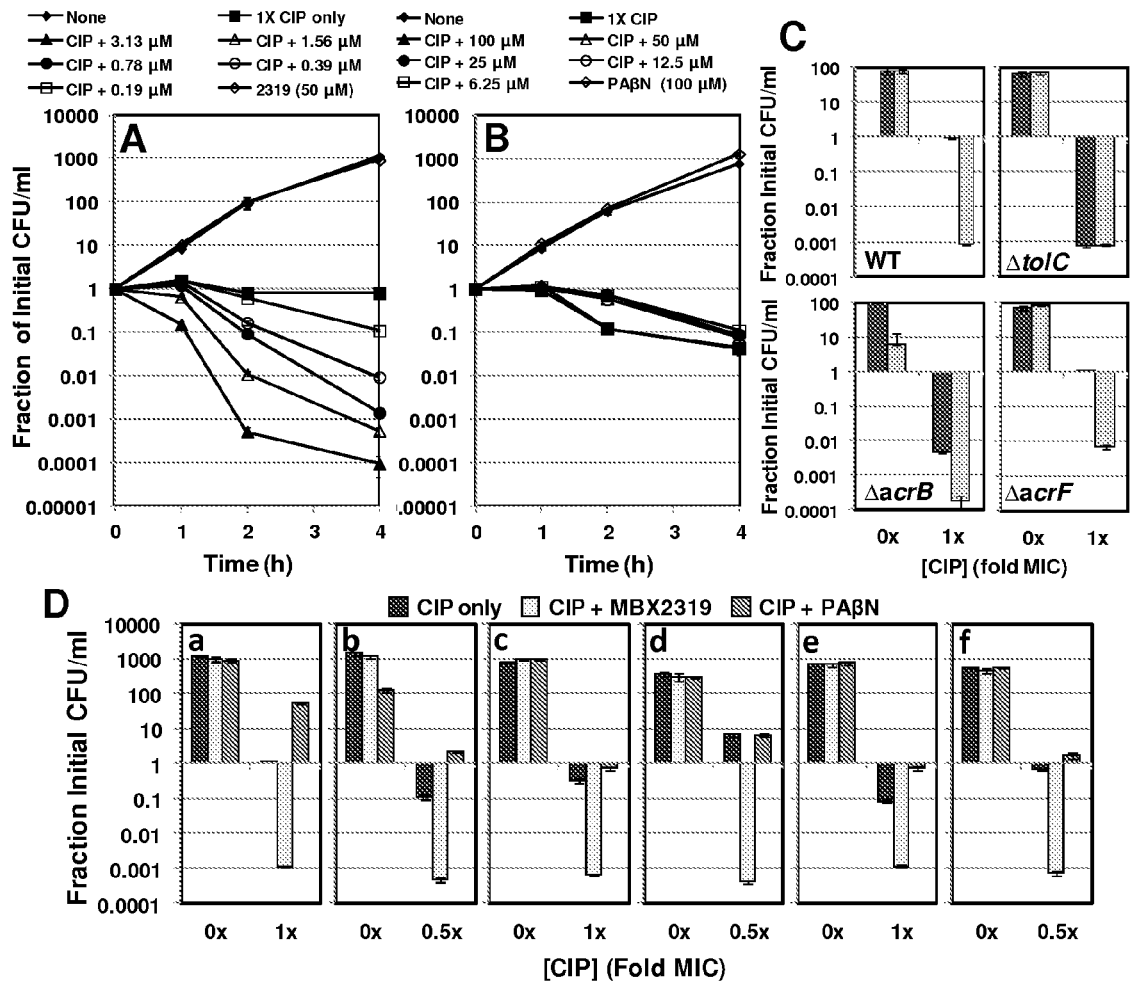
FIG. 2A-2D are graphs illustrating the effects of the efflux pump inhibitors MBX2319 and PAβN on the bactericidal activity of ciprofloxacin (CIP) in time-kill assays. Panel (A): Bactericidal activity of varying concentrations of MBX2319 (0.19-3.13 μM) combined with a bacteriostatic concentration of CIP (1×MIC, 0.01 μg/ml) against *E. coli* AB1157. Panel (B): Bactericidal activity of varying concentrations of PAβN (6.25-100 μM) combined with a bacteriostatic concentration of CIP (1×MIC, 0.01 μg/ml) against *E. coli* AB1157. Panel (C): Bactericidal activity of CIP alone, 25 μM MBX2319 alone, or 25 μM MBX2319 combined with a bacteriostatic concentration of CIP against *E. coli* AB1157 and isogenic efflux defective mutants after 2 hours exposure. Dark bars, CIP alone (0×(control) and 1×MIC, 0.01 μg/ml); Light bars CIP (Ox and 1×MIC, 0.01 μg/ml)+25 μM MBX2319. Panel (D): Bactericidal activity of CIP alone, 25 μM MBX2319 alone, 25 μM PAβN alone, and a bacteriostatic concentration of CIP combined with 25 μM MBX2319 or combined with 25 μM PAβN against the following organisms: a) *E. coli* AB1157, b) *E. coli* ATCC 25922, c) *K. pneumoniae* ATCC 700603, d) *S. flexneri* ATCC 12022, e) *S. enterica* ATCC 14028, f) *E. aerogenes* ATCC 13048.

We utilized the checkerboard assay to determine whether MBX2319 potentiates the activity of two fluoroquinolones, ciprofloxacin (CIP) and levofloxacin (LEV), and a β-lactam, piperacillin (PIP), against *E. coli* AB1157. The data, shown in Table 2, demonstrate that MBX2319 decreases the MICs of CIP, LEV, and PIP by 2, 4, and 8-fold, respectively. MBX2319 alone did not exhibit antibacterial activity (MIC≥100 µM). In addition, MBX2319 increased the bactericidal activity of 0.016 µg/ml CIP (1×MIC), which is a bacteriostatic against *E. coli* AB1157, in a dose-dependent manner (FIG. 2A). The highest concentration of MBX2319 (3.13 µM) decreased viability (CFU/ml) by 10,000 fold after 4 hr exposure, as compared to 1×MIC CIP alone. In contrast, MBX2319 alone at concentrations up to 50 µM did not affect growth. As a comparison, we measured the effect of various concentrations of phenyl-arginine-β-naphthylamide (PAβN), a known EPI (Lomovskaya, et al., Antimicrob Agents Chemother, vol. 45, pp. 105-116, (2001)), in combination with 0.016 µg/ml CIP in the time kill assay. The results of the assay are shown in FIG. 2B and demonstrate that PAβN at concentrations as high as 100 µM did not increase the bactericidal activity of 0.016 µg/ml CIP.

2.3. MBX2319 is an Efflux Pump Inhibitor (EPI).

To verify that the mechanism by which MBX2319 potentiates the antibacterial activity of fluoroquinolones and β-lactams is inhibition of efflux, we determined whether MBX2319 potentiated the antibacterial activity of CIP, LEV, and PIP against a panel of efflux-defective mutants of *E. coli* AB1157. We reasoned that the antibiotic sensitivity of mutants lacking the target of MBX2319 would not be affected by the compound. The results of a checkerboard assay, shown in Table 2, demonstrate that the MICs for the ΔtolC and ΔacrB mutants were not affected by MBX2319, whereas, mutants defective in other pumps that interact with TolC, such as AcrF (Table 2), MacB, and EmrB (data not shown) exhibited MIC shifts similar to WT Similarly, MBX2319 potentiated the bactericidal activity of CIP against the ΔacrF strain, but not against ΔtolC and ΔacrB strains (FIG. 2C). Finally, MBX2319 potentiated the antibacterial activity of CIP, LEV, and PIP by 4-8 fold against *E. coli* strains 285 and 287 (Table 2), which are CIP$^R$ mutants of *E. coli* AB1157 that were selected during a serial passage in subinhibitory concentrations of CIP, and exhibit increased efflux activity (see supplementary data). These findings indicate that the AcrAB-TolC efflux pump, which is the major efflux pump in *E. coli* (Okusu, et al., J Bacteriol, vol. 178, pp. 306-308, (1996)), is the target of MBX2319.

Figure 3:
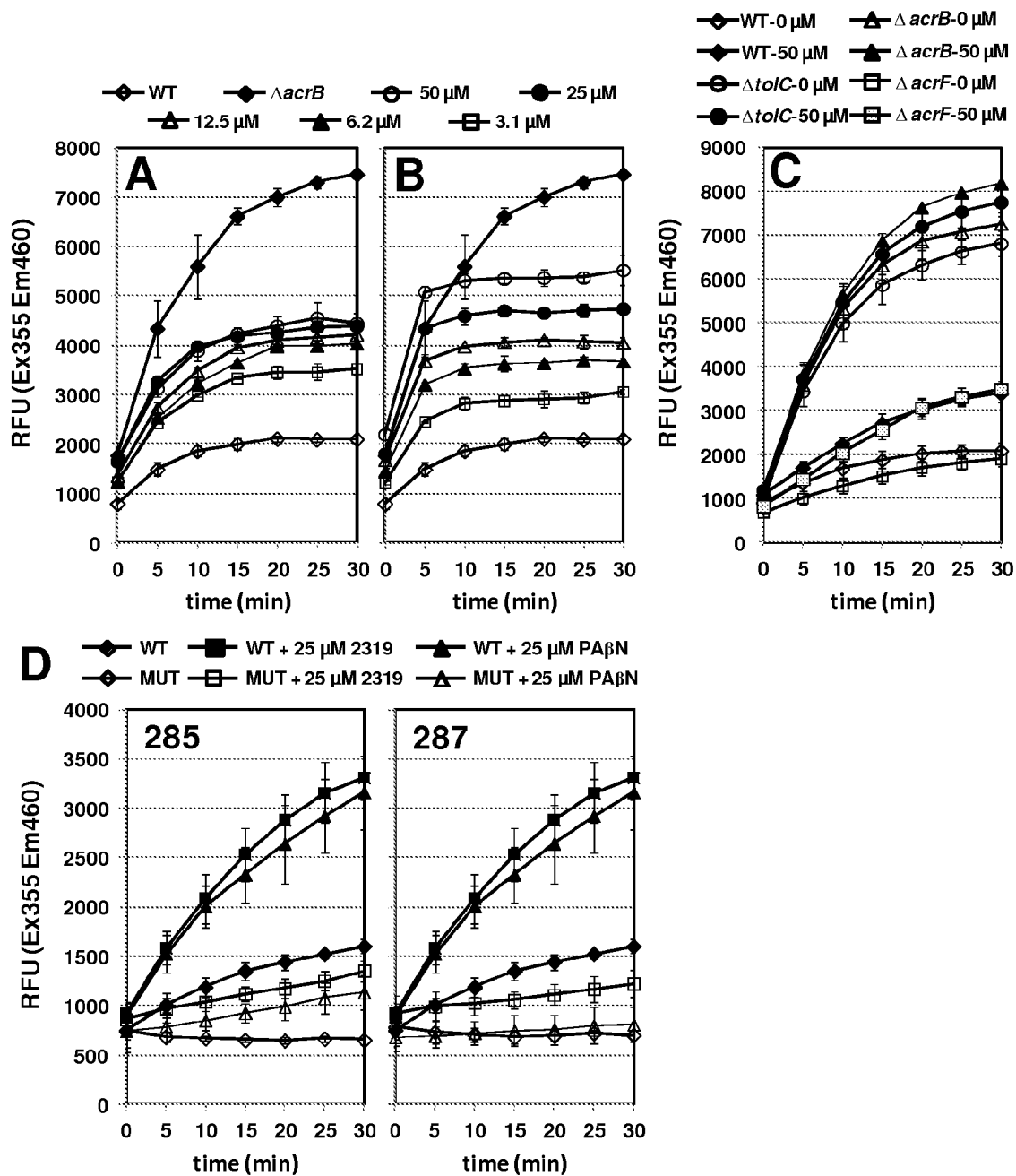
FIG. 3A-3D are graphs illustrating the effects of EPIs MBX2319 and PAβN on the accumulation of the fluorescent DNA-binding dye H33342, an AcrAB efflux pump substrate, in *E. coli* AB1157. Panel (A): effect of MBX2319 at varying concentrations (3.1-50 μM), Panel (B): effect of PAβN at varying concentrations (3.1-50 μM), Panel (C): effect of MBX2319 on H33342 accumulation in *E. coli* AB1157 and isogenic efflux-defective mutants, Panel (D): effect of MBX2319 on H33342 accumulation in *E. coli* AB1157 and isogenic mutants 285 and 287, which exhibit reduced susceptibility to Ciprofloxacin due to overexpression of efflux pumps.
Figure 4:
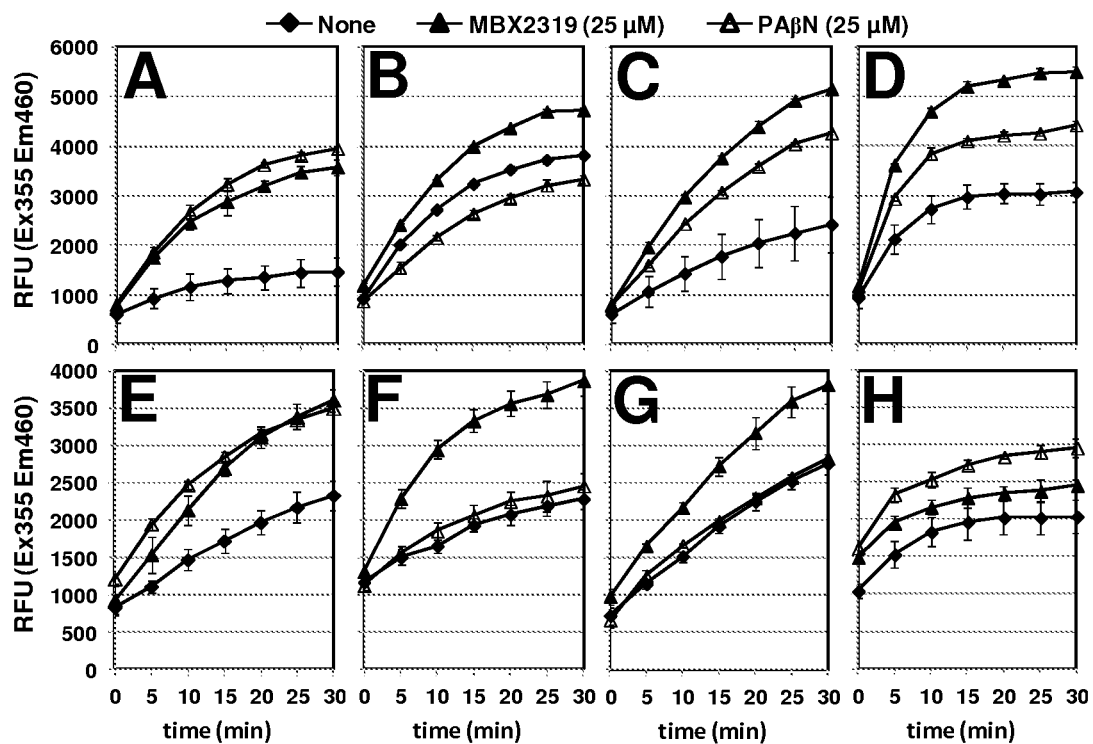
FIG. 4A-4H are graphs illustrating the effects of MBX2319 and PAβN on the accumulation of H33342 in various Gram-negative organisms. Panel (A): effects on *E. coli* AB1157, Panel (B): effects on *E. coli* 331, Panel (C): effects on *Shigella flexneri* ATCC 12022, Panel (D): effects on *Klebsiella pneumoniae* ATCC 13882, Panel (E): effects on *Salmonella enterica* (*typhimurium*) ATCC 14028, Panel (F): effects on *Enterobacter cloacae* subsp. *cloacae* ATCC 13047, Panel (G): effects on *Proteus mirabilis* ATCC 25933, Panel (H): effects on *Pseudomonas aeruginosa* ATCC 27835.

To confirm MBX2319 directly inhibits efflux, we used an assay that measures the accumulation of the fluorescent DNA-binding dye Hoechst 33342 (H33342), which is a substrate of the AcrAB-TolC pump, in *E. coli* AB1157. This assay has been used to estimate efflux activity in *E. coli* and *S. enterica* (Coldham, et al., J Antimicrob Chemother, vol. 65, pp. 1655-1663, (2010)). When H33342 enters the cell it binds to the minor DNA and becomes fluorescent and can be detected using a fluorescent plate reader (Ex 355, Em460). Efflux-competent cells extrude H33342 and accumulate the dye at a relatively slow rate, resulting in low levels of fluorescence. Conversely, efflux-defective cells accumulate intracellular levels of H33342, resulting in higher levels of fluorescence. The results of the H33342 accumulation assay are shown in FIGS. 3A and B. The ΔacrB strain was used as a positive control, indicating the maximum levels of H33342 accumulation possible. MBX2319 (FIG. 3A) and PAβN (FIG. 3B) increased accumulation of H33342 as compared to the untreated control in a dose-dependent manner. However, the dose response of MBX2319 was not proportional at higher concentrations (25-50 µM), probably due to decreased solubility of the compound in phosphate buffers (15-20 µMsolubility limit). At a concentration of 25 µM, MBX2319 and PAβN increased H33342 accumulation to levels that were about 45% and 52% of the ΔacrB strain, respectively. MBX2319 was more effective in this assay at lower concentrations (3.1-12.5 µM) than was PAβN. Both compounds increased H33342 accumulation in the hyper-efflux strains 285 and 287 (see FIG. 3D).

2.4. MBX2319 Potentiates the Activity of Multiple Antibiotics and Biocides.

Efflux pump inhibitors are known to increase the antibacterial activity of a diverse group of antibiotics and biocides (Nikaido, et al., FEMS Microbiol Rev, vol. 36, pp. 340-363, (2012)). To test this prediction, we measured the ability of MBX2319 to increase the susceptibility of *E. coli* AB1157 to a broad spectrum of antibiotics and biocides. The data, shown in Table 3, demonstrate that MBX2319 increased susceptibility to several known AcrAB-TolC substrates, such as CIP, LEV, nalidixic acid, PIP, oxacillin, and chloramphenical, but not to gentamicin and cephalexin, which are not substrates. In general, the MIC shifts produced by MBX2319 were lower than those of the ΔacrB strain, but were similar to those produced by PAβN for fluoroquinolone and β-lactam antibiotics.

2.5. Determination of Spectrum of Activity.

To determine whether MBX2319 inhibits the AcrAB-TolC orthologs of other Gram-negative pathogens, we measured the antibacterial activity of MBX2319 in combination with several antibiotics using two assays. First, we measured the MICs of several antibiotics, alone or in combination with MBX2319 or PAβN at a concentration of 25 µM against several Gram-negative pathogens. The data are shown in Table 5. For all species tested, with the exception of *P. aeruginosa*, MBX2319 significantly increased the activity of the fluoroquinolones CIP and LEV, whereas, PAβN did not significantly affect the MICs at the concentration tested (25 µM). MBX2319 and PAβN increased the activity of PIP and CEF against the majority of organisms tested; however, MBX2319 was active against more organisms than was PAβN. In addition, MBX2319 increased the activity of CIP and LEV against *E. coli* 331, which is resistant to fluoroquinolones. Interestingly, MBX2319 increased the activity of CEF against *P. aeruginosa*.

The time kill assay was used to verify the potentiating activity of 25 µM MBX2319 against Gram-negative pathogens (FIG. 2D). The combination of MBX2319 and a bacteriostatic concentration of CIP (0.5 or 1×MIC) decreased viability of *Shigella flexneri, Salmonella enterica, Enterobacter aerogenes*, and *Klebsiella pneumoniae*, by 100-1000 fold as compared to CIP alone. In contrast, 25 µM PAβN was not effective against any of the strains tested in this assay. The H33342 accumulation assay was used to verify that MBX2319 inhibits efflux in other Gram-negative pathogens. The results of this assay are shown in FIG. 4A-H. MBX2319 (25 µM) increased H33342 accumulation in the majority of organisms tested, including *Shigella flexneri, K pneumoniae, S. enterica, E. cloacae, Proteus mirabilis*, and showed weak activity against *E. coli* 331 (CIP$^R$) and *P. aeruginosa*.

2.6. MBX2319 Increases Antibacterial Activity of Levofloxacin and Piperacillin Against a Diverse Panel of *E. coli* Strains.

Figure 5:
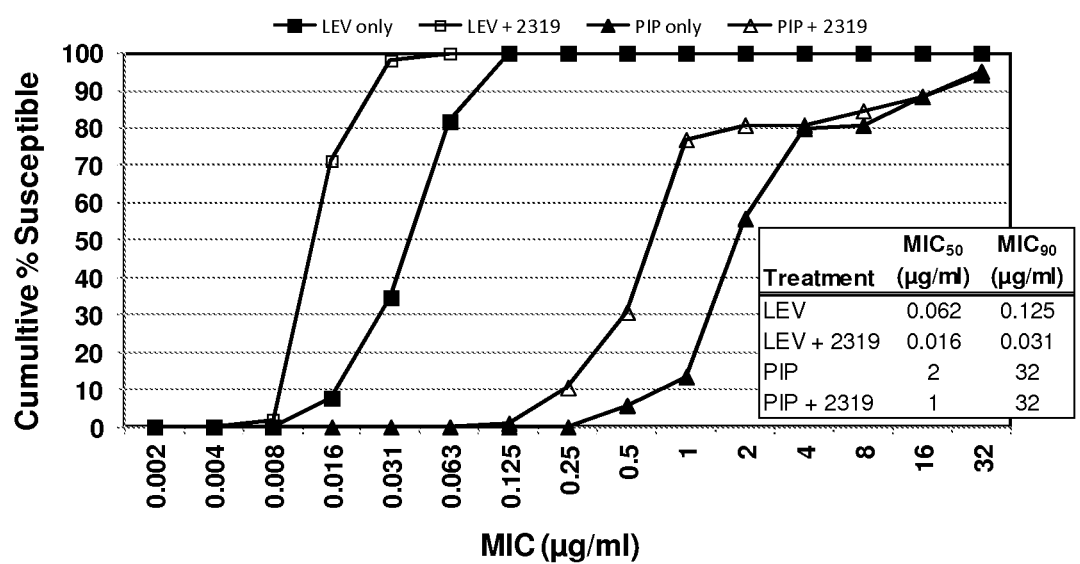
FIG. 5 is a graph showing the cumulative MICs for levofloxacin and piperacillin against a panel of 26 strains of *E. coli* strains in the absence and presence of 25 μM MBX2319.

To determine whether MBX2319 increases the antibacterial activity of LEV and PIP against a diverse panel of *E. coli* strains, we measured MICs for LEV and PIP in the absence and presence of 25 µM compound. The panel of 24 strains (see Table 5) is comprised of strains that were publically available clinical isolates; however, none of the strains were resistant to high levels of fluoroquinolones. MBX2319 decreased the MIC$_{50}$ and MIC$_{90}$ values for LEV (the concentration of LEV that inhibits growth of 50% and 90% of the strains, respectively) by four fold (FIG. 5). In contrast, MBX2319 did not have a significant effect on the $MIC_{50}$ or $MIC_{90}$ values for PIP, probably because ~20% of strains appeared to resistant to PIP, as evidenced by the plateau in the cumulative % susceptible at ~80%. The most likely reason for this observation is that these strains express a beta-lactamase enzyme that can reduce or eliminate the effectiveness of the beta-lactam antibiotic.

2.7. Antimicrobial Potentiating Effect of Selected Compounds Determined by MIC Reduction.

The ability of each analog to potentiate the activity of levofloxacin (LEV) and piperacillin (PIP) was measured using the checkerboard MIC assay as described above. The minimum potentiation concentration (MPG), which is the minimum concentration of compound that decreases the MIC by n-fold (n=2, 4, or 8 fold), was determined for each compound. The data, shown in Table 6, indicates that the analogs exhibited a wide range of MPC values for LEV and PIP.

Figure 6:
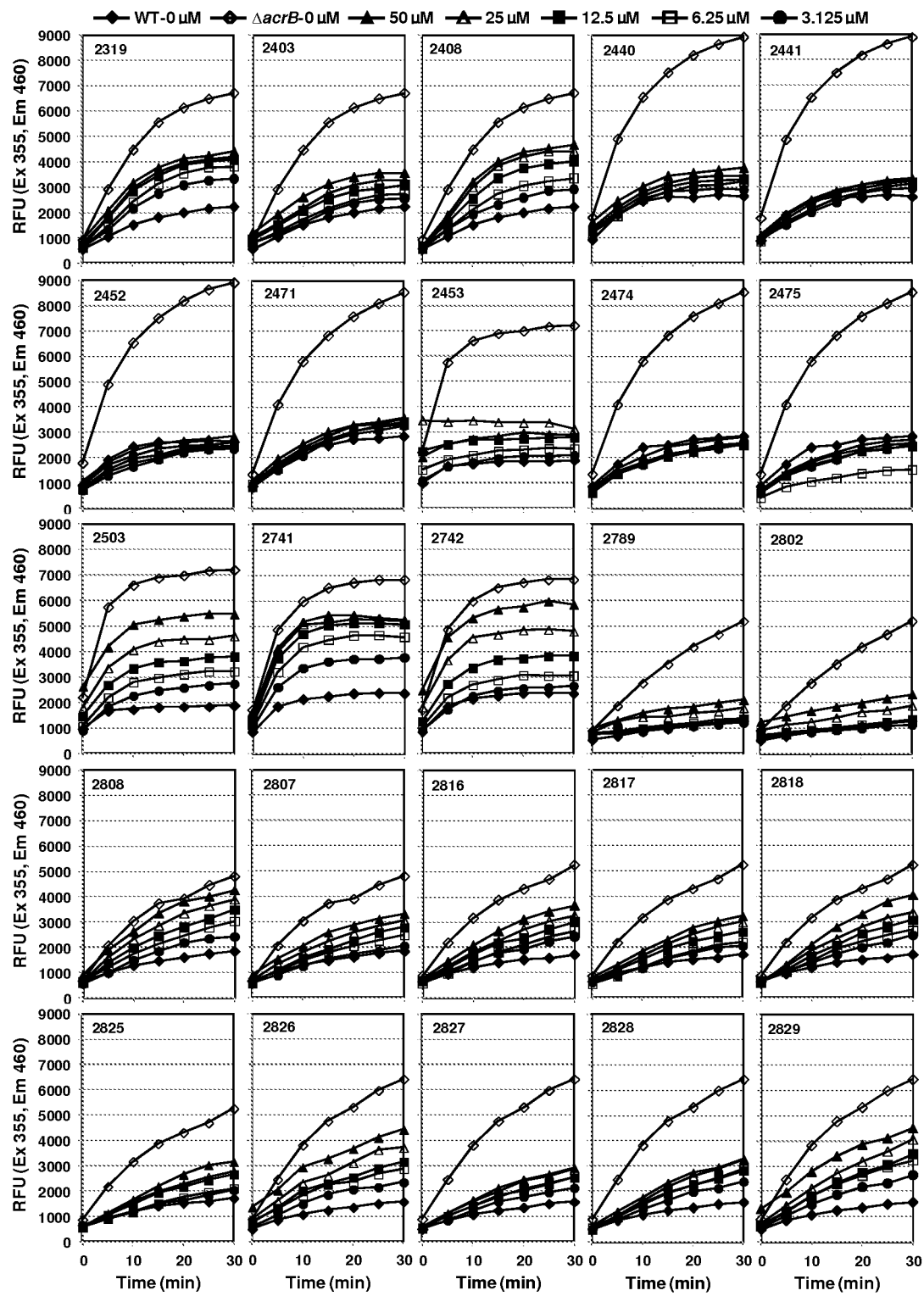
FIG. 6 shows a series of graphs evaluating the inhibition of efflux pump activity in *Escherichia coli* AB1157 by MBX2319 and several additional inhibitor compounds of the invention (see Example 1.4, infra) using the H33342 accumulation assay.

2.8. Antimicrobial Potentiating Effect of Selected Compounds Determined by Percent Increase in H33342 Accumulation Compounds with MPC4 values ≤25 µM for LEV or PIP were tested in the H33342 accumulation assay as described above. The data for each of these compounds are shown in FIG. 6. The percent increase in H33342 accumulation as compared to the ΔacrB strain was calculated for each compound at a concentration of 25 µM. The data from this analysis is presented in Table 7.

TABLE 1

Bacterial strains used in this study.

| Organism | Strain | Genotype/Description | Source (Ref) |
|---|---|---|---|
| *Escherichia coli* | AB1157 | thr-1, araC14, leuB6(Am), Δ(gpt-proA)62, lac Y1, tsx-33, qsr'-0, glnV44(AS), galK2(Oc), LAM-, Rac-0, hisG4(Oc), rfbC1, mgl-51, rpoS396(Am), rpsL31(strR), kdgK51, xylA5, mtl-1, argE3(Oc), thi-1 | (Dewitt, et al.: The Occurrence of a Genetic Transposition in a Strain of *Escherichia Coli*. In Genetics, vol. 47, pp. 577-585, (1962)) |
| *Escherichia coli* | ΔtolC | AB1157, ΔtolC::kan | this study |
| *Escherichia coli* | ΔacrB | AB1157, ΔacrB::kan | this study |
| *Escherichia coli* | ΔacrF | AB1157, ΔacrF::kan | this study |
| *Escherichia coli* | ΔmacB | AB1157, ΔmacB::kan | this study |
| *Escherichia coli* | ΔemrB | AB1157, ΔemrB::kan | this study |
| *Escherichia coli* | 285 | AB1157, $CIP^R$, Overexpresses efflux* | this study |
| *Escherichia coli* | 287 | AB1157, $CIP^R$, Overexpresses efflux* | this study |
| *Escherichia coli* | 331 | $CIP^R$, UTI isolate | Baylor College of Medicine |
| *Escherichia coli* | ATCC 25922 | | ATCC# |
| *Escherichia coli* | HN1157 | F', araD139, Δ(argF-lac)U169, rpsL150, rel-I, flb-5301, ptsF25, deoCI, thi-J, ΔlamB106, ΔompF80, zei06::Tn10, ompCI24, acrR::kan | (Nagano, et al.: Kinetic behavior of the major multidrug efflux pump AcrB of *Escherichia coli*. In Proc Natl Acad Sci USA, vol. 106, pp. 5854-5858, (2009)) |
| *Enterobacter cloacae* | ATCC 13047 | | ATCC# |
| *Enterobacter aerogenes* | ATCC 13048 | | ATCC# |
| *Klebsiella pneumoniae* | ATCC 700603 | | ATCC# |
| *Klebsiella pneumoniae* | ATCC 13882 | | ATCC# |
| *Shigella flexneri* | ATCC 12022 | | ATCC# |
| *Salmonella enterica* (typhimurium) | ATCC 14028 | | ATCC# |
| *Pseudomonas aeruginosa* | PA01 | | (Holloway: Genetic recombination in *Pseudomonas aeruginosa*. in J Gen Microbiol, vol. 13, pp. 572-581, (1955)) |
| *Pseudomonas aeruginosa* | ATCC 27853 | | ATCC# |

TABLE 1-continued

Bacterial strains used in this study.

| Organism | Strain | Genotype/Description | Source (Ref) |
|---|---|---|---|
| *Proteus mirabilis* | ATCC 25933 | | ATCC# |
| *Proteus mirabilis* | BAA-856 | UTI clinical isolate | ATCC# |

ATCC, American Type Culture Collection
*isolated as a ciprofloxacin resistant mutant during a serial passage in subinhibitory levels of ciprofloxacin

TABLE 2

MBX potentiates the antibacterial activity of fluoroquinolone and β-lactam antibacterial agents against *Escherichia coli* by inhibiting the AcrAB-TolC efflux pump.

| | MIC (μM) | | MIC (μg/ml) with MBX2319 at concn (μM) of: | | | | | | | MIC ratios | |
|---|---|---|---|---|---|---|---|---|---|---|---|
| Strain | MBX2319 | Drug | 0 | 1.56 | 3.13 | 6.25 | 12.5 | 25 | 50 | 2319[a] | mutant[b] |
| WT | ≥100 | CIP | 0.016 | 0.008 | 0.008 | 0.008 | 0.008 | 0.008 | 0.008 | 2 | 1 |
| | | LEV | 0.063 | 0.031 | 0.016 | 0.016 | 0.016 | 0.016 | 0.016 | 4 | 1 |
| | | PIP | 4 | 2 | 1 | 1 | 0.5 | 0.5 | 0.5 | 8 | 1 |
| ΔtolC | ≥100 | CIP | 0.004 | 0.004 | 0.004 | 0.004 | 0.004 | 0.004 | 0.004 | 1 | 4 |
| | | LEV | 0.016 | 0.016 | 0.016 | 0.008 | 0.008 | 0.008 | 0.008 | 2 | 4 |
| | | PIP | 0.125 | 0.125 | 0.125 | 0.125 | 0.125 | 0.125 | 0.125 | 1 | 32 |
| ΔacrB | ≥100 | CIP | 0.004 | 0.004 | 0.004 | 0.004 | 0.004 | 0.004 | 0.004 | 1 | 4 |
| | | LEV | 0.016 | 0.016 | 0.016 | 0.016 | 0.016 | 0.016 | 0.016 | 1 | 4 |
| | | PIP | 0.250 | 0.125 | 0.125 | 0.125 | 0.125 | 0.125 | 0.125 | 2 | 16 |
| ΔacrF | ≥100 | CIP | 0.016 | 0.008 | 0.008 | 0.008 | 0.008 | 0.008 | 0.008 | 2 | 1 |
| | | LEV | 0.063 | 0.031 | 0.031 | 0.016 | 0.016 | 0.016 | 0.016 | 4 | 1 |
| | | PIP | 4 | 2 | 1 | 0.5 | 0.5 | 0.5 | 0.5 | 8 | 1 |
| 285 | ≥100 | CIP | 1 | 0.25 | 0.125 | 0.125 | 0.125 | 0.125 | 0.125 | 8 | 0.016 |
| | | LEV | 2 | 0.5 | 0.25 | 0.25 | 0.25 | 0.25 | 0.25 | 8 | 0.031 |
| | | PIP | 8 | 4 | 2 | 2 | 2 | 2 | 2 | 4 | 0.5 |
| | | CEF | 0.25 | 0.125 | 0.063 | 0.063 | 0.063 | 0.031 | 0.031 | 8 | 0.25 |
| 287 | ≥100 | CIP | 1 | 0.5 | 0.25 | 0.25 | 0.25 | 0.25 | 0.25 | 4 | 0.016 |
| | | LEV | 2 | 0.5 | 0.5 | 0.5 | 0.5 | 0.25 | 0.25 | 8 | 0.031 |
| | | PIP | 16 | 8 | 4 | 4 | 2 | 2 | 2 | 8 | 0.25 |
| | | CEF | 0.25 | 0.125 | 0.125 | 0.063 | 0.063 | 0.063 | 0.063 | 4 | 0.25 |

[a] highest ratio of MIC (no compound)/MIC (MBX2319)
[b] MIC (WT)/MIC (mutant) in the absence of EPI
Abbreviations: CIP, Ciprofloxacin; LEV, Levofloxacin; PIP, piperacillin; CEF cefotaxime.

TABLE 3

MBX2319 potentiates the antibacterial activity of a broad range of antibiotics and biocides.

| | MICs* (μg/ml) ± EPIs‡ | | | | MIC Ratio | | |
|---|---|---|---|---|---|---|---|
| | WT | | | ΔacrB | | | |
| Compound | None | MBX2319 | PAβN | None | MBX2319[a] | PAβN[b] | ΔacrB[c] |
| Ciprofloxacin | 0.016 | 0.008 | 0.031 | 0.008 | 2 | 0.5 | 2 |
| Levofloxacin | 0.031 | 0.016 | 0.031 | 0.008 | 2 | 1 | 4 |
| Norfloxacin | 0.063 | 0.063 | 0.063 | 0.016 | 1 | 1 | 4 |
| Nalidixic acid | 16 | 8 | 1 | 8 | 2 | 16 | 2 |
| Piperacillin | 4 | 0.5 | 2 | 0.25 | 8 | 2 | 16 |
| Cloxacillin | 256 | 128 | 64 | 4 | 2 | 4 | 64 |
| Oxacillin | 512 | 64 | 128 | 4 | 8 | 4 | 128 |
| Cloramphenicol | 8 | 2 | 2 | 2 | 4 | 4 | 4 |
| Tetracycline | 1 | 1 | 1 | 0.5 | 1 | 1 | 2 |
| Ethidium Br | 256 | 256 | 16 | 8 | 1 | 16 | 32 |
| Irgasan | 0.25 | 0.125 | 0.031 | 0.031 | 2 | 8 | 8 |
| Gentamicin | 4 | 8 | 8 | 4 | 0.5 | 0.5 | 1 |
| Crystal violet | 16 | 8 | 1 | 1 | 2 | 16 | 16 |
| Cephalexin | 32 | 16 | 16 | 32 | 2 | 2 | 1 |

TABLE 3-continued

MBX2319 potentiates the antibacterial activity of a broad range of antibiotics and biocides.

| | MICs* (μg/ml) ± EPIs‡ | | | | MIC Ratio | | |
|---|---|---|---|---|---|---|---|
| | WT | | | ΔacrB | | | |
| Compound | None | MBX2319 | PAβN | None | MBX2319$^a$ | PAβN$^b$ | ΔacrB$^c$ |
| Amoxacillin | 4 | 4 | 4 | 8 | 1 | 1 | 0.5 |
| Rifampicin | 8 | 8 | 0.125 | 8 | 1 | 64 | 1 |

*Geometric mean of MICs from at least three replicate experiments.
‡The final concentration of the EPIs MBX2319 and PAβN was 25 μM.
$^a$MIC no cmpd/MIC + 25 μM MBX2319.
$^b$MIC no cmpd/MIC + 25 μM PAβN.
$^c$MIC WT/MIC ΔacrB

TABLE 4

The spectrum of activity of MBX2319 for antibacterial potentiation.

| | | MIC* (μg/ml) ± EPI‡ | | | MIC ratio | |
|---|---|---|---|---|---|---|
| Organism | Drug | None | MBX2319 | PAβN | MBX2319$^a$ | PAβN$^b$ |
| Escherichia coli | CIP | 0.016 | 0.008 | 0.031 | 2 | 0.5 |
| AB1157 | LEV | 0.031 | 0.016 | 0.031 | 2 | 1 |
| | PIP | 4 | 0.707 | 4 | 5.7 | 1 |
| | CEF | 0.1 | 0.022 | 0.25 | 4.8 | 0.42 |
| Escherichia coli | CIP | 0.016 | 0.005 | 0.022 | 2.8 | 0.7 |
| ATCC 25922 | LEV | 0.031 | 0.013 | 0.022 | 2.4 | 1.4 |
| | PIP | 2.83 | 1.68 | 4 | 1.7 | 0.7 |
| | CEF | 0.074 | 0.063 | 0.25 | 1.2 | 0.3 |
| Escherichia coli | CIP | 128 | 32 | 128 | 4 | 1 |
| 331 | LEV | 64 | 11.3 | 32 | 5.6 | 2 |
| | PIP | 4 | 0.707 | 4 | 5.6 | 1 |
| | CEF | 0.125 | 0.031 | 0.353 | 4 | 0.353 |
| Salmonella enterica | CIP | 0.031 | 0.008 | 0.044 | 4 | 0.7 |
| ATCC 14028 | LEV | 0.062 | 0.016 | 0.044 | 4 | 1.4 |
| | PIP | 2.4 | 0.5 | 4 | 4.8 | 0.6 |
| | CEF | 0.21 | 0.063 | 0.297 | 3.4 | 0.7 |
| Shigella flexneri | CIP | 0.031 | 0.008 | 0.031 | 4 | 1 |
| ATCC 12022 | LEV | 0.063 | 0.016 | 0.031 | 4 | 2 |
| | PIP | 1 | 0.25 | 1 | 4 | 1 |
| | CEF | 0.063 | 0.031 | 0.063 | 2 | 1 |
| Enterobacter aerogenes | CIP | 0.037 | 0.008 | 0.031 | 4.8 | 1.2 |
| ATCC 13048 | LEV | 0.177 | 0.044 | 0.063 | 4 | 2.8 |
| | PIP | 4 | 1.4 | 16 | 2.8 | 0.2 |
| | CEF | 2 | 2.4 | 6.7 | 0.8 | 0.3 |
| P. aeruginosa | CIP | 0.21 | 0.125 | 0.149 | 1.7 | 1.4 |
| ATCC 27853 | LEV | 1 | 1 | 0.5 | 1 | 2 |
| | PIP | 16 | 19 | 19 | 0.84 | 0.8 |
| | CEF | 53.8 | 8 | 19 | 6.7 | 2.8 |
| Klebsiella pneumoniae | CIP | 0.29 | 0.088 | 0.25 | 3.4 | 1.2 |
| ATCC 700603 | LEV | 0.71 | 0.149 | 0.5 | 4.7 | 1.4 |
| | PIP | 113 | 113 | 113 | 1 | 1 |
| | CEF | 8 | 8 | 8 | 1 | 1 |

*Geometric mean of MICs from at least three replicate experiments.
‡The final concentration of the EPIs MBX2319 and PAβN was 25 μM.
$^a$MIC no cmpd/MIC + 25 μM MBX2319.
$^b$MIC no cmpd/MIC + 25 μM PAβN.
Abbreviations: CIP, Ciprofloxacin; LEV, Levofloxacin; PIP, piperacillin; CEF, cefotaxime.

TABLE 5

E. coli strain panel used for cumulative MIC experiment shown in FIG. 5.

| Name | Description | Source (Reference) |
|---|---|---|
| AB1157 | lab strain | (Dewitt, et al.: The Occurrence of a Genetic Transposition in a Strain of Escherichia Coli. In Genetics, vol. 47, pp. 577-585, (1962)) |

TABLE 5-continued

E. coli strain panel used for cumulative MIC experiment shown in FIG. 5.

| Name | Description | Source (Reference) |
|---|---|---|
| ATCC 700336 | UTI isolate | ATCC |
| ECOR-11 | UTI isolate | ECOR |
| ECOR-14 | UTI isolate | ECOR |
| ECOR-35 | UTI isolate | ECOR |
| ECOR-38 | UTI isolate | ECOR |
| ECOR-40 | UTI isolate | ECOR |
| ECOR-48 | UTI isolate | ECOR |
| ECOR-50 | UTI isolate | ECOR |
| ECOR-55 | UTI isolate | ECOR |
| ECOR-60 | UTI isolate | ECOR |
| ECOR-62 | UTI isolate | ECOR |
| ECOR-63 | UTI isolate | ECOR |
| ECOR-64 | UTI isolate | ECOR |
| ECOR-71 | UTI isolate | ECOR |
| ECOR-72 | UTI isolate | ECOR |
| PUTI 308 | UTI isolate | BEI Resources |
| MS110-3 | colitis | BEI Resources |
| ZK57 | UTI isolate | (Barondess, et al.: bor gene of phage lambda, involved in serum resistance, encodes a widely conserved outer membrane lipoprotein. In J Bacteriol, vol. 177, pp. 1247-1253, (1995)) |
| O157:H7 | stool VTEC | BEI Resources |
| EH1533 | stool VTEC | BEI Resources |
| BAA-457 | UTI isolate | ATCC |
| 83972 | asymptomatic bacteuria | BEI Resources |
| PUTI 026 | UTI isolate | BEI Resources |
| CFT073 | UTI isolate | BEI Resources (Welch, et al.: Extensive mosaic structure revealed by the complete genome sequence of uropathogenic *Escherichia coli*. In Proc Natl Acad Sci USA, vol. 99, pp. 17020-17024, (2002)) |

UTI: urinary tract infection
ATCC: American Type Culture Collection
ECOR: reference
BEI Resources: The following reagent was obtained through BEI Resources, NIAID, NIH as part of the Human Microbiome Project: *Escherichia coli*, Strain MS 110-3, HM-343.

TABLE 6

The Minimum Potentiation Concentrations (MPC)* of MBX2319 and analogs in combination with Levofloxacin and Piperacillin against *Escherichia coli* AB1157.

| | Levofloxacin | | | Piperacillin | | |
|---|---|---|---|---|---|---|
| MBX# | MPC2* | MPC4* | MPC8* | MPC2* | MPC4* | MPC8* |
| 2319 | ≤1.56 | 3.13 | ≥100 | ≤1.56 | 3.13 | 12.5 |
| 2403 | ≤1.56 | ≥100 | ≥100 | 3.125 | ≥100 | ≥100 |
| 2408 | ≤1.56 | 6.25 | ≥100 | ≤1.56 | 6.25 | 12.5 |
| 2440 | ≤1.56 | 3.125 | ≥100 | ≤1.56 | ≤1.56 | 6.25 |
| 2441 | ≤1.56 | ≥100 | ≥100 | ≤1.56 | 6.25 | ≥100 |
| 2452 | 50 | ≥100 | ≥100 | 12.5 | >100 | ≥100 |
| 2453 | ≤1.56 | 12.5 | ≥100 | 3.13 | 12.5 | ≥100 |
| 2471 | ≤1.56 | ≥100 | ≥100 | ≤1.56 | ≤1.56 | ≥100 |
| 2503 | ≤1.56 | 12.5 | ≥100 | ≤1.56 | ≥25 | 25 |
| 2574 | ≤1.56 | ≥100 | ≥100 | ≤1.56 | ≥100 | ≥100 |
| 2575 | 100 | ≥100 | ≥100 | ≤1.56 | ≥100 | ≥100 |
| 2685 | ≥100 | ≥100 | ≥100 | ≥100 | ≥100 | ≥100 |
| 2687 | ≥100 | ≥100 | ≥100 | ≥100 | ≥100 | ≥100 |
| 2697 | ≤1.56 | ≥100 | ≥100 | ≥50 | 100 | ≥100 |
| 2698 | ≤1.56 | 25 | ≥100 | ≤1.56 | 3.13 | 25 |
| 2699 | ≤1.56 | 50 | ≥100 | 3.125 | 25 | 50 |
| 2741 | ≤0.2 | 6.25 | ≥12.5 | ≤0.2 | 0.4 | 6.25 |
| 2742 | ≤0.2 | ≥12.5 | ≥12.5 | ≤0.2 | 3.125 | ≥12.5 |
| 2743 | ≥12.5 | ≥12.5 | ≥12.5 | ≤0.2 | ≥12.5 | ≥12.5 |
| 2789 | 50 | ≥100 | ≥100 | ≤50 | 50 | ≥100 |
| 2802 | ≥100 | ≥100 | ≥100 | ≥100 | ≥100 | ≥100 |
| 2803 | ≥100 | ≥100 | ≥100 | ≥100 | ≥100 | ≥100 |
| 2804 | ≤1.56 | ≥100 | ≥100 | ≤1.56 | ≤1.56 | ≥100 |
| 2807 | 6.25 | ≥100 | ≥100 | 6.25 | 50 | ≥100 |
| 2808 | 3.13 | 100 | ≥100 | 6.25 | 25 | ≥100 |
| 2809 | 3.13 | 50 | ≥100 | 3.13 | 25 | ≥100 |
| 2810 | ≥100 | ≥100 | ≥100 | ≥100 | ≥100 | ≥100 |
| 2813 | ≥100 | ≥100 | ≥100 | ≥100 | ≥100 | ≥100 |
| 2814 | ≥100 | ≥100 | ≥100 | 12.5 | ≥100 | ≥100 |
| 2816 | ≤1.56 | 3.13 | ≥100 | ≤1.56 | 12.5 | ≥100 |
| 2817 | 6.25 | ≥100 | ≥100 | 3.125 | 25 | ≥100 |
| 2818 | 3.13 | 50 | ≥100 | 3.13 | 6.25 | 50 |
| 2825 | ≤1.56 | 50 | ≥100 | ≤3.125 | 3.125 | 25 |
| 2826 | ≤1.56 | 25 | ≥100 | 3.13 | 12.5 | 50 |
| 2827 | 3.125 | 25 | ≥100 | 3.13 | 25 | ≥100 |
| 2828 | ≤1.56 | 25 | ≥100 | 3.13 | 25 | ≥100 |
| 2829 | ≤1.56 | 12.5 | ≥100 | ≤1.56 | 6.25 | 50 |
| 2831 | ≥100 | ≥100 | ≥100 | ≥100 | ≥100 | ≥100 |
| 2842 | ≤1.56 | 12.5 | ≥100 | ≤1.56 | 3.125 | 12.5 |

TABLE 6-continued

The Minimum Potentiation Concentrations (MPC)* of MBX2319 and analogs in combination with Levofloxacin and Piperacillin against *Escherichia coli* AB1157.

| | Levofloxacin | | | Piperacillin | | |
|---|---|---|---|---|---|---|
| MBX# | MPC2* | MPC4* | MPC8* | MPC2* | MPC4* | MPC8* |
| 2843 | 50 | ≥100 | ≥100 | 25 | 50 | ≥100 |
| 2844 | 50 | ≥100 | ≥100 | 25 | ≥100 | ≥100 |
| 2845 | 3.13 | ≥100 | ≥100 | 6.25 | 25 | ≥100 |
| 2846 | ≤1.56 | ≥100 | ≥100 | 3.13 | 25 | ≥100 |
| 2847 | 6.25 | ≥100 | ≥100 | 6.25 | 25 | ≥100 |
| 2854 | ≤1.56 | 6.25 | ≥100 | ≤1.56 | ≤1.56 | 6.25 |
| 2885 | ≤1.56 | 3.13 | ≥100 | ≤1.56 | 3.13 | ≥100 |
| 2864 | ≤1.56 | ≥100 | ≥100 | ≤1.56 | 3.13 | ≥100 |
| 2865 | ≤1.56 | 50 | ≥100 | ≤1.56 | ≤1.56 | 6.25 |
| 2870 | ≤1.56 | 6.25 | ≥100 | ≤1.56 | ≤1.56 | 6.25 |
| 2871 | ≤1.56 | ≥100 | ≥100 | ≤1.56 | ≥100 | ≥100 |
| 2872 | ≤1.56 | 50 | ≥100 | ≤1.56 | ≤1.56 | ≤1.56 |
| 2873 | ≤1.56 | ≥100 | ≥100 | ≤1.56 | ≤1.56 | ≥100 |
| 2884 | ≤1.56 | 3.13 | >=100 | ≤1.56 | 3.13 | ≥100 |
| 2855 | ≤1.56 | 3.13 | >=100 | ≤1.56 | 3.13 | ≥100 |
| 2886 | ≤1.56 | 3.13 | ≥100 | ≤1.56 | 3.13 | ≥100 |
| 2893 | ≤1.56 | ≤1.56 | ≥100 | ≤1.56 | ≤1.56 | 6.25 |
| 2894 | ≤1.56 | 6.25 | ≥100 | ≤1.56 | 3.13 | 12.5 |
| 2895 | ≤1.56 | ≥100 | ≥100 | ≤1.56 | 6.25 | ≥100 |
| 2896 | ≤1.56 | ≤1.56 | ≥100 | ≤1.56 | ≤1.56 | 3.125 |
| 2897 | ≤1.56 | 6.25 | ≥100 | ≤1.56 | 3.13 | 25 |
| 2898 | ≤1.56 | 12.5 | ≥100 | ≤1.56 | 6.25 | 50 |
| 2900 | 12.5 | ≥100 | ≥100 | ≤1.56 | ≥100 | ≥100 |
| 2901 | 3.13 | ≥100 | ≥100 | ≤1.56 | 6.25 | ≥100 |
| 2903 | 3.13 | ≥100 | ≥100 | 3.13 | 12.5 | ≥100 |
| 2913 | ≤1.56 | 12.5 | ≥100 | ≤1.56 | 3.12 | 12.5 |
| 2923 | ≤1.56 | 12.5 | ≥100 | ≤1.56 | 6.25 | ≥100 |
| 2927 | ≤1.56 | 12.5 | ≥100 | ≤1.56 | ≤1.56 | 6.25 |
| 2928 | ≤1.56 | 25 | ≥100 | ≤1.56 | 3.12 | 12.5 |
| 2931 | ≤0.195 | 1.56 | ≥12.5 | ≤0.39 | 0.39 | 12.5 |
| 3097 | ≤1.56 | ≥100 | ≥100 | ≤1.56 | 3.125 | ≥100 |
| 3098 | ≤1.56 | 12.5 | ≥100 | 3.125 | 12.5 | 50 |
| 3099 | ≤0.195 | 0.78 | ≥12.5 | ≤0.39 | ≤0.39 | 1.56 |
| 3106 | ≤0.195 | 0.78 | ≥12.5 | ≤0.195 | 0.78 | 3.12 |
| 3132 | ≤0.049 | 0.097 | ≥3.125 | ≤0.049 | 0.097 | ≤0.39 |
| 3133 | ≤1.56 | ≥100 | ≥100 | 12.5 | 25 | ≥100 |
| 3134 | ≤1.56 | 6.25 | ≥100 | ≤1.56 | 6.25 | ≥100 |
| 3135 | ≤0.195 | ≤0.195 | 1.5625 | ≤0.195 | ≤0.195 | ≤0.195 |
| 3157 | ≤0.195 | 3.13 | ≥12.5 | ≤0.195 | 0.78 | 3.13 |
| 3193 | ≤1.56 | 6.25 | ≥100 | ≤1.56 | 3.13 | ≥100 |
| 3221 | 3.13 | ≥100 | ≥100 | 25 | ≥100 | ≥100 |
| 3223 | ≤1.56 | 3.13 | ≥100 | ≤1.56 | 3.13 | 12.5 |
| 3224 | ≤1.56 | 3.13 | ≥100 | ≤1.56 | 3.13 | ≥100 |
| 3225 | ≤1.56 | 12.5 | ≥100 | ≤1.56 | 12.5 | ≥100 |
| 3226 | ≤1.56 | 3.13 | ≥100 | ≤1.56 | 3.13 | ≥100 |
| 3229 | ≤1.56 | 6.25 | ≥100 | ≤1.56 | ≤1.56 | 12.5 |
| 3230 | ≤1.56 | ≤1.56 | ≥100 | ≤1.56 | ≤1.56 | ≥100 |
| 3249 | ≤1.56 | 3.13 | 100 | ≤1.56 | 6.25 | 25 |
| 3262 | ≤1.56 | 12.5 | ≥100 | ≤1.56 | 12.5 | ≥100 |
| 3263 | ≤1.56 | 3.13 | ≥100 | ≤1.56 | 3.13 | ≥100 |
| 3269A | ≥100 | ≥100 | ≥100 | ≤1.56 | ≤1.56 | ≥100 |
| 3309A | 50 | ≥100 | ≥100 | <=12.5 | 12.5 | ≥100 |
| 3310 | ≤1.56 | ≥100 | ≥100 | ≤1.56 | 3.13 | 12.5 |
| 3311A | ≤1.56 | 6.25 | ≥100 | ≤1.56 | ≤1.56 | 6.25 |
| 3324 | ≥100 | ≥100 | ≥100 | ≥100 | ≥100 | ≥100 |
| 3325 | ≤1.56 | 12.5 | ≥100 | ≤1.56 | ≤1.56 | 6.25 |
| 3327 | ≥100 | ≥100 | ≥100 | 3.13 | ≥100 | ≥100 |
| 3330 | ≤1.56 | ≥100 | ≥100 | ≤1.56 | 6.25 | ≥100 |
| 3335 | ≤1.56 | 3.13 | ≥100 | ≤1.56 | ≤1.56 | ≥100 |
| 3336 | ≤1.56 | 50 | ≥100 | ≤1.56 | ≤1.56 | 12.5 |
| 3347 | ≤1.56 | ≥100 | ≥100 | ≤1.56 | ≤1.56 | 12.5 |
| 3348 | ≤1.56 | ≥100 | ≥100 | ≤1.56 | 3.13 | ≥100 |
| 3353 | ≤1.56 | 1.25 | ≥100 | ≤0.195 | 0.781 | 1.5625 |
| 3354 | ≤1.56 | 6.25 | ≥100 | 0.78 | 3.13 | ≥100 |

*The Minimum Potentiation Concentrations (MPC) are the minimal concentration of a test compound that decreases the MIC of an antibacterial agent by 2 fold (MPC2), 4 fold (MPC4), or 8 fold (MPC8).
The MICs for Levofloxacin and Piperacillin against *E. coli* AB1157 are 0.06 ug/ml and 4 μg/ml, respectively.

TABLE 7

Inhibition of efflux against *Escherichia coli* AB1157 expressed as a fraction of total inhibition (ΔaacrB) at 25 μM EPI analog calculated from the data shown in FIG. 6.

| MBX# | Fraction ΔaacrB* |
|---|---|
| 2319 | 0.44 |
| 2403 | 0.24 |
| 2408 | 0.49 |
| 2440 | 0.13 |
| 2441 | 0.11 |
| 2452 | −0.01 |
| 2453 | 0.23 |
| 2471 | 0.12 |
| 2474 | −0.05 |
| 2475 | −0.05 |
| 2503 | 0.51 |
| 2635 | −0.01 |
| 2636 | −0.03 |
| 2685 | −0.07 |
| 2687 | 0.01 |
| 2697 | 0.22 |
| 2698 | 0.33 |
| 2699 | 0.36 |
| 2741 | 0.64 |
| 2742 | 0.54 |
| 2789 | 0.13 |
| 2802 | 0.15 |
| 2803 | 0.1 |
| 2804 | 0.22 |
| 2807 | 0.41 |
| 2808 | 0.69 |
| 2816 | 0.43 |
| 2817 | 0.36 |
| 2818 | 0.47 |
| 2825 | 0.3 |
| 2826 | 0.44 |
| 2827 | 0.26 |
| 2828 | 0.34 |
| 2829 | 0.51 |

*Fraction of ΔaacrB strain is the relative level of H33342 accumulation after 30 min in the presence of 25 μM compound as compared to the H33342 accumulation in the ΔaacrB strain (complete loss of AcrAB-TolC). Fraction of ΔaacrB was calculated as follows: Fluor (+cmpd) − Fluor (−cmpd) / Fluor (ΔaacrB) − Fluor (−cmpd).

All publications, patent applications, patents, and other documents cited herein are incorporated by reference in their entirety. The examples provided herein are illustrative only and are not intended to be limiting.

Obvious variations to the disclosed compounds and alternative embodiments of the invention will be apparent to those skilled in the art in view of the foregoing disclosure. All such obvious variants and alternatives are considered to be within the scope of the invention as described herein.

The invention claimed is:

1. A bacterial efflux inhibitor compound having the structure of Formula I, or a pharmaceutically acceptable salt thereof:

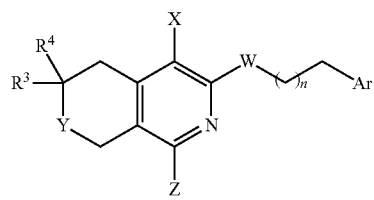

FORMULA I wherein, n is an integer from 1 to 5;

X is —CN, —F, —Cl, —Br, —I, —NO$_2$;

W is S, SO, SO$_2$, O, NH, or NR$^5$;

R$^5$ is alkyl, aralkyl, alkenyl, or alkynyl;

Y is O, S;

Z is NR$^1$R$^2$ or heterocycloalkyl;

R$^1$, R$^2$ are, independently, hydrogen, alkyl, aralkyl, alkenyl, alkynyl, or cycloalkyl and may be optionally substituted with halo, hydroxy, alkoxy, amino, alkylamino, carboxy, alkoxycarbonyl, or nitrile groups;

R$^3$ and R$^4$ are, independently, hydrogen, alkyl, aralkyl, alkenyl, alkynyl, or cycloalkyl and may be optionally substituted with halo, hydroxy, alkoxy, amino, alkylamino, carboxy, alkoxycarbonyl, or nitrile groups, and may together form a cyclic structure; and Ar is mono-, di-, or tri-substituted phenyl or heteroaryl.

2. A compound according to claim 1, wherein:

n is 1;

X is —CN;

W is S;

Y is O;

Z is heterocycloalkyl;

R$^3$ and R$^4$ are methyl; and

Ar is mono-, di, or tri-substituted phenyl or heteroaryl.

3. The compound according to claim 1, selected from the group consisting of:

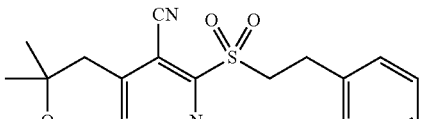

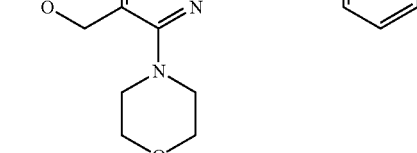

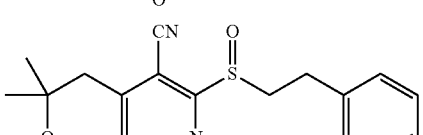

167
-continued
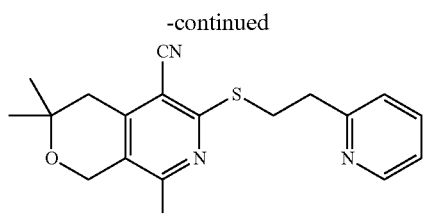
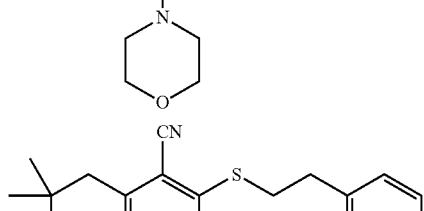
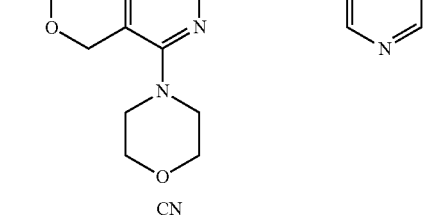
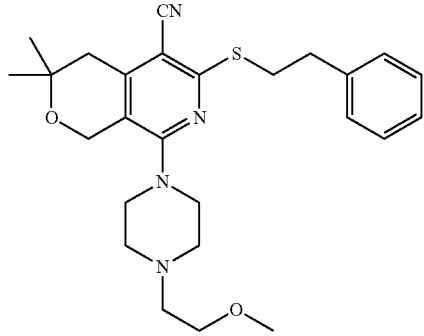
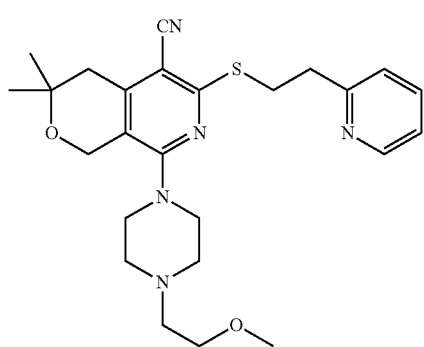
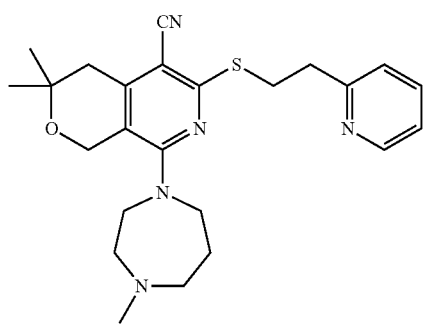
168
-continued
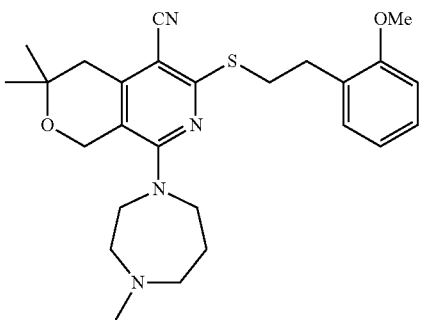
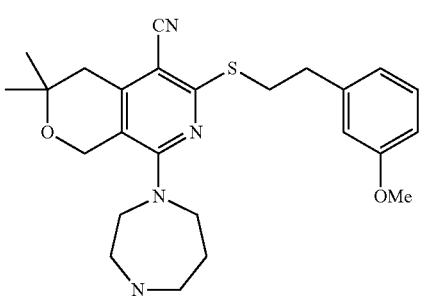
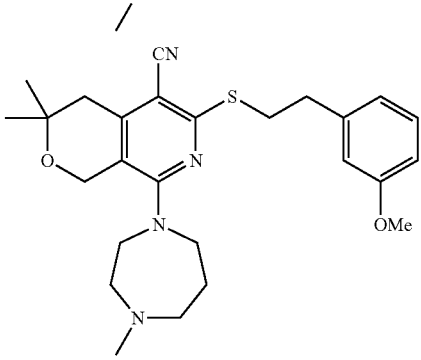
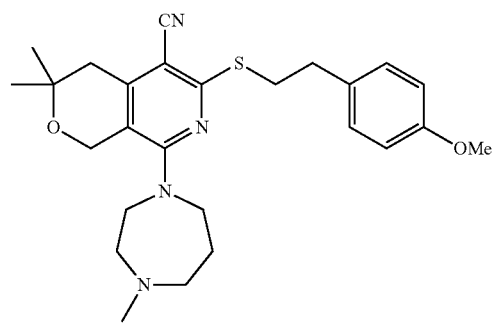
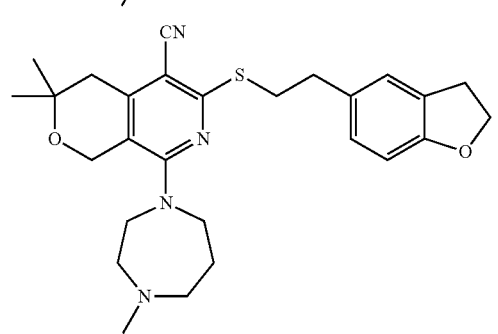

169
-continued
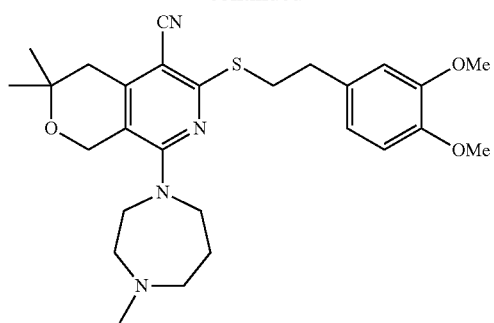
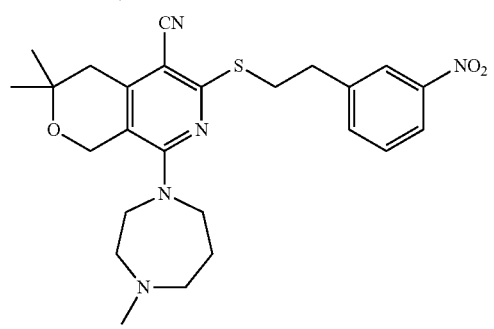
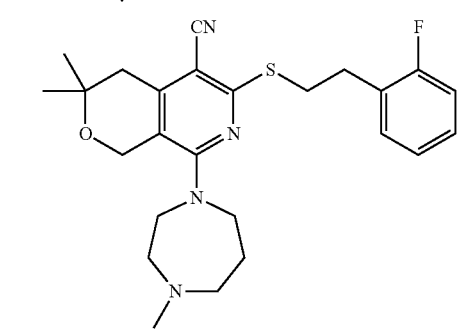
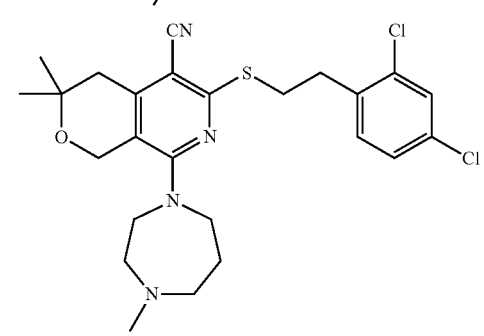
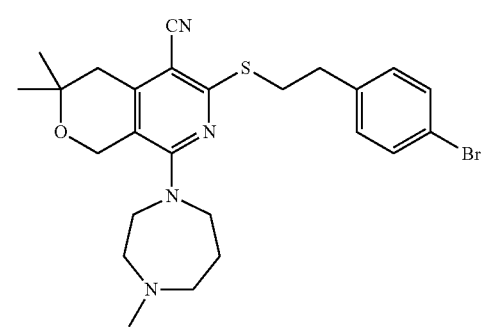
170
-continued
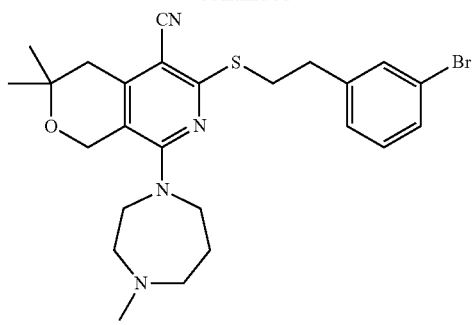
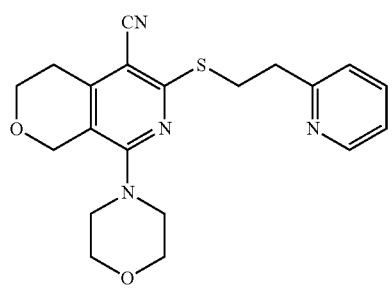
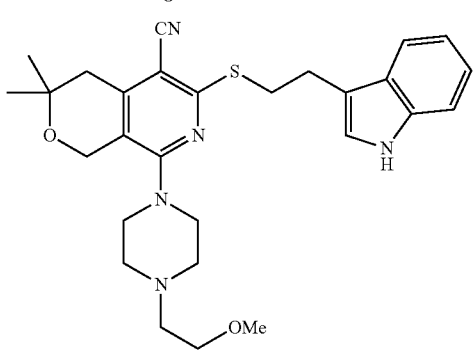
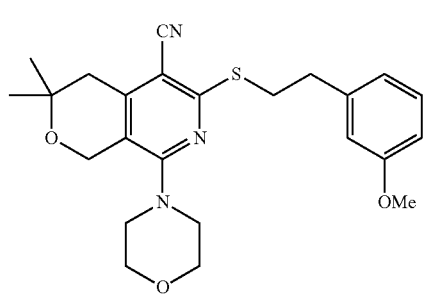
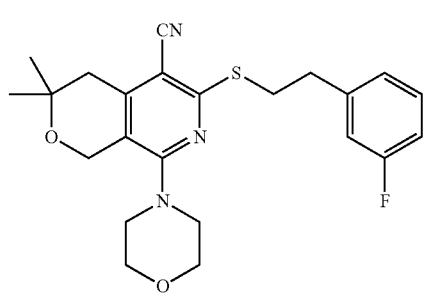

171
-continued
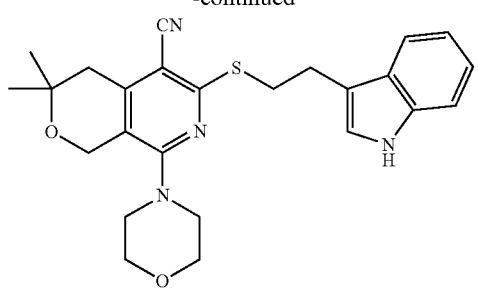
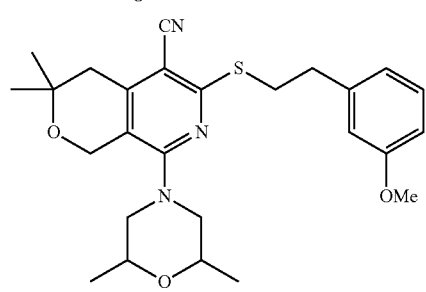
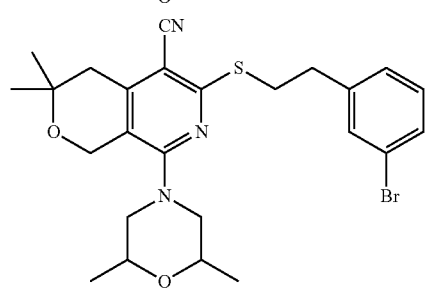
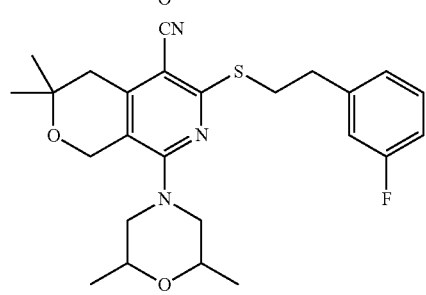
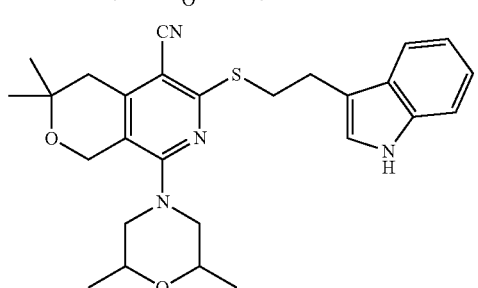
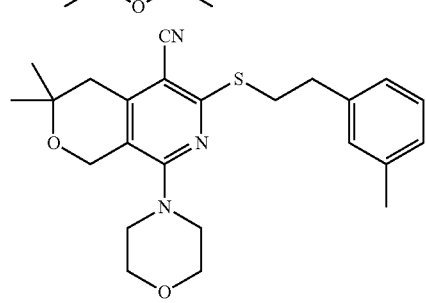
172
-continued
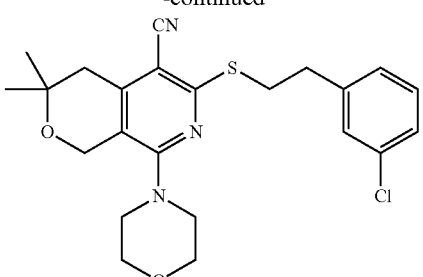
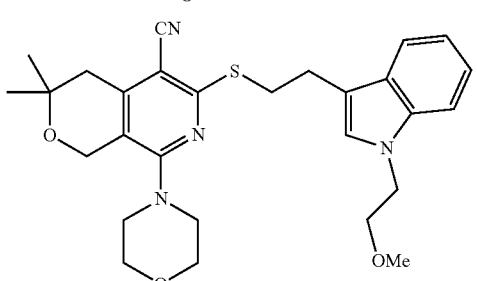
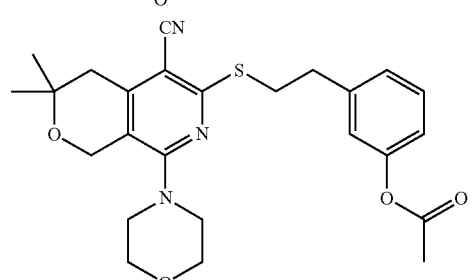
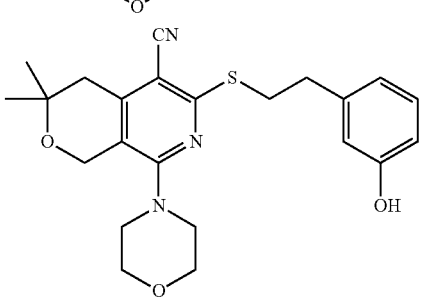
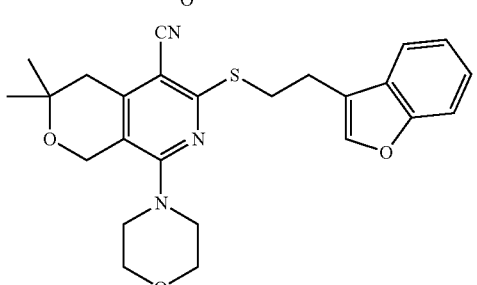
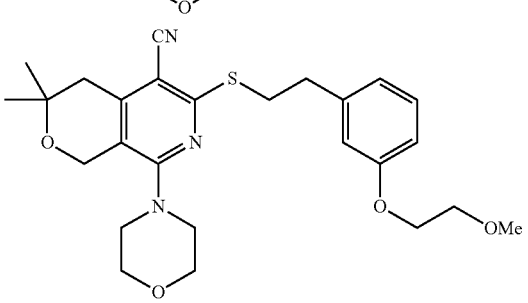

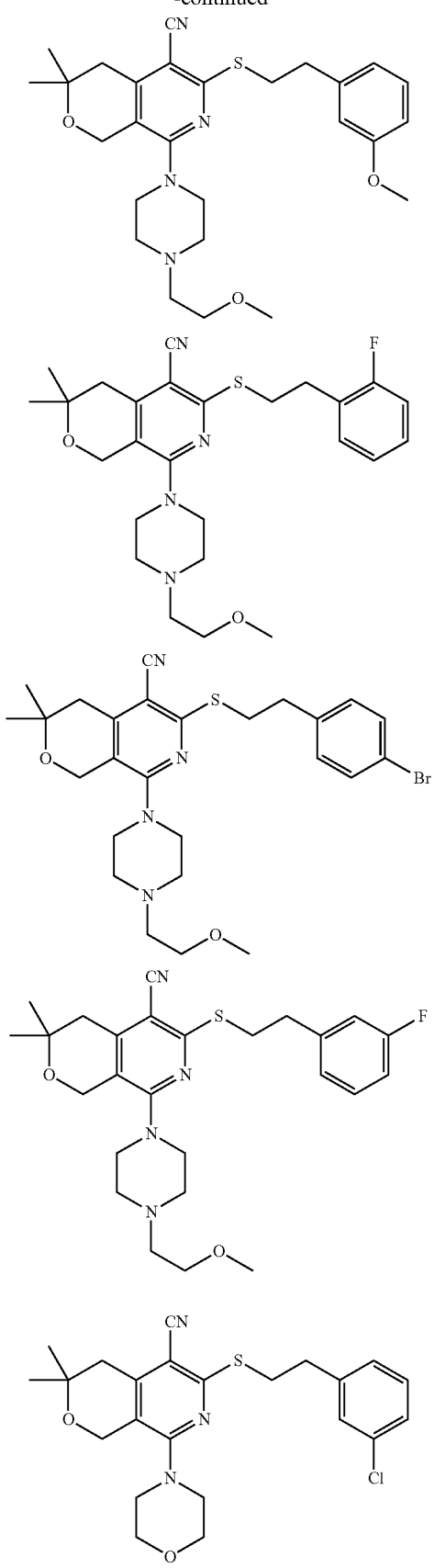
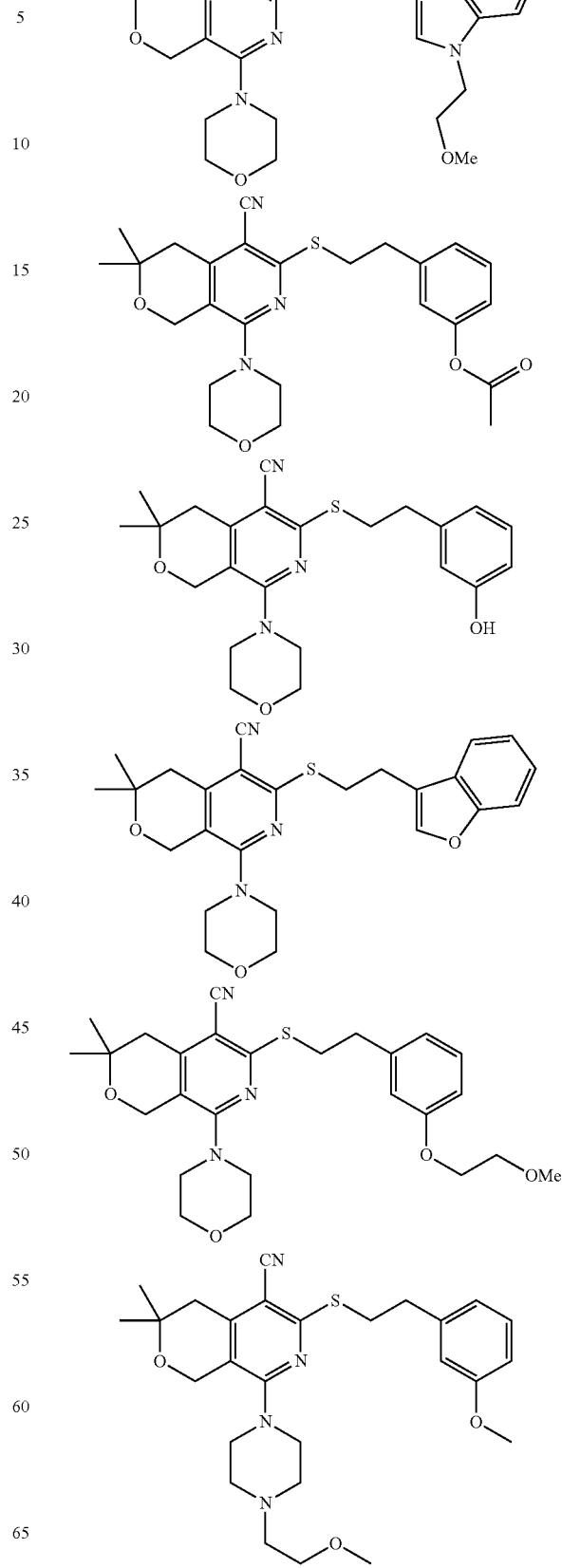

175
-continued
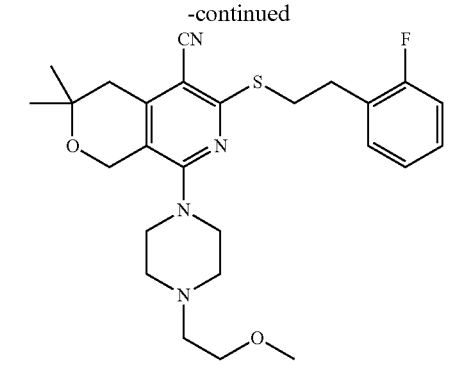
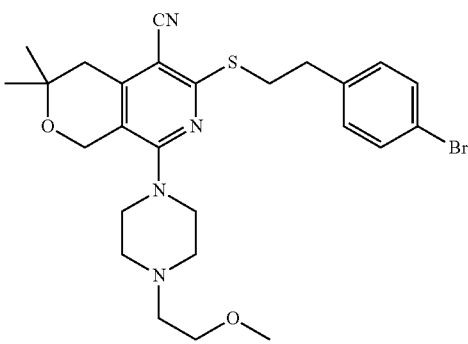
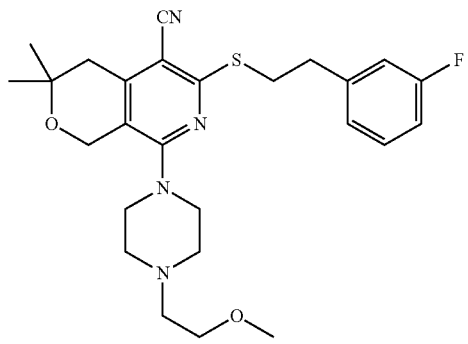
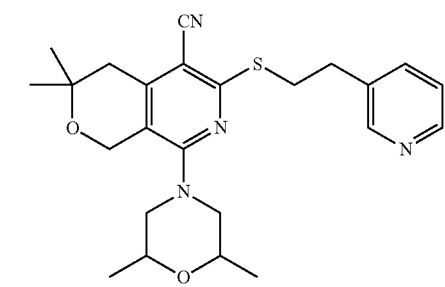
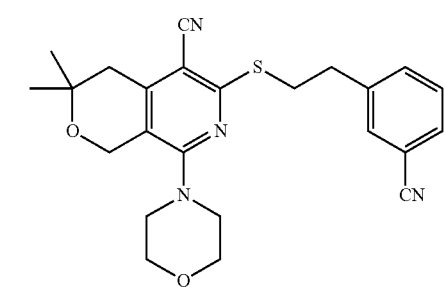
176
-continued
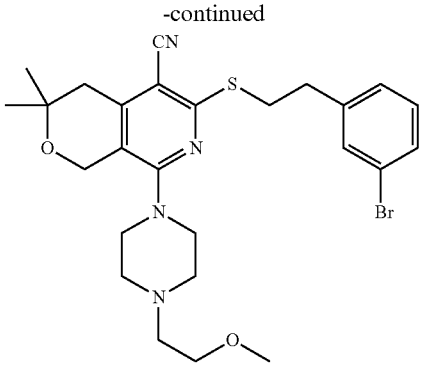
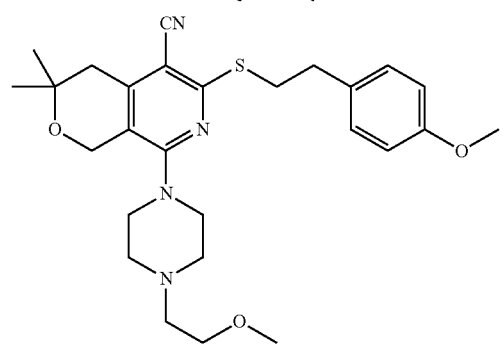
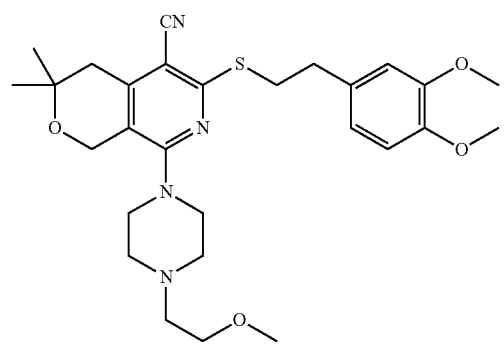
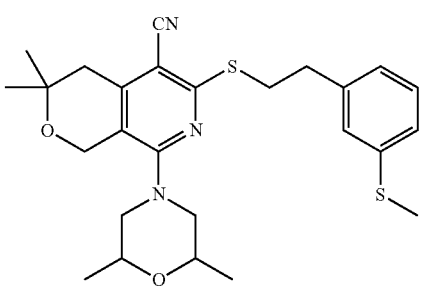
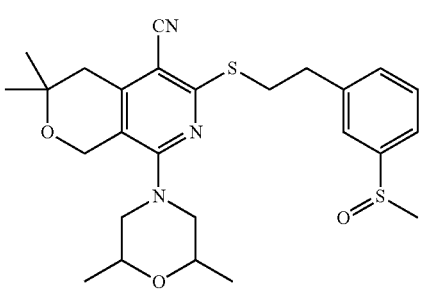

177
-continued
178
-continued
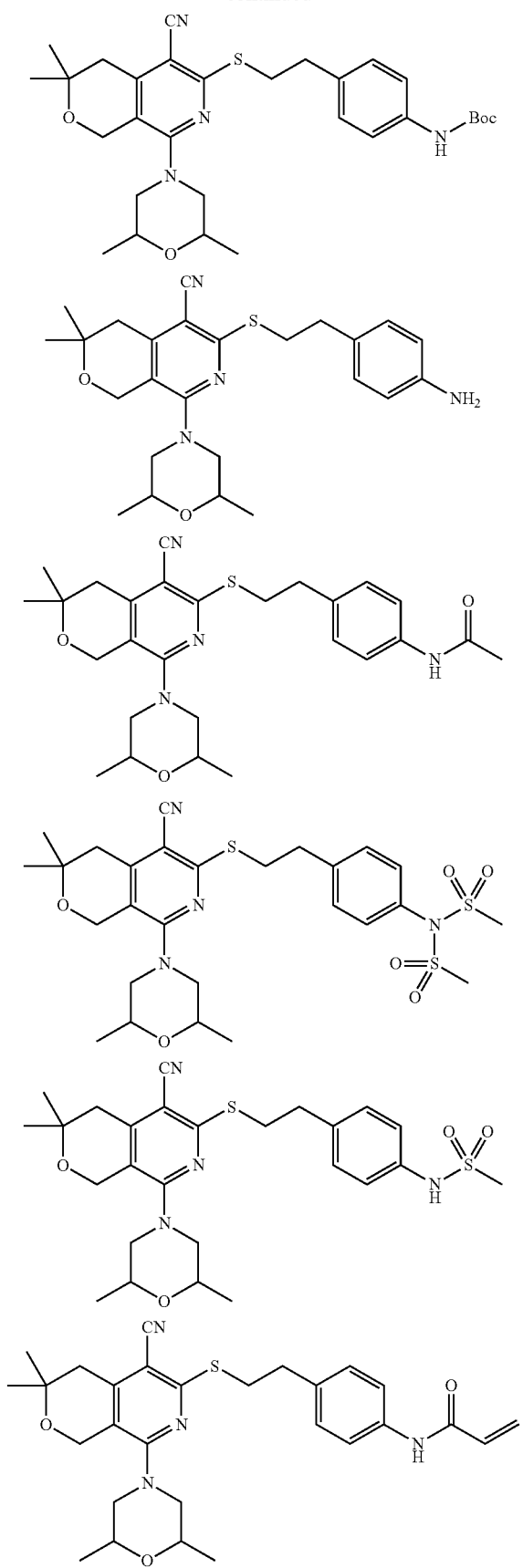
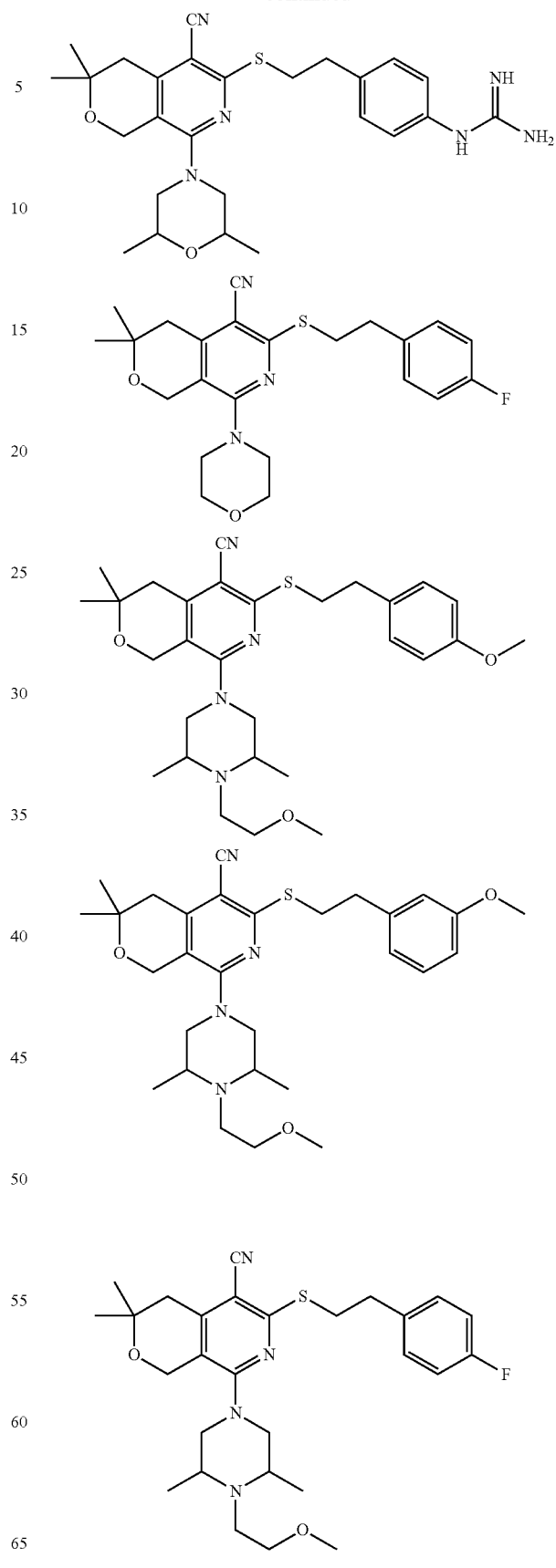

179
-continued
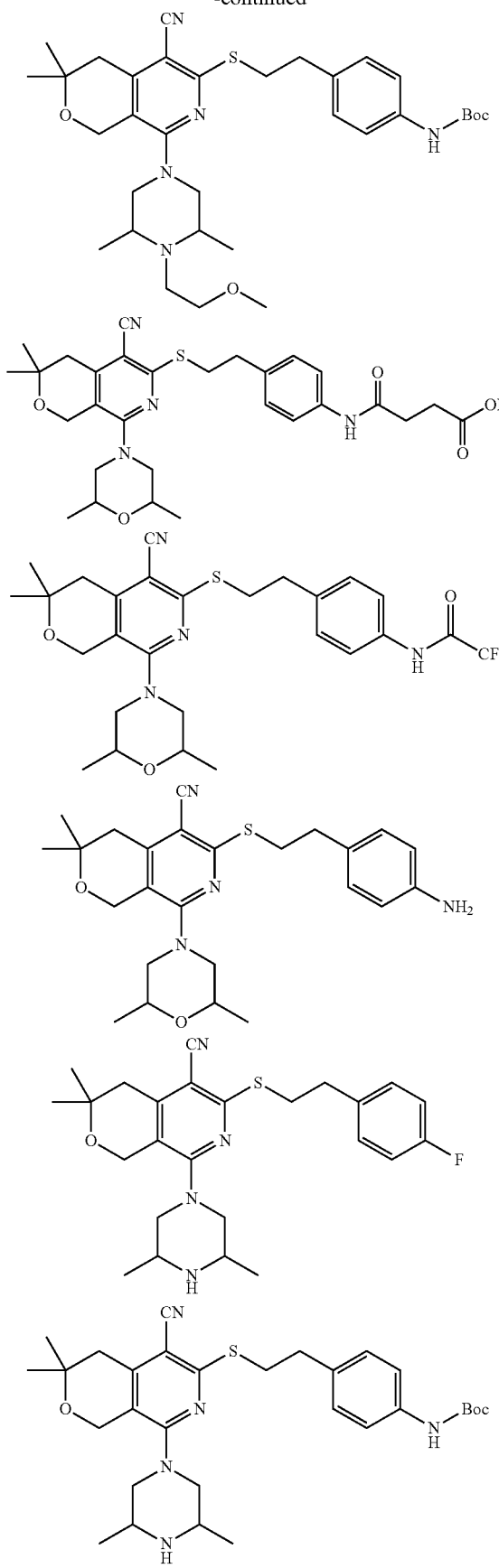
180
-continued
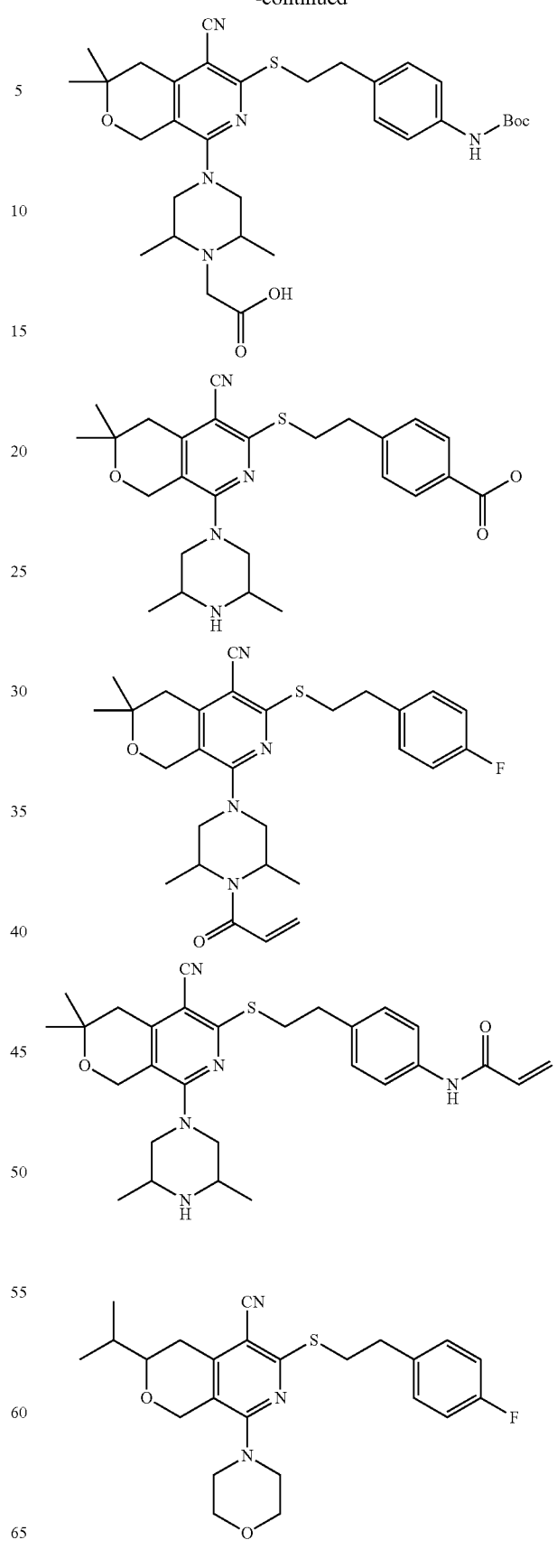

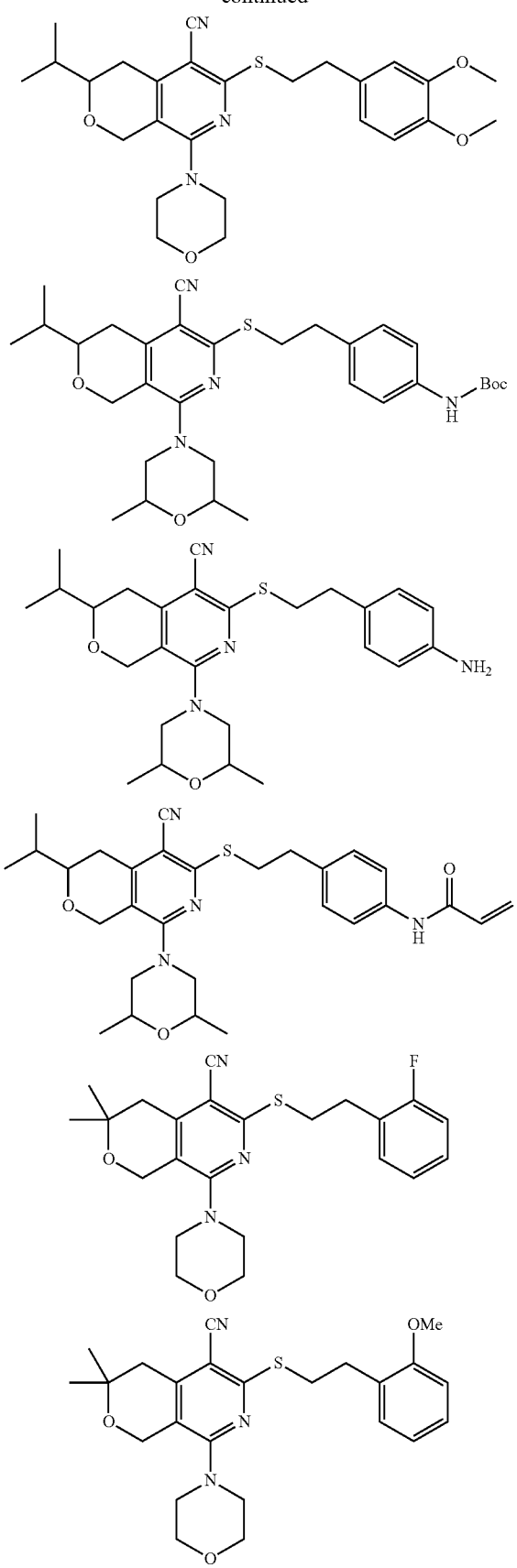

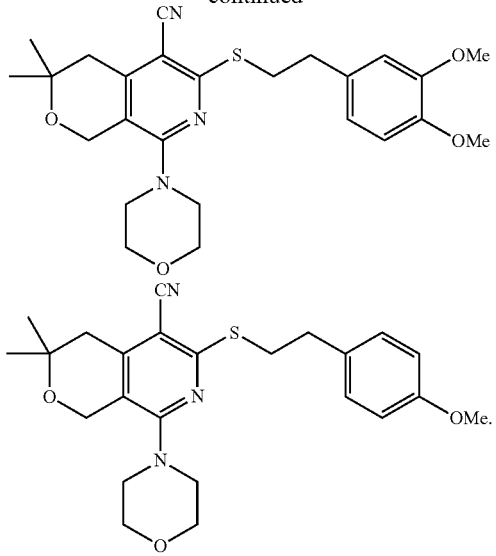

4. A pharmaceutical composition comprising a compound according to claim 1 and a pharmaceutically acceptable carrier or excipient.

5. A composition according to claim 4, further comprising an antimicrobial agent.

6. A composition according to claim 5, wherein said antimicrobial agent is a beta-lactam antibiotic with or without a beta-lactamase inhibitor, or a quinolone antibiotic.

7. A composition according to claim 6, wherein said antimicrobial agent is a beta-lactam antibiotic selected from amoxicillin, ampicillin, piperacillin, azlocillin, cefcapene, cefdaloxime, cefdinir, cefditoren, cefetamet, cefixime, cefmenoxime, cefodizime, cefotaxime, cefovecin, cefpimizole, cefpodoxime, cefteram, ceftibuten, ceftiofur, ceftiolene, ceftizoxime, ceftriaxone, cefoperazone, ceftazidime, cefclidine, cefepime, cefluprenam, cefoselis, cefozopran, cefpirome, cefquinome, ertapenem, doripenam, imipenam, meropenam, or aztronam, with or without a beta-lactamase inhibitor; or said antimicrobial agent is a quinolone antibiotic selected from ciprofloxacin, enoxacin, fleroxacin, lomefloxacin, nadifloxacin, norfloxacin, ofloxacin, pefloxacin, rufloxacin, balofloxacin, levofloxacin, pazufloxacin, sparfloxacin, tosufloxacin, clinafloxacin, gemifloxacin, moxifloxacin, sitafloxacin, trovafloxacin, or prulifloxacin.

8. A method of inhibiting bacterial efflux pumps in a mammal comprising administering an effective amount of at least one compound having the structure of Formula I:

FORMULA I

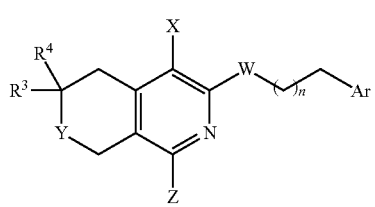

wherein,
n is an integer from 1 to 5;
X is —CN, —F, —Cl, —Br, —I, —NO$_2$;
W is S, SO, SO$_2$, O, NH, or NR$^5$;

$R^5$ is alkyl, aralkyl, alkenyl, or alkynyl;

Y is O, S;

Z is $NR^1R^2$ or heterocycloalkyl;

$R^1$, $R^2$ are, independently, hydrogen, alkyl, aralkyl, alkenyl, alkynyl, or cycloalkyl and may be optionally substituted with halo, hydroxy, alkoxy, amino, alkylamino, carboxy, alkoxycarbonyl, or nitrile groups;

$R^3$ and $R^4$ are, independently, hydrogen, alkyl, aralkyl, alkenyl, alkynyl, or cycloalkyl and may be optionally substituted with halo, hydroxy, alkoxy, amino, alkylamino, carboxy, alkoxycarbonyl, or nitrile groups, and may together form a cyclic structure; and Ar is mono-, di-, or tri-substituted phenyl or heteroaryl.

9. The method according to claim 8, wherein the compound, or pharmaceutically acceptable salt thereof, is used in combination with an antimicrobial agent.

10. The method according to claim 9, wherein said antimicrobial agent is a beta-lactam antibiotic with or without a beta-lactamase inhibitor, or a quinolone antibiotic.

11. The method according to claim 10, wherein said antimicrobial agent is a beta-lactam antibiotic selected from amoxicillin, ampicillin, piperacillin, azlocillin, cefcapene, cefdaloxime, cefdinir, cefditoren, cefetamet, cefixime, cefmenoxime, cefodizime, cefotaxime, cefovecin, cefpimizole, cefpodoxime, cefteram, ceftibuten, ceftiofur, ceftiolene, ceftizoxime, ceftriaxone, cefoperazone, ceftazidime, cefcclidine, cefepime, cefluprenam, cefoselis, cefozopran, cefpirome, cefquinome, ertapenem, doripenam, imipenam, meropenam, or aztronam, with or without a beta-lactamase inhibitor; or said antimicrobial agent is a quinolone antibiotic selected from ciprofloxacin, enoxacin, fleroxacin, lomefloxacin, nadifloxacin, norfloxacin, Ofloxacin, pefloxacin, rufloxacin, balofloxacin, levofloxacin, pazufloxacin, sparfloxacin, tosufloxacin, clinafloxacin, gemifloxacin, moxifloxacin, sitafloxacin, trovafloxacin, or prulifloxacin.

12. A method, for treating a bacterial infection in a mammal comprising administering to said mammal a composition comprising a compound having the structure of Formula I:

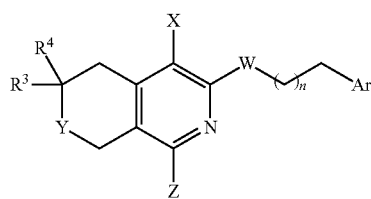

FORMULA I wherein, n is 1, 2, 3, 4 or 5;

X is —CN, —F, —Cl, —Br, —I, —NO$_2$;

W is S, SO, SO$_2$, O, NH, or $NR^5$;

$R^5$ is alkyl, aralkyl, alkenyl, or alkynyl;

Y is O, S;

Z is $NR^1R^2$ or heterocycloalkyl;

$R^1$, $R^2$ are, independently, hydrogen, alkyl, aralkyl, alkenyl, alkynyl, or cycloalkyl and may be optionally substituted with halo, hydroxy, alkoxy, amino, alkylamino, carboxy, alkoxycarbonyl, or nitrile groups;

$R^3$ and $R^4$ are, independently, hydrogen, alkyl, aralkyl, alkenyl, alkynyl, or cycloalkyl and may be optionally substituted with halo, hydroxy, alkoxy, amino, alkylamino, carboxy, alkoxycarbonyl, or nitrile groups, and may together form a cyclic structure; and Ar is mono-, di-, or tri-substituted phenyl or heteroaryl.

13. The method according to claim 12, wherein said composition is administered in combination with an antimicrobial agent.

14. The method according to claim 13, wherein said antimicrobial agent is a beta-lactam antibiotic with or without a beta-lactamase inhibitor, or a quinolone antibiotic.

15. The method according to claim 14, wherein said antimicrobial agent is a beta-lactam antibiotic selected from amoxicillin, ampicillin, piperacillin, azlocillin, cefcapene, cefdaloxime, cefdinir, cefditoren, cefetamet, cefixime, cefmenoxime, cefodizime, cefotaxime, cefovecin, cefpimizole, cefpodoxime, cefteram, ceftibuten, ceftiofur, ceftiolene, ceftizoxime, ceftriaxone, cefoperazone, ceftazidime, cefcclidine, cefepime, cefluprenam, cefoselis, cefozopran, cefpirome, cefquinome, ertapenem, doripenam, imipenam, meropenam, or aztronam, with or without a beta-lactamase inhibitor; or said antimicrobial agent is a quinolone antibiotic selected from ciprofloxacin, enoxacin, fleroxacin, lomefloxacin, nadifloxacin, norfloxacin, Ofloxacin, pefloxacin, rufloxacin, balofloxacin, levofloxacin, pazufloxacin, sparfloxacin, tosufloxacin, clinafloxacin, gemifloxacin, moxifloxacin, sitafloxacin, trovafloxacin, or prulifloxacin.

16. The method according to Claim 8, wherein said mammal is a human.

17. The method according to claim 12, wherein said mammal is a human.

* * * * *